United States Patent
Guillemont et al.

(10) Patent No.: US 7,115,608 B2
(45) Date of Patent: Oct. 3, 2006

(54) PYRIDINONE AND PYRIDINETHIONE DERIVATIVES HAVING HIV INHIBITING PROPERTIES

(75) Inventors: Jérôme Guillemont, Ande (FR); Abdellah Benjahad, Champigny-sur-Marne (FR); Dominique Mabire, La Saussaye (FR); Chi Hung N'Guyen, Antony (FR); David Grierson, Buc (FR); Claude Monneret, Paris (FR); Emile Bisagni, Orsay (FR); Gérard Sanz, Les Mesnil Esnard (FR); Laurence Decrane, Le Vaudreuil (FR)

(73) Assignees: Centre National de la Recherche Schentifique, (FR); Institute Curie, (FR)

( * ) Notice: Subject to any disclaimer, the term of this patent is extended or adjusted under 35 U.S.C. 154(b) by 142 days.

(21) Appl. No.: 10/380,784

(22) PCT Filed: Sep. 18, 2001

(86) PCT No.: PCT/IB01/02082

§ 371 (c)(1), (2), (4) Date: Mar. 18, 2003

(87) PCT Pub. No.: WO02/24650

PCT Pub. Date: Mar. 28, 2002

(65) Prior Publication Data

US 2004/0229847 A1    Nov. 18, 2004

(30) Foreign Application Priority Data

Sep. 19, 2000  (EP) .................................. 00402583

(51) Int. Cl.
C07D 213/02 (2006.01)
A61K 31/47 (2006.01)

(52) U.S. Cl. .................. 514/252.13; 514/340; 514/341; 514/345; 544/360; 546/268.1; 546/300; 546/301

(58) Field of Classification Search ................ 546/290, 546/300, 301, 79, 80, 81, 303, 268.1; 514/345, 514/351, 291, 292, 252.13, 340, 341; 544/360
See application file for complete search history.

(56) References Cited

FOREIGN PATENT DOCUMENTS

| WO | WO97/05113 | 2/1997 |
|---|---|---|
| WO | WO 97/19923 A1 * | 7/1997 |
| WO | WO97/37977 | 10/1997 |
| WO | WO99/55676 | 11/1999 |
| WO | WO00/00475 | 1/2000 |

OTHER PUBLICATIONS

Dolle, V. et al, "A New Series of Pyridinone Derivatives as Potent Non-Nucleoside Human Immunodeficiency Virus Type 1 Specific Reverse Transcriptase Inhibitors", J.Med.Chem, vol. 38, No. 23, Oct. 15, 1995, pp. 4679-4686.

Kolder, C.R. et al, "Tautomerism of Hydroxypyridines—(II) Bromination of 2,4-Dihydroxypyridines and its Ethyl Derivatives", Chemical Abstracts, No. CA55:1608f, XP-002190994.

Ran, C. et al, "Synthesis and bio-activity study of the 2(1H)-quinolone compounds", Chemical Abstracts, No. 134:56548, XP-002190976 (Zhongguo Yaoke Daxue Xuebao, 34(4) (2000), pp. 246-250).

Stadlbauer, W., Synthesis of 4-azido-2(1H)-quinolones, Chemical Abstracts, No. 107:134174, XP-002190977 (Monatsh. Chem., 117(11) (1986), pp. 1305-1323).

Earl, R. et al, "The preparation of 2(1H)-pyridinones and 2,3,-dihydro-5(1H)-indolizinones via transition metal mediated cocyclization of alkynes and isocyanates. A novel construction of the antitumor agent camptothecin", Chemical Abstracts, No. 102:6913, XP-002190978 (J. Org. Chem. 49(25) (1984), pp. 4786-4800).

Earl, R. et al, "Cobalt-catalyzed cocyclizations of isocyanato alkynes: a regiocontrolled entry into 5-indolizinones. Application to the total synthesis of camptothecin", Chemical Abstracts, No. 100:85968, XP-002190979 (J. Am. Chem. Soc. 105(23) (1983), pp. 6991-6993).

Fitton, A. et al, "Reactions of formylchromone derivatives. Part 1. Cycloadditions to 2- and 3-(aryliminomethyl)chromones", Chemical Abstracts, No. 88:22533, XP-002190980 (J. Chem. Soc., Perkin Trans. 1 (12) (1977), pp. 1450-1452).

(Continued)

Primary Examiner—Zinna Northington Davis
(74) Attorney, Agent, or Firm—Steptoe & Johnson LLP

(57) ABSTRACT

The present invention is concerned among others with compounds of formula (1), the N-oxides, the pharmaceutically acceptable addition salts, the quaternary amines and stereochemically isomeric forms thereof, wherein Q is halo, $C_{1-6}$ alkyl or $C_{2-6}$ alkenyl; X is (a-2) with q and r being O and Z being O, S or SO; $R_1$ is aryl; $R_2$ is selected from formyl; $C_{1-6}$alkyloxycarbonylalkyl; Het$^2$; Het$^2C_{1-6}$alkyl, $C_{1-6}$alkylthio; $C_{1-6}$alkyl optionally substituted with one or two substituents each independently selected from hydroxy, and halo; $R_3$ is selected from formyl; $C_{1-6}$alkyl optionally substituted with one or two $C_{1-6}$alkyloxy; $R_4$ is hydrogen, with HTV inhibiting properties (I)

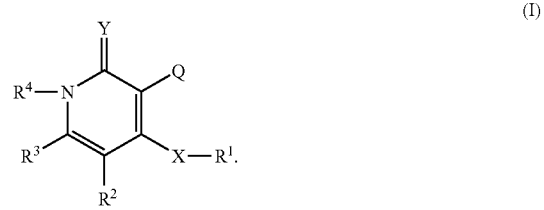

9 Claims, No Drawings

OTHER PUBLICATIONS

Moshchitskii, S. et al, "Reactions of diethyl 2,3,5,6-tetrachloro-4-pyridylmalonate", Chemical Abstracts, No. 73:120466, XP-002190981 (Khim. Geterotsikl. Soedin. (6) (1970), pp. 791-793).

Mao, C. et al, "Rational design of N-[2-(2,5-dimethoxyphenylethyl)]-N'-[2-(5-bromopridyl)]-thiourea (H1-236) as a potent non-nucleoside inhibitor of drug-resistant human immunodeficiency virus", Bioorganic & Medicinal Chemistry Letters, vol. 9, No. 11, Jun. 7, 1999, pp. 1593-1598.

* cited by examiner

PYRIDINONE AND PYRIDINETHIONE DERIVATIVES HAVING HIV INHIBITING PROPERTIES

The present invention is concerned with pyridinone and pyridinethione derivatives having Human Immunodeficiency Virus (HIV) replication inhibiting properties. It further relates to processes for their preparation and pharmaceutical compositions comprising them. The invention also relates to the use of said compounds in the manufacture of a medicament useful for the treatment of subjects suffering from HIV infection.

Compounds structurally related to the present compounds are disclosed in the prior art.

Naturforsch. B, Anorg. Chem., Org. Chem., 1983, 38 B (3), 398–403 discloses iodine, nitrogen and sulfurylides of 2-pyridones.

Pol. J. Chem., 1979, 53 (11), 2349–2354 discloses N-(tetrahalo-4-pyridyl) aminobenzoic acid derivatives and their use as herbicides.

J. Med. Chem., 1983, 26 (9), 1329–1333 discloses the synthesis of aza analogs of lucanthone useful as antitumor and bactericidal agents.

WO 86/01815 discloses the synthesis of monoazodyes and their use as dyestuffs.

Can. J. Chem., 1980, 58 (5), 501–526 discloses the chemistry of aurodox and related antibiotics.

WO 97/05113 discloses 4-aryl-thio-pyridin-2(1H)-ones and their use for treating HIV related diseases.

WO 99/55676 discloses 3-(amino- or aminoalkyl)pyridinone or pyridinethione derivatives and their use for the treatment of HIV related diseases.

However their activities are still moderate and their use in human therapy also could lead to the emergence of resistant strains. The most active thiopyridinones disclosed in WO 97/05113 have a 50% inhibitory concentration of virus multiplication (IC$_{50}$) for nevirapine resistant strains of about 260 nM, whereas the free amino or aminoalkyl pyridinone and pyridinone derivatives disclosed in WO 99/55676 have a 50% inhibitory concentration of virus multiplication for nevirapine resistant strains of more than 10 000 nM.

The Inventors have found a new family of pyridinones and pyridinethiones derivatives which show better HIV inhibitory properties.

The present invention is concerned with compounds of formula

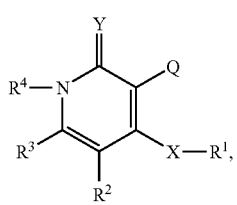

(I)

the N-oxides, the pharmaceutically acceptable addition salts, the quaternary amines and stereochemically isomeric forms thereof, wherein Y is O or S;

Q is hydrogen; halo; $C_{1-6}$alkyl; di($C_{1-4}$alkyl)amino; $C_{1-6}$alkyloxy, $C_{1-6}$alkyloxyC$_{1-6}$alkyl; $C_{1-6}$alkylthio; $C_{1-6}$alkylthioC$_{1-6}$alkyl; $C_{1-6}$alkylcarbonyl; $C_{1-6}$alkyloxycarbonyl; $C_{1-6}$alkyl-S(=O)—; $C_{1-6}$alkyl-S(=O)$_2$—; hydroxyC$_{1-6}$alkyl; polyhaloC$_{1-6}$alkyl; $C_{1-6}$akyloxycarbonylC$_{1-6}$alkyl; $C_{1-6}$alkyloxycarbonylC$_{1-6}$alkylthio; aminocarbonyl$_6$C$_{1-6}$alkylthio; $C_{1-6}$alkyloxyC$_{1-6}$alkyloxycarbonyl, $C_{2-6}$alkenyl optionally substituted with halo, hydroxy, cyano, formyl, —COOH, $C_{1-6}$alkyloxy, $C_{1-6}$alkylcarbonyl, $C_{1-6}$alkyloxycarbonyl, $C_{1-6}$alkylcarbonyloxy, N-hydroxy-imino or aryl; $C_{2-6}$alkynyl optionally substituted with halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino or aryl; $C_{3-6}$cycloalkyl optionally substituted with $C_{1-4}$alkyl; cyano; carboxyl; formyl; $R^5R^6N$—C(=O)—; $R^5R^6N$—C(=O)—$C_{1-6}$alkyl; N-hydroxy-imino; N—$C_{1-4}$alkyloxy-imino; aryl; aryloxy; arylthio; arylC$_{1-6}$alkyl; arylcarbonyl; arylC$_{1-6}$alkyloxycarbonyl; $C_{1-6}$alkyl substituted with hydroxy or aryl; Het$^1$; Het$^1$oxy, Het$^1$thio; Het$^1$C$_{1-6}$alkyl; Het$^1$carbonyl; Het$^1$C$_{1-6}$alkyloxycarbonyl; $C_{1-6}$alkyl-P(OR$^{15}$)$_2$=O or $C_{1-6}$alkyl-P(O—$C_{1-6}$alkyl-O)=O;

X is a bivalent radical of formula

(a-1)

or

(a-2);

wherein p is an integer of value 1 to 5;
q is an integer of value 0 to 5;
r is an integer of value 0 to 5;
Z is O, S, NR$^7$, C(=O), S(=O), S(=O)$_2$, CHOR$^{13}$, CH=CH, CH(NR$^7$R$^8$) or CF$_2$;
and wherein each hydrogen atom may be replaced by $C_{1-4}$alkyl or hydroxyC$_{1-4}$alkyl;

$R^1$ is $C_{1-6}$alkyl, $C_{3-6}$cycloalkyl, $C_{1-6}$alkenyl, $C_{1-6}$alkoxy, aryl or a monocyclic or bicyclic heterocycle selected from pyridyl, pyrimidyl, pyridazinyl, pyrazinyl, pyrrolyl, thienyl, furanyl, imidazolyl, thiazolyl, oxazolyl, benzopyrrolyl, benzofuranyl, benzothienyl, benzimidazolyl, benzothiazolyl, benzoxazolyl, or a radical of formula

(b-1)

or

(b-2)

with n being an integer of 1 or 2,
said monocyclic or bicyclic heterocycle or said radical of formula (b-1) or (b-2) optionally being substituted with one, two or three substituents each independently selected from halo, hydroxy, $C_{1-4}$alkyl, $C_{1-4}$alkyloxy, $C_{1-4}$alkylcarbonyl, polyhaloC$_{1-4}$alkyl or phenyl;

or Q and X—$R^1$ may be taken together with the pyridinone to form a tricyclic heterocycle of formula

(h-1)

with $R^{16}$ and $R^{17}$ being $C_{1-6}$alkyl or forming together =O.

$R^2$ and $R^3$ each independently are selected from hydrogen; halo; formyl; cyano; azido; hydroxy; oxiranyl; amino; mono- or di($C_{1-4}$alkyl)amino; formylamino; mercapto ($C_{1-6}$)alkyl; hydrazino; $R^{5a}R^{6a}N$—C(=O)—; $R^9$—N=C ($R^{10}$)—; $C_{2-6}$alkenyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, di($C_{1-4}$alkyl)carbamoyl, [di($C_{1-4}$alkyl)amino($C_{1-6}$alkyl)]($C_{1-4}$alkyl)carbamoyl, [di($C_{1-4}$alkyl)amino($C_{1-6}$alkyl)](aryl$C_{1-4}$alkyl)carbamoyl, di($C_{1-4}$alkyloxy)($C_{1-4}$alkyl)carbamoyl, (cyano$C_{1-6}$alkyl)($C_{1-6}$alkyl)amino$C_{1-6}$alkyl, N-hydroxy-imino, aryl, $Het^2$, $Het^2$carboxamido, $Het^2$($C_{1-6}$alkyl)carbamoyl; $C_{2-6}$alkynyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or $Het^2$; $C_{1-6}$alkyloxy; hydroxy $C_{1-6}$alkyloxy; amino$C_{1-6}$alkyloxy; mono- or di($C_{1-4}$alkyl)amino$C_{1-6}$alkyloxy; $C_{1-6}$alkylcarbonyl; arylcarbonyl; $Het^2$carbonyl; $C_{1-6}$alkyloxycarbonyl; $C_{1-6}$alkylcarbonyloxy; aryl; aryloxy; aryl$C_{1-6}$allyloxy; arylthio; aryl$C_{1-6}$alkylthio; mono- or di(aryl)amino; $Het^2$; $Het^2$oxy; $Het^2$thio; $Het^2C_{1-6}$alkyloxy; $Het^2C_{1-6}$alkylthio; $Het^2SO_2$; $Het^2SO$; mono- or di($Het^2$)amino; $C_{3-6}$cycloalkyl; $C_{3-6}$cycloalkyloxy; $C_{3-6}$cycloalkylthio; $C_{1-6}$alkylthio; hydroxy$C_{1-6}$alkylthio; amino$C_{1-6}$alkylthio; mono- or di($C_{1-4}$alkyl)amino$C_{1-6}$alkylthio; $C_{1-6}$alkyl optionally substituted with one or two substituents each independently selected from halo, hydroxy, cyano, carboxyl, $C_{1-6}$alkyloxy, $C_{1-6}$alkylthio, $C_{1-6}$alkylsulfonyl, $C_{1-6}$alkycarbamoyl$C_{1-4}$alkylthio, hydroxy$C_{1-6}$alkyloxy, $C_{1-6}$alkyloxy$C_{1-6}$alkyloxy, $C_{1-6}$alkyloxy$C_{1-6}$alkylthio $C_{1-6}$alkylcarbonyl, $C_{1-6}$alkylcarbonyloxy, aminocarbonyloxy, mono- or di($C_{1-4}$alkyl)aminocarbonyloxy, $C_{1-6}$alkyloxycarbonyl, $C_{1-6}$alkyloxycarbonyl$C_{1-6}$alkyloxy, $C_{1-6}$alkyloxycarbonyl$C_{1-6}$alkylthio, aryl, $Het^2$, aryloxy, arylthio, aryl$C_{1-6}$alkyloxy, aryl$C_{1-6}$alkylthio, $Het^2C_{1-6}$alkyloxy, $Het^2C_{1-6}$alkylthio, $C_{1-6}$alkyl-S(=O)$_2$-oxy, amino, mono- or di($C_{1-6}$alkyl)amino, di($C_{1-6}$alkyl)amino$C_{1-6}$alkylthio, [di($C_{1-6}$alkyl)amino($C_{1-6}$alkyl)]($C_{1-6}$alkyl)amino, di(cyano$C_{1-6}$alkyl)amino, $C_{1-6}$alkyloxycarbonylamino, $C_{1-6}$alkyloxy$C_{1-6}$alkylcarbonylamino, mono- or di(aryl)amino, mono- or di(aryl$C_{1-4}$alkyl)amino, mono- or di($C_{1-4}$alkyloxy$C_{1-4}$alkyl)amino, mono- or di($C_{1-4}$alkylthio $C_{1-4}$alkyl)amino, mono- or di($Het^2C_{1-4}$alkyl)amino, ($Het^2C_{1-4}$alkyl)($C_{1-4}$alkyl)amino, (cyano$C_{1-6}$alkyl)($C_{1-6}$alkyl)amino, $C_{3-6}$cycloalkylthio, $R^{11}$—(C=O)—NH—, $R^{12}$—NH—(C=O)—NH—, $R^{14}$—S(=O)$_2$—NH—, $C_{1-6}$alkyl-P(O—$R^{15}$)2=O, $C_{1-6}$alkyl-P(O—$C_{1-6}$alkyl-O)=O or a radical of formula

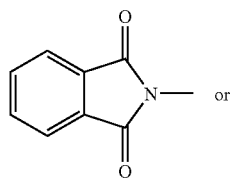

(c-1)

or

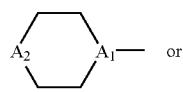

(c-2)

or

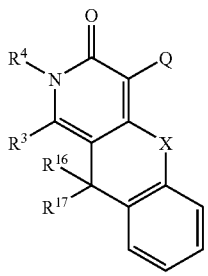

(c-3)

with $A_1$ being CH or N, and $A_2$ being $CH_2$, $NR^{13}$, S or O, provided that when $A_1$ is CH then $A_2$ is other than $CH_2$, said radical (c-1), (c-2) and (c-3) being optionally substituted with one or two substituents each independently selected from H, $C_{1-6}$alkyl, $C_{1-6}$alkyloxy, hydroxy $C_{1-4}$alkyl, $C_{1-6}$alkyloxycarbonyl, $C_{1-6}$alkyloxycarbonyl$C_{1-4}$alkyl, amino$C_{1-6}$alkyl, $C_{1-4}$alkylcarbonyl, arylcarbonyl, aryl, $Het^1$, $Het^1$-C=O)—, hydroxy, cyano, $C_{1-4}$alkylcyano, $CONR^{16}R^{17}$ with $R^{16}$ and $R^{17}$ being independently H or alkyl, mono or di($C_{1-4}$alkyl)aminoalkyl, 4-hydroxy-4-phenyl or 4-cyano-4-phenyl;

or $R^2$ and $R^3$ may be taken together to form a bivalent radical of formula

—(CH$_2$)$_t$—CH$_2$-A$_3$-CH$_2$— (d-1)

or

—CH=CH—CH=CH— (d-2)

with t being an integer of 0, 1 or 2 and $A_3$ being $CH_2$, O, S, $NR^{7a}$ or N[C(=O)$R^{8a}$] and wherein each hydrogen in said formula (d-1) or (d-2) may be substituted with halo, $C_{1-4}$alkyl, $C_{1-4}$alkyloxy, $C_{1-4}$alkylcarbonyl, halo$C_{1-4}$alkylcarbonyl or arylcarbonyl;

$R^4$ is hydrogen, hydroxy, $C_{1-6}$alkyl, $C_{1-6}$alkyloxy, $C_{1-6}$alkyloxy$C_{1-6}$alkyl, $C_{1-6}$alkyloxycarbonyl$C_{1-6}$alkyl, $C_{1-6}$alkylcarbonyloxy$C_{1-6}$alkyl, $C_{2-6}$alkenyl, amino, mono- or di($C_{1-4}$alkyl)amino, mono- or di($C_{1-4}$alkyl)amino$C_{1-6}$alkyl or aryl;

or $R^4$ and $R^3$ may be taken together to form a bivalent radical of formula

—(CH$_2$)$_t$—CH$_2$-A$_4$-CH$_2$— (e-1)

or

—CH=CH—CH=CH— (e-2)

with t being an integer of 0, 1 or 2 and $A_4$ being $CH_2$, O, S, $NR^{7b}$ or N[C(=O)$R^{8b}$] and wherein each hydrogen in said formula (e-1) or (e-2) may be substituted with halo, $C_{1-4}$alkyl, $C_{1-4}$alkyloxy, $C_{1-4}$alkylcarbonyl, halo$C_{1-4}$alkylcarbonyl or arylcarbonyl;

or X—$R^1$ and $R^2$ may be taken together to form a tricyclic heterocycle of formula

(h-2)

with $R^{16}$ and $R^{17}$ being $C_{1-6}$alkyl or forming together =O. $R^5$ and $R^6$ each independently are hydrogen, $C_{1-4}$alkyl or $C_{1-4}$alkyloxy;

$R^{5a}$ and $R^{6a}$ each independently are hydrogen; $C_{1-4}$alkyl optionally substituted with cyano, $C_{1-4}$alkyloxy, $C_{1-4}$alkylthio, amino, mono-or di($C_{1-4}$alkyl)amino or a radical of formula

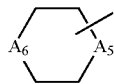
(f-1)

with $A_5$ and $A_6$ each independently being $CH_2$, $NR^{13}$ or O;

$R^7$, $R^{7a}$ and $R^{7b}$ each independently are hydrogen, formyl or $C_{1-4}$alkyl;

$R^8$, $R^{8a}$ and $R^{8b}$ each independently are hydrogen or $C_{1-4}$alkyl;

$R^9$ is hydrogen, hydroxy, $C_{1-4}$alkyloxy, carboxyl$C_{1-4}$alkyloxy, $C_{1-4}$alkyloxycarbonyl-$C_{1-4}$alkyloxy, $C_{2-4}$alkenyloxy, $C_{2-4}$alkynyloxy or aryl$C_{1-4}$alkyloxy;

$R^{10}$ is hydrogen, carboxyl or $C_{1-4}$alkyl;

$R^{11}$ is hydrogen; $C_{1-4}$alkyl optionally substituted with cyano, $C_{1-4}$alkyloxy, $C_{1-4}$alkyl-S(=O)$_2$—, aryl or Het$^3$; $C_{1-4}$alkyloxy; $C_{2-4}$alkenyl; aryl$C_{2-4}$alkenyl; Het$^3$$C_{2-4}$alkenyl; $C_{2-4}$alkynyl; Het$^3$$C_{2-4}$alkynyl, aryl$C_{2-4}$alkynyl; $C_{3-6}$cycloalkyl; aryl; naphthyl or Het$^3$;

$R^{12}$ is $C_{1-4}$alkyl, aryl$C_{1-4}$alkyl, aryl, arylcarbonyl, $C_{1-4}$alkylcarbonyl, $C_{1-4}$alkyloxycarbonyl or $C_{1-4}$alkyloxycarbonyl$C_{1-4}$alkyl;

$R^{13}$ is hydrogen, $C_{1-4}$alkyl or $C_{1-4}$alkylcarbonyl;

$R^{14}$ is $C_{1-4}$alkyl optionally substituted with aryl or Het$^4$; polyhalo$C_{1-4}$alkyl or $C_{2-4}$alkenyl optionally substituted with aryl or Het$^4$;

$R^{15}$ is $C_{1-4}$ alkyl;

Het$^1$ and Het$^2$ each independently are a heterocycle selected from pyrrolyl, furanyl, thienyl, imidazolyl, oxazolyl, isoxazolyl, thiazolyl, pyridyl, pyrmidinyl, pyrazinyl, pyridazinyl, pyrrolidinyl, tetrahydrofuranyl, tetrahydrothienyl, tetrahydropyrimidinyl, imidazolidinyl, oxazolidinyl, thiazolidinyl, piperidinyl, hexahydropyrimidinyl, piperazinyl, hexabydropyridazinyl, morpholinyl, thiomorpholinyl triazolyl, tetrazolyl, pyrrolyl, pyrazolyl, benzopyrrolyl, benzofuranyl, benzothienyl, benzimidazolyl, benzoxazolyl, benzothiazolyl, benzotriazolyl, indolyl, indazolyl, benzodioxanyl, quinolinyl, 2-oxo-1,2-dihydro-quinolinyl, imidazopyridinyl, dihydropyrrolyl or dihydroisoxazolyl, said heterocycle optionally being substituted with one, two or three substituents each independently selected from O, S, halo, formyl, amino, hydroxy, cyano, $C_{1-4}$alkyl, hydroxy$C_{1-4}$alkyl, carboxy$C_{1-4}$alkyl, carbamoyl$C_{1-4}$alkyl, carbamoyl$C_{1-4}$alkoxy, $C_{1-4}$alkyloxy, $C_{1-4}$alkylcarbonyl, $C_{1-4}$alkyloxy$C_{1-4}$alkyl, cyano$C_{1-4}$alkyl, di($C_{1-4}$alkyl)amino$C_{1-4}$alkyl, —OCONH$_2$, $C_{1-4}$alkoxy$C_{1-4}$alkyl, aryl, Het$^2$$C_{1-4}$alkyl, polyhalo$C_{1-4}$alkyl, $C_{3-6}$cycloalkyl or aryl$C_{2-6}$alkenyl, Het$^3$ is a monocyclic or bicyclic heterocycle selected from pyrrolyl, furanyl, thienyl, imidazolyl, oxazolyl, thiazolyl, pyridinyl, pyrimidinyl, pyrazinyl, pyridazinyl, benzopyrrolyl, benzofuranyl, benzothienyl, benzimidazolyl, benzoxazolyl, benzothiazolyl, quinolinyl, 2-oxo-1,2-dihydro-quinolinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl or a radical of formula

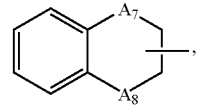
(g-1)

with $A_7$ or $A_8$ each independently being selected from $CH_2$ or O; each of said monocyclic or bicyclic heterocycles may optionally be substituted with one, two or three substituents each independently selected from halo, hydroxy,$C_{1-4}$alkyl, $C_{1-4}$alkyloxy, $C_{1-4}$alkylcarbonyl or polyhalo$C_{1-4}$alkyl;

Het$^4$ is a monocyclic heterocycle selected from pyrrolyl, furanyl, thienyl, imidazolyl, oxazolyl, thiazolyl, pyridyl, pyrimidinyl, pyrazinyl, pyridazinyl, said heterocycle optionally being substituted with one, two or three substituents each independently selected from halo, hydroxy, $C_{1-4}$alkyl, $C_{1-4}$alkyloxy, $C_{1-4}$alkylcarbonyl or polyhalo $C_{1-4}$alkyl;

Het$^5$ is pyridyl, pyrimidyl, pyridazinyl, pyrazinyl, pyrrolyl, thienyl, furanyl, imidazolyl, thiazolyl, oxazolyl, tetrazolyl, piperidinyl, morpholinyl or pyrrolidinyl;

aryl is phenyl optionally substituted with one, two or three substituents each independently selected from halo; hydroxy, carboxyl; cyano; formyl; acetyl; nitro; amino; mono- or di($C_{1-4}$alkyl)amino; $C_{1-4}$alkylcarbonylamino; mono- or di($C_{1-4}$alkyl)aminocarbonylamino; $C_{1-4}$alkyl-S(=O)$_2$—NH—; Het$^5$(=S)—S—$C_{1-4}$alkyl; $C_{1-6}$alkyloxy; sulfamoyl; ($C_{1-4}$alkyl)sulfamoyl; arylsulfamoyl; Het$^2$sulfamoyl; O—P=OR$^{15}$; $C_{1-6}$alkyl optionally substituted with halo, hydroxy, cyano, nitro, formyl, amino, mono- or di($C_{1-4}$alkyl)amino, $C_{1-6}$alkyloxycarbonyl, $C_{1-6}$alkyloxy, $C_{1-6}$alkyloxy$C_{1-6}$alkyloxy, $C_{2-6}$alkenyloxy, $C_{1-6}$alkylcarbonyloxy, $C_{1-6}$alkyloxycarbonylthio, N-hydroxyimino, phenyl or Het$^5$; $C_{2-6}$alkenyl optionally substituted with halo, hydroxy, cyano, nitro, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or Het$^5$; $C_{2-6}$alkynyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or Het$^5$; phenyl; phenyloxy; phenyl($C_{1-4}$alkyl)thio$C_{1-4}$alkyl; ($C_{3-6}$)cyclohexylthio$C_{1-4}$alkyl or isoxazolinyl optionally substituted by $C_{1-4}$alkyloxycarbonyl or morpholinyl$C_{1-4}$alkyl provided that 5,6,7,8-tetrahydro-3-iodo-4-phenoxy-1-phenyl-2(1H)quinolinone;

3-iodo-6-methyl-4-phenoxy-2(1H)-pyridinone;

2-[(3,5,6-trifluoro-1,2-dihydro-2-oxo-4-pyridinyl)amino] benzoic acid;

1,2-dihydro-6-hydroxy-2-oxo-4-(2-phenylethyl)-3-pyridinecarbonitrile;

1,2-dihydro-6-hydroxy-2-oxo-4-(4-pyridinylmethyl)-3-pyridinecarbonitrile;

4-[(4-bromophenyl)methoxy]-3,5-diodo-1-methyl-2(1H)-pyridinone;

4-[(4-bromophenyl)methoxy]-1,2-dihydro-1-methyl-2-oxo-3-pyridinecarboxylic acid; 1,2-dihydro-6-methyl-2-oxo-4-(phenylthio)-3-pyridinecarboxylic acid and the alkyl-4-arylthio-1,2-dihydro-5-methyl-6-methyl-2-oxo-3-pyridine carboxylate 3-bromo-4-[[[2-(3,4-dimethoxyphenyl)ethyl]amino]methyl-2(1H)quinolinone;
3-iodo-7-methoxy-1-methyl-4-phenoxy-2(1H)quinolinone;
1-ethyl-3-iodo-7-methoxy-4-phenoxy-2(1H)quinolinone;
3-iodo-7-methoxy-4-(4-methoxyphenoxy)-1-methyl-2(1H) quinolinone;
1-ethyl-3-iodo-7-methoxy-4-(4-methoxyphenoxy)-1-methyl-2(1H)quinolinone;
3-iodo-7-methoxy-4-(3-methoxyphenoxy)-1-methyl-2(1H) quinolinone;
1-ethyl-3-iodo-7-methoxy-4-(3-methoxyphenoxy)-1-methyl-2(1H)quinolinone;
3-iodo-7-methoxy-4-phenoxy-2(1H)quinolinone;
4-(3-chloro-4-methoxyphenoxy)-3-iodo-7-methoxy-2(1H) quinolinone;
3-iodo-4-phenoxy-2(1H)quinolinone;
3-iodo-4-phenoxy-1-phenyl-2(1H)quinolinone;
3-iodo-4-(4-methylphenoxy)-2(1H)quinolinone;
3-iodo-4-(4-methoxyphenoxy)-2(1H)quinolinone;

are not included.

As used herein $C_{1-4}$alkyl as a group or part of a group defines straight or branched chain saturated hydrocarbon radicals having from 1 to 4 carbon atoms such as methyl, ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylpropyl, 2-methylbutyl and the like; $C_{2-4}$alkenyl as a group or part of a group defines straight or branched chain hydrocarbon radicals having from 2 to 4 carbon atoms and containing a double bond such as ethenyl, propenyl, butenyl and the like; $C_{2-6}$alkenyl as a group or part of a group defines straight or branched chain hydrocarbon radicals having from 2 to 6 carbon atoms and containing at least one double bond such as the groups defined for $C_{2-4}$alkenyl and pentenyl, hexenyl, 2,4-hexadienyl, 1,3-butadienyl, 3-methylbutenyl and the like; $C_{2-4}$alkynyl as a group or part of a group defines straight or branched chain hydrocarbon radicals having from 2 to 4 carbon atoms and containing one triple bond such as ethynyl, propynyl, butynyl and the like; $C_{2-6}$alkynyl as a group or part of a group defines straight or branched chain hydrocarbon radicals having from 2 to 6 carbon atoms and containing one triple bond such as the groups defined such as ethynyl, propynyl, butynyl, pentynyl, hexynyl, 3-methylbutynyl and the like; $C_{3-6}$cycloalkyl is generic to cyclopropyl, cyclobutyl, cyclopentyl and cyclohexyl.

As used hereinbefore, the term (=O) forms a carbonyl moiety when attached to a carbon atom, a sulfoxide moiety when attached to a sulfur atom, a sulfonyl moiety when two of said terms are attached to a sulfur atom, a phosphonate when attached to a phosphorus atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoroethyl and the like. In case more than one halogen atom is attached to an alkyl group within the definition of polyhalomethyl or polyhalo$C_{1-6}$alkyl, they may be the same or different.

The $R^1$ or $Het^1$, $Het^2$, $Het^3$, $Het^4$ or $Het^5$ radical as described above for the compounds of formula (I) may be attached to the remainder of the molecule of formula (I) through any ring carbon or heteroatom as appropriate. For example, when $Het^1$ is pyridyl, it may be 2-pyridyl, 3-pyridyl or 4-pyridyl.

Lines drawn into ring systems indicate that the bond may be attached to any suitable ring atom.

When any variable (e.g. aryl) occurs more than one time in any constituent, each definition is independent.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used herein before defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates, quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic) malonic, succinic (i.e. butanedioic acid), maleic, fumaric, malic, tartaric, citric, methanesulfonic, ethanesulfonic, benzensulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, thiehylamine, tripropylamine, quinuclidine, pyridine, quinoline and isoquinoline; the benzathine, N-methyl-D-glucamine, hydrabamine salts, and salts with amino acids such as, for example, arginine, lysine and the like.

Conversely the salt forms can be converted by treatment with acid into the free acid form.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions include chloro, bromo, iodo, trifluoroacetate and acetate. The counterion of choice can be introduced using ion exchange resins.

Some of the compounds of formula (I) may also exist in their tautomeric form. Such forms although not explicitly indicated in the above formula are intended to be included within the scope of the present invention.

Whenever used hereinafter, the term "compounds of formula (I)" or "compounds of formula (I-a)" is meant to include also the N-oxides, the addition salts, the quaternary amines and all stereoisomeric forms.

A special group of compound contains those compounds of formula (I) wherein

Q is halo; $C_{1-6}$alkyl; $C_{1-6}$alkyloxy; $C_{1-6}$alkyloxy$C_{1-6}$alkyl; $C_{1-6}$alkylthio; $C_{1-6}$alkylthio$C_{1-6}$alkyl; $C_{1-6}$alkylcarbonyl; $C_{1-6}$alkyloxycarbonyl$C_{1-6}$alkyl-S(=O)—; $C_{1-6}$alkyl-S(=O)$_2$—; hydroxy$C_{1-6}$alkyl; polyhalo$C_{1-6}$alkyl; $C_{1-6}$alkyloxycarbonyl$C_{1-6}$alkyl; $C_{1-6}$alkyloxy$C_{1-6}$alkyloxycarbonyl; $C_{2-6}$alkenyl optionally substituted with halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino or aryl; $C_{2-6}$alkynyl optionally substituted with halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino or aryl; $C_{3-6}$cycloalkyl optionally substituted with $C_{1-4}$alkyl; cyano; carboxyl; formyl; $R^5R^6N$—C(=O)—; $R^5R^6N$—C(=O)—$C_{1-6}$alkyl; N-hydroxy-imino; N—$C_{1-4}$alkyloxy-imino; aryl; aryloxy; arylthio; aryl$C_{1-6}$alkyl; arylcarbonyl; aryl$C_{1-6}$alkyloxycarbonyl; $C_{1-6}$alkyl substituted with both hydroxy and aryl; Het$^1$; Het$^1$oxy; Het$^1$thio; Het$^1$$C_{1-6}$alkyl; Het$^1$carbonyl; Het$^1$$C_{1-6}$alkyloxycarbonyl; $C_{1-6}$alkyl-P(OR$^{15}$)$_2$=O or $C_{1-6}$alkyl-P(O—$C_{1-6}$alkyl-O)=O X is a bivalent radical of formula

(a-1)

or

(a-2);

wherein p is an integer of value 1 to 5;
q is an integer of value 0 to 5;
r is an integer of value 0 to 5;
Z is O, S, NR$^7$, C(=O), S(=O), S(=O)$_2$, CHOR$^{13}$, CH=CH, CH(NR$^7$R$^8$) or CF$_2$;
and wherein each hydrogen atom may be replaced by $C_{1-4}$alkyl or hydroxy$C_{1-4}$alkyl;

R$^1$ is $C_{3-6}$cycloalkyl, aryl or a monocyclic or bicyclic heterocycle selected from pyridyl, pyrimidyl, pyridazinyl, pyrazinyl, pyrrolyl, thienyl, furanyl, imidazolyl, thiazolyl, oxazolyl, benzopyrrolyl, benzofuranyl, benzothienyl, benzimidazolyl, benzothiazolyl, benzoxazolyl, or a radical of formula

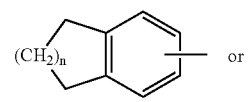

(b-1)

or

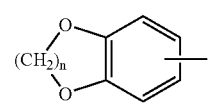

(b-2)

with n being an integer of 1 or 2,
said monocyclic or bicyclic heterocycle or said radical of formula (b-1) or (b-2) optionally being substituted with one, two or three substituents each independently selected from halo, hydroxy, $C_{1-4}$alkyl, $C_{1-4}$alkyloxy, $C_{1-4}$alkylcarbonyl, polyhalo$C_{1-4}$alkyl or phenyl;

R$^2$ and R$^3$ each independently are selected from hydrogen; halo; formyl; cyano; azido; hydroxy; oxiranyl; amino; mono- or di($C_{1-4}$alkyl)amino; formylamino; R$^{5a}$R$^{6a}$N—C(=O)—; R$^9$—N=C(R$^{10}$)—; $C_{2-6}$alkenyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or Het$^2$; $C_{2-6}$alkynyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or Het$^2$; $C_{1-6}$alkyloxy; hydroxy$C_{1-6}$alkyloxy; amino$C_{1-6}$alkyloxy; mono- or di($C_{1-4}$alkyl)amino$C_{1-6}$alkyloxy; $C_{1-6}$alkylcarbonyl; arylcarbonyl; Het$^2$carbonyl; $C_{1-6}$alkyloxycarbonyl; $C_{1-6}$alkylcarbonyloxy, aryl; aryloxy; aryl$C_{1-6}$alkyloxy; arylthio; aryl$C_{1-6}$alkylthio; mono- or di(aryl)amino; Het$^2$; Het$^2$oxy; Het$^2$thio; Het$^2$$C_{1-6}$alkyloxy; Het$^2$$C_{1-6}$alkylthio; mono- or di(Het$^2$)amino; $C_{3-6}$cycloalkyl; $C_{3-6}$cycloalkyloxy; $C_{3-6}$cycloalkylthio; $C_{1-6}$alkylthio; hydroxy$C_{1-6}$alkylthio; amino$C_{1-6}$alkylthio; mono- or di($C_{1-4}$alkyl)amino$C_{1-6}$ alkylthio; $C_{1-6}$alkyl optionally substituted with one or two substituents each independently selected from halo, hydroxy, cyano, $C_{1-6}$alkyloxy, $C_{1-6}$alkylthio, hydroxy$C_{1-6}$alkyloxy, $C_{1-6}$alkyloxy$C_{1-6}$alkyloxy, $C_{1-6}$alkylcarbonyl, $C_{1-6}$alkylcarbonyloxy, aminocarbonyloxy, mono- or di($C_{1-4}$alkyl)aminocarbonyloxy, $C_{1-6}$alkyloxycarbonyl, $C_{1-6}$alkyloxycarbonyl$C_{1-6}$alkyloxy, $C_{1-6}$alkyloxycarbonyl$C_{1-6}$ alkylthio, aryl, Het$^2$, aryloxy, arylthio, aryl$C_{1-6}$alkyloxy, aryl$C_{1-6}$alkylthio, Het$^2$$C_{1-6}$alkyloxy, Het$^2$$C_{1-6}$alkylthio, $C_{1-6}$alkyl-S(=O)$_2$-oxy, amino, mono- or di($C_{1-6}$alkyl) amino, $C_{1-6}$alkyloxy-carbonylamino, $C_{1-6}$alkyloxy$C_{1-6}$ alkylcarbonylamino, mono- or di(aryl)amino, mono- or di(aryl$C_{1-4}$alkyl)amino, mono- or di($C_{1-4}$alkyloxy$C_{1-4}$ alkyl)amino, mono- or di($C_{1-4}$alkylthio$C_{1-4}$alkyl)amino, mono or di(Het$^2C_{1-4}$alkyl)amino, $R^{11}$—(C=O)—NH—, $R^{12}$—NH—(C=O)—NH—, $R^{14}$—S(=O)$_2$—NH—, $C_{1-6}$alkyl-P(O—$R^{15}$)$_2$=O, $C_{1-6}$alkyl-P(O—$C_{1-6}$alkyl-O)=O or a radical of formula

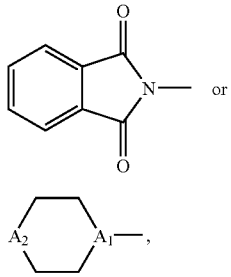

(c-1)

(c-2)

with $A_1$ being CH or N, and $A_2$ being CH$_2$, NR$^{13}$, S or O, provided that when $A_1$ is CH then $A_2$ is other than CH$_2$, said radical (c-1) and (c-2) being optionally substituted with one or two substituents each independently selected from H, $C_{1-6}$alkyl, $C_{1-6}$alkyloxy, hydroxy $C_{1-4}$alkyl, $C_{1-6}$alkyloxycarbonyl, $C_{1-6}$alkyloxycarbonyl$C_{1-4}$alkyl, amino$C_{1-6}$alkyl, carbonyl, hydroxy, cyano, CONR$^{16}$R$^{17}$ with R$^{16}$ and R$^{17}$ being independently H or alkyl, mono or di($C_{1-4}$alkyl)aminoalkyl, 4-hydroxy-4-phenyl or 4-cyano-4-phenyl;

or R$^2$ and R$^3$ may be taken together to form a bivalent radical of formula

  (d-1)

or

—CH=CH—CH=CH—  (d-2)

with t being an integer of 0, 1 or 2 and $A_3$ being CH$_2$, O, S, NR$^{7a}$ or N[C(=O)R$^{8a}$] and wherein each hydrogen in said formula (d-1) or (d-2) may be substituted with halo, $C_{1-4}$alkyl, $C_{1-4}$alkyloxy, $C_{1-4}$alkylcarbonyl, halo$C_{1-4}$alkylcarbonyl or arylcarbonyl;

R$^4$ is hydrogen, hydroxy, $C_{1-6}$alkyl, $C_{1-6}$alkyloxy, $C_{1-6}$alkyloxy$C_{1-6}$alkyl, $C_{1-6}$alkyloxycarbonyl$C_{1-6}$alkyl, $C_{1-6}$alkylcarbonyloxy$C_{1-6}$alkyl, $C_{2-6}$alkenyl, amino, mono- or di($C_{1-4}$alkyl)amino, mono- or di($C_{1-4}$alkyl)amino$C_{1-4}$alkyl or aryl;

or R$^4$ and R$^3$ may be taken together to form a bivalent radical of formula

  (e-1)

or

—CH=CH—CH=CH—  (e-2)

with t being an integer of 0, 1 or 2 and $A_4$ being CH$_2$, O, S, NR$^{7b}$ or N[C(=O)R$^{8b}$] and wherein each hydrogen in said formula (e1) or (e-2) may be substituted with halo, $C_{1-4}$alkyl, $C_{1-4}$alkyloxy, $C_{1-4}$alkylcarbonyl, halo$C_{1-4}$alkylcarbonyl or arylcarbonyl;

R$^5$ and R$^6$ each independently are hydrogen, $C_{1-4}$alkyl or $C_{1-4}$alkyloxy, R$^{5a}$ and R$^{6a}$ each independently are hydrogen; $C_{1-4}$alkyl optionally substituted with cyano, $C_{1-4}$alkyloxy, $C_{1-4}$alkylthio, amino, mono- or di($C_{1-4}$alkyl)amino; or a radical of formula

(f-1)

with $A_5$ and $A_6$ each independently being CH$_2$, NR$^{13}$ or O;

R$^7$, R$^{7a}$ and R$^{7b}$ each independently are hydrogen, formyl or $C_{1-4}$alkyl;

R$^8$, R$^{8a}$ and R$^{8b}$ each independently are hydrogen or $C_{1-4}$alkyl;

R$^9$ is hydrogen, hydroxy, $C_{1-4}$alkyloxy, carboxyl$C_{1-4}$alkyloxy, $C_{1-4}$alkyloxycarbonyl-$C_{1-4}$alkyloxy, $C_{2-4}$alkenyloxy, $C_{2-4}$alkynyloxy or aryl$C_{1-4}$alkyloxy;

R$^{10}$ is hydrogen, carboxyl or $C_{1-4}$alkyl;

R$^{11}$ is hydrogen; $C_{1-4}$alkyl optionally substituted with cyano, $C_{1-4}$alkyloxy, $C_{1-4}$alkyl-S(=O)$_2$—, aryl or Het$^3$; $C_{1-4}$alkyloxy, $C_{2-4}$alkenyl; aryl$C_{2-4}$alkenyl; Het$^3C_{2-4}$alkenyl; $C_{2-4}$alkynyl; Het$^3C_{2-4}$alkynyl; aryl$C_{2-4}$alkynyl; $C_{3-6}$cycloalkyl; aryl; naphthyl or Het$^3$;

R$^{12}$ is $C_{1-4}$alkyl, aryl$C_{1-4}$alkyl, aryl, arylcarbonyl, $C_{1-4}$alkylcarbonyl, $C_{1-4}$alkyloxycarbonyl, or $C_{1-4}$alkyloxycarbonyl$C_{1-4}$alkyl;

R$^{13}$ is hydrogen, $C_{1-4}$alkyl or $C_{1-4}$alkylcarbonyl;

R$^{14}$ is $C_{1-4}$alkyl optionally substituted with aryl or Het$^4$; polyhalo$C_{1-4}$alkyl or $C_{2-4}$alkenyl optionally substituted with aryl or Het$^4$;

R$^{15}$ is $C_{1-4}$alkyl;

Het$^1$ and Het$^2$ each independently are a heterocycle selected from pyrrolyl, furanyl, thienyl, imidazolyl, oxazolyl, thiazolyl, pyridyl, pyrimidinyl, pyrazinyl, pyridazinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl, benzopyrrolyl, benzofuranyl, benzothienyl, benzimidazolyl, benzoxazolyl, benzothiazolyl, quinolinyl or 2-oxo-1,2-dihydro-quinolinyl, said heterocycle optionally being substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

Het$^3$ is a monocyclic or bicyclic heterocycle selected from pyrrolyl, furanyl, thienyl, imidazolyl, oxazolyl, thiazolyl, pyridinyl, pyrimidinyl, pyrazinyl, pyridazinyl, benzopyrrolyl, benzofuranyl, benzothienyl, benzimidazolyl, benzoxazolyl, benzothiazolyl, quinolinyl, 2-oxo-1,2-dihydroquinolinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl or a radical of formula

(g-1)

with $A_7$ or $A_8$ each independently being selected from CH$_2$ or O; each of said monocyclic or bicyclic heterocycles may optionally be substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

Het$^4$ is a monocyclic heterocycle selected from pyrrolyl, furanyl, thienyl, imidazolyl, oxazolyl, thiazolyl, pyridyl, pyrimidinyl, pyrazinyl, pyridazinyl, said heterocycle optionally being substituted with one, two or three substituents each independently selected from halo, hydroxy, $C_{1-4}$alkyl, $C_{1-4}$alkyloxy, $C_{1-4}$alkylcarbonyl or polyhalo $C_{1-4}$alkyl;

Het$^5$ is pyridyl, pyrimidyl, pyridazinyl, pyrazinyl, pyrrolyl, thienyl, furanyl, imidazolyl, thiazolyl or oxazolyl;

aryl is phenyl optionally -substituted with one, two or three substituents each independently selected from halo; hydroxy; carboxyl; cyano; formyl; nitro; amino; mono- or di($C_{1-4}$alkyl)amino; $C_{1-4}$alkylcarbonylamino; mono- or di($C_{1-4}$alkyl)aminocarbonylamino; $C_{1-4}$alkyl-S(=O)$_2$—NH—; $C_{1-6}$alkyloxy; $C_{1-6}$alkyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkyloxy$C_{1-6}$alkyloxy, $C_{1-6}$alkylcarbonyloxy, N-hydroxy-imino, phenyl or Het$^5$; $C_{2-6}$alkenyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino phenyl or Het$^5$; $C_{2-6}$alkynyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or Het$^5$; phenyl or phenyloxy;

A special group of compound contains those compounds of formula (I) wherein

Q is halo, $C_{1-6}$alkyl or $C_{2-6}$alkenyl;

X is (a-2) with q and r being 0 and Z being O, S or SO;

$R_1$ is aryl;

$R_2$ is selected from formyl; $C_{1-6}$alkyloxycarbonylalkyl; Het$^2$; Het$^2C_{1-6}$alkyl; $C_{1-6}$alkylthio; $C_{1-6}$alkyl optionally substituted with one or two substituents each independently selected from hydroxy or halo;

$R_3$ is selected from formyl; $C_{1-6}$alkyl optionally substituted with one or two $C_{1-6}$alkyloxy;

$R^4$ is hydrogen.

Particular compounds are those compounds of formula (I) wherein Q is iodo.

Preferred compounds are those compounds of formula (I) wherein Q is iodo, X—$R_1$ is a 3,5-dimethylphenylthio or a 3,5-dimethylphenyloxy and $R_2$ is a hydroxymethyl or a N-morpholinomethyl or a 3-phenylpropyl or a furan-2-ylmethylthiomethyl. Also preferred compounds are those compounds of formula (I) wherein Q is iodo, X—$R_1$ is a 3-(2-cyano-vinyl)-5-iodophenyloxy or 5-bromo-3-(2-cyano-vinyl) and $R_2$ is ethyl.

Most preferred compounds are compounds n° 242, 255, 43, 264, 124, 249, 298, 326, 133, 241, 253, 306, 328, 46, 105, 234, 254, 256, 272, 284, 296, 319, 83, 88, 108, 109, 115, 277, 286, 299, 45, 85, 86, 231, 244, 297, 250, 257, 307, 324, 81, 92, 140, 143, 217, 221, 230, 232, 245, 309, 321, 322, 31, 218, 222, 314, 8, 99, 121, 219, 233, 280, 551, 470, 375, 483, 547, 606, 618, 662, 694, 700, 709 and 713 of table 1.

The present invention also relates to a method of treating warm-blooded animals suffering from HIV infection. Said method comprises the administration of the therapeutically effective amount of a compound of formula (I) or any sub group thereof, a N-oxide form, a pharmaceutically acceptable addition salt or a stereochemically isomeric form thereof in admixture with a pharmaceutical carrier.

The compounds of formula (I) can be prepared according to art-known procedures.

In general, compounds of formula (I) wherein X is an oxygen and $R_1$ a 3,5-dimethylphenyl, said compound being represented by formula (I-a) can be prepared by reacting an intermediate of formula (II) with a derivative of formula (III)

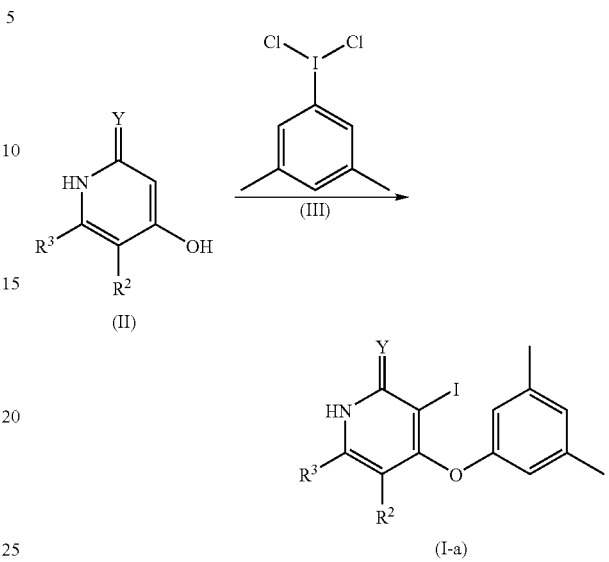

In this and the following preparations, the reaction products may be isolated from the reaction medium and, if necessary, further purified according to methodologies generally known in the art such as, for example, extraction, crystallization, distillation, trituration and chromatography.

The compounds of formula (I) wherein X is a sulphur, said compound being represented by formula (I-b) can be prepared by reacting an intermediate of formula (IV) with a derivative of formula (V) in an appropriate solvent such as for example methanol, ethanol, propanol, butanol, dioxane, tetrahydrofurane, 2-methoxyethylether or toluene, and the like. This reaction can be performed at a temperature comprised between 20 and 130° C.

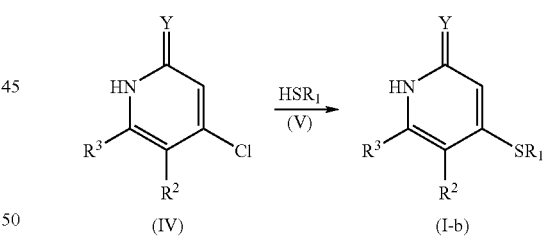

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization of chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography using a chiral stationary phase.

Some of the intermediates and starting materials are known compounds and may be commercially available or may be prepared according to art-known procedures.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in '*Protective Groups in Organic Chemistry*', edited by J W F McOmie, Plenum Press (1973), and '*Protective Groups in Organic Synthesis*' $2^{nd}$ edition, T W Greene & P G M Wutz, Wiley Interscience (1991).

The compounds of the present invention show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as progressive dysarthria, ataxia and disorientation. HIV infection further has also been associated with peripheral neuropathy progressive generalized lymphadenopathy (PGL) and AIDS-related complex (ARC).

The present compounds also show activity against HIV-1 strains that have acquired resistance to art-know non-nucleoside reverse transcriptase inhibitors. They also have little or no binding affinity to human α-1 acid glycoprotein.

Due to their antiretroviral properties, particularly their anti-HIV properties, especially their anti-HIV-1-activity, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid sugars, kaolin, lubricants, binders, disintegrating agent and the like in the case of powders pills, capsules, and tablets. Because of their ease in administration, tablets and capsules represent the list advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

To aid solubility of the compounds of formula (I), suitable ingredients, e.g. cyclodextrins, may be included in the compositions. Appropriate cyclodextrins are α, β, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles obtainable by melt-extruding a mixture comprising a compound of formula (I) and an appropriate water-soluble polymer and subsequently milling said melt-extruded mixture. Said particles can then be formulated by conventional techniques into pharmaceutical dosage forms such as tablets and capsules.

Said particles consist of a solid dispersion comprising a compound of formula (I) and one or more pharmaceutically acceptable water-soluble polymers. The preferred technique for preparing solid dispersions is the melt-extrusion process comprising the following steps:

a) mixing a compound of formula (I) and an appropriate water-soluble polymer, b) optionally blending additives with the thus obtained mixture, c) heating the thus obtained blend until one obtains a homogenous melt, d) forcing the thus obtained melt through one or more nozzles; and e) cooling the melt till it solidifies.

The solid dispersion product is milled or ground to particles having a particle size of less than 1500 μm, preferably less than 400 μm, more preferably less than 250 μm and most preferably less than 125 μm.

The water-soluble polymers in the particles are polymers that have an apparent viscosity, when dissolved at 20° C. in an aqueous solution at 2% (w/v), of 1 to 5000 mPa.s, more preferably of 1 to 700 mPa.s, and most preferred of 1 to 100 mPa.s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, polysaccharides, polyacrylic acids and the salts thereof, polymethacrylic acids and the salts and esters thereof, methacrylate copolymers, polyvinylalcohol, polyalkylene oxides and copolymers of ethylene oxide and propylene oxide. Preferred water-soluble polymers are Eudragit E® (Röhm GmbH, Germany) and hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β, γ-cyclodextrins or the pharmaceutically acceptable derivatives thereof.

Substituted cyclodextrins which can be used include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl.

Of particular utility are the β-cyclodextrin ethers, e.g. dimethyl-β-cyclodextrin as described by M. Nogradi (*Drugs of the Future*, (1984) Vol. 9, No. 8, p. 577–578) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

A more novel type of substituted cyclodextrins is sulfobutylcyclodextrines.

The ratio of the compound of formula (I) over cyclodextrin may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

Those of skill in the treatment of HIV-infection could determine the effective daily amount from the test results presented here. In general, it is contemplated that an effective daily amount would be from 0.01 mg/kg to 50 mg/kg body weight, more preferably from 0.1 mg/kg to 10 mg/kg body weight. It may be appropriate to administer the required dose at two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, the weight and general physical condition of the particular patient as well as other medication the individual may be taking, as is well known to those skilled in the art. Furthermore, it is evident that said effective daily amount may be lowered or increased of the response of the treated subject and/or depending on the evaluation of the physician prescribing the compounds of the instant invention. The effective daily amount ranges mentioned hereinabove are therefore only guidelines and are not intended to limit the scope or use of the invention to any extent.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as nucleoside reverse transcriptase inhibitors, e.g. zidovudine (3'-azido-3'-deoxythymidine; AZT), didanosine (dideoxy inosine; ddI), zalcitabine (dideoxycytidine; ddC) or lamivudine (3'-thia-2'-3'-dideoxycytidine; 3TC) and the like; non-nucleoside reverse transcriptase inhibitors such as suramine, pentamidine, thymopentin, castanospermine, efavirenz, rescriptor (BHAP derivative), dextran (dextran sulfate), foscarnet-sodium (trisodium phosphono formate), nevirapine (11-cyclopropyl-5, 11-dihydro-4-methyl-6Hdipyrido[3,2-b:2',3'-e][1,4]diazepin-6-one), tacrine (tetrahydroaminoacridine) and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl) imidazo-[4,5,1-jk][1,4]benzodiazepine-2(1H)-thione compounds of the α-APA (α-anilino phenyl acetamide) type e.g. α-[(2-nitro-phenyl)amino]-2,6-dichloro-benzene-acetamide and the like; TAT-inhibitors, e.g. RO-5-3335 and the like; protease inhibitors e.g. indinavir, ritonavir, saquinovir, ABT-378 and the like; fusion inhibitors; integrase inhibitors; or immunomodulating agents, e.g. levamisole and the like. The compound of formula (I) can also be combined with another compound of formula (I).

The following examples are intended to illustrate the present invention. The numbers under the formulas correspond to the numbers in the table (I).

EXAMPLE 1

Ethyl 2-azido-4-(3,5-dimethylphenoxy)-1,6-dihydro-5-iodo-6-oxo-3-pyridinecarboxylate (compound 106)

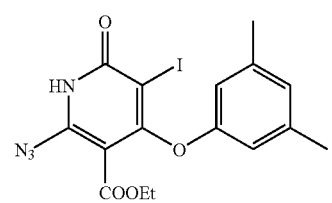

106

2-chloro-4-hydroxy-6-oxo-1,6-dihydro-pyridine-3-carboxylic acid ethyl ester (intermediate 1) was obtained as described by J. A. Elvidge and N. A. Zaidi (*J. Chem. Soc.*, (1968), 17, 2188) and dichloro-3,5-dimethyliodobenzene (intermediate 2) as described by H. J. Lucas, E. R. Kennedy, Org. Synth. (1955) Vol-III, 482–483.

1.1.: Ethyl 2-chloro-4-(3,5-dimethylphenoxy)-1,6-dihydro-5-iodo-6-oxo-3-pyridinecarboxylate (intermediate 3)

Intermediate 2 (0.73 g, 2.2 mmol) was suspended in 10 ml of water containing sodium carbonate (0.24 g, 2.2 mmol) and stirred for 30 min. at room temperature. To this mixture a solution of intermediate 1 (0.44 g, 2 mmol) in 10 ml of water containing also sodium carbonate (0.22 g; 2 mmol) was added. After stirring for one hour at 20° C. the precipitate was filtered off, washed with water, dried in vacuo and suspended in diglyme (5 ml). After heating at 100° C. for 10 min., the solvent was removed in vacuo. Purification by flash chromatography ($SiO_2$, $CH_2Cl_2$/ethanol 98:2) gave the titled compound (0.6 g, 67%) as yellow microcrystals, m.p. 180–182° C.

1.2.: Ethyl 2-azido-4-(3,5-dimethylphenoxy)-1,6-dihydro-5-iodo-6-oxo-3-pyridinecarboxylate (compound 106)

Sodium azide (0.20 g, 3.12 mmol) was added to a solution of intermediate 3 (0.50 g, 1.56 mmol) in DMSO (5 ml), and the mixture was heated at 50° C. for 5 hours Reaction mixture was partitioned between water (30 ml) and ethyl acetate (40 ml). The organic layer was dried over magnesium sulfate and concentred. Flash chromatography ($SiO_2$, $CH_2Cl_2$/ethanol 95:5) gave the desired product (0.49 g, 70%) as a white solid, m.p.=216–218° C.

EXAMPLE 2

4-[3,5-dimethylphenyl)-sulfinyl]-5-ethyl-3-iodo-6-methyl-2(1H)-pyridinone (compound 108)

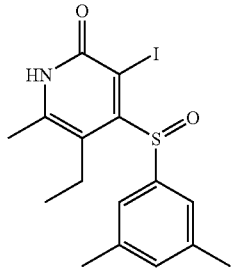

108

4-[3,5-dimethylphenyl)-thio]-5-ethyl-6-methyl-2(1H)-pyridinone (intermediate 4) was obtained as described by Dollé et al. (*J. Med. Chem.*, (1995), 38, 4679–4686).

2.1.: 4-[3,5-dimethylphenyl)-thio]-5-ethyl-3-iodo-6-methyl-2(1H)-pyridinone (intermediate 5)

The intermediate 4 (273 mg, 1 mmol) was dissolved in acetic acid (4 ml) and ethyl acetate (4 ml). At room temperature and in the dark N-iodosuccinimide (225 mg; 1 mmol) was added in one portion. After 4 hours under stirring at room temperature, the mixture was poured into water (15 ml) and the pH of the solution was adjusted to 7 with 28% ammonia. The combined organic layers obtained by extraction with ethyl acetate (3×30 ml) were washed with brine (10 ml), dried over magnesium sulfate and evaporated to give a gum. It was then purified by flash chromatography on silica gel column with $CH_2Cl_2$-ethanol (98:2) as the eluent to give the main fraction containing the titled compound which was recristallized from ethanol furnishing the pure intermediate 5 as yellow microcrystals (122 mg; 51%), m.p.=252° C.

2.2.: 4[-3,5-dimethylphenyl)-sulfinyl]-5-ethyl-3-iodo-6-methyl-2(1H)-pyridinone (compound 108)

m-chloroperbenzoic acid and water (70%, 123 mg; 0.5 mmol) in chloroform (15 ml) was dried over magnesium sulfate and filtered. To this solution at 0° C. was added the intermediate 5 (200 mg; 0.5 mmol) and the mixture was kept under stirring for 1 hour. A saturated solution of sodium carbonate (5 ml) was added and the combined organic layers obtained by extraction with $CH_2Cl_2$ (3×30 ml) were dried over magnesium sulfate and evaporated. The residue obtained was then chromatographed ($SiO_2$, $CH_2Cl_2$/ethanol 98:2) to give the titled compound (113 mg; 50%).

1H NMR. (200 MHz, CDCl3), d: 0.66 (t, 3H, CH3-CH2, J=6.9 Hz); 2.20–2.90 (m, 11H, CH3-6,3',5', CH2CH3); 7.08 (s, 1H, H-4'); 7.25 (s, 2H, H-2',6'); 12.9 (s, 1H, NH).

EXAMPLE 3

4-(3,5-dimethylphenoxy)-1,6-dihydro-5-iodo-2-methyl-6-oxo-3-pyridinecarboxaldehyde (compound 269)

269

Ethyl 4-hydroxy-6-methyl-2-oxo-1,2-dihydro-3-pyridinecarboxylate (intermediate 6) was described by E. Knoevenagel and A. Fries (*Ber.*, (1898), 31, 768).

3.1.: Ethyl 4-hydroxy-5-hydroxymethyl-6-methyl-2-oxo-1,2-dihydro-3-pyridinecarboxylate (intermediate 7)

The mixture of intermediate 6 (1.8 g; 9.1 mmol), $Na_2CO_3$ (970 mg; 9.1 mmol) and water (30 ml) was heated in an oil bath at 90° C. Three portions of 37% formaldehyde solution in water (1.46 ml; 18.2 mmol each) were added every 45 min. The homogeneous mixture obtained was kept at the same temperature for 30 min. further and the oil bath was removed. When the internal temperature reaches 60° C., ethyl acetate (40 ml) and acetic acid (1.8 ml) were added and after extraction with hot ethyl acetate (4×40 ml) the organic layer was evaporated under reduced pressure. The residue was then purified by flash chromatography on a silica gel column with $CH_2Cl_2$/ethanol (95:5) as the eluent to give the expected intermediate 7 (830 mg; 40%), m.p.=262–265° C.

3.2.: Ethyl 5-formyl-4-hydroxy-6-methyl-2-oxo-1,2-dihydro-3-pyridine-3-carboxylate (intermediate 8)

To a stirred solution of intermediate 7 (500 mg; 2.2 mmol) in $CH_2Cl_2$ (80 ml) was added at reflux $MnO_2$ (4 g; 46 mmol) and the reflux was maintained for 50 hours. The hot mixture was filtered off, the solid was washed successively with hot methanol (3×50 ml) and hot ethyl acetate (3×50 ml). The solvents were evaporated and the solid residue obtained was then purified by flash chromatography on a column of silica gel with $CH_2Cl_2$/ethanol (98:2) as the eluent to give the intermediate 8 (420 mg; 85%); m.p.=248–250° C.

3.3.: 4-hydroxy-2-methyl-6-oxo-1,6-dihydro-3-pyridinecarboxaldehyde (intermediate 9)

To a solution of intermediate 8 (350 mg; 1.5 mmol) in 1,4-dioxane (15 ml) was added water (7.6 ml) and 1N HCl (2.4 ml) and the mixture was heated under reflux for 24 hours. The hot solution was extracted with ethyl acetate (3×30 ml) and the solvent was removed under reduced pressure furnishing the titled intermediate 9 as yellow microcrystals (110 mg; 47%); m.p.>260° C. This compound was used for the next step without any further purification.

3.4.: 4-(3,5-dimethylphenoxy)-1,6-dihydro-5-iodo-2-methyl-6-oxo-3-pyridinecarboxaldehyde (compound 269)

Intermediate 2 (1.31 g, 4.32 mmol) was suspended in 25 ml of water containing sodium carbonate (0.46 g, 4.32 mmol) and stirred for 30 min. at room temperature. To this mixture a solution of intermediate 9 (0.55 g, 3.6 mmol) in 25 ml of water containing also sodium carbonate (0.38 g; 3.6 mmol) was added. After stirring for 1 hour at 20° C. the precipitate was filtered off, washed with water, dried in vacuo and suspended in dimethylformamide (15 ml). After heating under reflux for 1 h the solvent was removed in vacuo. Purification by flash chromatography (SiO$_2$, CH$_2$Cl$_2$/EtOH 95:5) gave the titled compound (1.01 g, 73%) as yellow microcrystals, m.p.>260° C.

EXAMPLE 4

4-(3,5-dimethylphenoxy)-5-(hydroxymethyl)-3-iodo-6-methyl-2(1H)-pyridinone (compound 257)

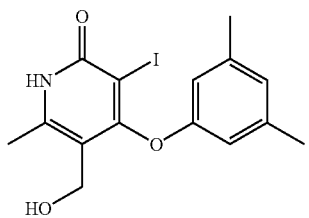

257

To a stirred solution of compound 269 (500 mg; 1.3 mmol) in methanol (50 ml) was added NaBH$_4$ (350 mg; 9.2 mmol) in small portions for a period of 10 min. After 1 hour on stirring at room temperature, water (20 ml) and a solution 10% potassium carbonate (30 ml) were added. The mixture was extracted with ethyl acetate (3×60 ml) and the organic layer was washed with brine, dried over magnesium sulfate and the solvent was removed under reduced pressure giving colorless microcrystals which correspond to the titled compound (490 mg; 97%) m.p.=248–250° C.

EXAMPLE 5

5-(chloromethyl)-4-(3,5-dimethylphenoxy)-3-iodo-6-methyl-2(1H)-pyridinone (compound 125)

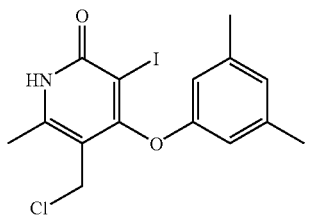

125

The heterogeneous solution of compound 257 (450 mg; 1.2 mmol) in CH$_2$Cl$_2$ (30 ml) became homogeneous mixture by addition at room temperature of SOCl$_2$ (2.6 ml). After 2 hours on stirring at room temperature, all the volatiles were removed under reduced pressure giving a yellow solid which corresponds to the expected compound 125 in quantitative yield (470 mg); m.p.=256–258° C. This compound was used for the next step without any further purification.

EXAMPLE 6

4-(3,5-dimethylphenoxy)-5-(ethoxymethyl)-3-iodo-6-methyl-2(1H)-pyridinone (compound 255)

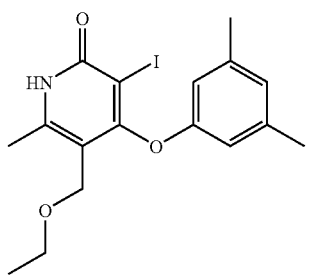

255

A solution of compound 125 (60 mg; 0.15 mmol) in absolute ethanol (5 ml) and potassium carbonate (60 mg; 0.44 mmol) was heated under reflux for 16 hours. After evaporation under reduced pressure, water (5 ml) was added and the mixture was extracted with ethyl acetate (3×10 ml). The organic layer was washed with brine (5 ml), dried over magnesium sulfate and the solvent was removed. The colorless solid residue was then purified by flash chromatography on a silica gel column with CH$_2$Cl$_2$/ethanol (98:2) as the eluent to give the titled compound 255 (59 mg; 95%); m.p.=234–236° C.

EXAMPLE 7

4-(3,5-dimethylphenoxy)-5-ethyl-3-iodo-6-methyl-2(1H)-pyridinone (compound 258)

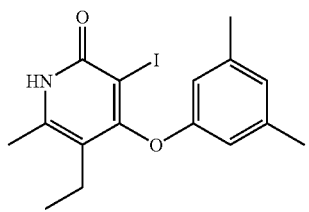

258

This compound was prepared starting from the 5-ethyl-6-methyl-4-hydroxypyridin-2(1H)-one (intermediate 10) which was obtained as described by Dollé et al. (*J. Med. Chem.*, (1995), 38, 4679–4686).

Intermediate 2 (3.75 g; 12.4 mmol) was suspended in water (50 ml) containing sodium carbonate (1.31 g; 12.4 mmol) and stirred for 30 min at room temperature. To this mixture a solution intermediate 10 (1.9 g; 12.4 mmol) in water (50 ml) containing also sodium carbonate (1.31 g; 12.4 mmol) was added. After stirring for 1 hour at 20° C. the precipitate was filtered off, washed with water, dried under vacuum at room temperature and suspended in dimethylformamide (20 ml). The mixture was refluxed for 1 hour. The solvent was removed in vacuo. Purification by flash chromatography (SiO$_2$, CH$_2$Cl$_2$/Et OH 98:2) gave the titled compound (4.3 g; 90%) as colorless microcrystals; m.p.=240° C.

EXAMPLE 8

4-(3,5-dimethylphenoxy)-3-ethenyl-5-ethyl-6-methyl-2(1H)-pyridinone (compound 234)

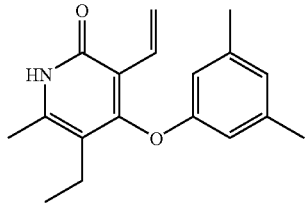

Compound 258 (300 mg, 0.1783 mmol) and palladium tetrakistriphenylphosphine (45 mg, 5% mol) were dissolved in toluene (6 ml). Tributyl(vinyl)tin (358 mg, 0.94 mmol) was added at room temperature. The mixture was refluxed for 12 hours. Water (8 ml) was added and the aqueous layer was extracted with dichloromethane and dried over magnesium sulfate. The solvent was removed under vacuum and the residue was purified by flash chromatography (SiO$_2$, CH$_2$Cl$_2$/ethanol 98:2) to give the titled compound 234 as colorless microcrystals (87 mg, 39%); m.p.=200° C.

EXAMPLE 9

4-(3,5-dimethylphenoxy)-3,5-diethyl-6-methyl-2(1H)-pyridinone (compound 231)

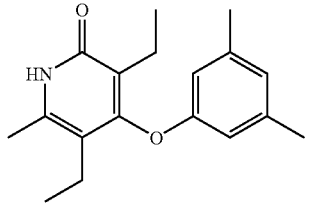

Compound 234 (90 mg, 0.318 mmol) was dissolved in absolute ethanol (10 ml). The catalyst palladium on carbon 10% (44 mg) was added. The mixture was stirred under hydrogen atmosphere at room temperature for 12 hours. The catalyst was filtered off and the solvent was evaporated under vacuum. The residue was purified by flash chromatography (SiO$_2$, CH$_2$Cl$_2$/ethanol 98:2) to give the desired compound as colorless microcrystals (60 mg, 66%);, m.p.=180° C.

EXAMPLE 10

4-[3,5-dimethylphenyl]-thio]-5-(ethoxymethyl)-3-iodo-6-methyl-2(1H)-pyridinone (compound 86)

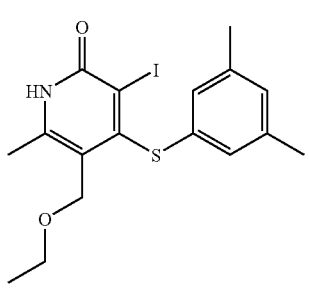

10.1. Ethyl 4-hydroxy-2-methyl-6-oxo-1,6-dihydro-3-pyridinecarboxylate (intermediate 12)

This compound was prepared starting from the di-(2,4,6-trichlorophenyl)malonate (intermediate 11) which was obtained as described by Kappe, Th., (Mh. Chem. (1967), 98, 874).

A solution of ethyl 3-aminocrotonate (12.6 g, 97.5 mmol) and of intermediate 11 in diglyme (400 ml) was heated at 100° C. for 3 hours during which the product separated out. After cooling, diethylether (1.5 l) was added and the desired intermediate 12 was filtered (14.2 g, 75%). m.p. 243–245° C.

10.2.: Ethyl 4-chloro-2-methyl-6-oxo-1,6-dihydro-3-pyridinecarboxylate (intermediate 13)

To a solution of intermediate 12 (2 g; 10 mmol) and benzyltriethylammonium chloride (9.1 g; 40 mmol) in acetonitrile (40 ml) was added in one portion phosphorus oxychloride (2.2 ml; 24 mmol). The obtained mixture was stirred at room temperature under nitrogen atmosphere for 5 min. and heated under reflux for 2 hours. After evaporation of the solvent, cool water (40 ml) was added and the mixture was stirred for 0.5 hour. Extraction with CH$_2$Cl$_2$ followed by a silica gel column chromatography using CH$_2$Cl$_2$/ethanol (99:1) as eluent gave i) ethyl 2,4-dichloro-6-methylpyridin-5-ylcarboxylate (1.7 g; 72%) (which can be transformed into the intermediate 13 and ii) intermediate 13 (506 mg; 24%) m.p.=161–163° C.

10.3.: Ethyl 4-[(3,5-dimethylphenyl)-thio]-1,6-dihydro-2-methyl-6-oxo-3-pyridinecarboxylate (intermediate 14)

A mixture of the intermediate 13 (1.2 g; 5.6 mmol) in ethanol (15 ml), triethylamine (1.5 ml) and 3,5-dimethylthiophenol (1.45 ml; 11 mmol) was heated under reflux for 16 hours. After evaporation under reduced pressure, diethylether (50 ml) was added and the precipitate was filtered off. The intermediate 14 was obtained (1.42 g; 80%) as a colorless solid m.p.=233–235° C.

10.4.: 4-[(3,5-dimethylphenyl)-thio]-5-(hydroxymethyl)-6-methyl-2(1H)-pyridinone (intermediate 15)

Under nitrogen atmosphere, the intermediate 14 (500 mg; 1.6 mmol) was suspended in dry tetrahydrofurane (20 ml) and LiAlH$_4$ (120 mg; 3.2 mmol) was added at 0° C. The mixture was stirred at room temperature for 18 hours and poured in ethyl acetate (50 ml) at 0° C. and a solution 10% H$_2$SO$_4$ (100 ml) was added dropwise. The mixture was extracted with ethyl acetate (2×100 ml) and the organic layer was removed under reduced pressure giving the intermediate 15 (310 mg; 71%) m.p.=268–270° C.

10.5.: 4-[(3,5-dimethylphenyl)-thio]-5-(chloromethyl)-6-methyl-2(1H)-pyridinone (intermediate 16)

A suspension of intermediate 15 (275 mg; 1 mmol) in dichloromethane (10 ml) became homogeneous by addition of SOCl$_2$ (2.3 ml) at room temperature. After 2 hours of stirring at room temperature, all the volatiles were removed under reduced pressure giving a yellow solid which corresponds to the expected intermediate 16 in quantitative yield (294 mg).

This compound was used for the next step without further purification.

10.6.: 4-[(3,5-dimethylphenyl)-thio]-5-(ethoxymethyl)-6-methyl-2(1H)-pyridinone (intermediate 17)

A solution of intermediate 16 (250 mg; 0.85 mmol) in absolute ethanol (10 ml) and triethylamine (0.24 ml) was heated at 50° C. for 18 hours. After evaporation under reduced pressure the residue was purified by flash chromatography on a silica gel column with CH$_2$Cl$_2$/ethanol (99:1) as the eluent to give the titled intermediate 17 (243 mg; 94%) m.p.=203–205° C.

10.7.: 4-[3,5-dimethylphenyl)-thio]-5-(ethoxymethyl)-3-iodo-6-methyl-2(1H)-pyridinone (compound 86)

The intermediate 17 (100 mg; 0.33 mmol) was dissolved in acetic acid (2 ml) and ethyl acetate (2 ml). At room temperature and in the dark N-iodosuccinimide (75 mg; 0.33 mmol) was added in one portion. After 2.5 h under stirring at room temperature, the mixture was poured into water (5 ml) and the pH of the solution was adjusted to ca.7 with 28% ammonia. The combined organic layers obtained by extraction with $CH_2Cl_2$ (3×10 ml) were washed with water (15 ml), dried over magnesium sulfate and evaporated to give a solid residue. It was then chromatographed on silica gel column with $CH_2Cl_2$/ethanol (99:1) as the eluent to give the titled compound 86 as colorless microcrystals (96 mg; 68%) m.p.=220–222° C.

EXAMPLE 11

3-bromo-4-[3,5-dimethylphenyl)-thio]-5-(ethoxymethyl)-6-methyl-2(1H)-pyridinone (compound 85)

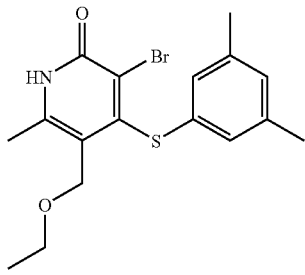

85

The intermediate 17 (50 mg; 0.16 mmol) was dissolved in acetic acid (3 ml) and ethyl acetate (3 ml). At room temperature and in the dark N-bromosuccinimide (29 mg; 0.16 mmol) was added in one portion. After 30 min. under stirring at room temperature, the mixture was poured into water (10 ml) and the pH of the solution was adjusted to ca.7 with 28% ammonia. The combined organic layers obtained by extraction with ethyl acetate (3×15 ml) were dried over magnesium sulfate and evaporated to give a solid residue. It was then purified by flash chromatography on silica gel column with $CH_2Cl_2$/ethanol (99:1) as the eluent to give the titled compound 85 as colorless microcrystals (48 mg; 76%) m.p.=183–184° C.

EXAMPLE 12

Ethyl 4-[3,5-dimethylphenyl)-thio]-1,6-dihydro-5-iodo-2-methyl-6-oxo-3-pyridinecarboxylate (compound 71)

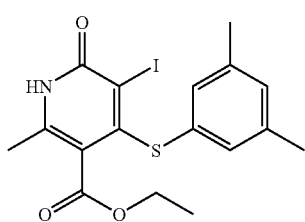

71

12.1.: Ethyl 4-[3,5-dimethylphenyl)-thio]-1,6-dihydro-2-methyl-1-6-oxo-3-pyridinecarboxylate (intermediate 18)

3,5-dimethylthiophenol (0.69 ml; 5.1 mmol) was added to a mixture of intermediate 13 (1 g; 4.6 mmol) in triethylamine (1 ml) and ethanol (10 ml). The mixture was stirred and refluxed then brought to room temperature and poured out into water. The precipitate was filtered. The residue was crystallized from diethyl ether. The precipitate was filtered off and dried to yield (1.2 g; 80%) of intermediate 18; m.p.=230° C.

12.2.: Ethyl 4-[3,5-dimethylphenyl)-thio]-1,6-dihydro-5-iodo-2-methyl-6-oxo-3-pyridinecarboxylate (compound 71)

N-iodosuccinimide (0.085 g; 0.4 mmol) was added at room temperature to a solution of intermediate 18 (0.1 g; 0.3 mmol) in ethyl acetate (0.3 ml) and acetic acid (0.3 ml) under nitrogen. The mixture was stirred 48 hours in darkness. The solvent was evaporated. The residue was purified by column chromatography over Kromasil® ($CH_2Cl_2$; 100). Two fractions were collected and the solvent was evaporated to give 0.052 g of a compound which was crystallized from diisopropyl ether. The precipitate was filtered off and dried to yield (32 mg; 23%) of compound 71; m.p.=210° C.

EXAMPLE 13

4-[3,5-dimethylphenyl)-thio]-5-(hydroxymethyl)-3-iodo-6-methyl-2(1H)-pyridinone (compound 61)

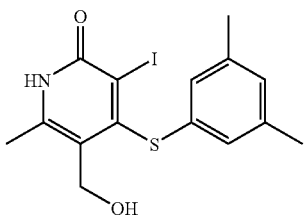

61

Diisobutylaluminium hydride (20 wt. % solution in toluene) (0.75 ml; 0.9 mmol) was added at −70° C. to a mixture of compound 71 (0.1 g; 0.2 mmol) in toluene (10 ml). The mixture was stirred at 0° C. for 1 hour, poured out into water and extracted with ethyl acetate. The residue was crystallized from diisopropyl ether. The precipitate was filtered off and dried to yield (56 mg; 70%) of compound 61; m.p.=240° C.

EXAMPLE 14

5-(chloromethyl)-4-[-3,5-dimethylphenyl)-thio]-3-iodo-6-methyl-2(1H)-pyridinone (compound 60)

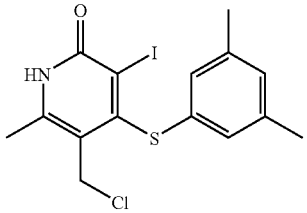

60

$SOCl_2$ (0.9 ml; 12.3 mmol) was added dropwise at 0° C. to a solution of compound 61 (0.8 g; 1.9 mmol) in $CH_2Cl_2$ (90 ml). The mixture was stirred at room temperature overnight and evaporated till dryness. The residue was taken up in CH$_2$Cl$_2$ and evaporated (3 times) to yield 0.7 g (89%) m.p.=218° C. The product was used without further purification in the next reaction step.

EXAMPLE 15

4-[3,5-dimethylphenyl)-thio]-5-[(ethylthio)methyl]-3-iodo-6-methyl-2(1H)-pyridinone (compound 45)

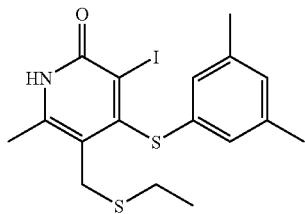

45

A mixture of compound 60 (0.1 g; 0.2 mmol) and ethanethiol (0.0361 ml; 0.5 mmol) in triethylamine (0.1 ml) and ethanol (2 ml) was stirred and refluxed for 4 hours. The solvent was evaporated. The residue (0.06 g) was purified by column chromatography over silica gel (eluent: CH$_2$Cl$_2$/CH$_3$OH/NH$_4$OH; 95/5/0.1). The pure fractions were collected and the solvent was evaporated. The residue (0.02 g) was crystallized from diisopropylether. The precipitate was filtered off and dried to yield 0.018 g (17%); m.p.=210° C.

EXAMPLE 16

4-[(3,5-dimethylphenyl)-thio]-3-iodo-6-methyl-5-morpholinomethyl-1H-pyridin-2-one (compound 43)

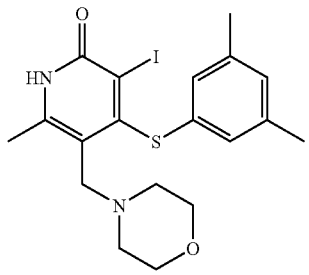

43

A mixture of compound 60 (0.05 g; 0.1 mmol), morpholine (0.02 ml; 0.0002 mol) and K$_2$CO$_3$ (0.082 g; 0.6 mmol) in acetonitrile (2 ml; 0.6 mmol) was stirred at 50° C. in a sealed tube for 2 hours, poured out into water and extracted with ethylacetate. The solvent was evaporated. The residue was crystallized from diisopropyl ether. The precipitate was filtered off and dried. The residue (0.057 g) was crystallized from isopropanol. The precipitate was filtered off and dried to yield 0.041 g (73%), m.p.=230° C.

EXAMPLE 17

6-(diethoxymethyl)-4-(3,5-dimethylphenoxy)-5-ethyl-3-iodo-2(1H)-pyridinone (compound 134)

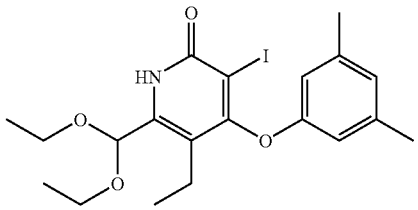

134

17.1.: 6-(diethoxymethyl)-5-ethyl-4-hydroxy-2H-pyran-2-one (intermediate 19)

A solution of sodium hydride (60% dispersion in mineral oil) in tetrahydrofurane (500 ml) was cooled at 0° C. under nitrogen. 3-oxo-hexanoic-acid ethyl ester (25 g; 158 mmol) was added dropwise and the mixture was stirred at 0° C. for 15 minutes. Butyllithium 1.6 M (99 ml; 158 mmol) was added dropwise and the mixture was stirred at 0° C. for 1 hour. Diethoxy-acetic acid ethyl ester (27.8 g; 0.178 mol) was added drop wise and the mixture was stirred at 0° C. for 1 hour. Hydrochloric acid 12 N (50 ml) was added and the mixture was stirred at room temperature for 1 hour and extracted with diethyl ether to yield 20 g (53%) of intermediate 19. The product was used without further purification in the next reaction step.

17.2.: 6-(diethoxymethyl)-5-ethyl-4-hydroxy-2(1H)-pyridinone (intermediate 20)

A mixture of intermediate 19 (20 g; 82 mmol) in CH$_3$OH/NH$_3$ (150 ml) was stirred at 60° C. for 4 hours, evaporated till dryness and taken up in diisopropyl ether. The precipitate was filtered to yield 1.5 g of intermediate 20 (7.5%). The product was used without further purification in the next reaction step.

17.3.: [6-diethoxymethyl-5-ethyl-4-hydroxy-2-oxo-3-pyridinyl]-3,5-dimethylphenyl)-iodonium, hydroxide, inner salt (intermediate 21)

A mixture of intermediate 20 (3.4 g; 14 mmol) and Na$_2$CO$_3$ (3 g; 28 mmol) in water (50 ml) was stirred at room temperature for 15 min to give residue 1. A mixture of intermediate 2 (4.66 g; 15.4 mmol) and Na$_2$CO$_3$ (3 g; 28 mmol) in water (50 ml) was stirred at room temperature for 15 min to give residue 2. Residue 1 and residue 2 were combined and then stirred at room temperature for 2 hours. The precipitate was filtered off, washed with water and dried. Yield 8 g of intermediate 21; m.p.=125° C.).

17.4.: 6-(diethoxymethyl)-4-(3,5-dimethylphenoxy)-5-ethyl-3-iodo-2(1H)-pyridinone (compound 134)

A mixture of intermediate 21 (6 g; 12.7 mmol) in DMF (20 ml) was stirred at 120° C. for 1 hour. The solvent was evaporated till dryness to yield 5 g of compound 134 (83%). The residue was used immediately without further purification.

EXAMPLE 18

4-(3,5-dimethylphenoxy)-3-ethyl-1,6-dihydro-5-iodo-6-oxo-2-pyridinecarboxaldehyde (compound 159)

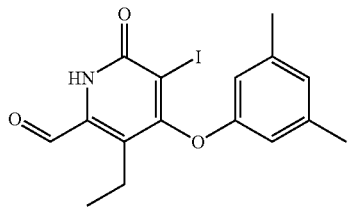

159

A mixture of compound 134 (5 g; 10 mmol) in HCl 3N (30 ml) and tetrahydrofurane (5 ml) was stirred at 100° C. for 30 min. and then extracted with $CH_2Cl_2$. The organic layer was separated, dried, filtered and the solvent was evaporated. The residue (5 g) was crystallized from diisopropyl ether. The precipitate was filtered off and dried to yield 3.5 g of titled compound 159 (83%), m.p.=158° C.

The residue was used without further purification.

EXAMPLE 19

4-(3,5-dimethylphenoxy)-5-ethyl-6-(hydroxymethyl)-3-iodo-2(1H)-pyridinone (compound 133)

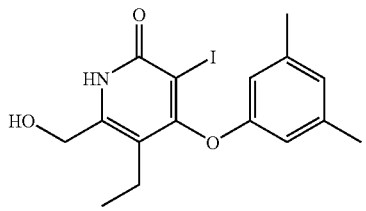

133

$NaBH_4$ (0.047 g; 1.3 mmol) was added to a mixture of compound 159 (0.5 g; 0.013 mol) in methanol (3 ml). The mixture was stirred at room temperature for 1 hour. Water was added. The precipitate was filtered off, taken up in diisopropyl ether and dried to yield 0.26 g (52%), m.p.=70° C.).

EXAMPLE 20

[3-(5-ethyl-3-iodo-6-methyl-2-oxo-1,2-dihydro-pyridin-4-yloxy)-5-iodo-phenyl]-acetonitrile (compound n° 426)

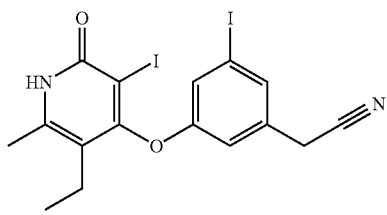

426

A mixture of compound 81 (0.1 g; 0.001 mol) and potassium cyanide (0.024 g; 0.0003 mol) in ethanol (2 ml) was stirred at 80° C. in a celled tube overnight. $H_2O$ was added. The mixture was extracted with $CH_2Cl_2$. The solvent was evaporated. The residue was purified by column chromatography over silica gel (eluent: $CH_2Cl_2/CH_3OH$ 99/1; 15–40 μm). The pure fractions were collected and the solvent was evaporated. The residue (0.03 g) was crystallized from DIPE. The precipitate was filtered off and dried to yield 0.21 g (21%), m.p.=220° C.

EXAMPLE 21

4-(3,5-dimethylphenoxy)-3-iodo-6-methyl-5-[2-methylthiazol-4-ylmethylsulfanylmethyl)-1H-pyridin-2-one (compound n° 483)

21.1: 4-(3,5-dimethylphenoxy)-3-iodo-5-mercaptomethyl-6-methyl-1H-pyridin-2-one (compound n° 451)

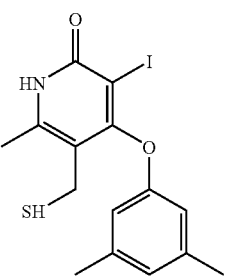

451

A mixture of compound 125 (1.5 g; 0.0037 mol) and thiourea (0.31 g; 0.00408 mol) in DMSO (30 ml) was stirred at room temperature for 1 hour. NaOH 3N was added. The mixture was stirred for 15 minutes, acidified with HCl 3N and extracted with ethylacetate (EtOAc). The organic layer was separated, dried on magnesium sulfate ($MgSO_4$), filtered and the solvent was evaporated. The residue was taken up in DIPE and filtered. The precipitate (1.2 g) was purified by column chromatography over silica gel (eluent: EtOAc 100%; 35–70 μm) and dried to yield 0.3 g (20%).

21.2: 4-(3,5-dimethylphenoxy)-3-iodo-6-methyl-5-[2-methylthiazol-4-ylmethyl-sulfanylmethyl)-1H-pyridin-2-one (compound n° 483)

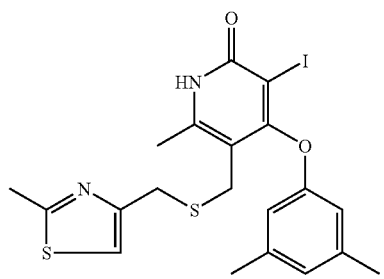

483

A mixture of compound 451 (0.07 g; 0.0001 mol) and 4-chloromethyl-2-methylthiazole (0.16 g, 0.0008 mol) in ethanol (3 ml) and triethylamine (0.2 ml) was stirred at 80° C. for 1 hour. $H_2O$ was added. The mixture was extracted with EtOAc. The organic layer was separated, dried ($MgSO_4$), filtered and the solvent was evaporated. The residue (0.04 g) was purified by column chromatography over silica gel (eluent: $CH_2Cl_2/CH_3OH$ 98/2; 15–40 μm). The pure fractions were collected and the solvent was evaporated and dried to yield 0.018 g.

EXAMPLE 22

4-(3,5-dimethylphenoxy)-3-iodo-6-methyl-5-(3-phenyl-propyl)-1H-pyridin-2-one (compound 547)

22.1: 2-(1-amino-ethylidene)-5-phenyl-pentanoic acid ethyl ester (intermediate 23)

Ammonium nitrate (3.1 g; 0.039 mol) was added to a solution of intermediate 22 (2-acethyl-5-phenyl-pentanoic acid ethyl ester) (8.8 0.0354 mol) in tetrahydrofuran (90 ml). Ammoniac was bubbled. The mixture was stirred and refluxed for 6 hours, then stirred at room temperature for 12 hours, poured out into $H_2O$ and extracted with $CH_2Cl_2$. The organic layer was separated, dried on magnesium sulfate ($MgSO_4$), filtered and the solvent was evaporated and dried to yield 8.3 g.

22.2: ethyl 4-hydroxy-6-methyl-2-oxo-5-(3-phenyl-propyl)-1,2dihydro-pyridine-3-carboxylic acid ethyl ester (intermediate 24)

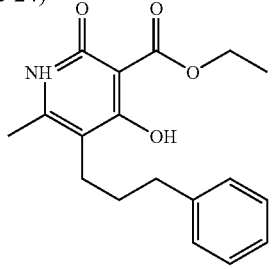

Sodium ethoxide in ethanol (27.5 ml; 0.0738 mol) was stirred and refluxed. Malonic acid diethyl ester (11.8 ml; 0.0738 mol) was added dropwise. A solution of intermediate 23 (8.3 g; 0.0335 mol) in ethanol (30 ml) was added dropwise. The mixture was stirred and refluxed for 15 hours. Three-quarters of EtOH were evaporated. The mixture was poured out in ice, acidified with HCl 3N and extracted with EtOAc. The organic layer was separated, dried ($MgSO_4$), filtered and the solvent was evaporated The residue (19.5 g) was purified by column chromatography over silica gel (eluent: $CH_2Cl_2/NH_4OH$ 96/4/0.1; 15–35 μm). Two fractions were collected and the solvent was evaporated and dried to yield 0.43 g (4%).

22.3: 4-hydroxy-6-methyl-5-(3-phenyl-propyl)-1H-pyridin-2-one (intermediate 25)

A mixture of intermediate 24 (0.1 g; 0.003 mol) and sodium hydroxide (0.038 g; 0.0009 mol) in $H_2O$ (1.5 ml) was stirred and refluxed for 15 hours, then cooled to 5° C. with HCl 3N. The precipitate was filtered, washed with $H_2O$, then with isopropanol and dried to yield 0.07 g (91%).

22.4: 4-(3,5-dimethylphenoxy)-3-iodo-6-methyl-5-(3-phenyl-propyl)-1H-pyridin-2-one (compound 547)

A mixture of dichloro-3,5-dimethyliodobenzene (0.096 g; 0.0003 mol) and sodium carbonate (0.12 g; 0.0005 mol) in dimethylformamide (1 ml; 0.5 ml) was stirred at room temperature for 30 minutes. A solution of intermediate 25 (0.07 g; 0.0002 mol) and sodium carbonate (0.6 g; 0.0005 mol) in $H_2O$ (0.5 ml) was added. The mixture was stirred at room temperature for 1 hour. The precipitate was filtered, washed with $H_2O$, then with DIPE and dried. The residue (0.12 g) was taken up in DMF and stirred at 100° C. for 30 minutes. The solvent was evaporated till dryness. The residue (0.1 g) was purified by column chromatography over silica gel (eluent: $CH_2Cl_2/CH_3OH/NH_4OH$ 98/2/0 to 95/5/0.1; 35–70 μm). The pure fractions were collected and the solvent was evaporated. The residue (0.07 g) was taken up in iPrOH. The precipitate was filtered off and dried to yield 0.06 g (44%), m.p.=220° C.

EXAMPLE 23

6-methyl-5-ethyl-3-iodo-4-[(3-bromo,5-acrylonitrile-phenoxy]pyridin-2(1H)-one (compound 470)

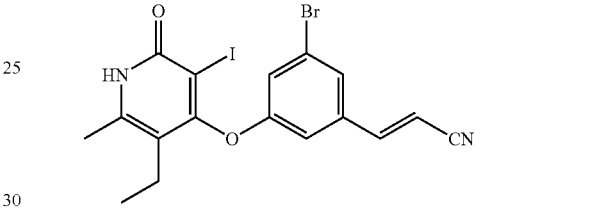

23.1. 3-Bromo-5-iodobenzaldehyde dichloride (intermediate 26)

3-Bromo-5-iodobenzaldehyde dichloride (intermediate 26) was obtained as described by H. J. Lucas and E. R. Kennedy, Org. Synth. (1955), III, 482–483.

23.2. 6-methyl-5-ethyl-3-iodo-4-[(3-bromo,5-formylphenoxy]pyridin-2(1H)-one (compound 469)

Intermediate 26 (311 mg, 1 mmol) was suspended in 10 ml of water containing sodium carbonate (106 mg, 1 mmol) and stirred for 30 min. at room temperature. To this mixture a solution of 5-ethyl-6-methyl-4-hydroxypyridin-2(1H)-one (153 mg, 1 mmol) in 10 ml of water containing also $Na_2CO_3$ (106 mg, 1 mmol) was added. After stirring for 1 h at 20° C. the precipitate was filtered off, washed with water, dried in vacuo and suspended in dimethylformamide (5 mL). After heating at 120° C. for 10 min., the solvent was removed. Purification by flash chromatography ($SiO_2$, $CH_2Cl_2$/EtOH 98:2) gave the titled compound (205 mg, 44%) as yellow microcrystals, m.p.>260° C.

23.3. 6-methyl-5-ethyl-3-iodo-4-[(3-bromo,5-acrylonitrile-phenoxy]pyridin-2(1H)-one (compound 470)

To a 0° C. magnetically stirred solution of diethyl(cyanomethyl)-phosphonate (113 μL, 0.68 mmol) in anhydrous THF (3 mL), NaH (28 mg; 0.68 mmol) was added (60% in mineral water). After stirring at room temperature for 1 h, compound 469 (80 mg; 0.17 mmol) was added and the reaction mixture was stirred 18 h at room temperature and poured into water (5 ml). The resulting solution was extracted with AcOEt, dried over $MgSO_4$ and evaporated. The oily residue obtained was then crystallized from $Et_2O$ to give the pure titled compound (65 mg; 77%), m.p.>260° C.

Table 1 lists intermediates and compounds of formula (I) which were made analogous to one of the above examples.

| N° | Y | Q | X—R1 | R2 | R3 | R4 | mp. °C./[MH+] |
|---|---|---|---|---|---|---|---|
| 1 | O | H | 3,5-dimethylphenyl-S- (Chemistry 5) | cyclopentyl-S-CH2- (Chemistry 6) | Me | H | 245 |
| 2 | O | H | 3,5-dimethylphenyl-O- (Chemistry 11) | -C(O)NH-(4-pyridyl) (Chemistry 12) | Me | H | >250 |
| 3 | O | H | 3,5-dimethylphenyl-O- (Chemistry 17) | -C(O)NH-cyclopropyl (Chemistry 18) | Me | H | >250 |

-continued
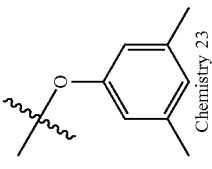
| N°= | Y | Q | X—R1 | R2 | R3 | R4 | mp. °C/[MH+] |
|---|---|---|---|---|---|---|---|
| 4 | O | H | 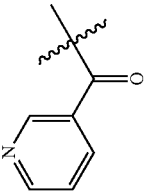 Chemistry 23 | Et |  Chem 25 | H | 210 |
| 5 | O | H |  Chemistry 29 | 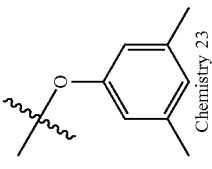 Chemistry 30 | Me | H | >250 |
| 6 | O | H | 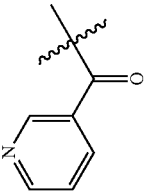 Chemistry 35 |  Chemistry 36 | Me | H | [520] |

-continued
| N° | Y | Q | X—R1 | R2 | R3 | R4 | mp. °C/[MH+] |
|----|---|------|------|------|------|------|------|
| 7 | O | I—Pr | 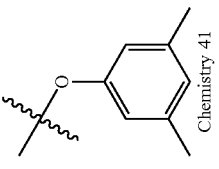 Chemistry 41 | Et | Me | H | 260–262 |
| 8 | O | I | 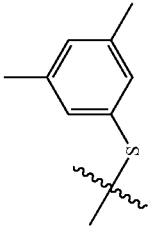 Chemistry 47 | 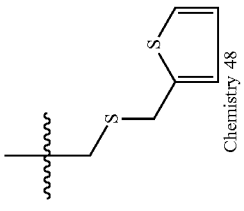 Chemistry 48 | Me | H | 230 |
| 9 | O | I | 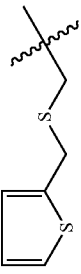 Chemistry 53 |  Et |  Chem 55 | H | 125 |

-continued
| N° | Y | Q | X—R1 | R2 | R3 | R4 | mp. °C./[MH+] |
|---|---|---|---|---|---|---|---|
| 10 | O | I | 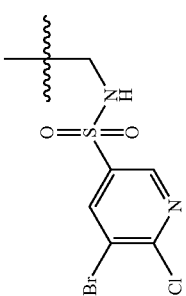 Chemistry 59 | 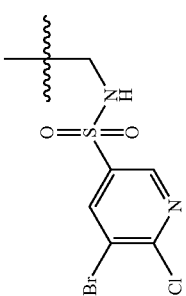 Chemistry 60 | Me | H | [639] |
| 11 | O | I | 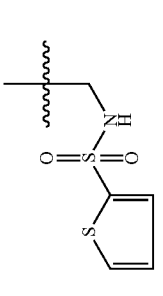 Chemistry 65 | 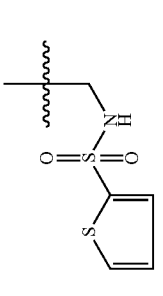 Chemistry 66 | Me | H | [569] |
| 12 | O | I | 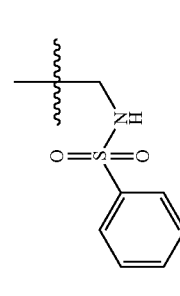 Chemistry 71 | 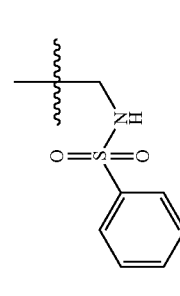 Chemistry 72 | Me | H | [593] |

-continued
| N° = | Y | Q | X—R1 | R2 | R3 | R4 | mp. °C./[MH+] |
|---|---|---|---|---|---|---|---|
| 13 | O | I | 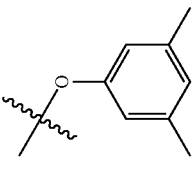 Chemistry 77 | 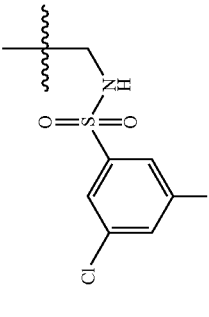 Chemistry 78 | Me | H | [539] |
| 14 | O | I | 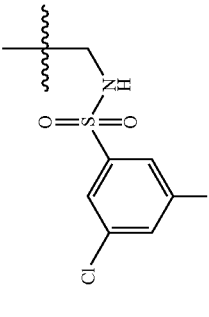 Chemistry 83 | 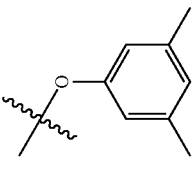 Chemistry 84 | Me | H | [543] |
| 15 | O | I | 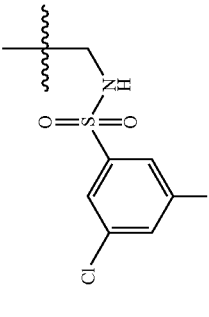 Chemistry 89 | 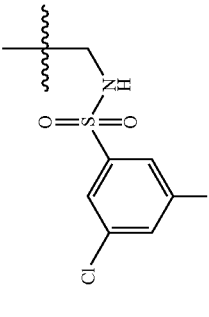 Chemistry 90 | Me | H | [551] |

-continued
| N° = | Y | Q | X—R1 | R2 | R3 | R4 | mp. °C./[MH+] |
|---|---|---|---|---|---|---|---|
| 16 | O | I | 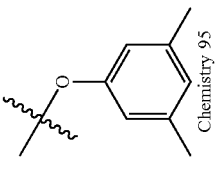 Chemistry 95 | 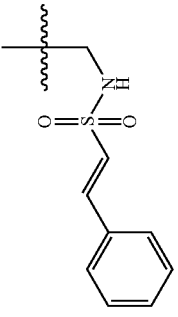 Chemistry 96 | Me | H | [539] |
| 17 | O | I | 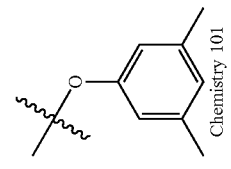 Chemistry 101 | 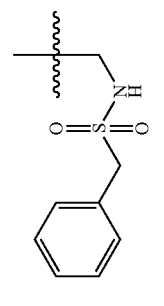 Chemistry 102 | Me | H | [531] |
| 18 | O | I | 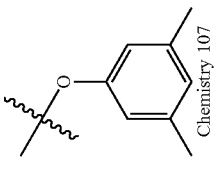 Chemistry 107 | 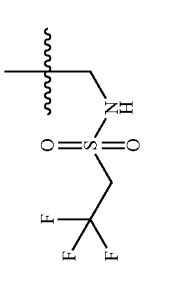 Chemistry 108 | Me | H | [477] |

-continued

[Structure: pyridine-type ring with Y=, Q, X—R1, R2, R3, R4, N—R4]

| N° = | Y | Q | X—R1 | R2 | R3 | R4 | mp. °C/[MH+] |
|---|---|---|---|---|---|---|---|
| 19 | O | I | 3,5-dimethylphenyloxy (Chemistry 113) | ethylsulfonamidomethyl (Chemistry 114) | Me | H | [463] |
| 20 | O | I | 3,5-dimethylphenyloxy (Chemistry 119) | methylsulfonamidomethyl (Chemistry 120) | Me | H | [531] |
| 21 | O | ethoxymethyl (Chem 124) | 3,5-dimethylphenyloxy (Chemistry 125) | I | Me | H | 240–244 |

-continued
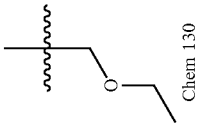
| N° | Y | Q | X—R1 | R2 | R3 | R4 | mp. °C./[MH+] |
|---|---|---|---|---|---|---|---|
| 22 | O | 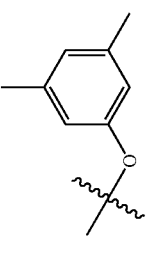 Chem 130 | 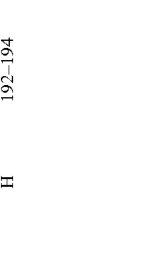 Chemistry 131 | H | Me | H | 192–194 |
| 23 | O | I | 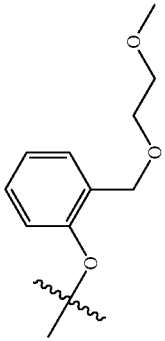 Chemistry 137 | Et | Me | H | 102–104 |
| 24 | O | I | 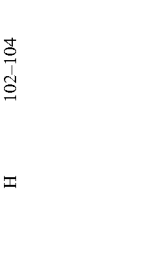 Chemistry 143 | Et | Me | H | 170–172 |
| 25 | O | I | 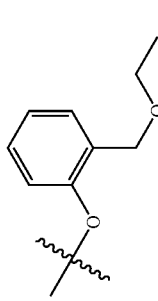 Chemistry 149 | Et | Me | H | 225–226 |

-continued

| N° | Y | Q | X—R1 | R2 | R3 | R4 | mp. °C/[MH+] |
|---|---|---|---|---|---|---|---|
| 26 | O | I | Chemistry 155 (2-hydroxymethylphenoxy) | Et | Me | H | 236–238 |
| 27 | O | I | Chemistry 161 (2-formylphenoxy) | Et | Me | H | 260–262 |
| 28 | O | I | Chemistry 167 (3,5-dimethylphenoxy) | Et | CH(OH)CH2CN | H | 118 |
| 29 | O | I | (3,5-dimethylphenoxy) | Et | Chem 169 (CH(OH)CH2C(O)OEt) | H | 184 |

-continued

Chem 175:

[Structure: pyridine-type ring with Q at position 3, X–R1 at position 4, R2 at position 5, R3 at position 6, N–R4, and Y at position 2]

| N° | Y | Q | X—R1 | R2 | R3 | R4 | mp. °C/[MH+] |
|---|---|---|---|---|---|---|---|
| 30 | O | I | Chemistry 173 (3,5-dimethylphenyl-O-) | Chemistry 180 (-C(=O)NH-CH2CH2CH2-N(Me)2) | Me | H | 160 |
| 31 | O | I | Chemistry 179 (3,5-dimethylphenyl-S-) | Chemistry 186 (-CH=N-O-CH2-Ph) | Me | H | 165 |
| 32 | O | I | Chemistry 185 (3,5-dimethylphenyl-S-) | -CH=NOH | Me | H | >250 |
| 33 | O | I | Chemistry 191 (3,5-dimethylphenyl-S-) | Chemistry (-S-CH2CH2-N(Et)2) | Me | H | 150 |

-continued
| N°= | Y | Q | X—R1 | R2 | R3 | R4 | mp. °C./[MH+] |
|---|---|---|---|---|---|---|---|
| 34 | O | I | 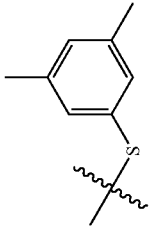 Chemistry 197 | 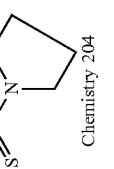 Chemistry 198 | Me | H | >250 |
| 35 | O | I | 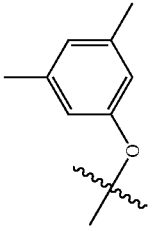 Chemistry 203 | 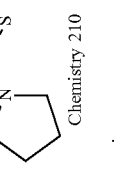 Chemistry 204 | Me | H | >250 |
| 36 | O | I | 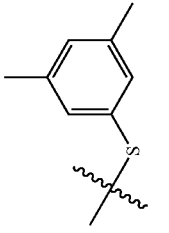 Chemistry 209 |  Chemistry 210 | Me | H | 200 |

-continued

| N° | Y | Q | X—R1 | R2 | R3 | R4 | mp. °C/[MH+] [519] |
|---|---|---|---|---|---|---|---|
| 37 | O | I | 3,5-dimethylphenoxy (Chemistry 221) | Et | CH(CH3)(OH)CH2NHCH2Ph (Chem 223) | H | — |
| 38 | O | I | 3,5-dimethylphenoxy (Chemistry 227) | Et | 2-methyloxiranyl (Chem 229) | H | — |
| 39 | O | I | 3,5-dimethylphenylthio (Chemistry 233) | CH2CH2SPh (Chemistry 234) | Me | H | 210 |

-continued

| N° | Y | Q | X—R1 | R2 | R3 | R4 | mp. °C./[MH+] |
|---|---|---|---|---|---|---|---|
| 40 | O | I | 3,5-dimethylphenoxy (Chemistry 239) | Et | 1-(pyridin-3-yl)-1-hydroxymethyl (Chem 241) | H | 210 |
| 41 | O | I | 3,5-dimethylphenoxy (Chemistry 245) | Et | CH=NOH | H | >250 |
| 42 | O | I | 3,5-dimethylphenoxy (Chemistry 251) | CH2NHC(=S)NHEt (Chemistry 252) | C=NOH Me | H | >250 |

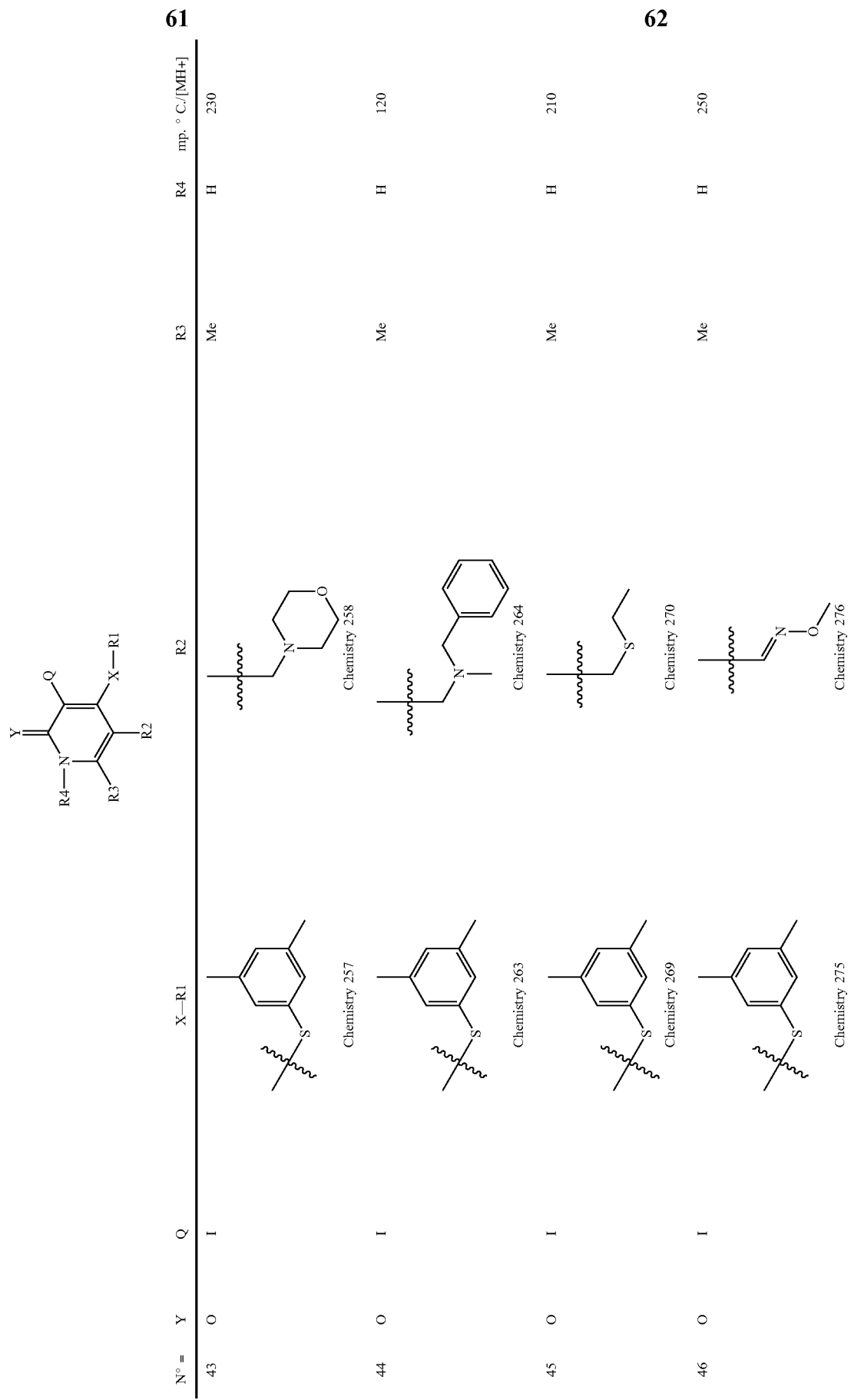

-continued

| N° | Y | Q | X—R1 | R2 | R3 | R4 | mp. °C./[MH+] |
|---|---|---|---|---|---|---|---|
| 47 | O | I | Chemistry 281 | Chemistry 282 | Me | H | >250 |
| 48 | O | I | Chemistry 287 | Et | Chem 289 | H | 218 |
| 49 | O | I | Chemistry 293 | Chemistry 294 | Me | H | >250 |

-continued

| N° | Y | Q | X—R1 | R2 | R3 | R4 | mp. °C/[MH+] |
|----|---|---|------|----|----|----|--------------|
| 50 | O | I | 3,5-dimethylphenoxy (Chemistry 299) | Et | benzothiazol-2-yl-carbonyl (Chem 301) | H | 226 |
| 51 | O | I | 3,5-dimethylphenoxy (Chemistry 305) | -C(O)NH-CH2CH2-OMe (Chemistry 306) | Me | H | 236 |
| 52 | O | I | 3,5-dimethylphenoxy (Chemistry 311) | -C(O)NH-CH2CH2-SMe (Chemistry 312) | Me | H | >250 |
| 53 | O | I | 3,5-dimethylphenoxy (Chemistry 317) | -C(O)NH-CH2CH2-morpholine (Chemistry 318) | Me | H | >250 |

-continued
| N° | Y | Q | X—R1 | R2 | R3 | R4 | mp. °C./[MH+] |
|---|---|---|---|---|---|---|---|
| 54 | O | I | 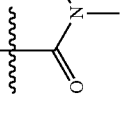 Chemistry 323 | 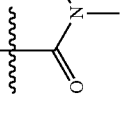 Chemistry 324 | Me | H | 150 |
| 55 | O | I | 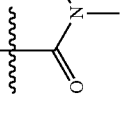 Chemistry 329 | 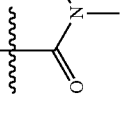 CN | Me | H | >250 |
| 56 | O | H | 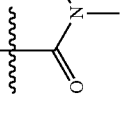 Chemistry 335 | 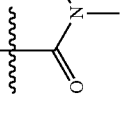 CN | Me | H | >250 |
| 57 | O | I | 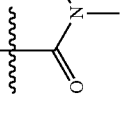 Chemistry 341 | 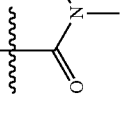 Formyl | Me | H | >250 |

-continued

![structure with Q, X-R1, R2, R3, R4, Y]

| N° | Y | Q | X—R1 | R2 | R3 | R4 | mp. °C/[MH+] |
|---|---|---|---|---|---|---|---|
| 58 | O | I | 3,5-dimethylphenoxy (Chemistry 347) | Et | CH2SEt (Chem 349) | H | 182 |
| 59 | O | I | 3,5-dimethylphenylthio (Chemistry 353) | CH2NMe2 | Me | H | 245 |
| 60 | O | I | 3,5-dimethylphenylthio (Chemistry 359) | CH2Cl | Me | H | 218 |
| 61 | O | I | 3,5-dimethylphenylthio (Chemistry 365) | CH2OH | Me | H | 240 |

-continued

| N° = | Y | Q | X—R1 | R2 | R3 | R4 | mp. °C./[MH+] |
|---|---|---|---|---|---|---|---|
| 62 | O | I | 3,5-dimethylphenoxy (Chemistry 371) | Et | benzyl(methyl)aminoethyl (Chem 373) | H | 165 |
| 63 | O | I | 3,5-dimethylphenoxy (Chemistry 377) | Et | (1-methylimidazol-2-yl)carbonyl (Chem 379) | H | 235 |
| 64 | O | I | 3,5-dimethylphenoxy (Chemistry 383) | benzofuran-2-ylcarbonyl (Chemistry 384) | Me | H | >250 |

-continued

[Structure: pyridine ring with Y=, Q, X-R1, R2, R3, R4-N substituents]

| N° | Y | Q | X—R1 | R2 | R3 | R4 | mp. °C/[MH+] |
|---|---|---|---|---|---|---|---|
| 65 | O | I | [3,5-dimethylphenoxy] | [CH(OH)CO2H] | Me | H | >250 |
| 66 | O | I | [3,5-dimethylphenoxy] Chemistry 389 | CO2H Et | [CH2CH2CN] | H | 240 |
| 67 | O | I | [3,5-dimethylphenoxy] Chemistry 395 | Et | CH2CN | H | [502] |
| 68 | O | Me | [3,5-dimethylphenoxy] Chemistry 401 | Et | [CH2SCH2CO2Et] Chem 403 | H | 207–209 |

| N° | Y | Q | X—R1 | R2 | R3 | R4 | mp. °C./[MH+] |
|---|---|---|---|---|---|---|---|
| 69 | O | H | Chemistry 407 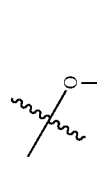 | Et | Me | H | — |
| 70 | O | I | Chemistry 413 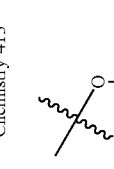 | Et | Chem 421 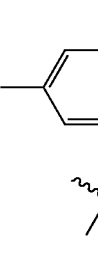 | H | 224 |
| 71 | O | I | Chemistry 425 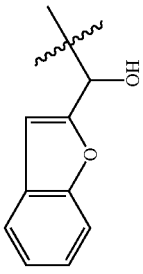 | CO2Et 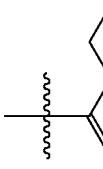 | Me | H | 210 |

-continued
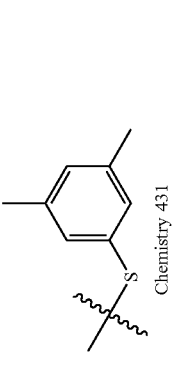
| N° | Y | Q | X—R1 | R2 | R3 | R4 | mp. °C./[MH+] |
|---|---|---|---|---|---|---|---|
| 72 | O | H | 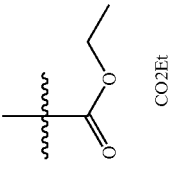 Chemistry 431 | 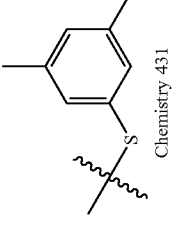 CO2Et | Me | H | 230 |
| 73 | O | I | 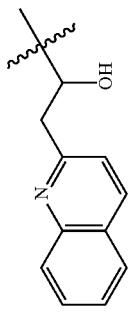 Chemistry 437 | Et | 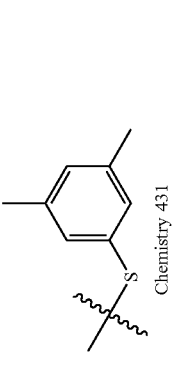 Chem 439 | H | 181 |
| 74 | O | I | 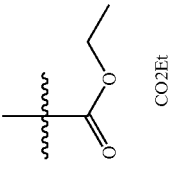 Chemistry 443 | Et | 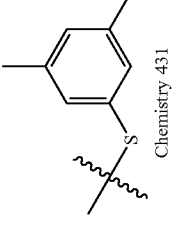 Chem 445 | H | 170 |

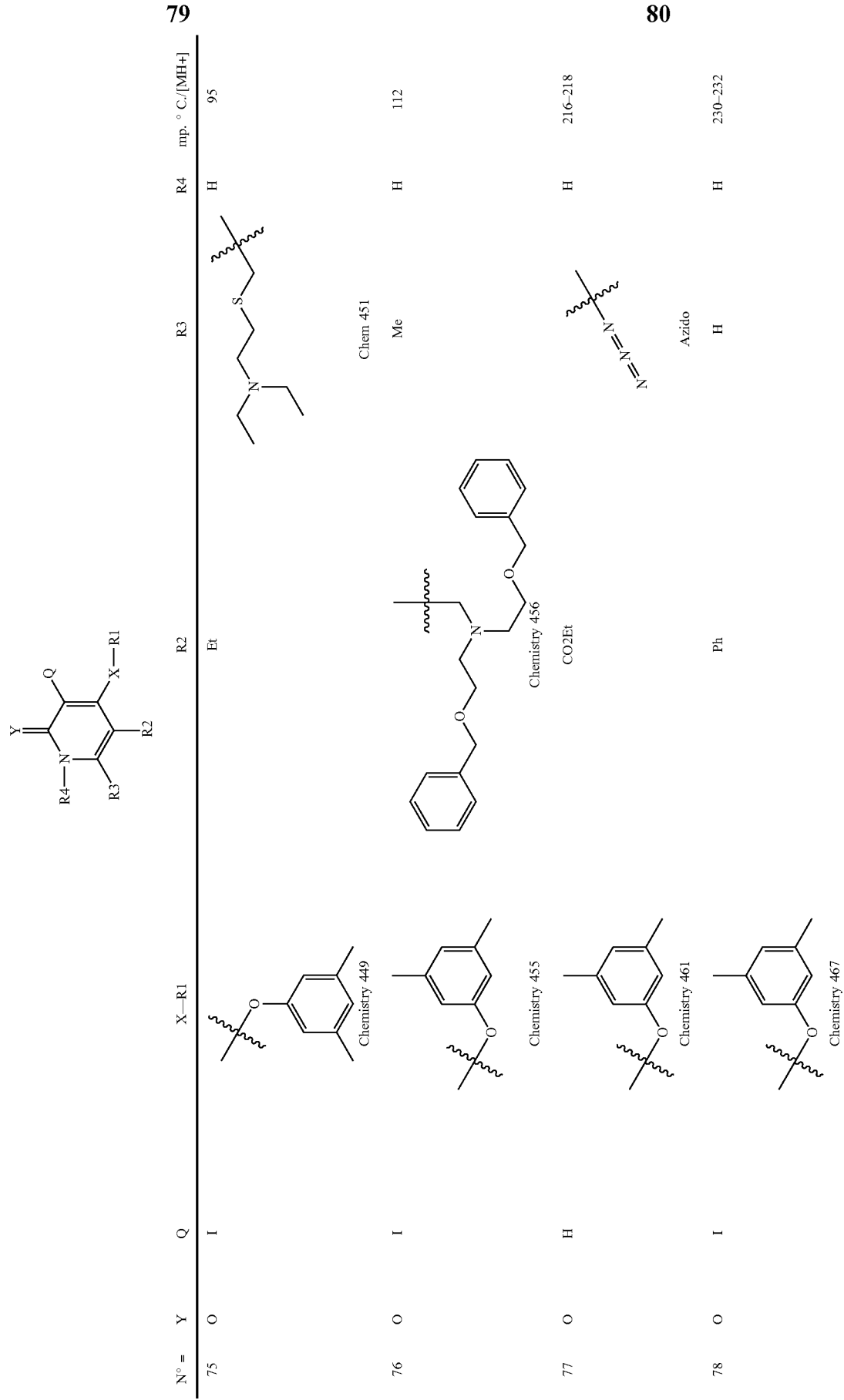

-continued

| N°= | Y | Q | X—R1 | R2 | R3 | R4 | mp. °C./[MH+] |
|---|---|---|---|---|---|---|---|
| 79 | O | I | Chemistry 473 (3-methyl-5-(2-methoxyethoxymethyl)phenoxy) | Et | Me | H | 138–139 |
| 80 | O | I | Chemistry 479 (3-methyl-5-(ethoxymethyl)phenoxy) | Et | Me | H | 178–149 |
| 81 | O | I | Chemistry 485 (3-methyl-5-(chloromethyl)phenoxy) | Et | Me | H | 248–250 |
| 82 | O | I | Chemistry 491 (3-(ethoxycarbonyl)phenoxy) | Et | Me | H | 202–204 |

-continued

| N° | Y | Q | X—R1 | R2 | R3 | R4 | mp. °C./[MH+] |
|---|---|---|---|---|---|---|---|
| 83 | O | I | 3-methyl-5-(2-cyanovinyl)phenoxy (Chemistry 497) | Et | Me | H | 258–260 |
| 84 | O | H | 3,5-dimethylphenylthio (Chemistry 503) | ethoxymethyl (Chemistry 504) | Me | H | 205–207 |
| 85 | O | Br | 3,5-dimethylphenylthio (Chemistry 509) | ethoxymethyl (Chemistry 510) | Me | H | 183–184 |
| 86 | O | I | 3,5-dimethylphenylthio (Chemistry 515) | ethoxymethyl (Chemistry 516) | Me | H | 220–222 |

-continued

Structure: pyridine with Y=, Q, X-R1, R2, R3, R4-N

| N° | Y | Q | X—R1 | R2 | R3 | R4 | mp. °C./[MH+] |
|---|---|---|---|---|---|---|---|
| 87 | O | CO2Et | 2,6-difluorophenoxy (Chemistry 521) | Et | Me | H | 189–191 |
| 88 | O | I | 3-methylphenylthio (Chemistry 527) | Et | Me | H | — |
| 89 | O | H | 3-methylphenylthio (Chemistry 533) | Et | Me | H | 229–231 |
| 90 | O | I | 3-(carboxy)phenoxy (Chemistry 539) | Et | Me | H | 288–290 |

-continued

| N° | Y | Q | X—R1 | R2 | R3 | R4 | mp. °C./[MH+] |
|---|---|---|---|---|---|---|---|
| 91 | O | I | 3,5-dimethylphenoxy (Chemistry 545) | CH2NMe2 | Me | H | 238 |
| 92 | O | I | 3,5-dimethylphenoxy (Chemistry 551) | benzyl-S-CH2 (Chemistry 552) | Me | H | 220 |
| 93 | O | I | 3,5-dimethylphenoxy (Chemistry 557) | Et | piperidinylmethyl (Chem 559) | H | 160 |

-continued

| N° = | Y | Q | X—R1 | R2 | R3 | R4 | mp. °C./[MH+] |
|---|---|---|---|---|---|---|---|
| 94 | O | I | 3,5-dimethylphenoxy | (quinolin-2-yl)CH(OH)CH2- (Chemistry 563/564) | Me | H | 218 |
| 95 | O | I | 3,5-dimethylphenoxy-CH2- (Chemistry 569) | Et | (1-methylimidazol-2-yl)CH(OH)- (Chem 571) | H | 214 |
| 96 | O | I | 3,5-dimethylphenoxy-CH2- (Chemistry 575) | Et | PhS-CH2- (Chem 577) | H | 190 |

-continued

| N° | Y | Q | X—R1 | R2 | R3 | R4 | mp. °C./[MH+] |
|---|---|---|---|---|---|---|---|
| 97 | O | I | Chemistry 581 | Chemistry 582 | Me | H | >250 |
| 98 | O | I | Chemistry 587 | Et | Chem 589 | H | 240 |
| 99 | O | I | Chemistry 593 | Chemistry 594 | Me | H | 180 |

| N° | Y | Q | X—R1 | R2 | R3 | R4 | mp. °C./[MH+] |
|---|---|---|---|---|---|---|---|
| 100 | O | I | Chemistry 599 | 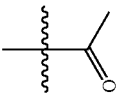 | Me | H | >250 |
| 101 | O | I | Chemistry 605 | Ac | 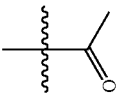 | H | 210 |
| 102 | O | I | Chemistry 611 | Et | (CH2)3 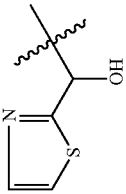 | H | 170 |
| 103 | O | I | Chemistry 617 | Et | Chem 613 / Chem 619 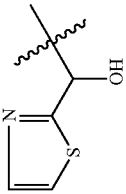 | H | 170 |

-continued

| N° = | Y | Q | X—R1 | R2 | R3 | R4 | mp. °C/[MH+] |
|---|---|---|---|---|---|---|---|
| 104 | O | I | Chemistry 623 | Et | Chem 625 | H | 200 |
| 105 | O | I | Chemistry 629 | Et | Chemistry 631 | H | >250 |
| 106 | O | I | Chemistry 635 | CO2Et | Azido | H | 216–218 |
| 107 | O | I | | Et | Me | H | 263–265 |

-continued
| N° | Y | Q | X—R1 | R2 | R3 | R4 | mp. °C./[MH+] |
|---|---|---|---|---|---|---|---|
| 108 | O | I | 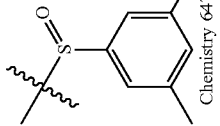 Chemistry 641 | Et | Me | H | — |
| 109 | O | Br | 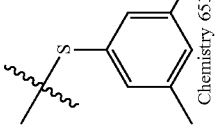 Chemistry 647 | Et | Me | H | 187–189 |
| 110 | O | I | 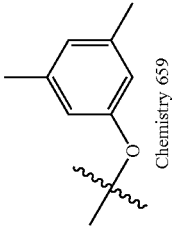 Chemistry 659 | 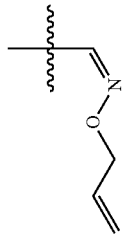 Chemistry 660 | Me | H | 240 |

-continued

| N° | Y | Q | X—R1 | R2 | R3 | R4 | mp. °C/[MH+] |
|---|---|---|---|---|---|---|---|
| 111 | O | CO2Et | Chemistry 665 (3,5-dimethylphenyl sulfinyl) | Et | Me | H | 202–204 |
| 112 | O | H | Chemistry 671 (3,5-dimethylphenoxy) | CN | NH2 | H | 282–283 |
| 113 | O | I | Chemistry 677 (3,5-dimethylphenoxy) | CN | NH2 | H | 283–285 |

-continued

| N° | Y | Q | X—R1 | R2 | R3 | R4 | mp. °C./[MH+] |
|---|---|---|---|---|---|---|---|
| 114 | O | H | 3-Methylbenzyl | Et | Me | H | 166–168 |
| 115 | O | I | S-(3,5-dichlorophenyl) Chemistry 695 | Et | Me | H | 229–231 |
| 116 | O | Br | S-(3,5-dimethylphenyl) Chemistry 701 | Et | CH2Br | H | [430] |

-continued
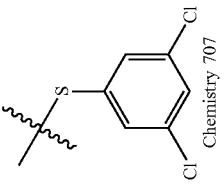
| N° = | Y | Q | X—R1 | R2 | R3 | R4 | mp. °C./[MH+] |
|---|---|---|---|---|---|---|---|
| 117 | O | H | 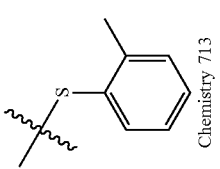 Chemistry 707 | Et | Me | H | — |
| 118 | O | I | 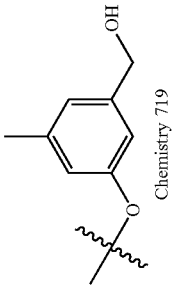 Chemistry 713 | Et | Me | H | — |
| 119 | O | I | 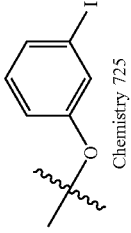 Chemistry 719 | Et | Me | H | 266–267 |
| 120 | O | I | Chemistry 725 | Et | Me | H | 186–187 |

-continued
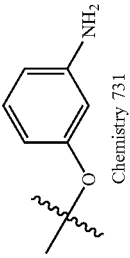
| N° = | Y | Q | X—R1 | R2 | R3 | R4 | mp. °C./[MH+] |
|---|---|---|---|---|---|---|---|
| 121 | O | I | Chemistry 731 | Et | Me | H | 225–226 |
| 122 | O | I | Chemistry 737 | CN | Chemistry (N=N=N) | H | 225–227 |
| 123 | O | I | Chemistry 743 | Chemistry 744 | Azido | H | [539] |
| 124 | O | I | Chemistry 749 | Chemistry 750 | Me | H | 140 |

-continued
| N° = | Y | Q | X—R1 | R2 | R3 | R4 | mp. °C./[MH+] |
|---|---|---|---|---|---|---|---|
| 125 | O | I |  Chemistry 755 | CH2Cl | Me | H | 256–258 |
| 126 | O | I |  Chemistry 761 | 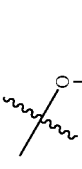 Chemistry 762 | Me | H | >250 |
| 127 | O | I |  Chemistry 767 |  | Me | H | — |
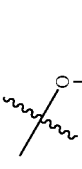

-continued
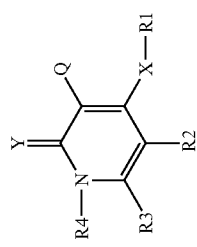
| N° = | Y | Q | X—R1 | R2 | R3 | R4 | mp. °C./[MH+] |
|---|---|---|---|---|---|---|---|
| 128 | O | I | 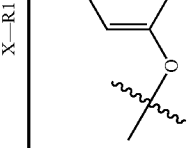 Chemistry 773 | 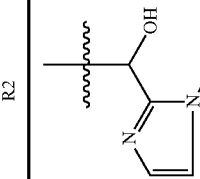 Chemistry 774 | Me | H | >240 |
| 129 | O | I | 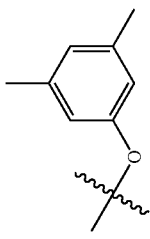 Chemistry 779 | 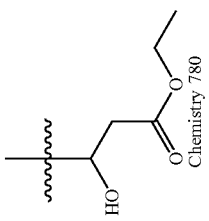 Chemistry 780 | Me | H | 230 |
| 130 | O | I | 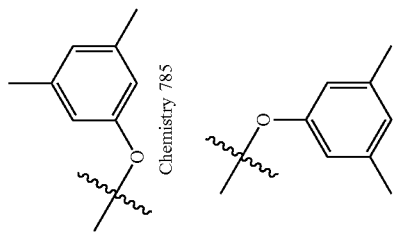 Chemistry 785 | Et | 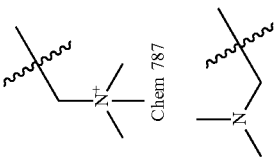 Chem 787 | H | 180 |
| 131 | O | I | 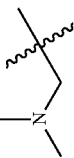 | Et | 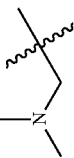 | H | 130 |

-continued
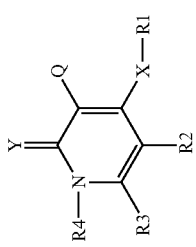
| N° | Y | Q | X—R1 | R2 | R3 | R4 | mp. °C./[MH+] |
|----|---|---|------|----|----|----|---------------|
| 132 | O | I | Chemistry 791 | Et | CH2NMe2 CH2Cl | H | >240 |
| 133 | O | I | Chemistry 797 | Et | CH2OH | H | 97 |
| 134 | O | I | Chemistry 803 | Et | 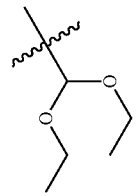 Chem 811 | H | — |
Chemistry 809

-continued
| N° = | Y | Q | X—R1 | R2 | R3 | R4 | mp. °C/[MH+] |
|---|---|---|---|---|---|---|---|
| 135 | O | I | 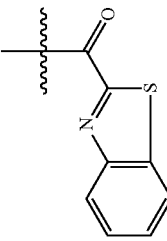 Chemistry 815 | 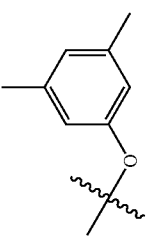 Chemistry 816 | Me | H | >250 |
| 136 | O | I | 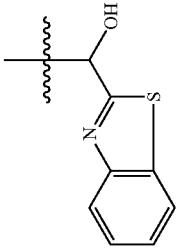 Chemistry 821 | 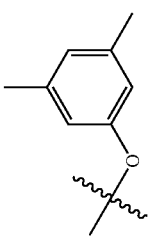 Chemistry 822 | Me | H | >250 |
| 137 | O | I | 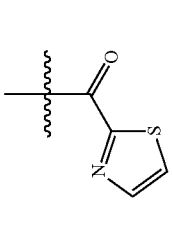 Chemistry 827 | 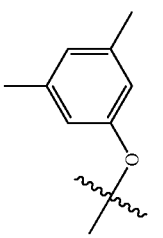 Chemistry 828 | Me | H | >250 |
| 138 | O | I | 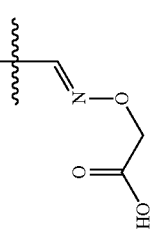 | 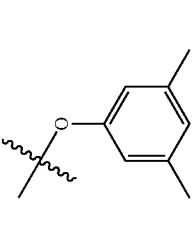 | Me | H | 250 |

-continued

| N° = | Y | Q | X—R1 | R2 | R3 | R4 | mp. °C./[MH+] |
|---|---|---|---|---|---|---|---|
| 139 | O | I | Chemistry 833 | Chemistry 834 Et | Chemistry 841 | H | [442] |
| 140 | O | I | Chemistry 839 | Chemistry 845 CH=CHCN | Me | H | >250 |
| 141 | O | I | Chemistry 851 | Chemistry 852 | Me | H | [508] |

-continued
| N° | Y | Q | X—R1 | R2 | R3 | R4 | mp. °C./[MH+] |
|---|---|---|---|---|---|---|---|
| 142 | O | I | 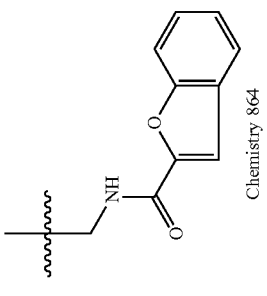 Chemistry 857 | 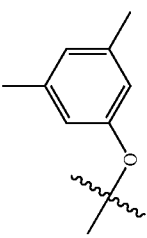 Chemistry 858 | Me | H | [491] |
| 143 | O | I | 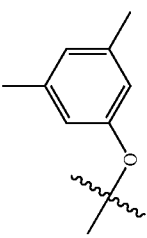 Chemistry 863 | 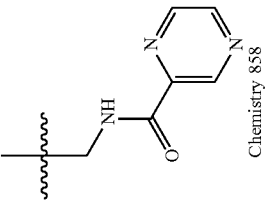 Chemistry 864 | Me | H | [529] |
| 144 | O | I | 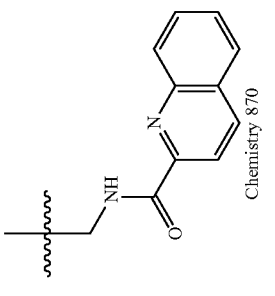 Chemistry 869 | 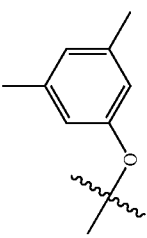 Chemistry 870 | Me | H | [540] |

-continued
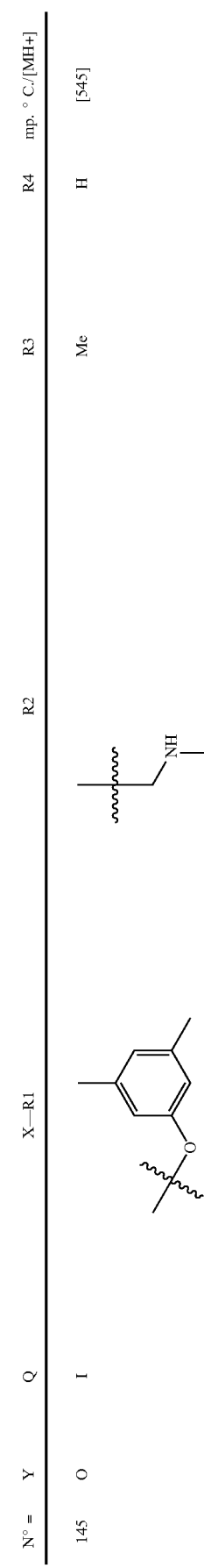
| N°  | Y | Q | X—R1 | R2 | R3 | R4 | mp. °C./[MH+] |
|-----|---|---|------|----|----|----|----------------|
| 145 | O | I | Chemistry 875 | Chemistry 876 | Me | H | [545] |
| 146 | O | I | Chemistry 881 | Chemistry 882 | Me | H | [543] |

-continued
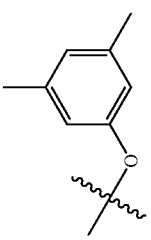
| N°= | Y | Q | X—R1 | | R2 | | R3 | R4 | mp. °C/[MH+] |
|---|---|---|---|---|---|---|---|---|---|
| 147 | O | I |  Chemistry 887 | | 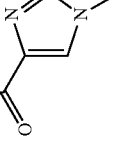 Chemistry 888 | | Me | H | [593] |
| 148 | O | I | 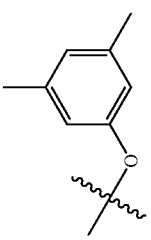 Chemistry 893 | |  Chemistry 894 | | Me | H | [544] |

-continued

| N° | Y | Q | X—R1 | R2 | R3 | R4 | mp. °C/[MH+] |
|---|---|---|---|---|---|---|---|
| 149 | O | I | Chemistry 899 | Chemistry 900 | Me | H | [570] |
| 150 | O | I | Chemistry 899 | Chemistry 906 | Me | H | [516] |
| 151 | O | I | Chemistry 905 | Chemistry 906 | Me | H | [519] |

| N° = | Y | Q | X—R1 | R2 | R3 | R4 | mp. °C./[MH+] |
|---|---|---|---|---|---|---|---|
| | | | Chemistry 911 | Chemistry 912 | | | |
| 152 | O | I | Chemistry 917 | Chemistry 918 | Me | H | [569] |
| 153 | O | I | Chemistry 923 | Chemistry 924 | Me | H | [535] |
| 154 | O | I | Chemistry 929 | Chemistry 930 | Me | H | [572] |

-continued
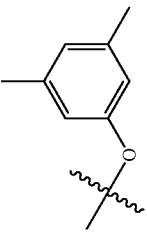
| N° = | Y | Q | X—R1 | R2 | R3 | R4 | mp. °C./[MH+] |
|---|---|---|---|---|---|---|---|
| 155 | O | I | 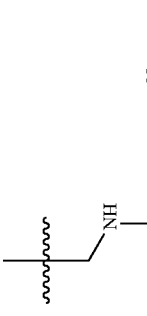<br>Chemistry 935 | 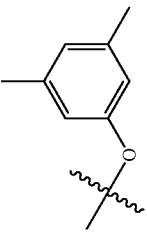<br>Chemistry 936 | Me | H | [586] |
| 156 | O | I | 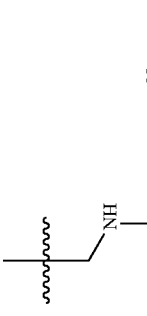<br>Chemistry 941 | 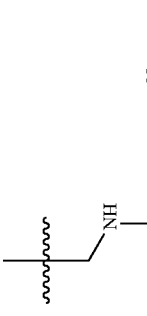<br>Chemistry 942 | Me | H | [518] |

-continued
| N° | Y | Q | X—R1 | R2 | R3 | R4 | mp. °C./[MH+] |
|---|---|---|---|---|---|---|---|
| 157 | O | I | Chemistry 947 | Et | Chem 949 | H | 195 |
| 158 | O | I | Chemistry 953 | Et | Chem 955 | H | 200 |
| 159 | O | I | Chemistry 959 | Et | 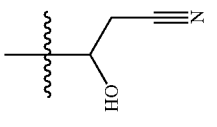 | H | 158 |
| 160 | O | I | 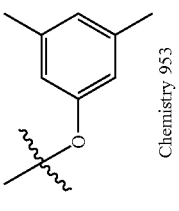 | 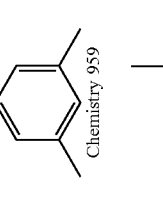 | Formyl Me | H | >250 |

| N° = | Y | Q | X—R1 | R2 | R3 | R4 | mp. °C./[MH+] |
|---|---|---|---|---|---|---|---|
| 161 | O | I | Chemistry 965 (3,5-dimethylphenoxy) | Chemistry 966 (CH₂-C(=O)-NH-CH₂- attached to 2,5-dimethylphenyl) | Me | H | 195 |
| 162 | O | I | Chemistry 971 (3,5-dimethylphenoxy) | Chemistry 972 (CH(OH)-benzofuran-2-yl) | Me | H | 220 |
| 163 | O | I | Chemistry 983 (3,5-dimethylphenoxy) | Chemistry 978 (CH=CH-C(=O)-CH₃, C=CHAc) | Me | H | >240 |

-continued

| N° = | Y | Q | X—R1 | R2 | R3 | R4 | mp. °C./[MH+] |
|---|---|---|---|---|---|---|---|
| 164 | O | I | 3,5-dimethylphenoxy (Chemistry 989) | 2-methyl-pent-2-enenitrile (Chemistry 990) | Me | H | >240 |
| 165 | O | I | 3,5-dimethylphenoxy (Chemistry 995) | 3-(dimethylamino)-N-ethylbenzamide (Chemistry 996) | Me | H | >240 |
| 166 | O | I | 3,5-dimethylphenoxy (Chemistry 1001) | N-ethyl-2-(thiophen-3-yl)acetamide (Chemistry 1002) | Me | H | >250 |

-continued
| N° | Y | Q | X—R1 | R2 | R3 | R4 | mp. °C/[MH+] |
|---|---|---|---|---|---|---|---|
| 167 | O | I | 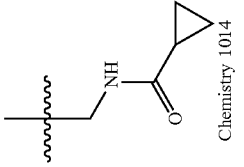 Chemistry 1007 | 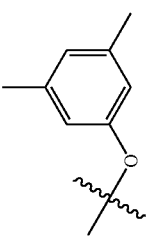 Chemistry 1008 | Me | H | 242 |
| 168 | O | I | 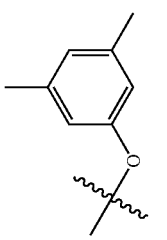 Chemistry 1013 | 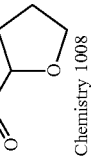 Chemistry 1014 | Me | H | 262 |
| 169 | O | I | 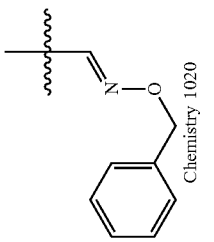 Chemistry 1019 | 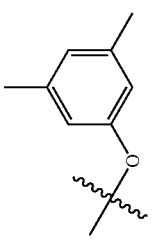 Chemistry 1020 | Me | H | >250 |

| N° | Y | Q | X—R1 | R2 | R3 | R4 | mp. °C/[MH+] |
|---|---|---|---|---|---|---|---|
| 170 | O | I | 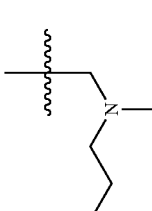 Chemistry 1025 | 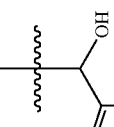 Chemistry 1026 | Me | H | 230 |
| 171 | O | I | 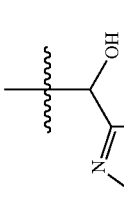 Chemistry 1031 | 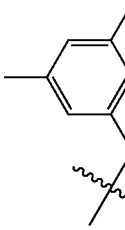 Chemistry 1032 | Me | H | [573] |
| 172 | O | I | 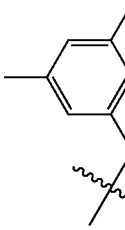 Chemistry 1037 | 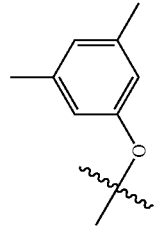 Chemistry 1038 | Me | H | [561] |

-continued
| N° = | Y | Q | X—R1 | R2 | R3 | R4 | mp. °C./[MH+] |
|---|---|---|---|---|---|---|---|
| 173 | O | I | 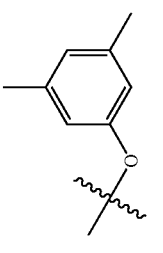 Chemistry 1043 | 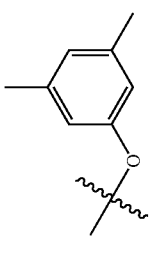 Chemistry 1044 | Me | H | [593] |
| 174 | O | I |  Chemistry 1049 | 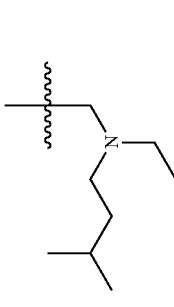 Chemistry 1050 | Me | H | [526] |
| 175 | O | I |  Chemistry 1055 | 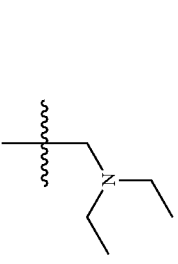 Chemistry 1056 | Me | H | [441] |

-continued
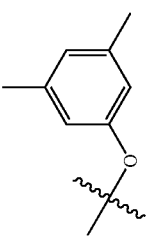
| N° | Y | Q | X—R1 | R2 | R3 | R4 | mp. °C./[MH+] |
|---|---|---|---|---|---|---|---|
| 176 | O | I | 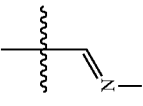 Chemistry 1061 | 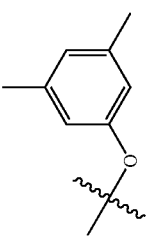 | Me | H | >250 |
| 177 | O | H | 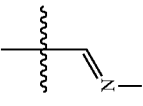 Chemistry 1067 | Et | Me | H | — |
| 178 | O | CO2Et | 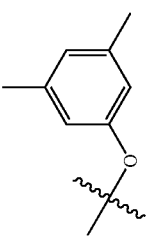 Chemistry 1073 | Et | Me | H | — |

-continued

Structure: pyridine ring with substituents Y=, Q, X—R1, R2, R3, N—R4

| N° | Y | Q | X—R1 | R2 | R3 | R4 | mp. °C/[MH+] |
|---|---|---|---|---|---|---|---|
| 179 | O | CO2Et | S-(2-methylphenyl), Chemistry 1079 | Et | Me | H | — |
| 180 | O | n-Pr | O-(3,5-dimethylphenyl), Chemistry 1085 | Et | Me | H | 158–160 |
| 181 | O | I | O-(3,5-dimethylphenyl), Chemistry 1091 | Me | H | H | >260 |

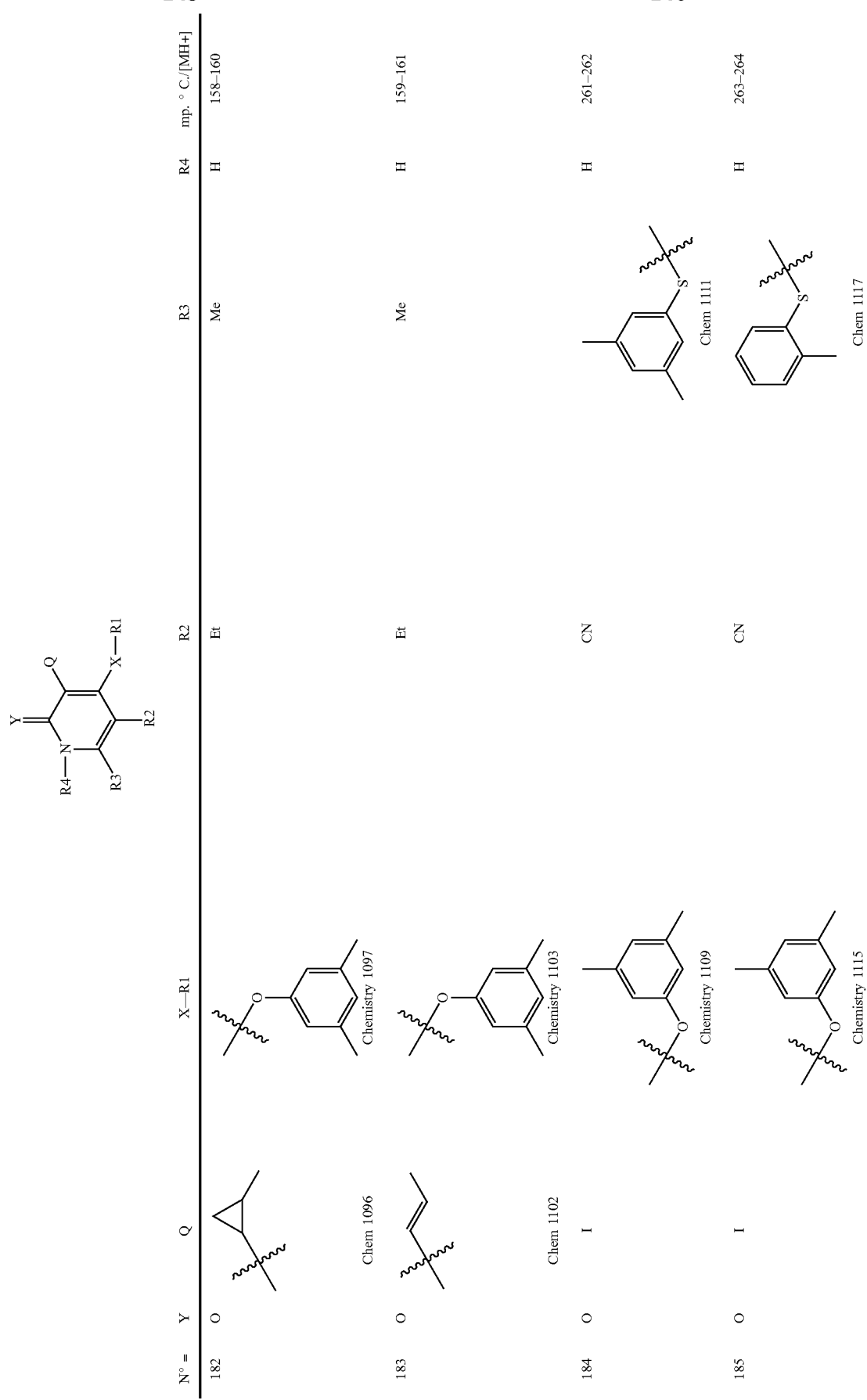

-continued
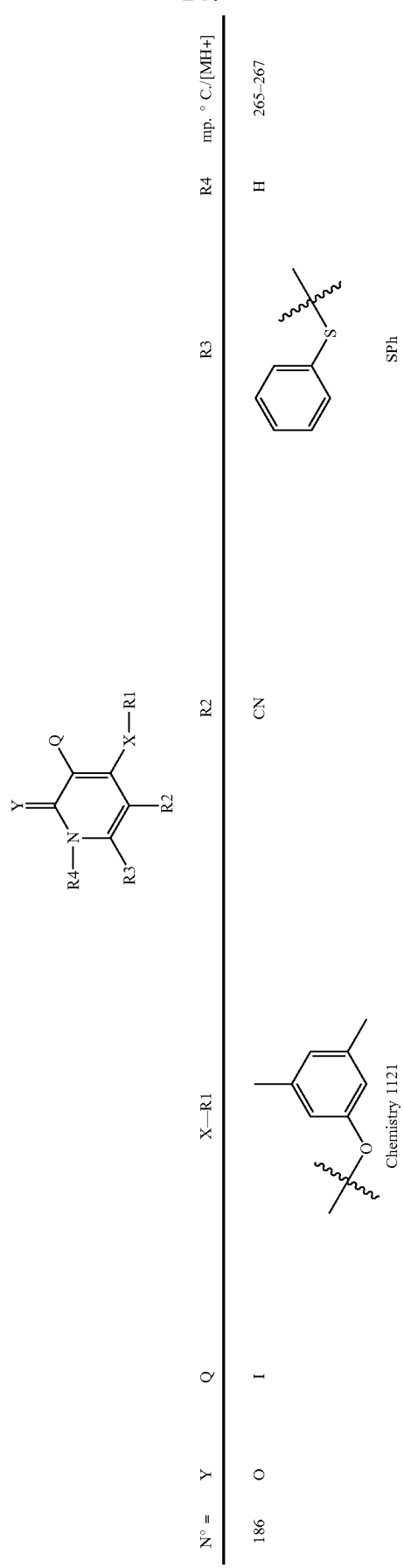
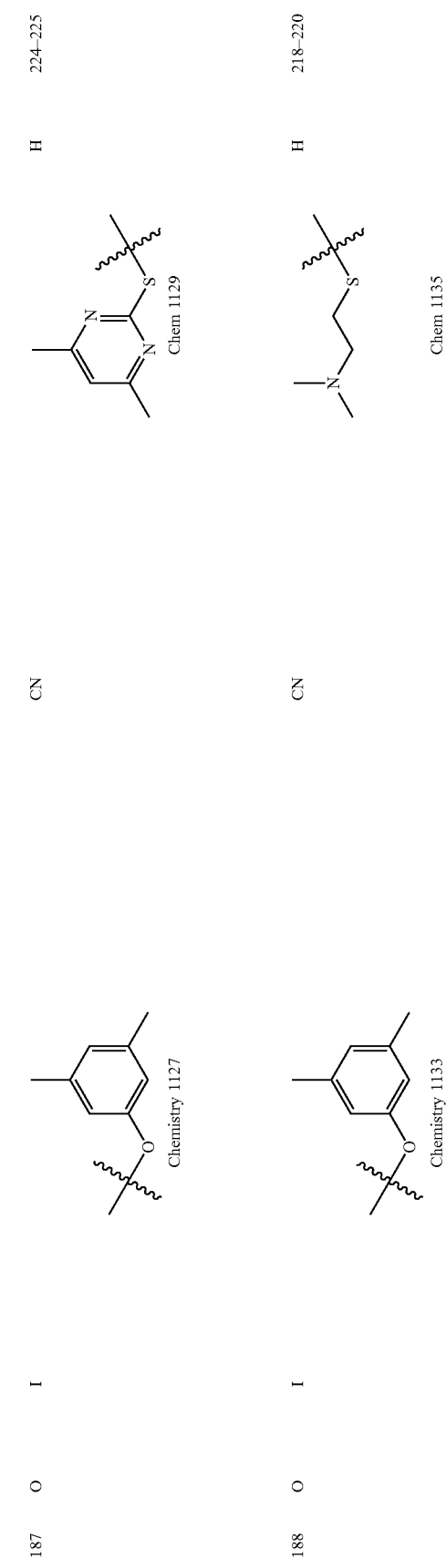
| N° | Y | Q | X—R1 | R2 | R3 | R4 | mp. °C./[MH+] |
|---|---|---|---|---|---|---|---|
| 186 | O | I | Chemistry 1121 | CN | SPh | H | 265–267 |
| 187 | O | I | Chemistry 1127 | CN | Chem 1129 | H | 224–225 |
| 188 | O | I | Chemistry 1133 | CN | Chem 1135 | H | 218–220 |

-continued

| N° | Y | Q | X—R1 | R2 | R3 | R4 | mp. °C/[MH+] |
|---|---|---|---|---|---|---|---|
| 189 | O | I | 3,5-dimethylphenoxy (Chemistry 1139) | CN | -S-CH2CH2-NH2 (Chem 1141) | H | 235–237 |
| 190 | O | I | 3,5-dimethylphenoxy (Chemistry 1145) | CN | -S-CH2CH2-OH (Chem 1147) | H | 242–244 |
| 191 | O | I | 3,5-dimethylphenoxy (Chemistry 1151) | Et | CH2CH2Ph | H | 240 |

| | | | | | | |
|---|---|---|---|---|---|---|
| 192 | O | I |  Chemistry 1157 |  Chemistry 1158 | Me | H | [514] |
| 193 | O | I |  Chemistry 1163 |  Chemistry 1164 | Me | H | [529] |
| 194 | O | I |  Chemistry 1169 |  Chemistry 1170 | Me | H | [580] |
| 195 | O | I |  Chemistry 1175 |  Chemistry 1176 | Me | H | [504] |

-continued
| | | | | | |
|---|---|---|---|---|---|
| 196 | O | H | 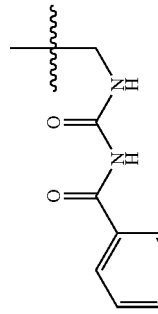<br>Chemistry 1181 | 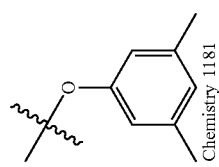<br>Chemistry 1182 | Me | H | [562] |
| 197 | O | H | Chemistry 1187 | 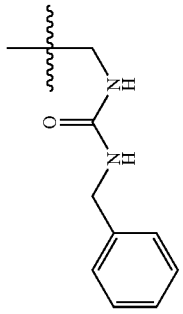<br>Chemistry 1188 | Me | H | [518] |
| 198 | O | H | Chemistry 1193 | 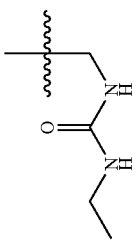<br>Chemistry 1194 | Me | H | [456] |
| 199 | O | H | Chemistry 1199 | 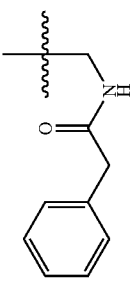<br>Chemistry 1200 | Me | H | [503] |

| | | | | | |
|---|---|---|---|---|---|
| 200 | O | 3,5-dimethylphenoxy (Chemistry 1205) | chroman-2-carboxamide-CH2- (Chemistry 1206) | Me | H | [545] |
| 201 | O | 3,5-dimethylphenoxy (Chemistry 1211) | isovaleramide-CH2- (Chemistry 1212) | Me | H | [469] |
| 202 | O | 3,5-dimethylphenoxy (Chemistry 1217) | 3-phenylpropiolamide-CH2- (Chemistry 1218) | Me | H | [513] |
| 203 | O | 3,5-dimethylphenoxy (Chemistry 1223) | 1-acetylpiperidine-4-carboxamide-CH2- (Chemistry 1224) | Me | H | [538] |

-continued

| | | | | | |
|---|---|---|---|---|---|
| 204 | O | H | 3,5-dimethylphenoxy (Chemistry 1229) | cyclopentyl-C(O)NH-CH2- (Chemistry 1230) | Me | H | [481] |
| 205 | O | H | 3,5-dimethylphenoxy (Chemistry 1235) | pyridin-3-yl-C(O)NH-CH2- (Chemistry 1236) | Me | H | [490] |
| 206 | O | H | 3,5-dimethylphenoxy (Chemistry 1241) | 1-methylpyrrol-2-yl-C(O)NH-CH2- (Chemistry 1242) | Me | H | [492] |
| 207 | O | H | 3,5-dimethylphenoxy (Chemistry 1247) | 1-methylindol-2-yl-C(O)NH-CH2- (Chemistry 1248) | Me | H | [542] |

| | | | | | |
|---|---|---|---|---|---|
| 208 | O | I | ![3,5-dimethylphenoxy] Chemistry 1253 | ![CH2NHC(O)CH2S(O)2Me] Chemistry 1254 | Me | H | [505] |
| 209 | O | I | ![3,5-dimethylphenoxy] Chemistry 1259 | ![CH2NHC(O)CH2OMe] Chemistry 1260 | Me | H | [487] |
| 210 | O | I | ![3,5-dimethylphenoxy] Chemistry 1265 | ![CH2NHC(O)CH2CN] Chemistry 1266 | Me | H | [452] |
| 211 | O | I | ![3,5-dimethylphenoxy] Chemistry 1271 | ![CH2NHC(O)CH=CHPh] Chemistry 1272 | Me | H | [516] |

| | | | | | |
|---|---|---|---|---|---|
| 212 | O | I | ![3,5-dimethylphenoxy, Chemistry 1277] | ![3-cyanobenzamide-CH2-, Chemistry 1278] | Me | H | [514] |
| 213 | O | I | ![3,5-dimethylphenoxy, Chemistry 1283] | ![acetamide-CH2-, Chemistry 1284] | Me | H | [427] |
| 214 | O | I | ![3,5-dimethylphenoxy, Chemistry 1289] | ![furan-2-carboxamide-CH2-, Chemistry 1290] | Me | H | >250 |
| 215 | O | I | ![3,5-dimethylphenoxy, Chemistry 1295] | CH=CHCO2Et | Me | H | >250 |

| | | | | |
|---|---|---|---|---|
| 216 | O | I | 3,5-dimethylphenoxy (Chemistry 1301), Et | CH2CH2CH2OC(O)CH3 (Chem 1303), H | 160 |
| 217 | O | I | 3,5-dimethylphenoxy (Chemistry 1307), Et | CH2CH2CH2OH (Chem 1309), H | 230 |
| 218 | O | I | 3,5-dimethylphenoxy (Chemistry 1313), CH2NHC(O)OEt (Chemistry 1314) | Me, H | >250 |
| 219 | O | I | 3,5-dimethylphenoxy (Chemistry 1319), CH2NHCHO (Chemistry 1320) | Me, H | >250 |
| 220 | O | I | 3,5-dimethylphenoxy (Chemistry 1325), CH2NH2 | Me, H | 240 |

-continued
| | | | | | |
|---|---|---|---|---|---|
| 221 | O | H | 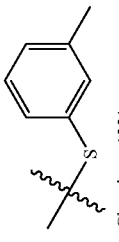 Chemistry 1331 | 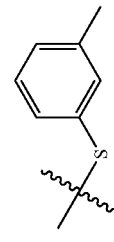 Chemistry 1332 | H | 264–266 |
| 222 | O | H | 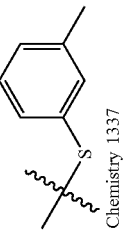 Chemistry 1337 | 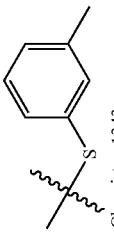 (CH2)4 | H | 252–253 |
| 223 | O | H | 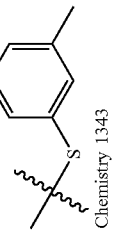 Chemistry 1343 | (CH2)3 | H | 243–244 |
| 224 | O | H | 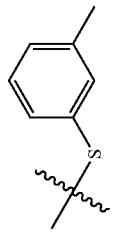 Chemistry 1349 | 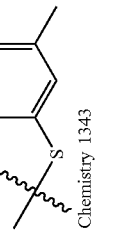 Chemistry 1350 | H | 260–262 |
| 225 | O | H | 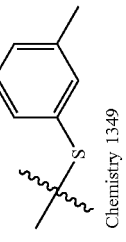 CO2Et Chemistry 1355 | Me | H | 190 |
| 226 | O | H | 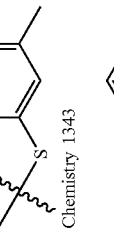 Et Chemistry 1361 | Cl | NH2 | 146–147 |

| | | | | |
|---|---|---|---|---|
| 227 | O | I | <br>Chemistry 1367 | CN | <br>Chem 1369 | H | 282–284 |
| 228 | O | I | <br>Chemistry 1373 | CO2Et | Cl | 180–182 |
| 229 | O | H | <br>Chemistry 1379 | CN | Cl | 240–242 |
| 230 | O | <br>Chem 1384 | Chemistry 1385 | Et | Me | 188–190 |
| 231 | O | Et | Chemistry | Et | Me | 179–181 |

-continued

| | | | | | |
|---|---|---|---|---|---|
| 232 | O | I | Chemistry 1391 | ![Chemistry 1398](N-OMe oxime) Chemistry 1398 | Me | H | >240 |
| 233 | O | I | Chemistry 1397 | Chemistry 1404 | Me | H | [539] |
| 234 | O | Vinyl | Chemistry 1403 | Et | Me | H | 198–200 |
| 235 | O | H | Chemistry 1409 Chemistry 1415 | | (CH2)3 | H | — |

| | | | | | |
|---|---|---|---|---|---|
| 236 | O | I | ![3,5-dimethylphenoxy](Chemistry 1421) | CN | Cl | H | 276–277 |
| 237 | O | I | ![3,5-dichlorophenoxy](Chemistry 1427) | Et | Me | H | 280–282 |
| 238 | O | I | ![3,5-dimethylphenoxy](Chemistry 1433) | CN | Me | H | >240 |
| 239 | O | I | ![3,5-dimethylphenoxy](Chemistry 1439) | ![morpholinoethyl](Chemistry 1440) | Me | H | >240 |
| 240 | O | I | ![3,5-dimethylphenoxy](Chemistry 1445) | ![mesyloxyethyl](Chemistry 1446) | Me | H | — |

| | | | | | |
|---|---|---|---|---|---|
| 241 | O | I | Chemistry 1451 (3,5-dimethylphenoxy) | Chemistry 1452 (CH₂CH₂OH) | Me | H | >240 |
| 242 | O | I | Chemistry 1457 (3,5-dimethylphenoxy) | Chemistry 1458 ((CH₂)₃OH) | Me | H | 220 |
| 243 | O | I | Chemistry 1463 (3,5-dimethylphenoxy) | Chemistry 1464 (CH₂NH-C₆H₄-OMe) | Me | H | 216–217 |
| 244 | O | I | Chemistry 1469 (3,5-dimethylphenoxy) | Chemistry 1470 (CH₂OCH₂-thiophene) | Me | H | 216–218 |

-continued

| | | | | | |
|---|---|---|---|---|---|
| 245 | O | (3,5-dimethylphenoxy, Chemistry 1475) | (benzyloxy-methyl, Chemistry 1476) | Me | 212–214 |
| 246 | O | I | (N-methoxy-N-methylamide, Chem 1480) | Me | — |
| 247 | S | H | 3-Methylbenzyl | Me | >240 |
| 248 | S | I | (3,5-dimethylphenoxy, Chemistry 1487) | Me | 210 |
| 249 | O | I | (3,5-dimethylphenoxy, Chemistry 1493) | Me | 156 |

(additional entry: 2-Methoxybenzyl, Chemistry 1505)

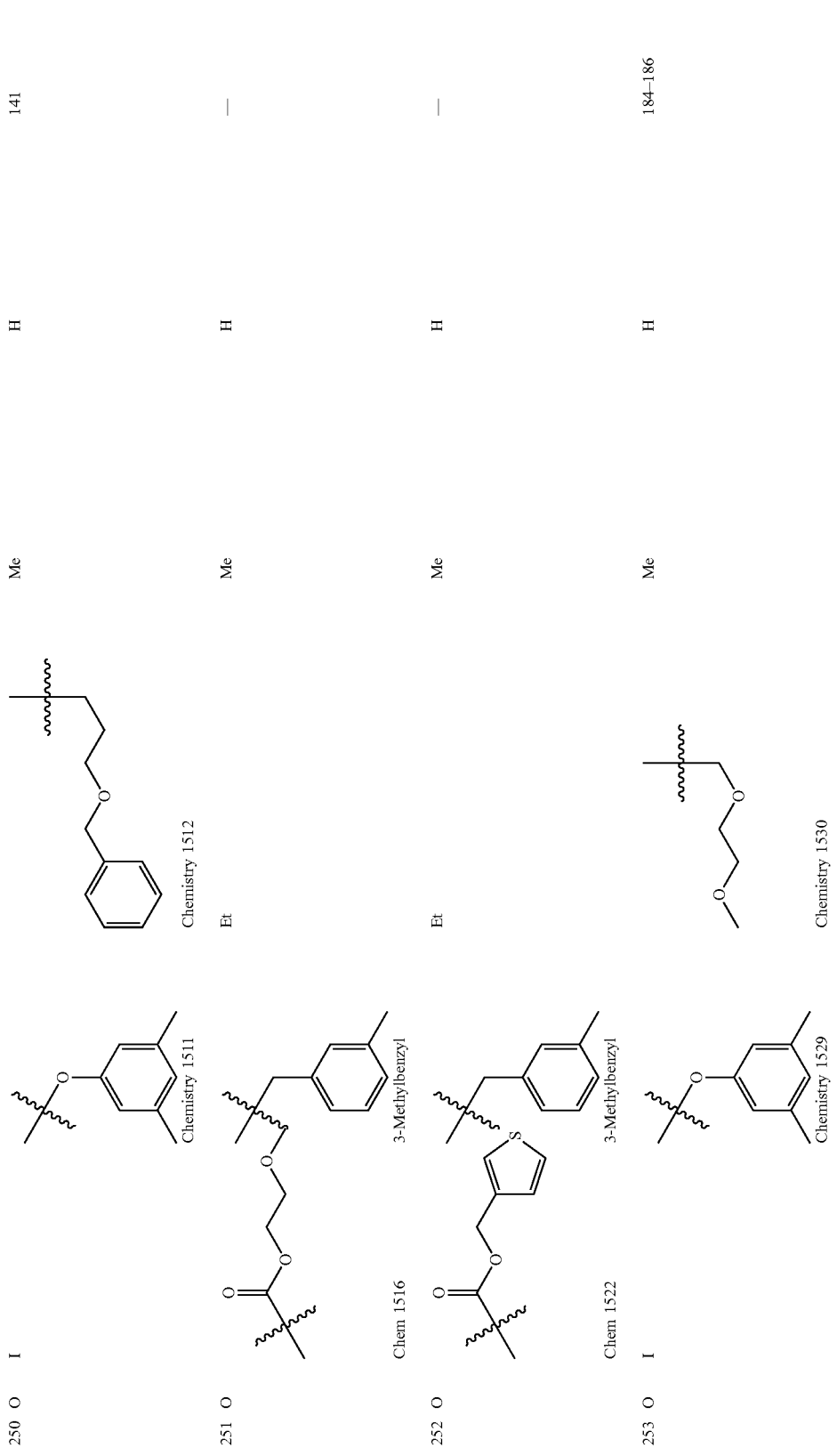

| | | | | | |
|---|---|---|---|---|---|
| 254 | O | H | Chemistry 1535 (3,5-dimethylphenoxy) | Chemistry 1536 (-CH2-O-CH2CH2OH) | Me | H | 224–226 |
| 255 | O | H | Chemistry 1541 (3,5-dimethylphenoxy) | Chemistry 1542 (-CH2-O-Et) | Me | H | 234–236 |
| 256 | O | H | Chemistry 1547 (3,5-dimethylphenoxy) | Chemistry 1548 (-CH2-O-Et) | H | H | 160–162 |
| 257 | O | H | Chemistry 1553 (3,5-dimethylphenoxy) | CH2OH | Me | H | 248–250 |

-continued

| | | | | | |
|---|---|---|---|---|---|
| 258 | O | I | ![3,5-dimethylphenoxy] Chemistry 1559 | Et | Me | Me | 240 |
| 259 | O | I | ![3,5-dimethylphenoxy] Chemistry 1565 | Et | Me | ![CH2-C(=O)-O-Et] Chem 1562 | 179 |
| 260 | O | SOMe | ![3,5-dimethylphenoxy] Chemistry 1571 | Et | Me | H | 196–197 |
| 261 | O | I | ![3,5-dimethylphenyl ether] Chemistry 1577 | Et | Cl | H | 186–187 |
| 262 | O | H | ![3,5-dimethylphenyl ether] Chemistry 1583 | Me | Cl | H | 210–242 |

-continued

| # | | | | | | | |
|---|---|---|---|---|---|---|---|
| 263 | O | I | 3,5-dimethylphenoxy (Chemistry 1589) | Me | Cl | H | 240–242 |
| 264 | O | I | 3,5-dimethylphenoxy (Chemistry 1595) | 2-Methoxyethyl | Me | H | 212 |
| 265 | O | H | 3-Methylbenzoyl | Me | oxime (Chem 1603) | H | 176 |
| 266 | O | I | 3-Methylbenzoyl | Me | oxime (Chem 1609) | H | >260 |
| 267 | O | H | 3,5-dimethylphenoxy (Chemistry 1613) | Et | Cl | H | 210–211 |

-continued

| 268 | O | CH2OH | [3,5-dimethylphenoxy-C(Me)2- Chemistry 1619] | H | Me | H | 212–214 |
| 269 | O | I | [3,5-dimethylphenoxy-C(Me)2- Chemistry 1625] | Formyl | Me | H | 282–284 |
| 270 | O | [isopropyl ester, Chem 1630] | [3,5-dimethylphenoxy-C(Me)2- Chemistry 1631] | Et | Me | H | 192 |
| 271 | O | [benzyl ester, Chem 1636] | [3,5-dimethylphenoxy-C(Me)2- Chemistry 1637] | Et | Me | H | 182 |
| 272 | O | SMe | [3,5-dimethylphenoxy-C(Me)2- Chemistry 1643] | Et | Me | H | 186–188 |

-continued

| | | | | | | |
|---|---|---|---|---|---|---|
| 273 | O | ![Chem 1648](imidazole carbonyl) Chem 1648 | Et | | Me | H | [336] |
| 274 | S | ![Chem 1654](N,N-dimethyl amide) Chem 1654 | Et | 3-Methylbenzyl | Me | H | [313] |
| 275 | O | CO2Me | Et | 3-Methylbenzyl | Me | H | [300] |
| 276 | O | C=NOH | Et | ![Chemistry 1667](aryl ether) Chemistry 1667 | Me | H | 262 |

-continued

| | | | | | | |
|---|---|---|---|---|---|---|
| 277 | O | OMe | ![](Chemistry 1673) 3,5-dimethylphenoxy | Et | Me | H | 178 |
| 278 | O | ![](Chem 1678) N-methoxy imine | ![](Chemistry 1679) 3,5-dimethylphenoxy | Et | Me | H | 225 |
| 279 | O | ![](Chem 1684) N,N-dimethylamide | ![](Chemistry 1685) 3,5-dimethylphenoxy | Et | Me | H | 166 |
| 280 | O | SPh | ![](Chemistry 1691) 3,5-dimethylphenoxy | Et | Me | H | 211 |

-continued

| | | | | | | |
|---|---|---|---|---|---|---|
| 281 | O | CH(OH)Ph | 3,5-dimethylphenoxy (Chemistry 1697) | Et | Me | H | 198 |
| 282 | O | CO2Et | 3-Methylbenzyl | Et | Me | H | — |
| 283 | O | CO2H | 3-Methylbenzyl | Et | Me | H | — |
| 284 | O | Br | 3,5-dimethylphenoxy (Chemistry 1715) | Et | Me | H | 240–241 |

-continued

| | | | | | | |
|---|---|---|---|---|---|---|
| 285 | O | CN | ~O~-(3,5-dimethylphenyl) Chemistry 1721 | Et | Me | H | 282–284 |
| 286 | O | I | ~CH2~-(3-methylphenyl) 3-Methylbenzyl | Et | Me | H | 204–206 |
| 287 | O | I | ~O~-(3,5-dimethylphenyl) Chemistry 1733 | H | Me | H | 274–275 |
| 288 | O | CCPh | ~O~-(3,5-dimethylphenyl) Chemistry 1739 | Et | Me | H | 260 |

-continued
| | | | | | | |
|---|---|---|---|---|---|---|
| 289 | O | CH=CHCO2Et |  Chemistry 1745 | Et | Me | H | 256 |
| 290 | O | Formyl |  Chemistry 1751 | Et | Me | H | 228 |
| 291 | O | 3-Thiophenyl |  Chemistry 1757 | Et | Me | H | 222 |

| | | | | | | | |
|---|---|---|---|---|---|---|---|
| 292 | O | 3-Cl-phenyl | 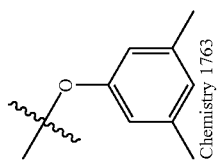 Chemistry 1763 | Et | Me | H | 223 |
| 293 | O | 2-Furyl | 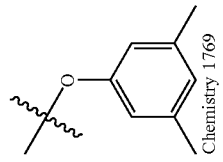 Chemistry 1769 | Et | Me | H | 228 |
| 294 | O | CH2OH | 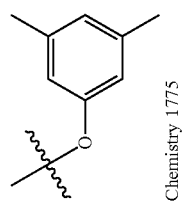 Chemistry 1775 | Et | Me | H | 200 |
| 295 | O | CO2H | 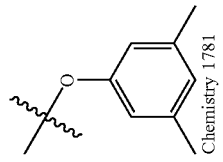 Chemistry 1781 | Et | Me | H | 221 |

-continued
| | | | | | | |
|---|---|---|---|---|---|---|
| 296 | O | H | Chemistry 1787 | Et | Me | H | 232–234 |
| 297 | O | H | Chemistry 1793 | Et | Me | H | 248–250 |
| 298 | O | H | Chemistry 1799 | Et | Me | H | 250 |
| 299 | O | H | 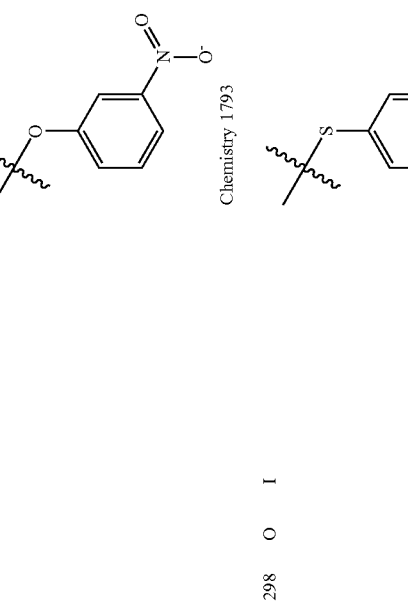Chemistry 1805 | Et | Me | H | 265–266 |

-continued

| | | | | | | | |
|---|---|---|---|---|---|---|---|
| 300 | O | I | S—⟨2,6-diMe-phenyl⟩ Chemistry 1811 | Et | Me | H | 275–276 |
| 301 | O | CO2H | CH2—⟨2,5-dimethoxybenzyl⟩ 2,5-Dimethoxybenzyl | H | H | H | [290] |
| 302 | O | H | NH—⟨5-Me-tetrahydronaphthyl⟩ Chemistry 1823 | H | Me | H | [283] |
| 303 | O | CO2Et | NH—⟨5-Me-tetrahydronaphthyl⟩ Chemistry 1829 | H | Me | H | [355] |
| 304 | O | CO2H | NH—⟨tetrahydronaphthyl⟩ | H | Me | H | [299] |

-continued

| # | | | | | | |
|---|---|---|---|---|---|---|
| 305 | O | CO2Et | H | Me | H | [303] |
| | | | Chemistry 1835 | | | |
| 306 | O | I | Et (4-methoxyanilino, Chemistry 1841) | Me | H | 200–202 |
| 307 | O | I | Et (3-methylphenoxy, Chemistry 1859) | Me | H | 238–240 |
| 308 | O | H | Et (3-bromophenoxy, Chemistry 1865) | Me | H | 212–214 |
| 309 | O | I | Et (3,5-Dimethylbenzyl) | Me | H | 258–260 |
| 310 | O | I | Et (3-(3-(hydroxyimino)propenyl)phenoxy, Chemistry 1877) | Me | H | — |
| 311 | O | I | Et (3-(3-oxopropenyl)phenoxy, Chemistry 1883) | Me | H | — |

| | | | | | |
|---|---|---|---|---|---|
| 311 | O | ![Chemistry 1889: 3-(3-hydroxyprop-1-en-1-yl)phenoxy] Chemistry 1889 | Et | Me | H | 198–199 |
| 312 | O | ![Chemistry 1895: 3-(ethoxycarbonylvinyl)phenoxy] Chemistry 1895 | Et | Me | H | 182–183 |
| 313 | O | ![Chemistry 1901: 4-chloro-3,5-dimethylphenoxy] Chemistry 1901 | Et | Me | H | 265–266 |
| 314 | O | ![Chemistry 1907: 3-methylphenoxy] Chemistry 1907 | Et | H | H | 210–212 |
| 315 | O | ![Chemistry 1913: 3-methylphenoxy] Chemistry 1913 | Me | Me | H | 261–262 |

-continued
| | | | | | | |
|---|---|---|---|---|---|---|
| 316 | O | H |  Chemistry 1919 | | H | 218–219 |
| 317 | O | H |  Chemistry 1925 | | H | 230–232 |
| 318 | O | H |  Chemistry 1931 | (CH2)4 | H | 206–208 |
| 319 | O | H |  Chemistry 1937 | (CH2)3 Et | Me | 242–243 |
| 320 | O | H |  Chemistry 1943 | Et | Me | 241–242 |

| | | | | | |
|---|---|---|---|---|---|
| 321 | O | I | 3-formylphenoxy (Chemistry 1949) | Et | Me | H | 198–200 |
| 322 | O | I | 3-(hydroxymethyl)phenoxy (Chemistry 1955) | Et | Me | H | — |
| 323 | O | CO2Et | 3,5-dimethylphenoxy (Chemistry 1961) | Et | Me | H | 198 |
| 324 | O | CO2Et | 3,5-Dimethylbenzyl | Et | Me | H | 184–185 |
| 325 | O | H | 3,5-dimethylphenoxy (Chemistry 1973) | Et | Me | H | 232–233 |

-continued

| # | | | | | | | |
|---|---|---|---|---|---|---|---|
| 326 | O | I | 3,5-dimethylphenoxy (Chemistry 1979) | Et | Me | H | 240 |
| 327 | O | H | OPh | Et | Me | H | 228–229 |
| 328 | O | I | OPh | Et | Me | H | 180–182 |
| 329 | O | I | OPh | H | Me | H | 265–266 |
| 330 | O | CO2Et | 3,5-dimethylphenylamino (Chemistry 2003) | Et | Me | H | 228–229 |
| 331 | O | C(=O)N(Me)2 (Chem 2008) | 3,5-Dimethylbenzyl phenoxy | Et | Me | H | 192–193 |
| 332 | O | CO2H | 3,5-Dimethylbenzyl phenoxy | Et | Me | H | — |

-continued

| | | | | | | | |
|---|---|---|---|---|---|---|---|
| 333 | O | CN | Benzyl | H | n-Pr | H | 132 |
| 334 | O | Chem 2026 (N,N-diethyl amide) | 3-Methylbenzoyl | Et | Me | H | 207 |
| 335 | O | Chem 2032 (N,N-diethyl amide) | 3-Methylbenzyl (ether) | Et | Me | H | 216 |
| 336 | O | CH2NMe2 | 3-Methylbenzyl (ether) | (CH2)4 | | H | 185 |
| 337 | O | CH2NH2 | 3-Methylbenzyl (ether) | (CH2)4 | | H | — |

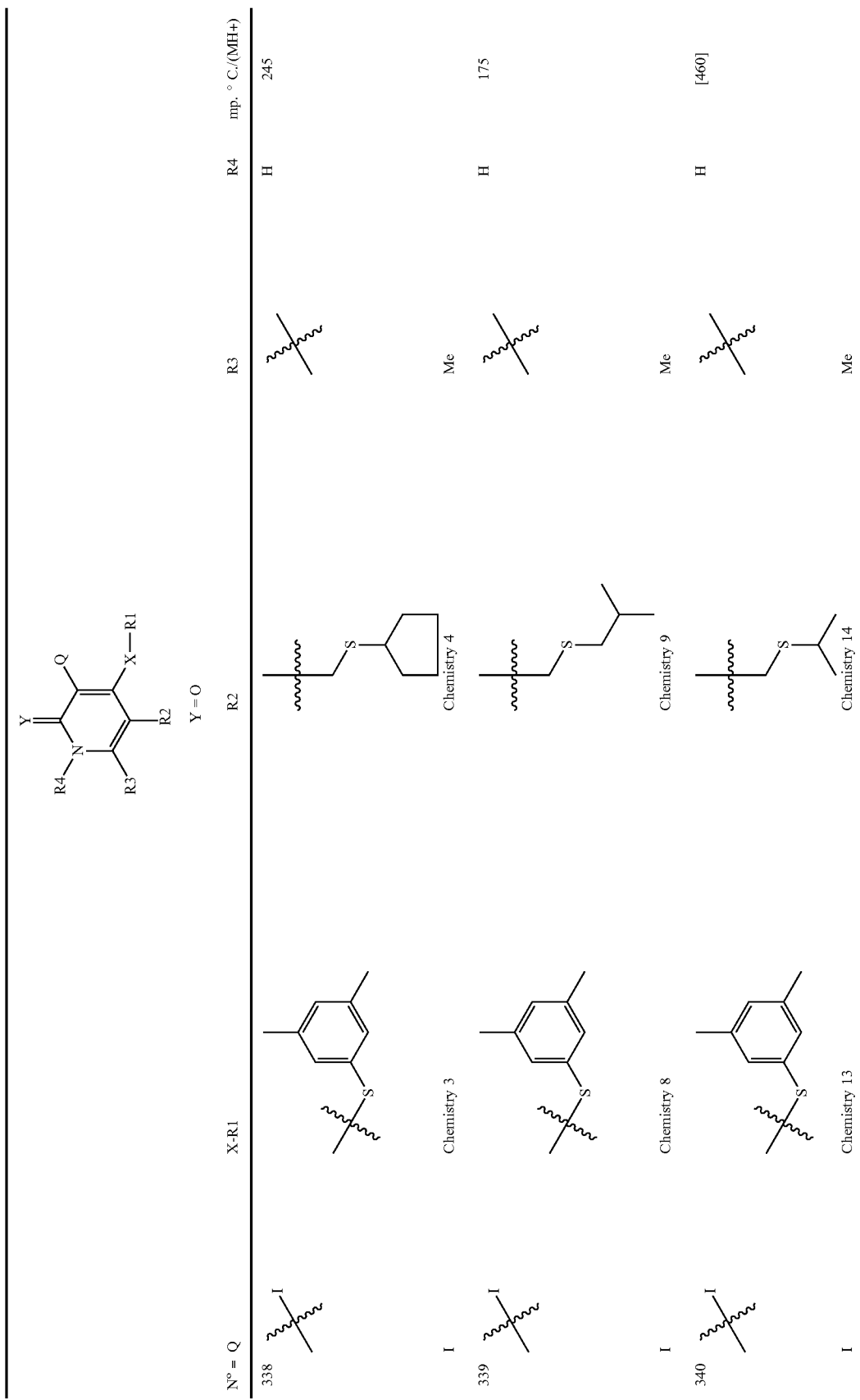

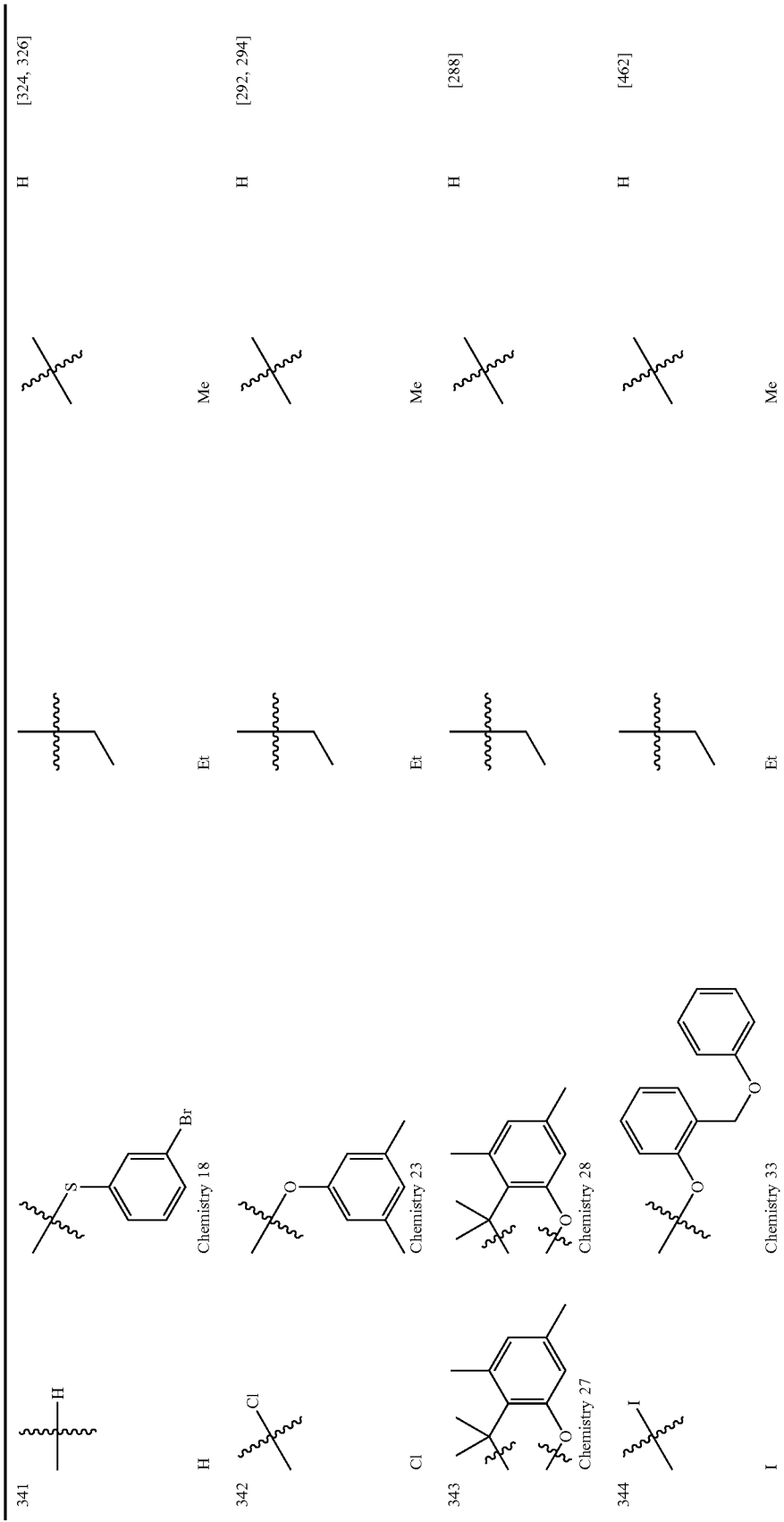

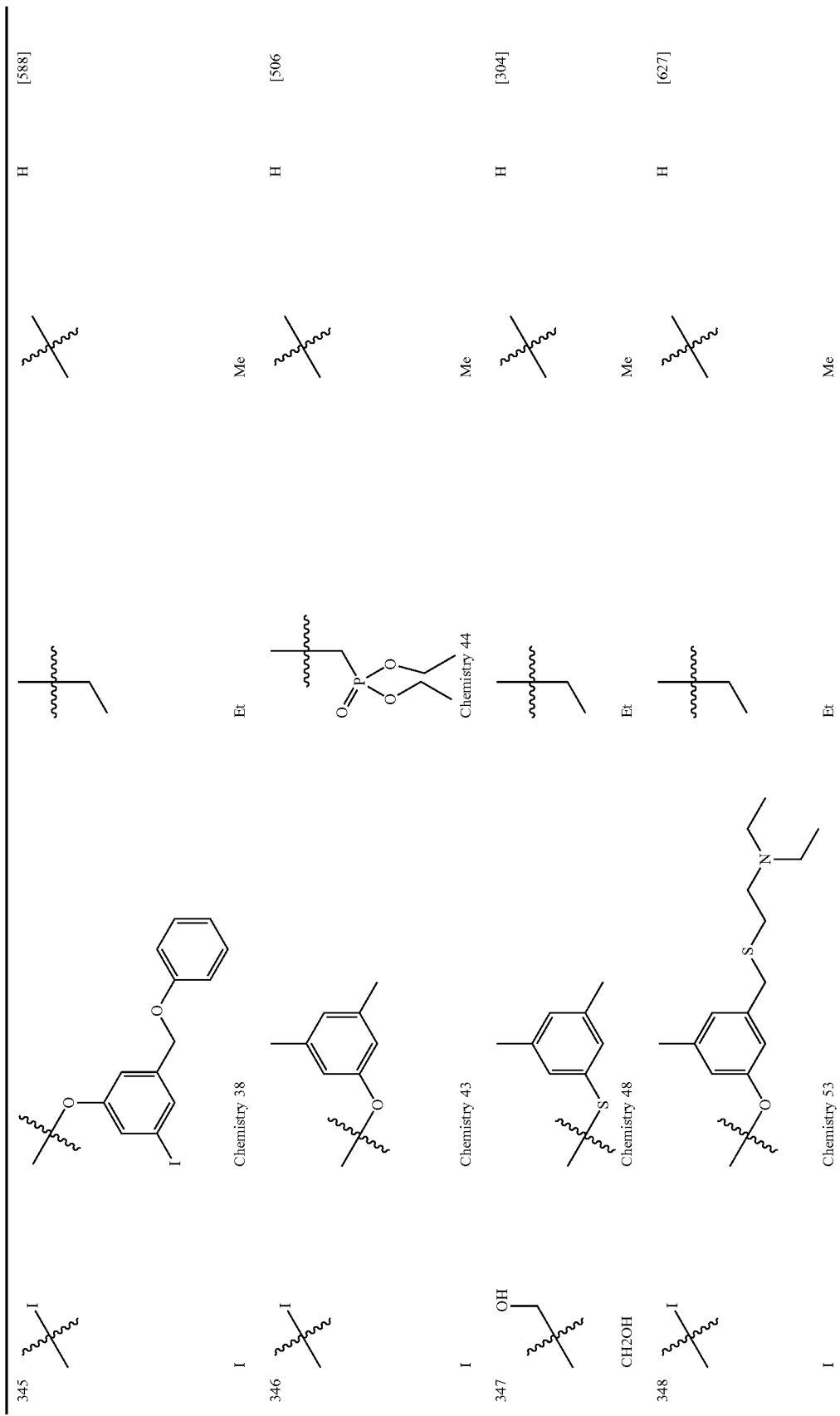

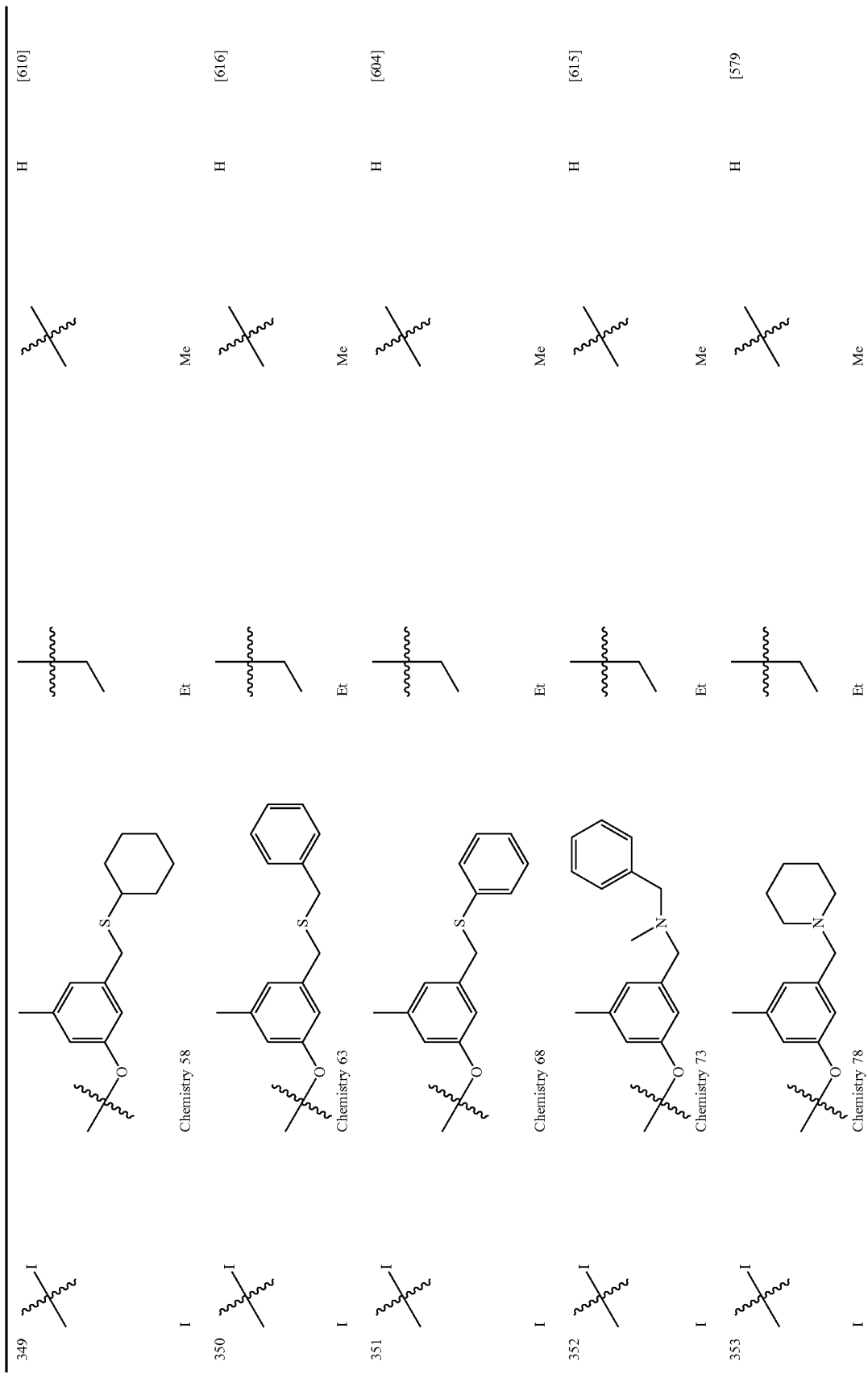

-continued

| | | | | |
|---|---|---|---|---|
| 354 | Chemistry 83 (dimethylaminoethyl-methylamino group on methylphenoxy) | (wavy) | (wavy) | H | [596] |
| 355 | Chemistry 88 (pyrrolidine-thiocarbonyl-S-CH2 on methylphenoxy) | Et | Me | H | [640] |
| 356 | Chemistry 93 (ethoxycarbonylmethyl-S-CH2 on methylphenoxy) | Et | Me | H | [614] |
| 357 | Chemistry 98 (dimethylphenylthio) | Et | Me | H | 205 |
| | Chemistry 99 (furfuryl-S-CH2) | | Me | | |

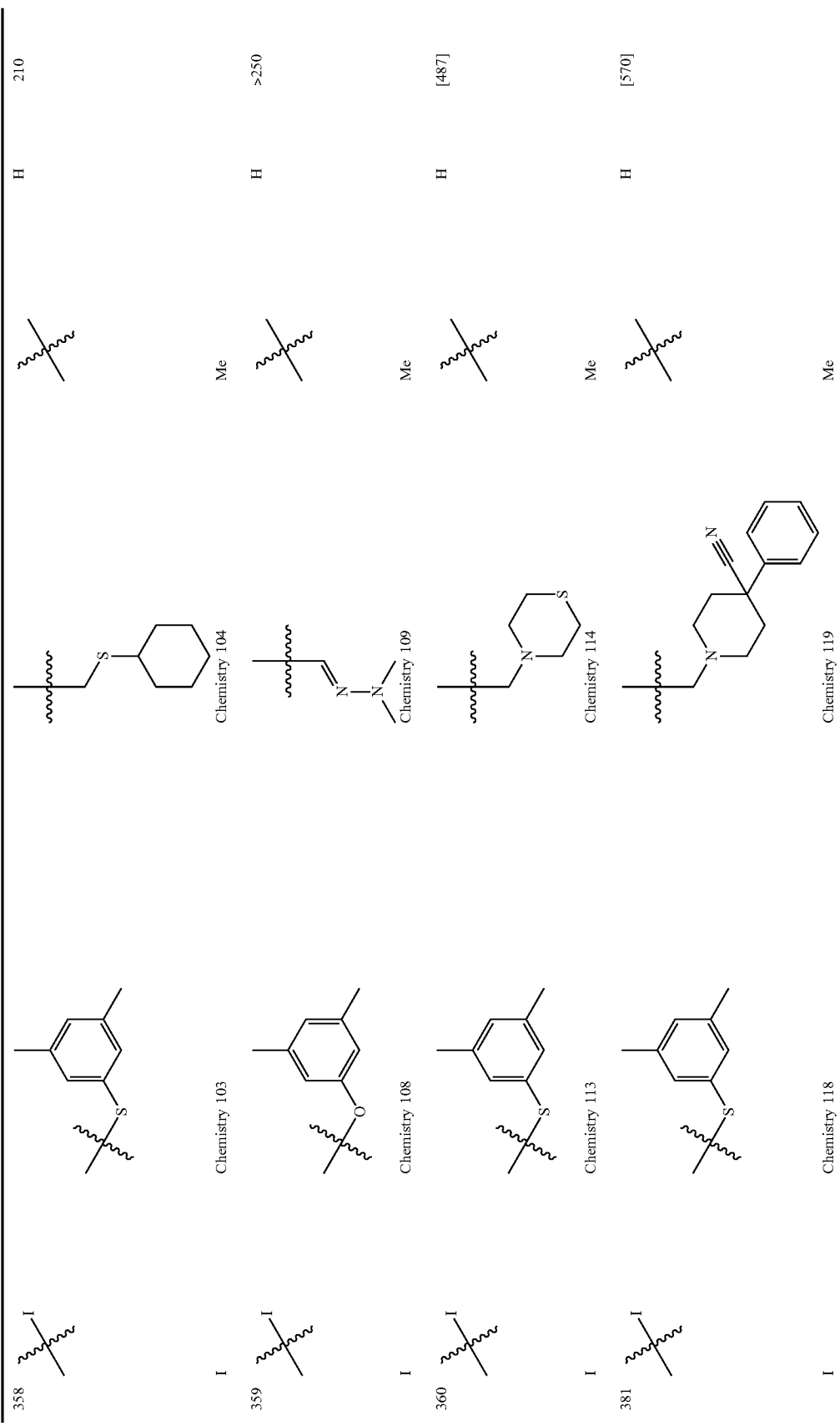

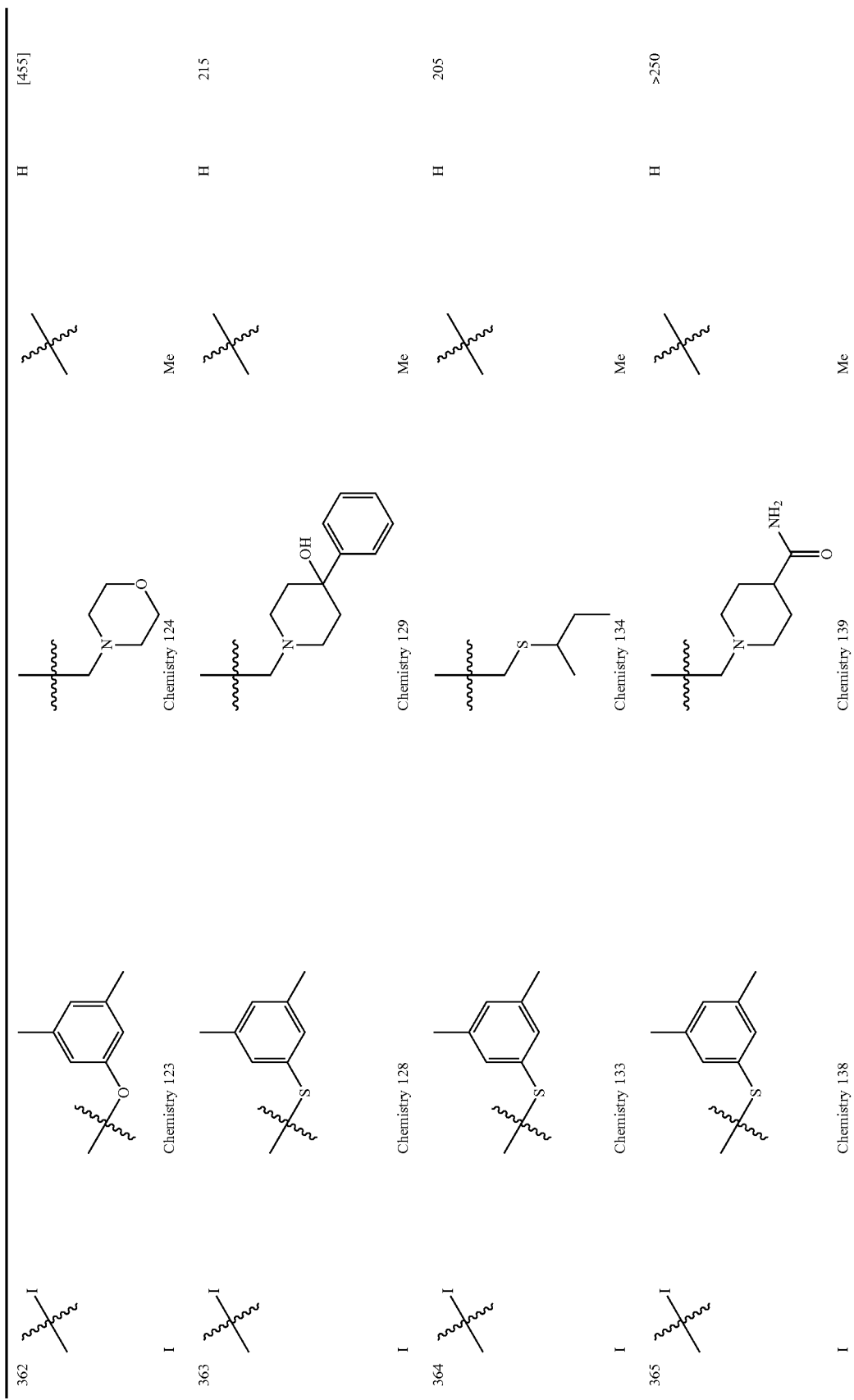

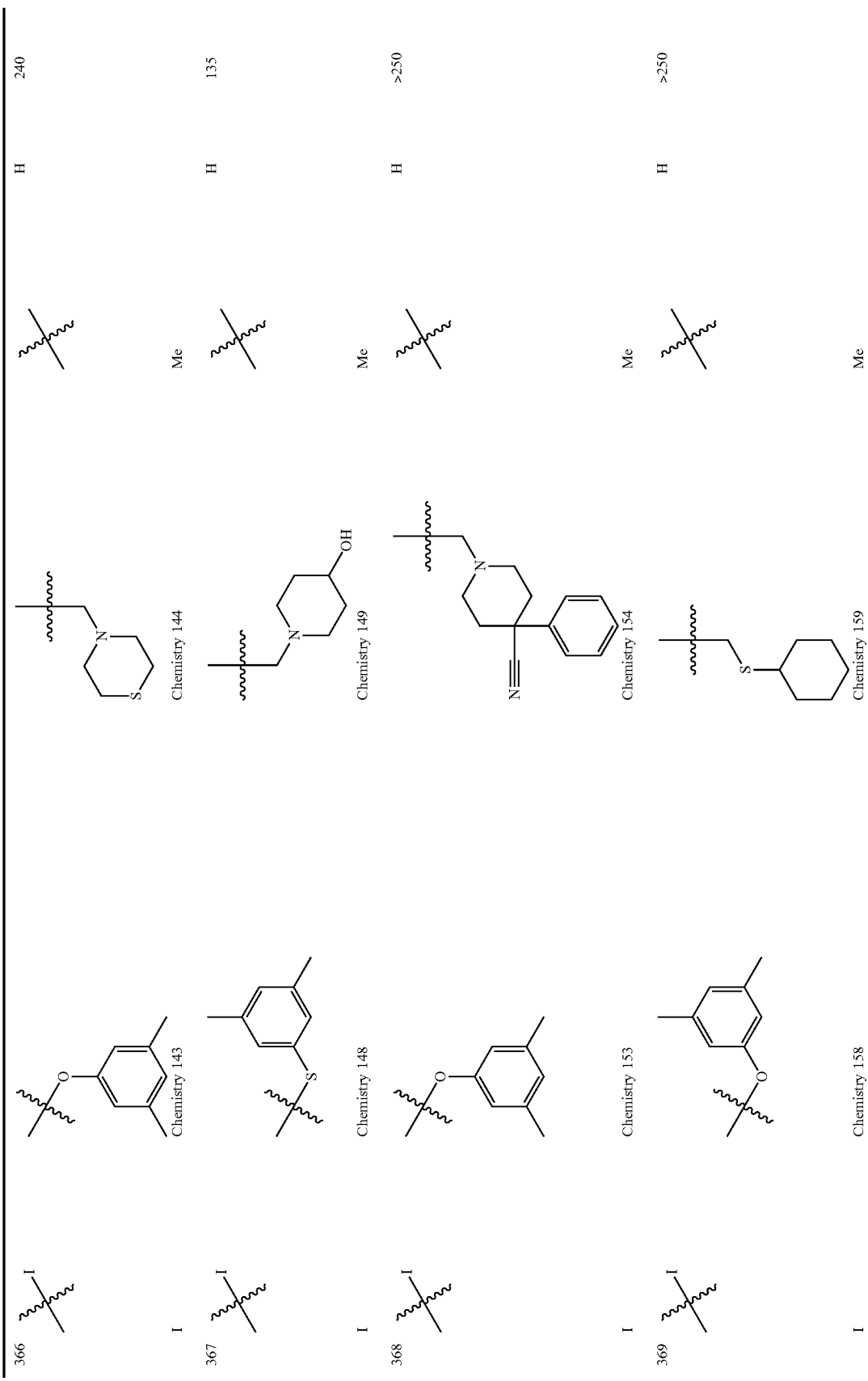

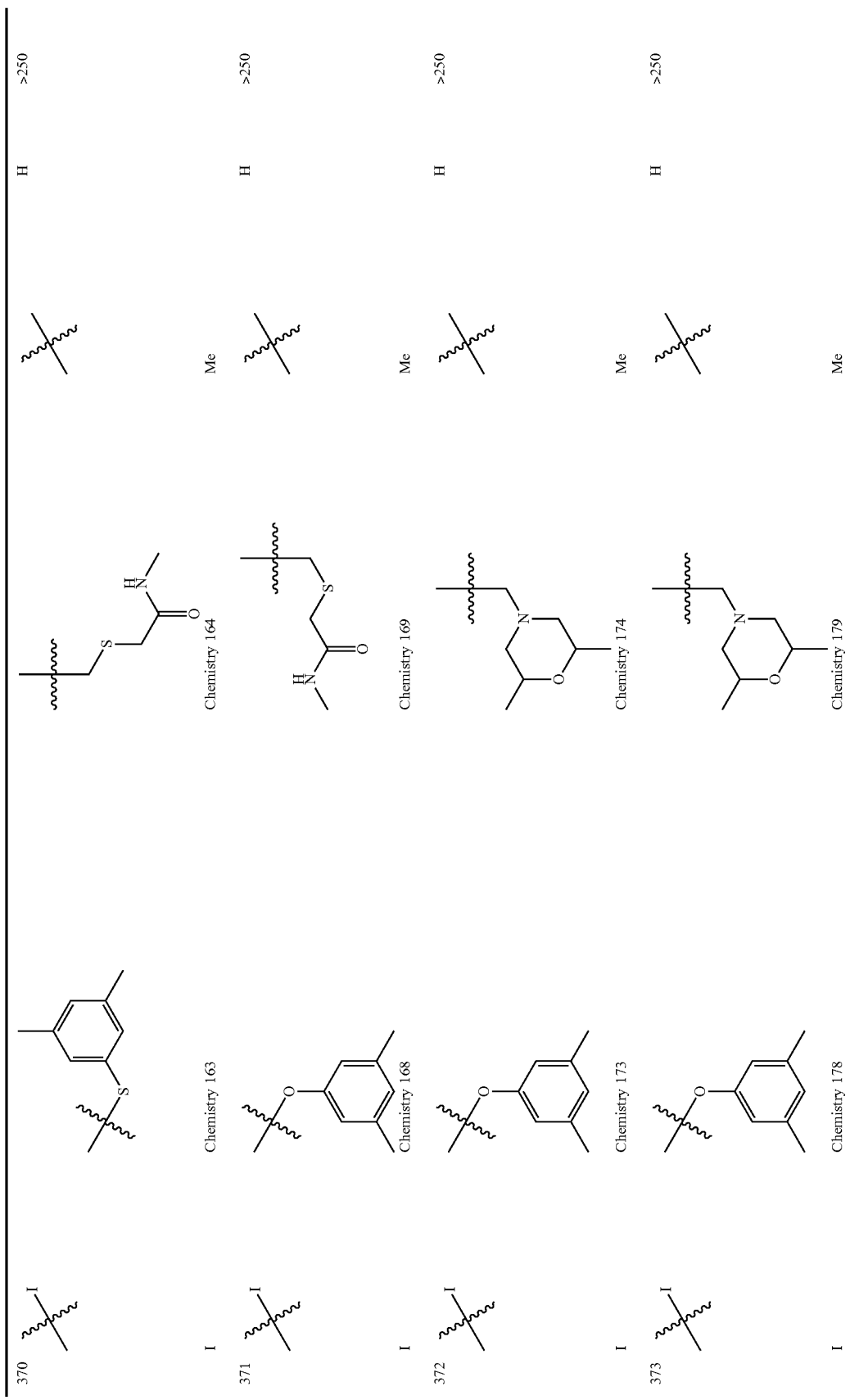

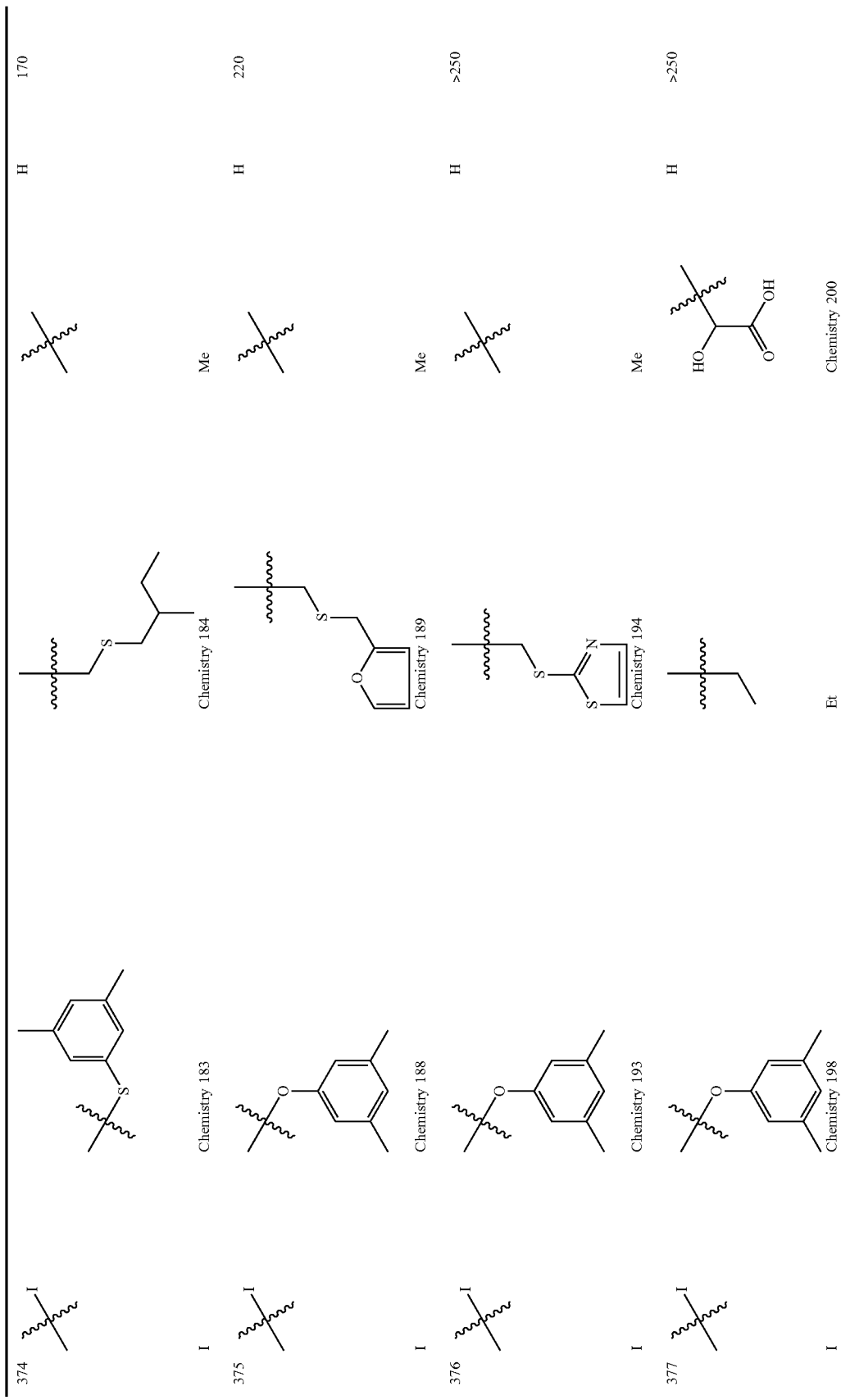

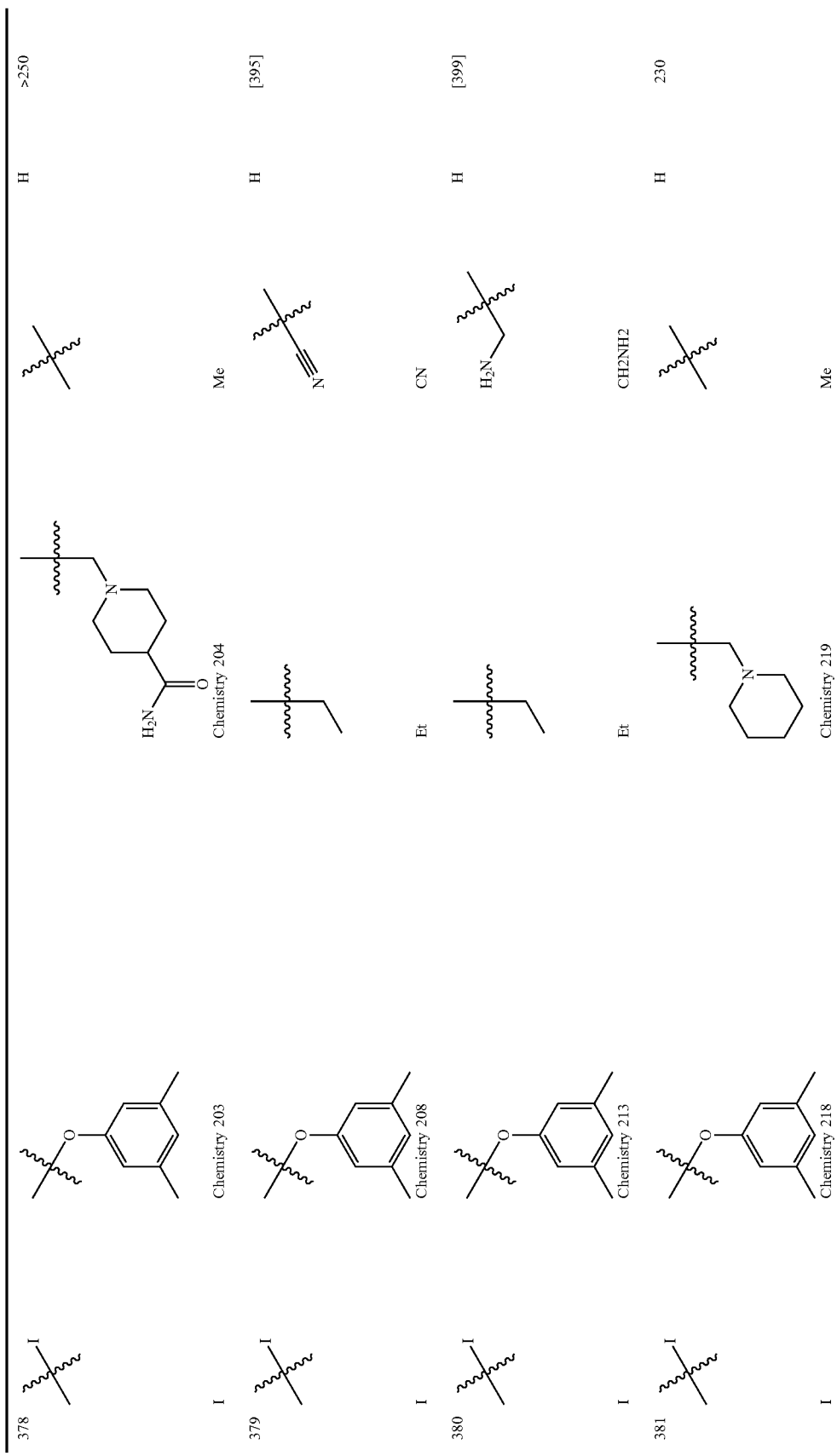

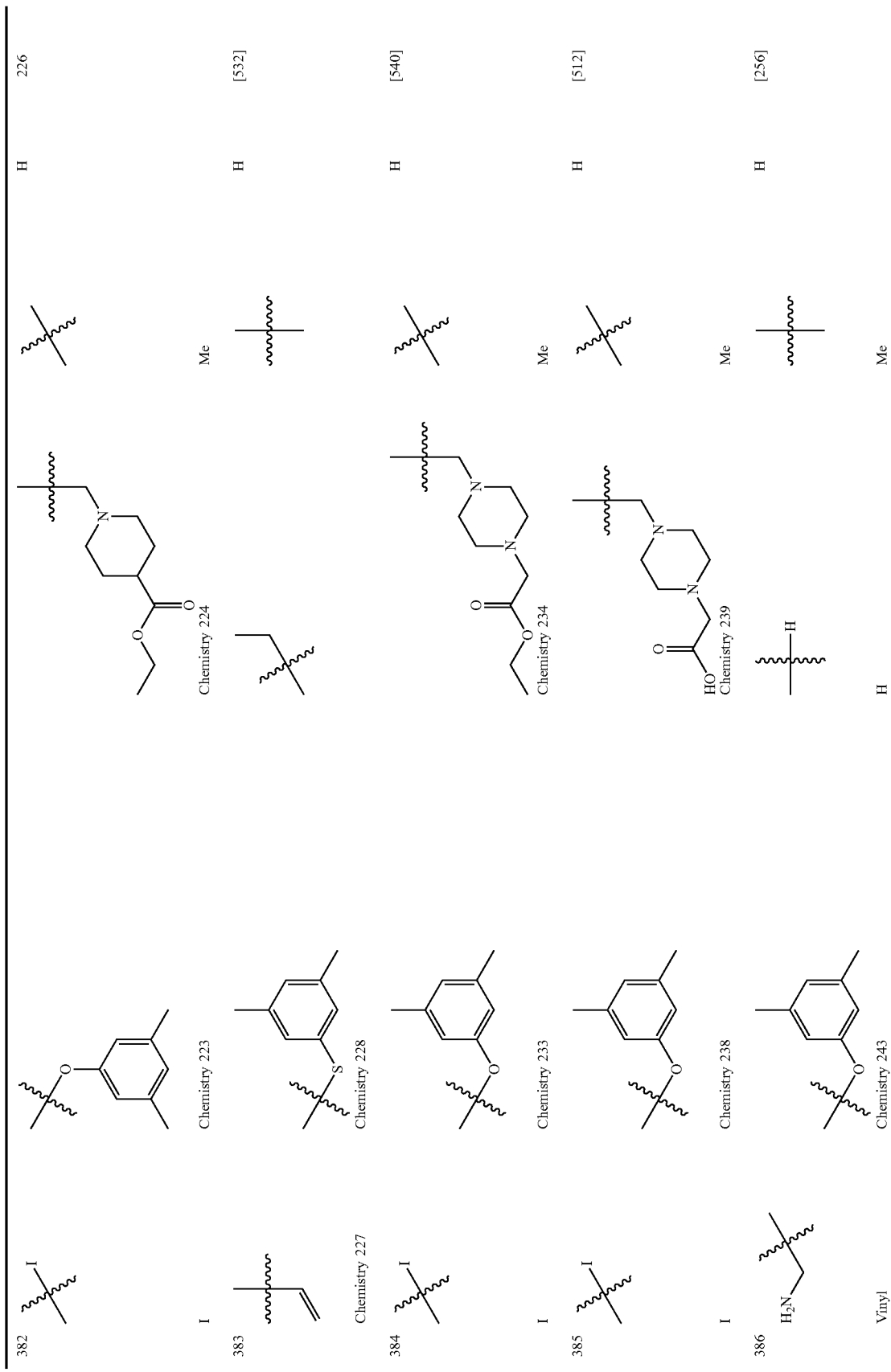

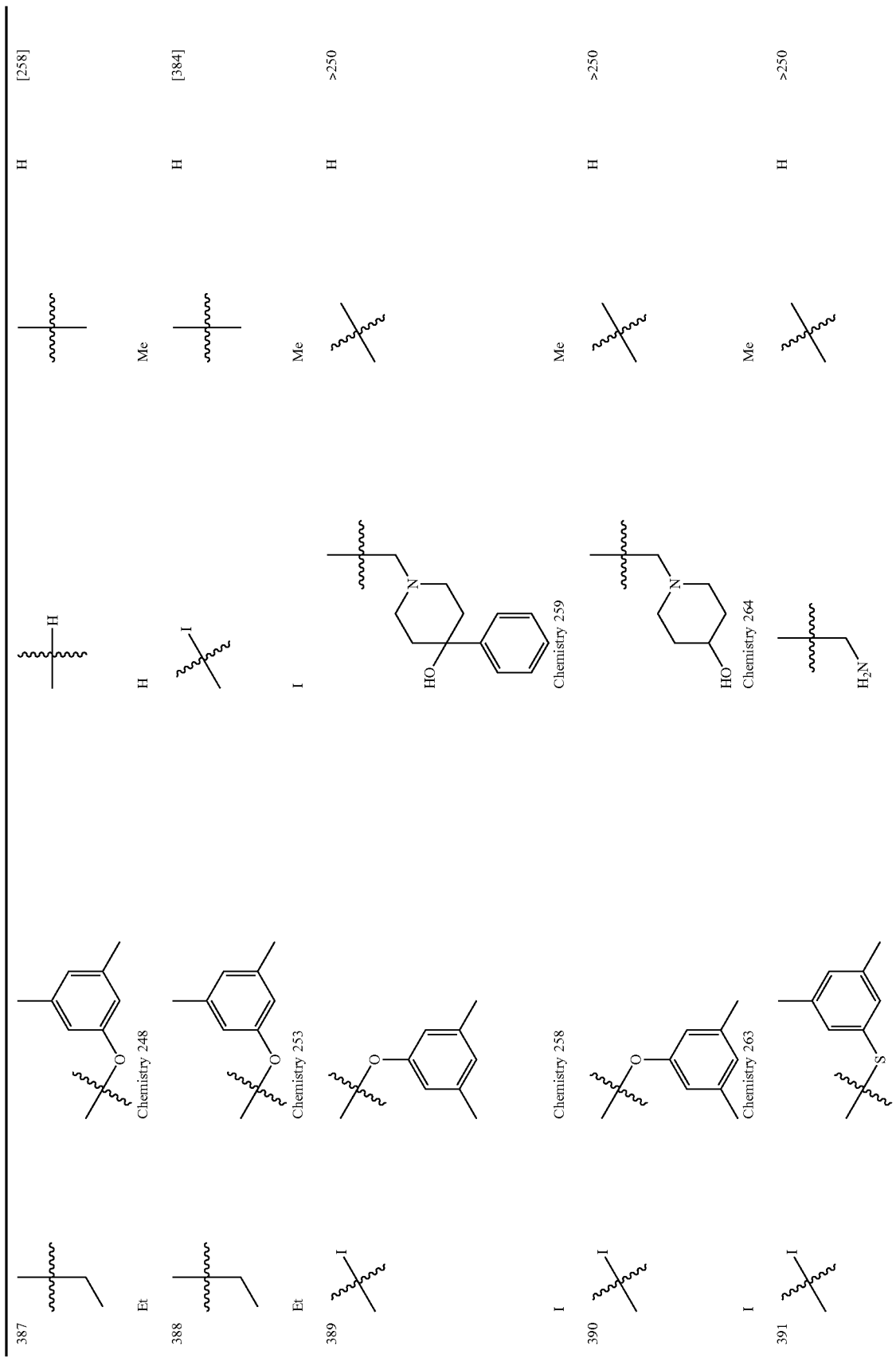

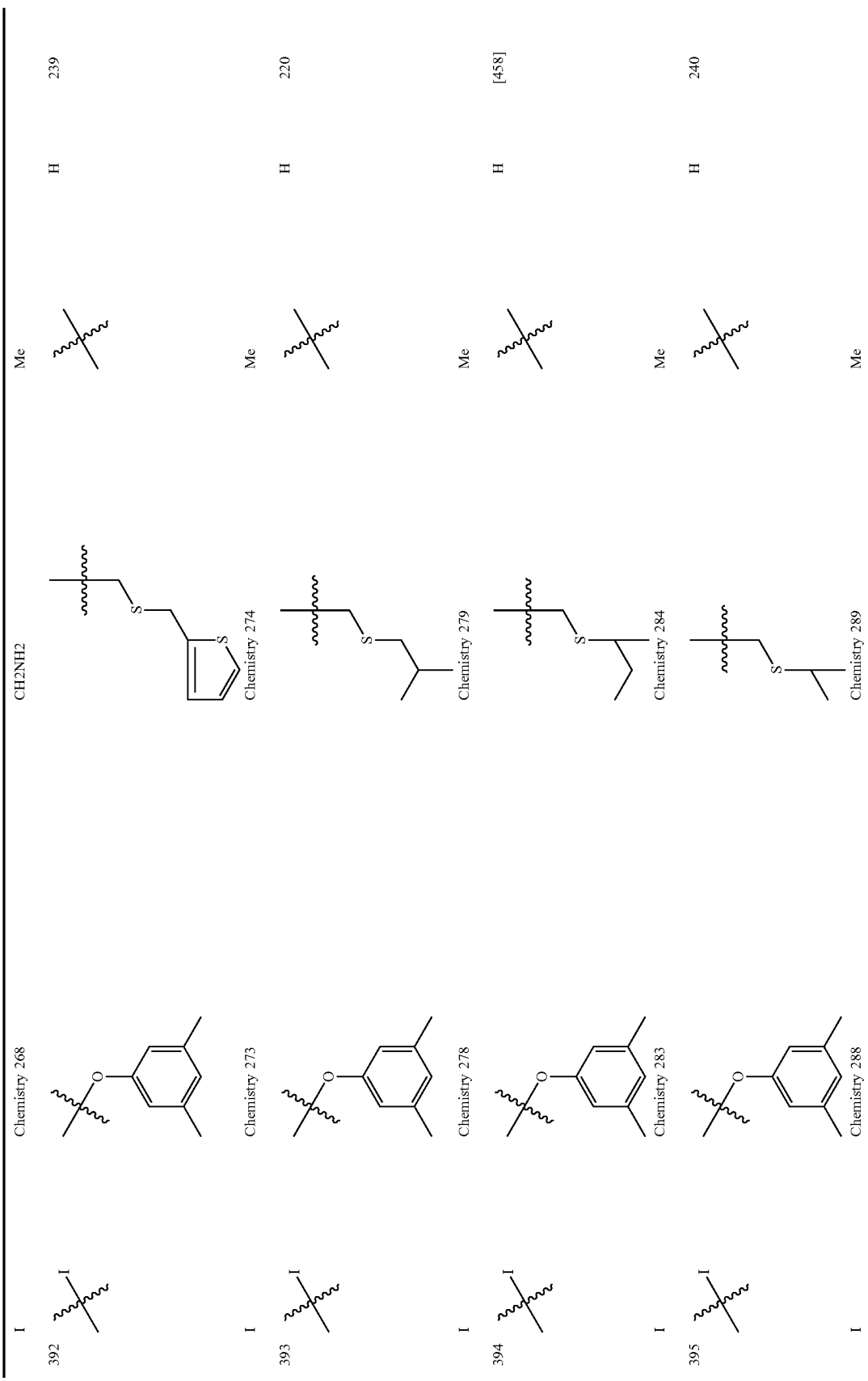

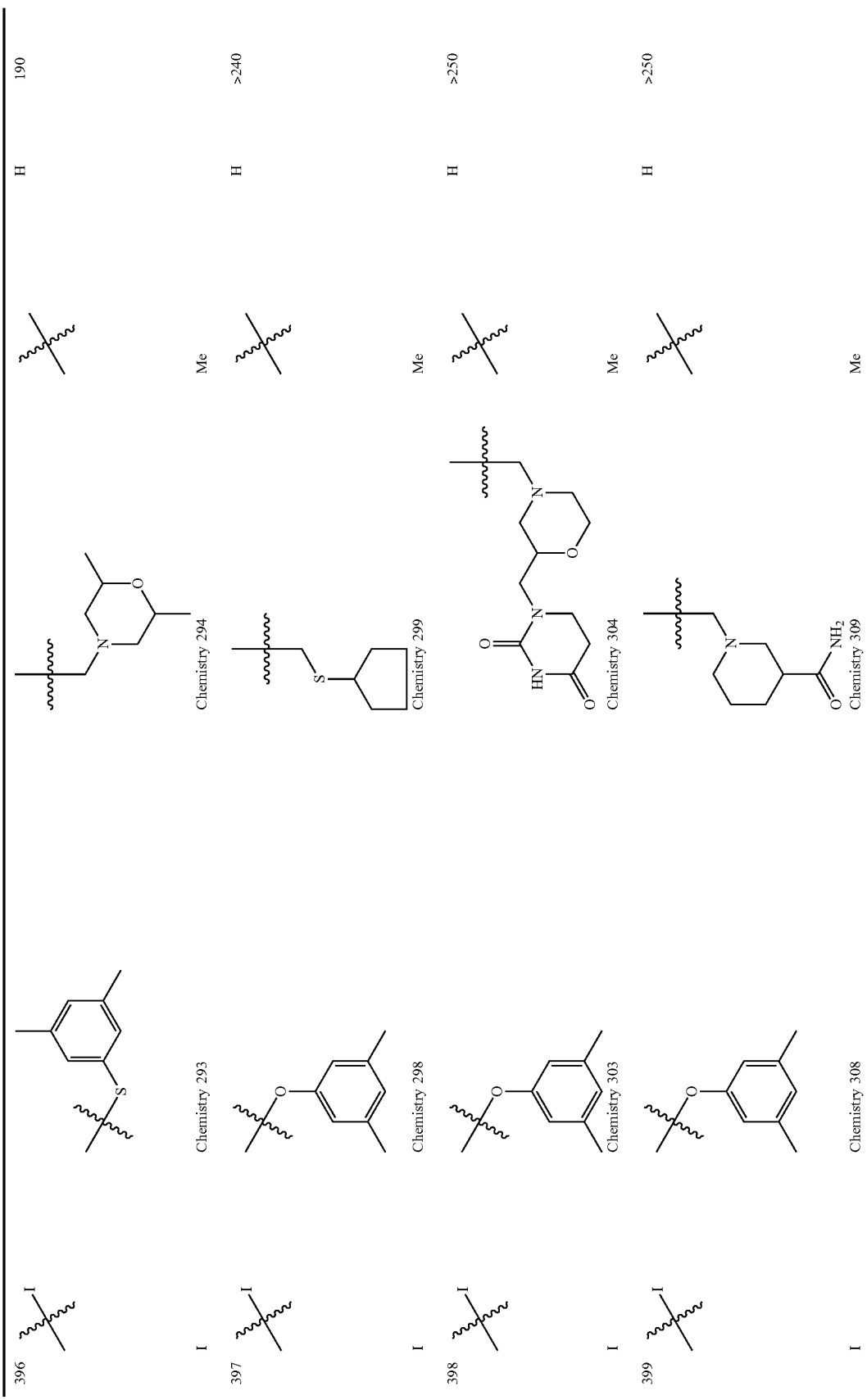

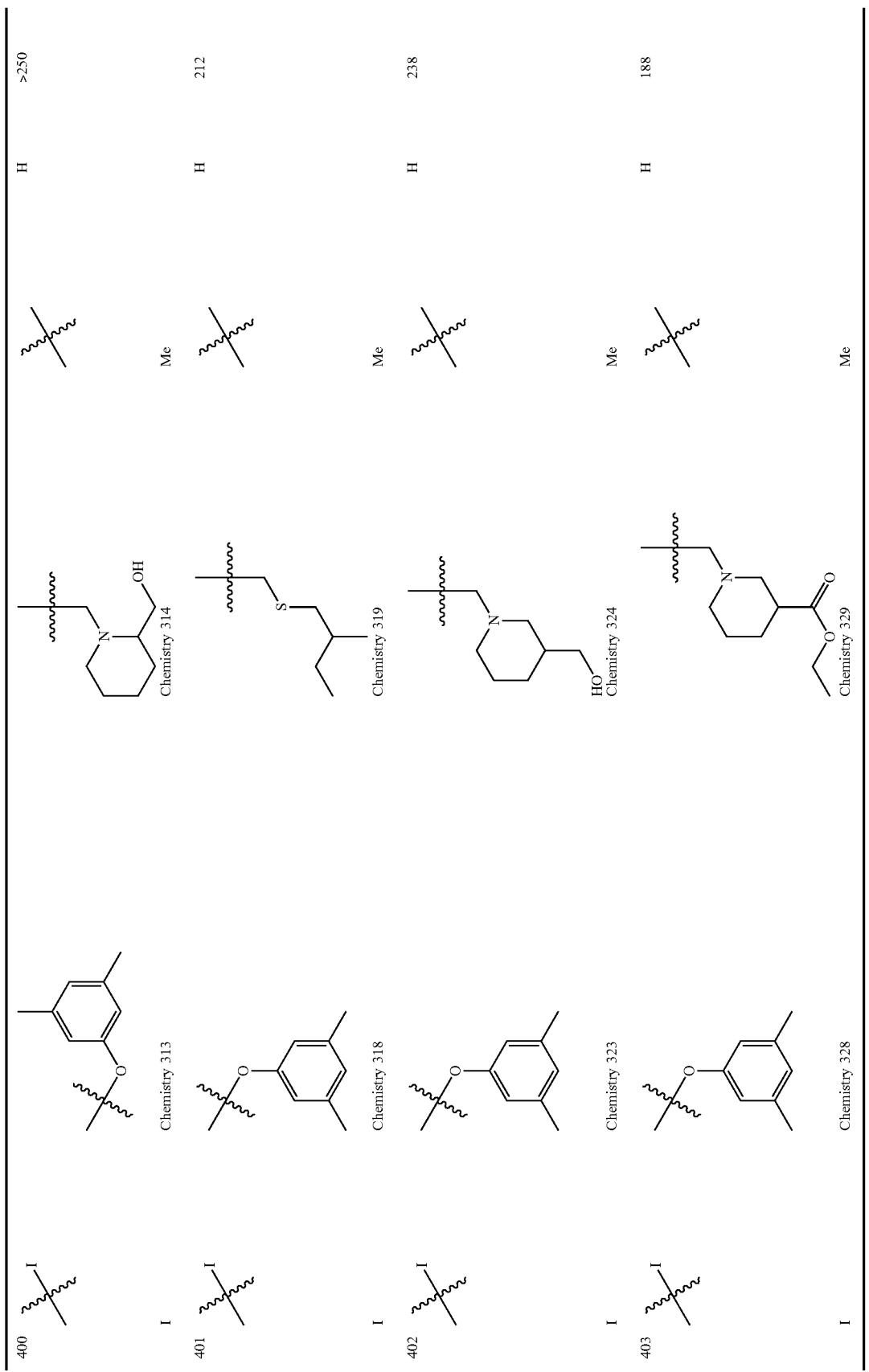

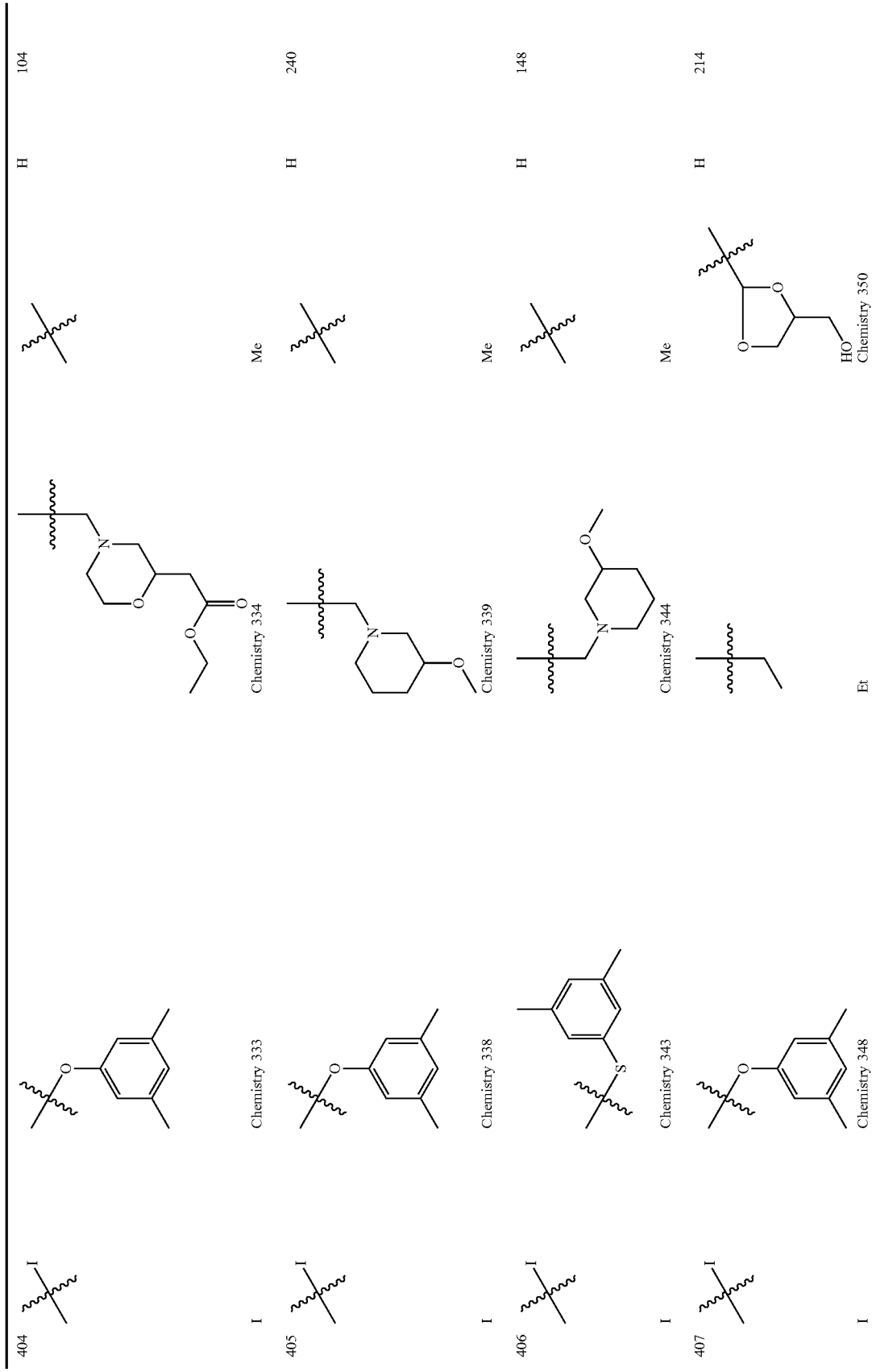

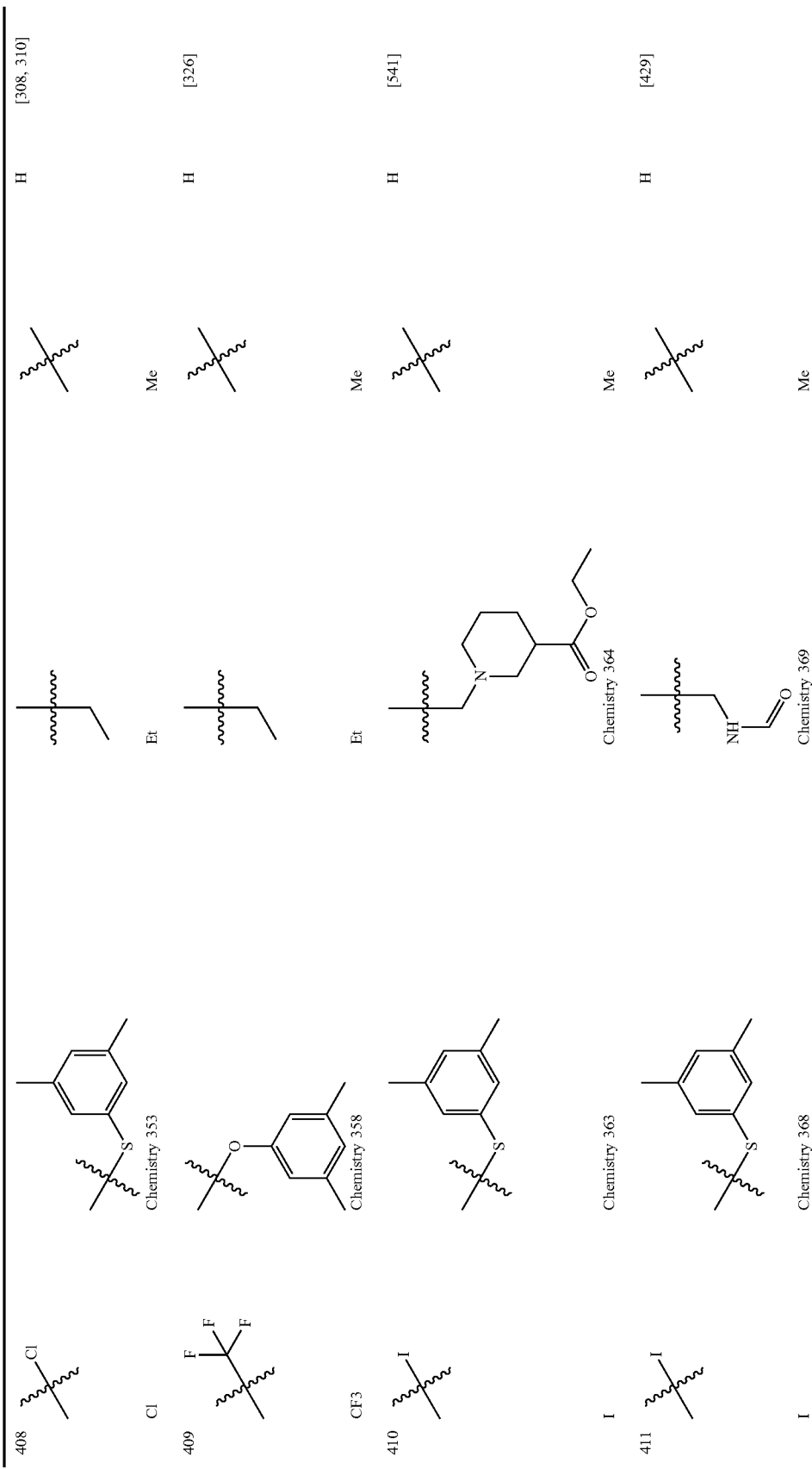

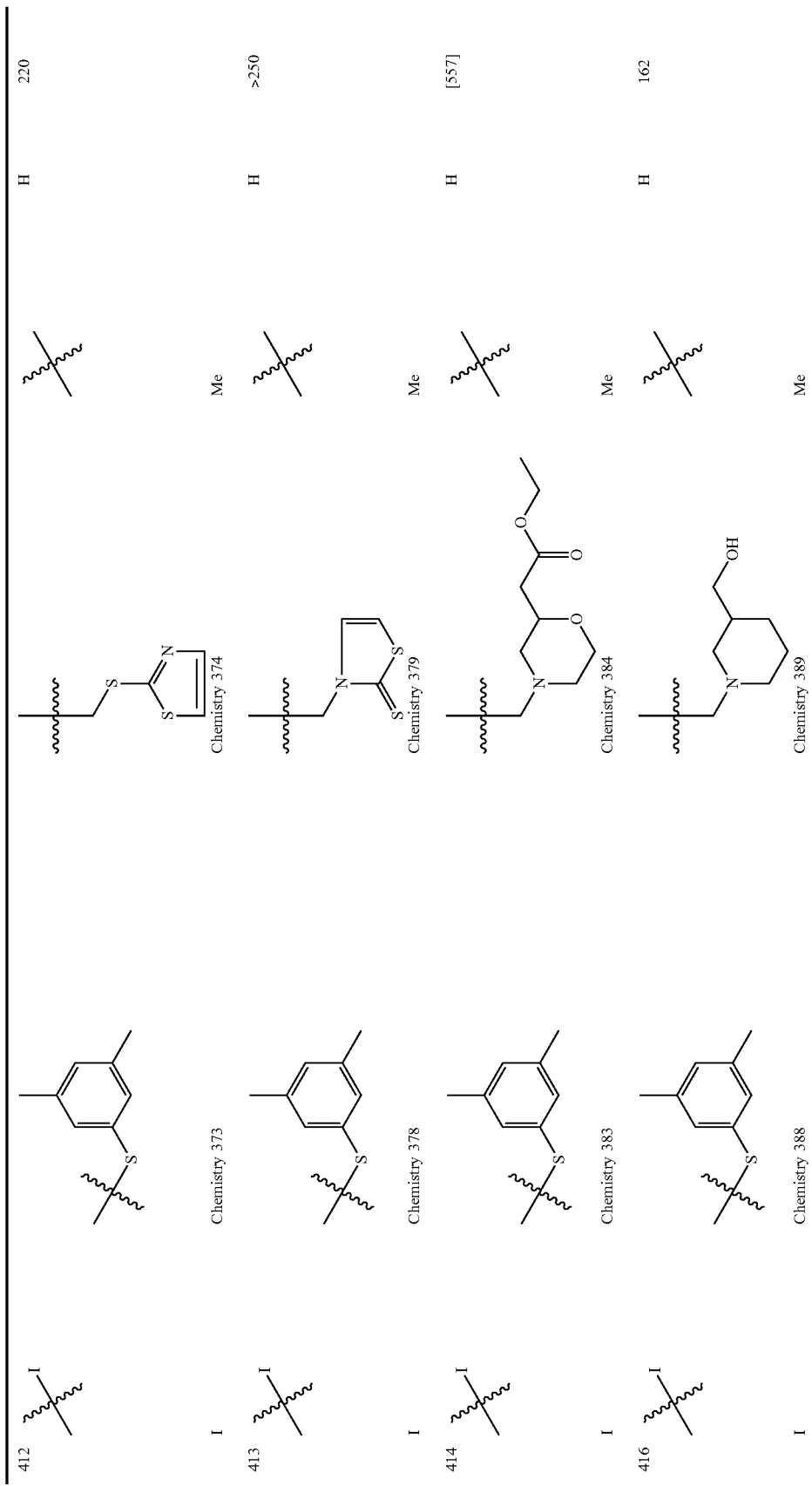

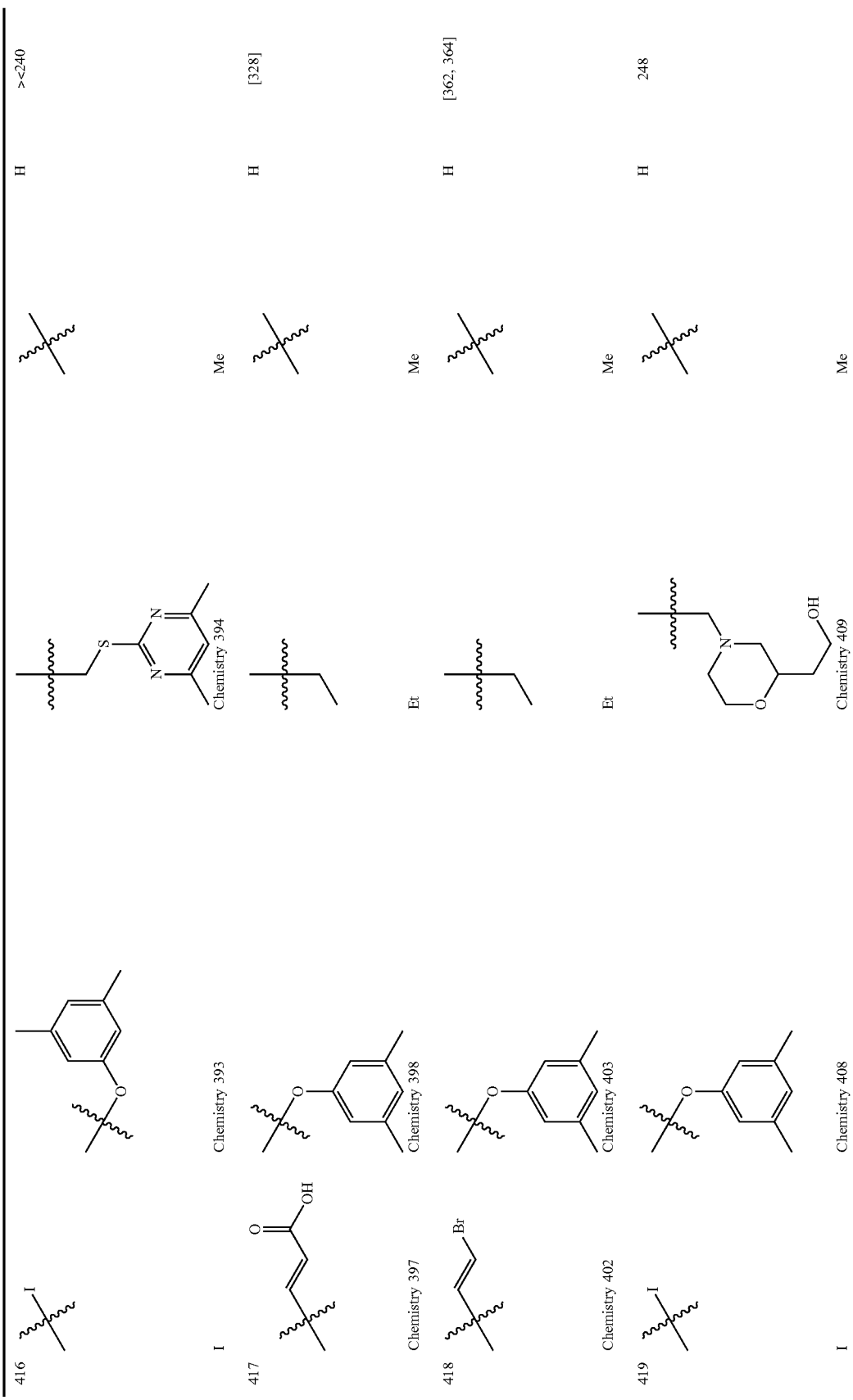

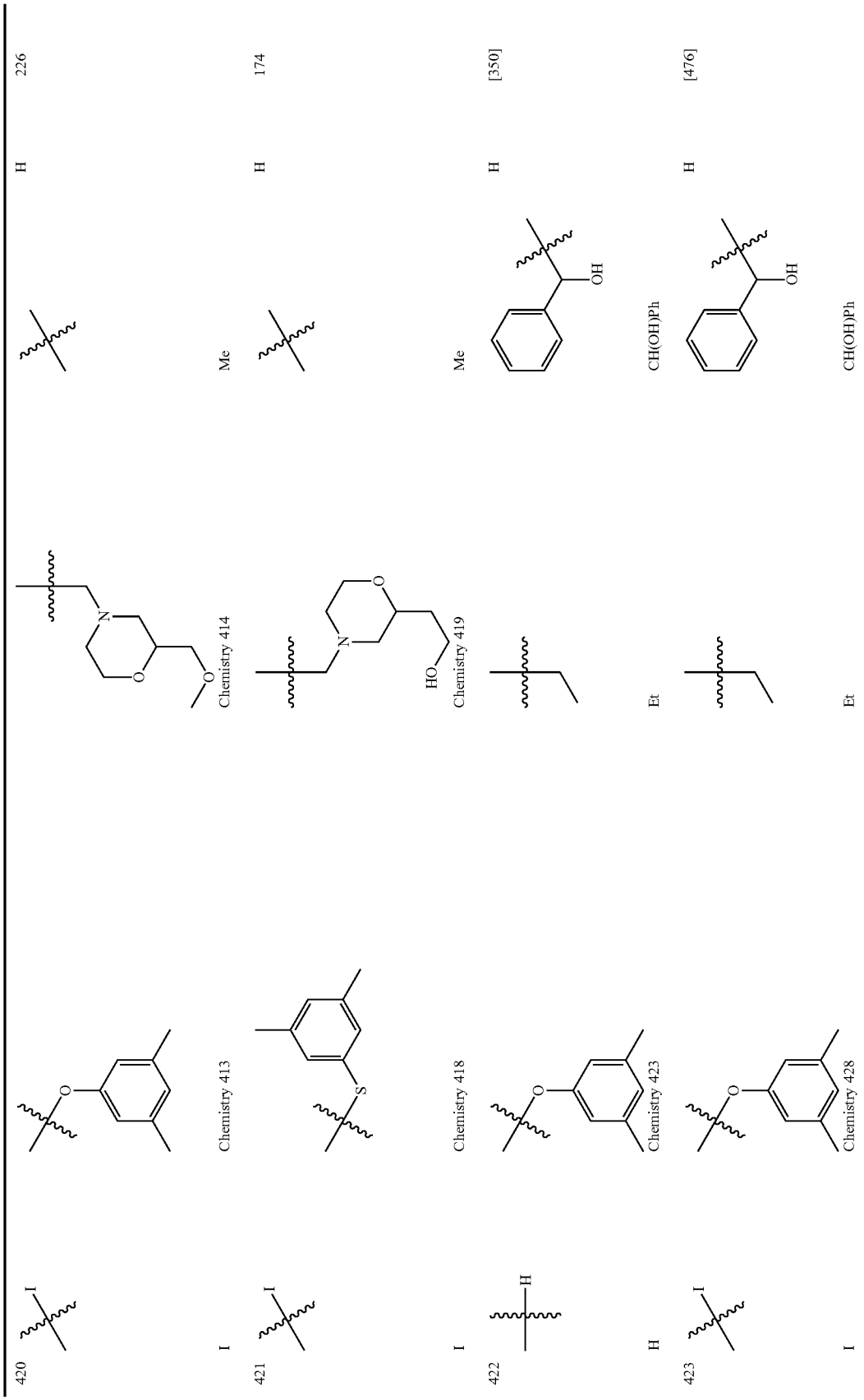

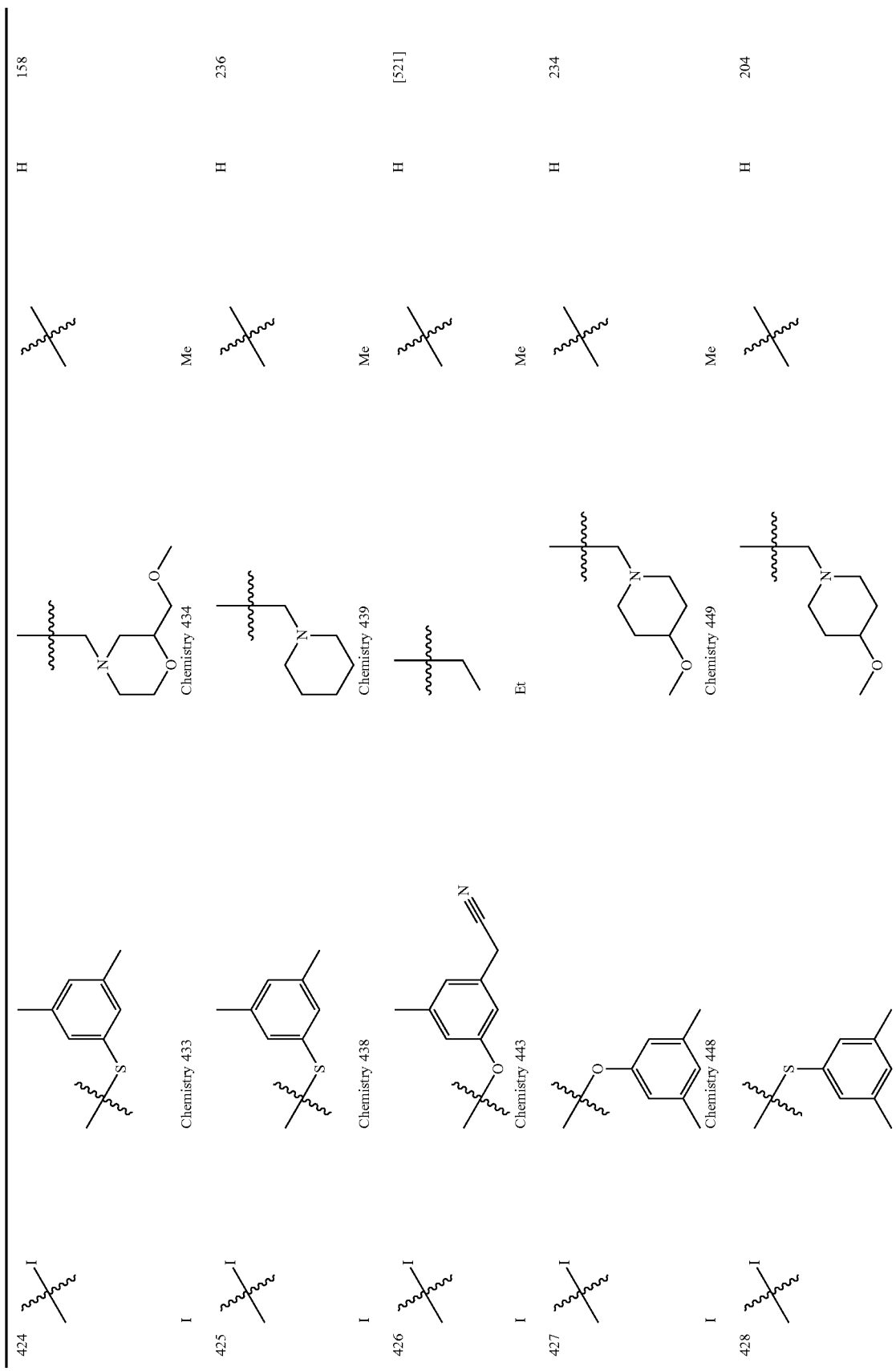

-continued

| | | | | |
|---|---|---|---|---|
| 429 | I | Chemistry 463 / Chemistry 458 | Chemistry 464 | Me | H | [556] |
| 430 | I | Chemistry 463 / Chemistry 463 | CO2Et | Me | H | [574] |
| 431 | Chemistry 467 | Chemistry 468 | Et | Me | H | [410] |
| 432 | Chemistry 472 | Chemistry 473 | Et | Me | H | [432] |
| 433 | I | Chemistry 478 | Et | Me | H | 236 |
| | | Chemistry 479 | | Me | |

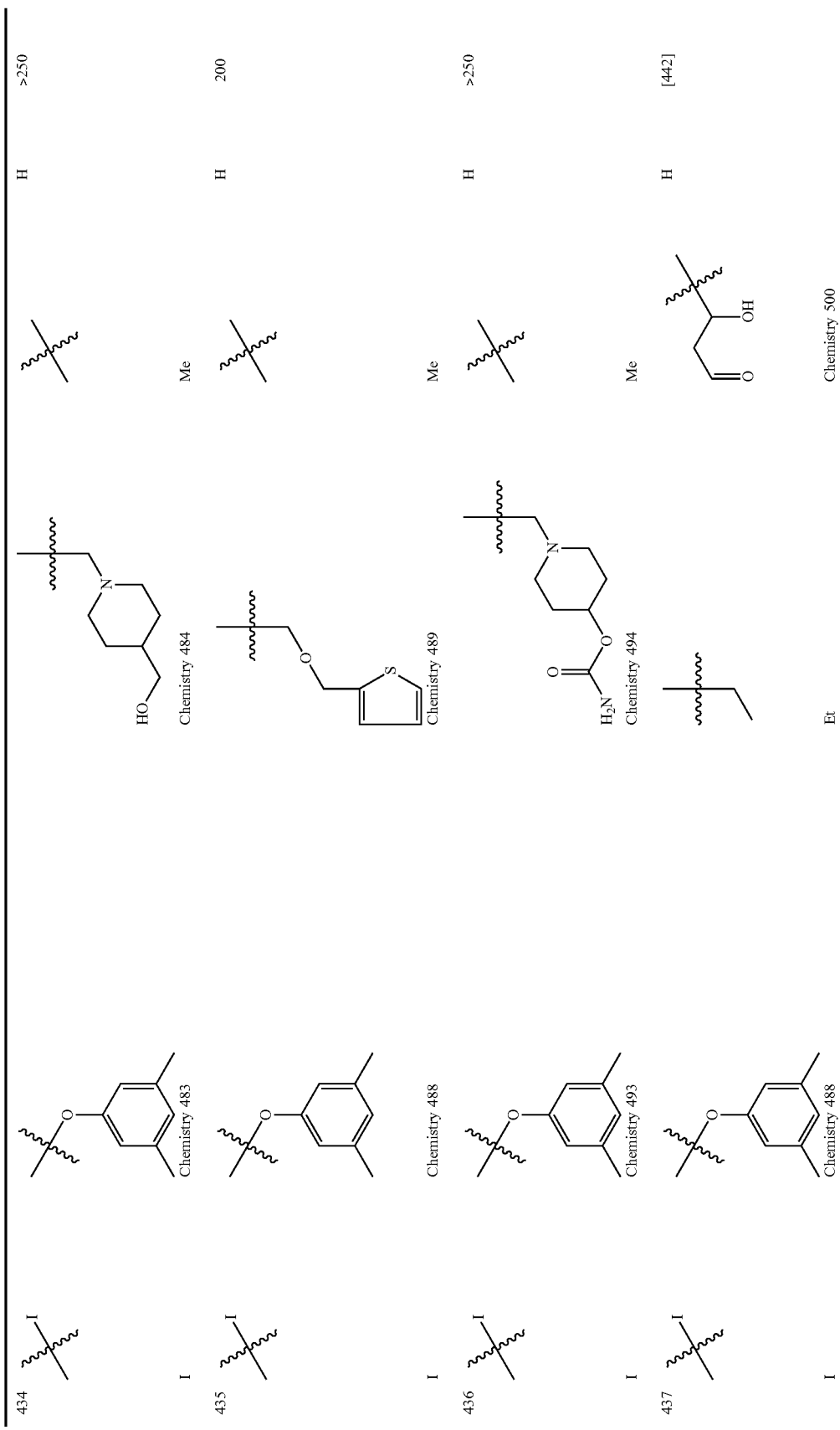

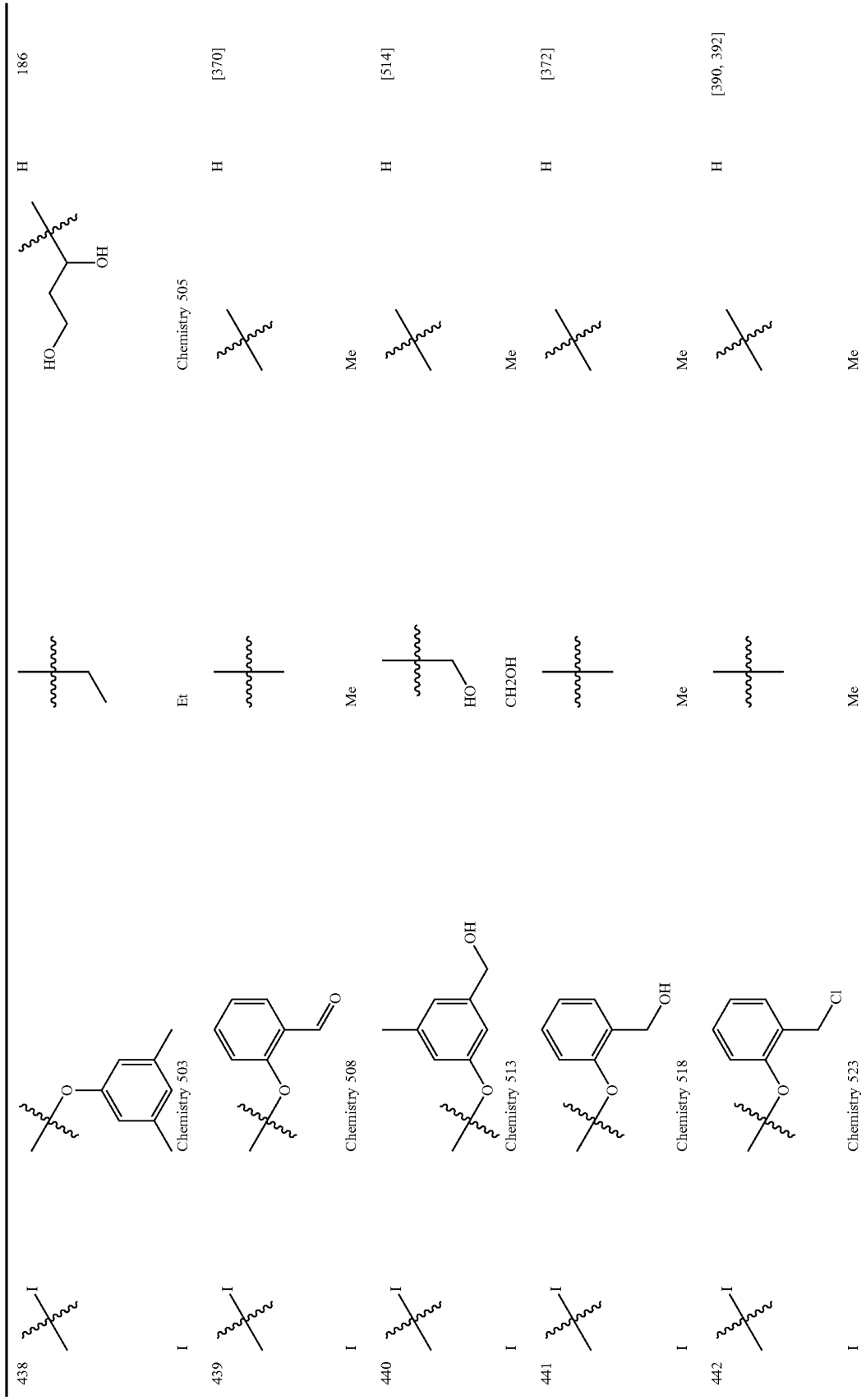

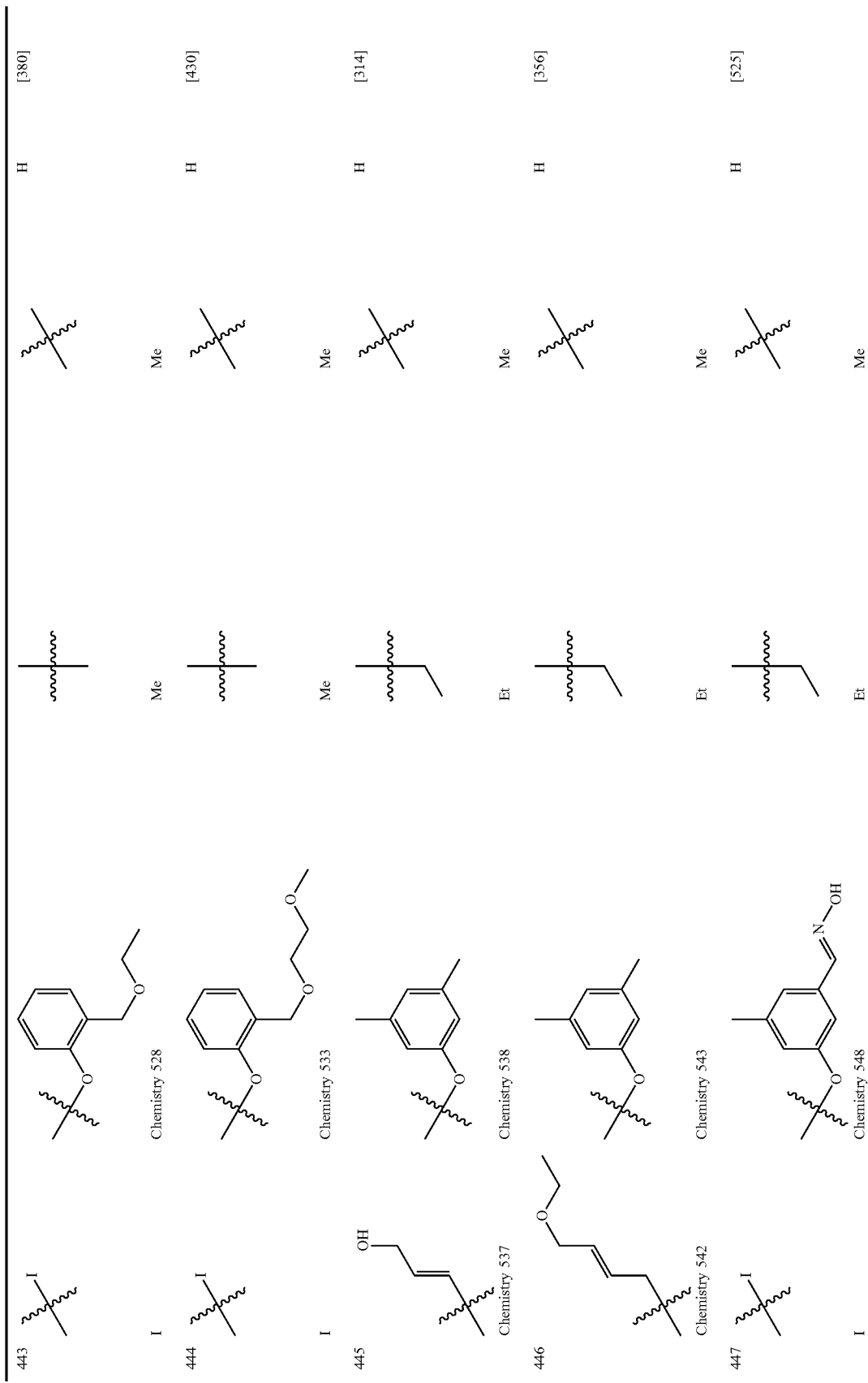

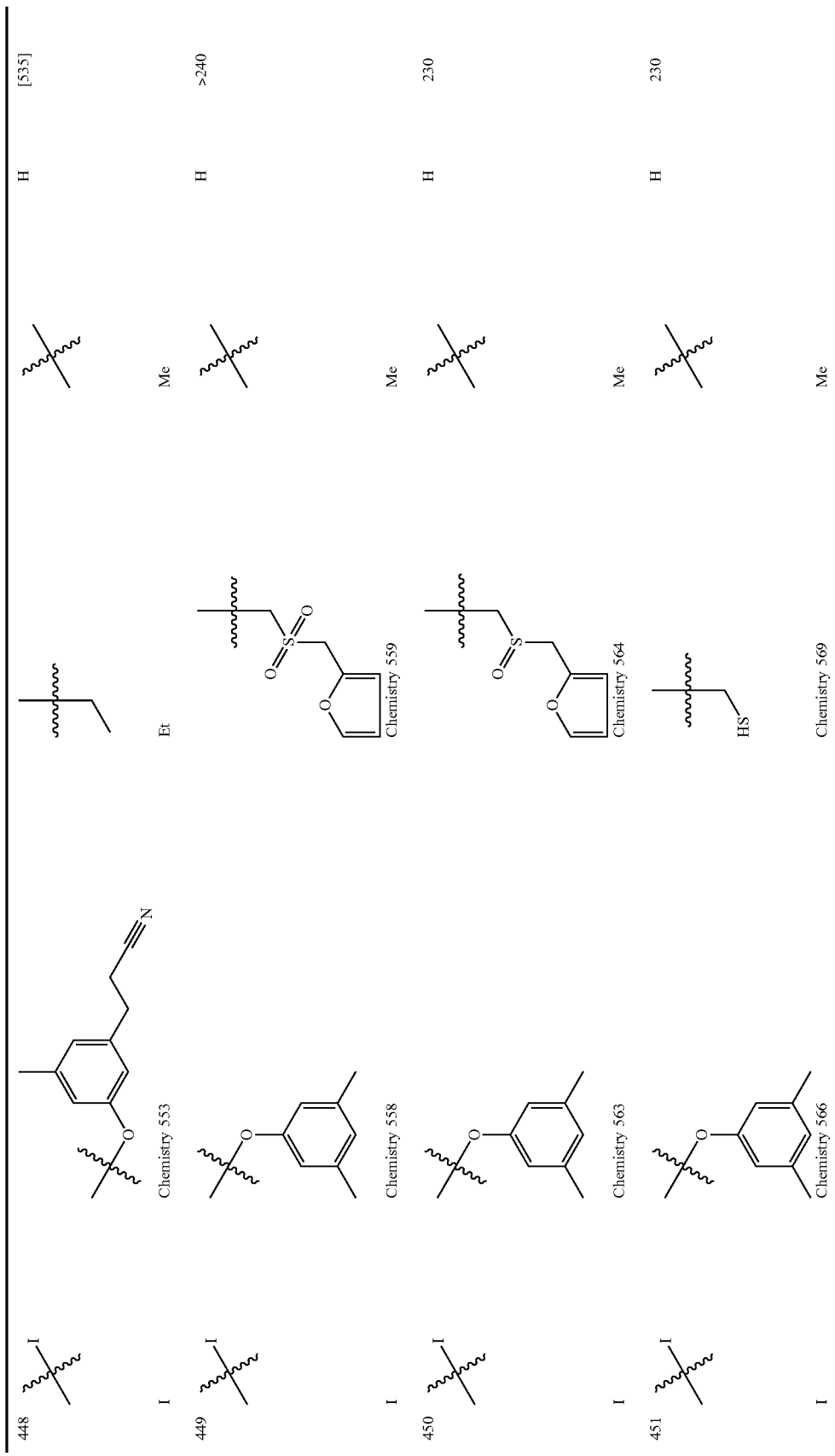

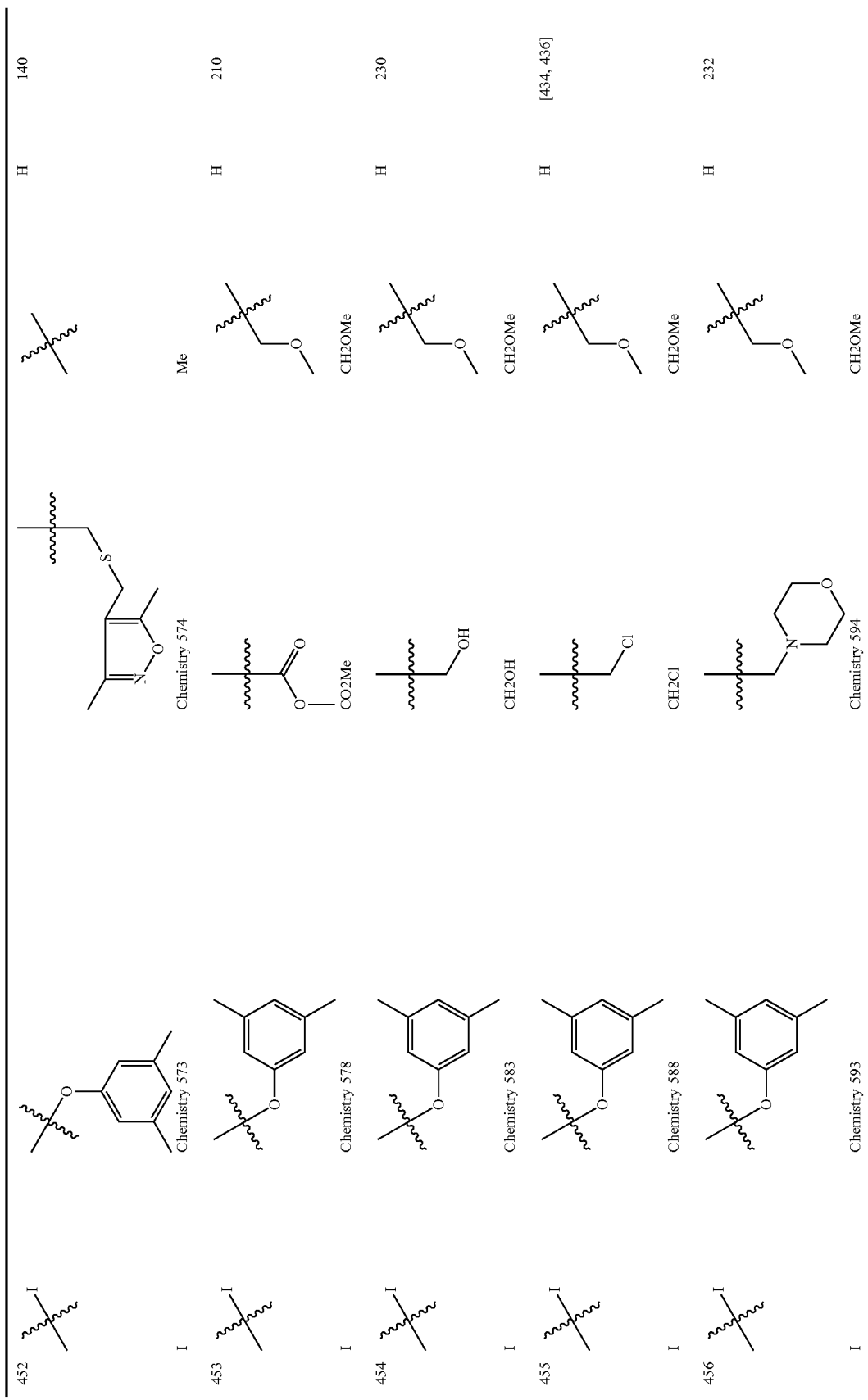

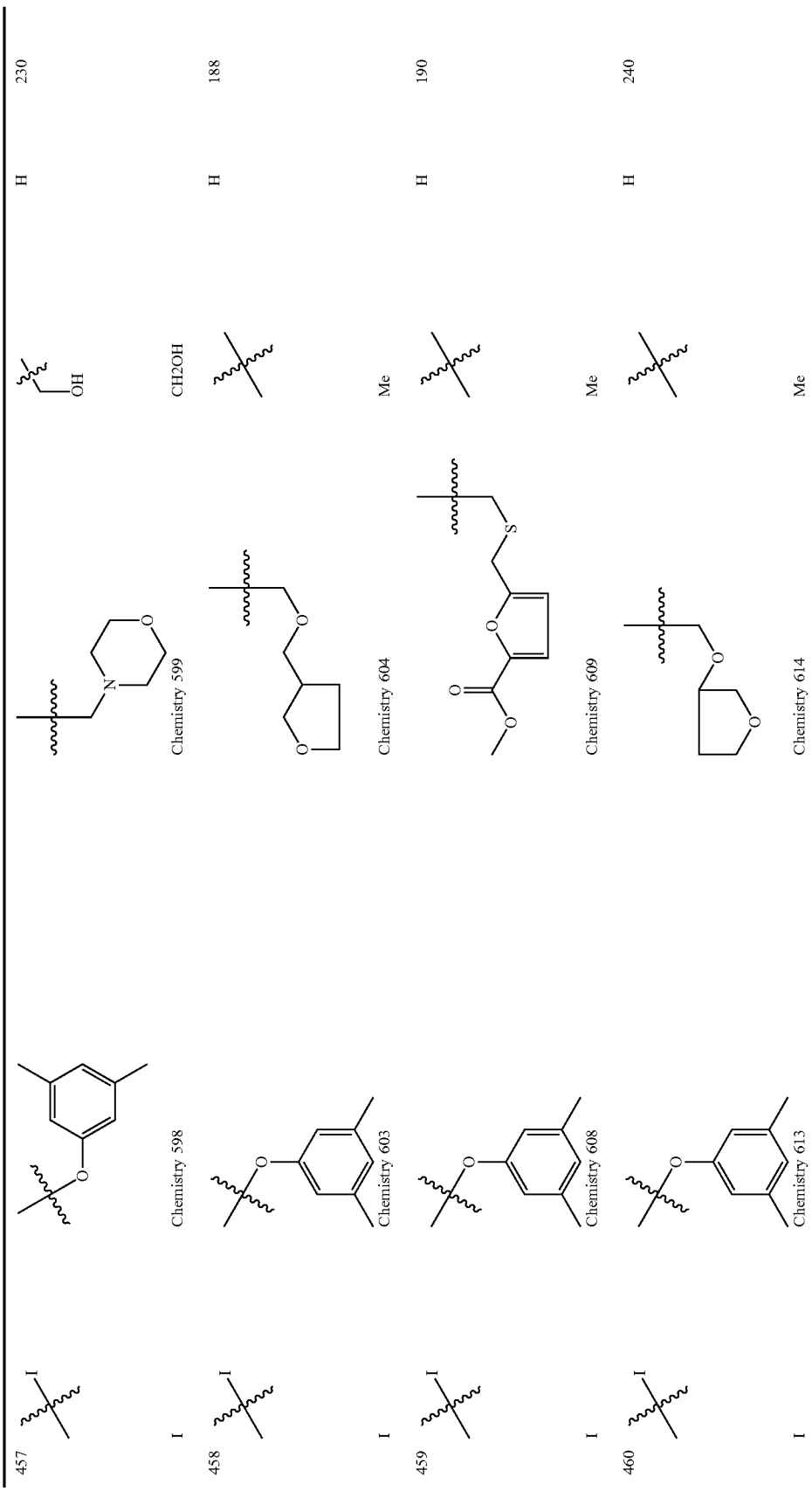

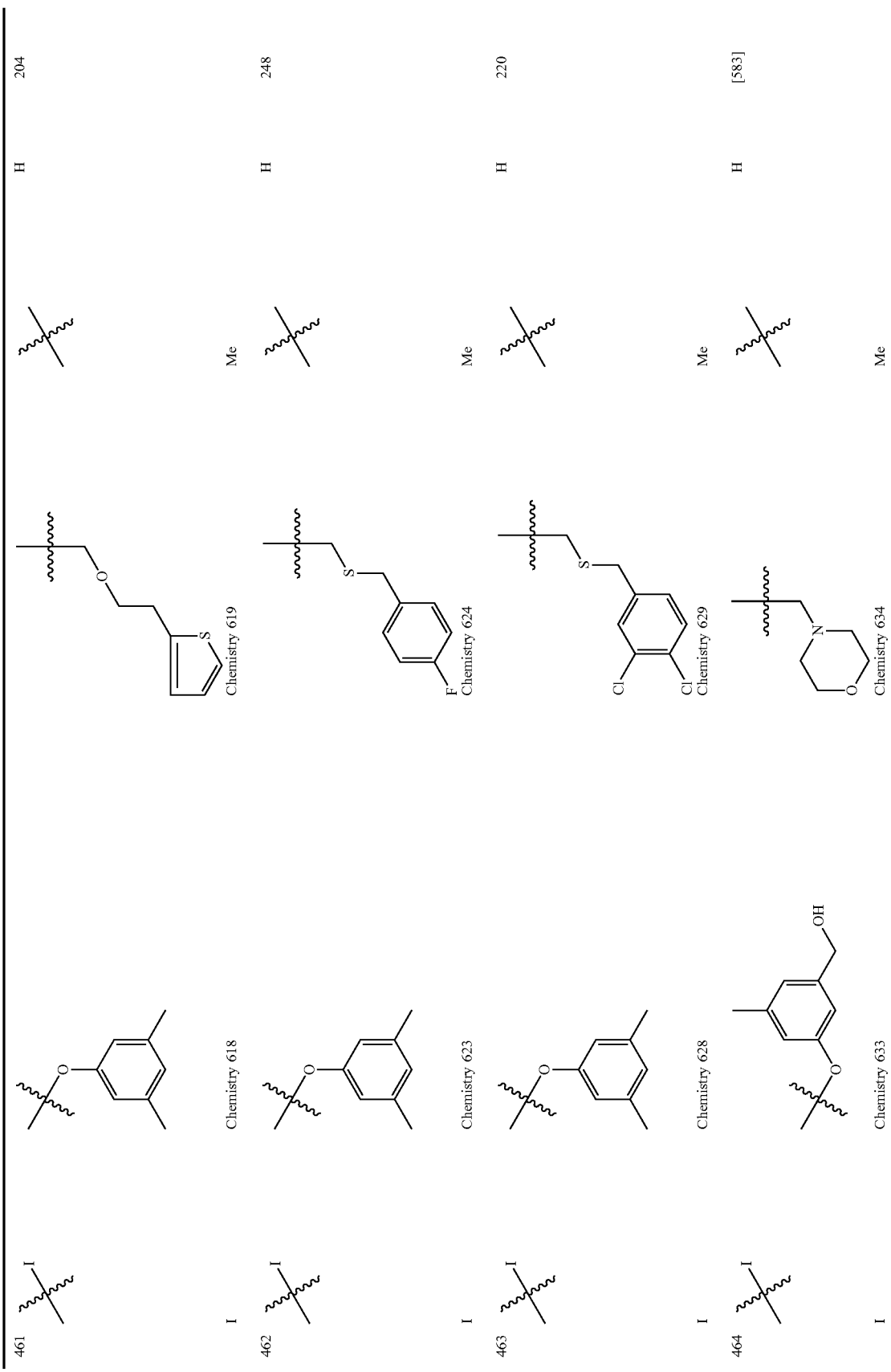

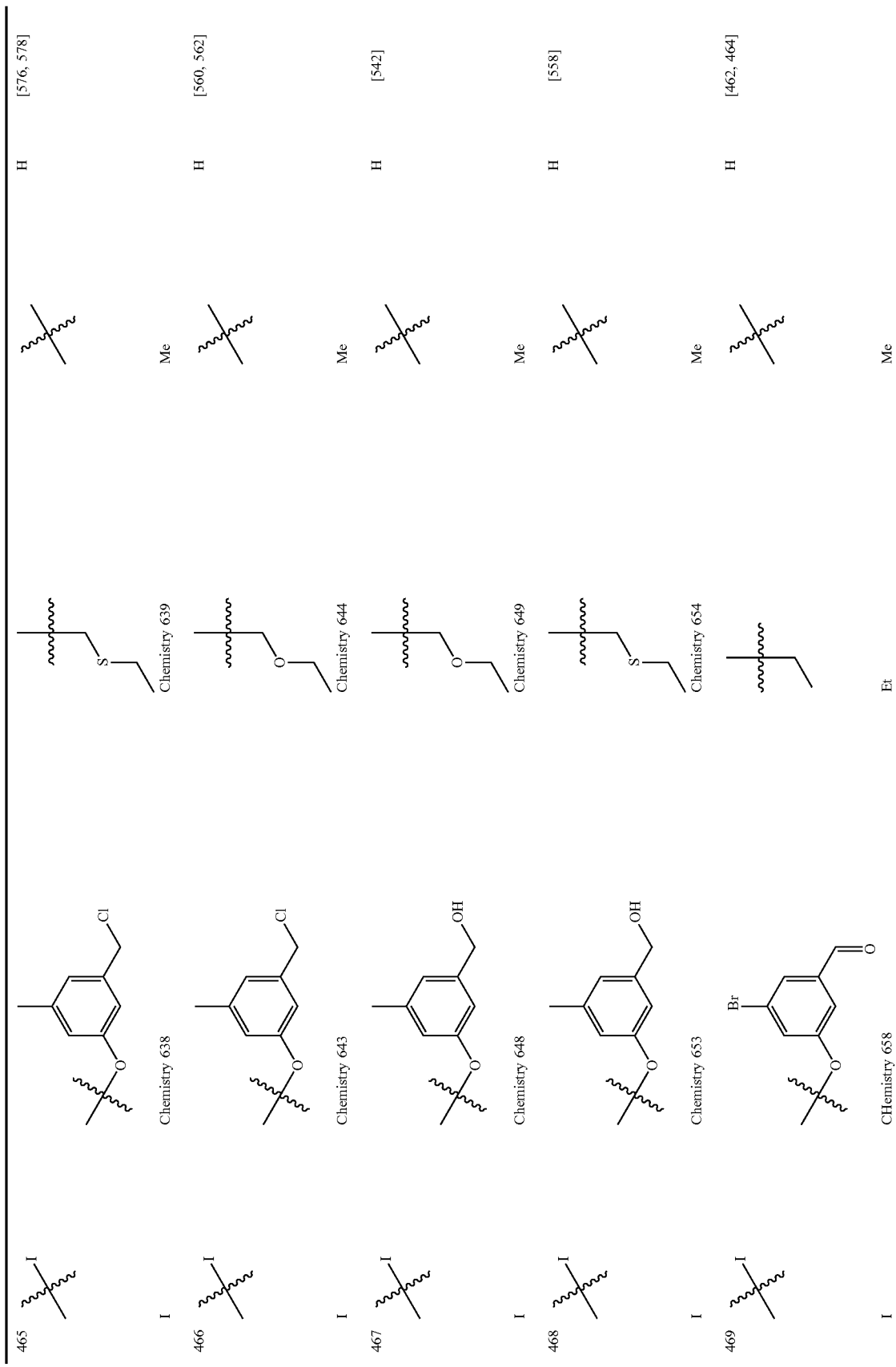

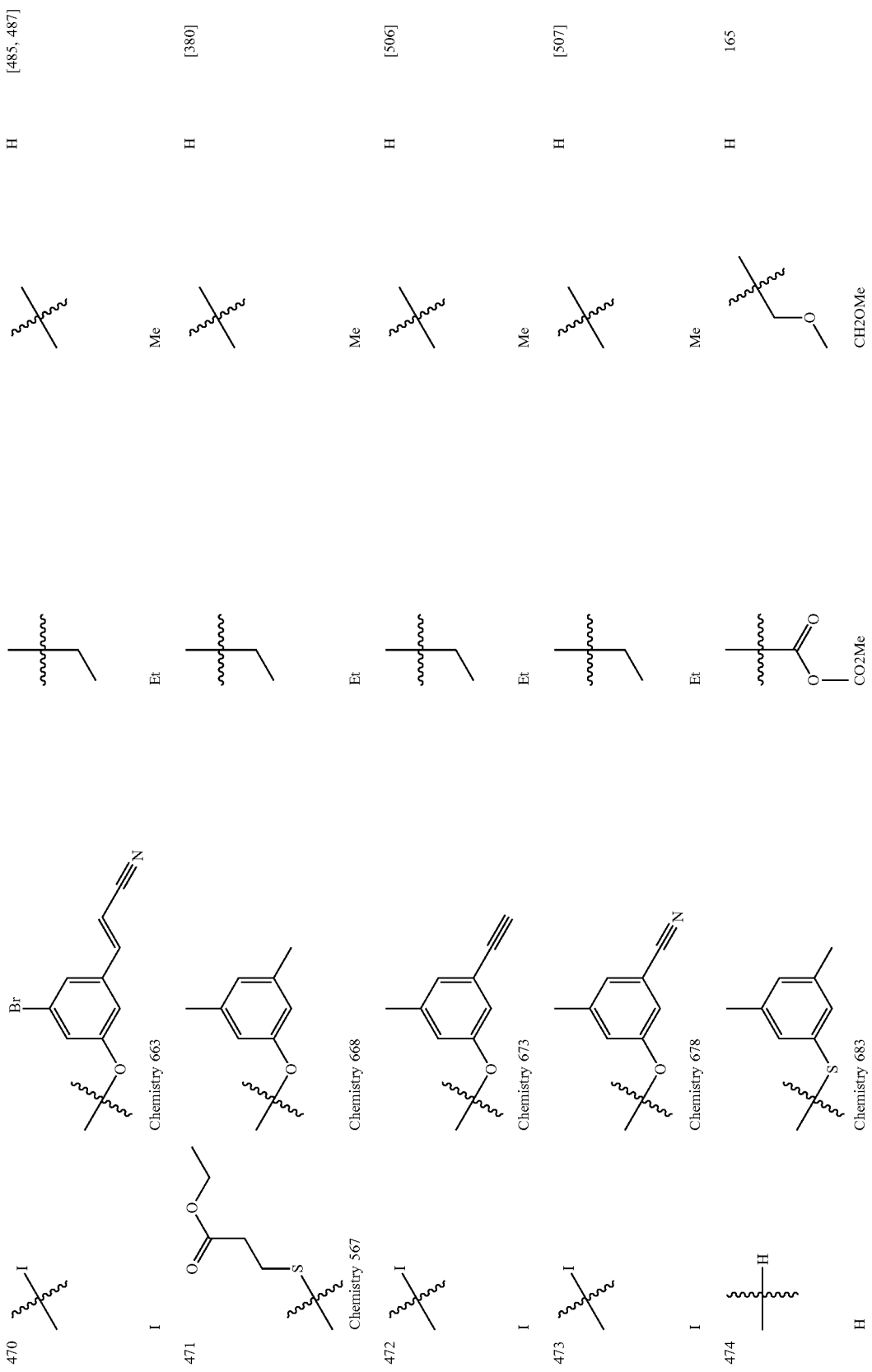

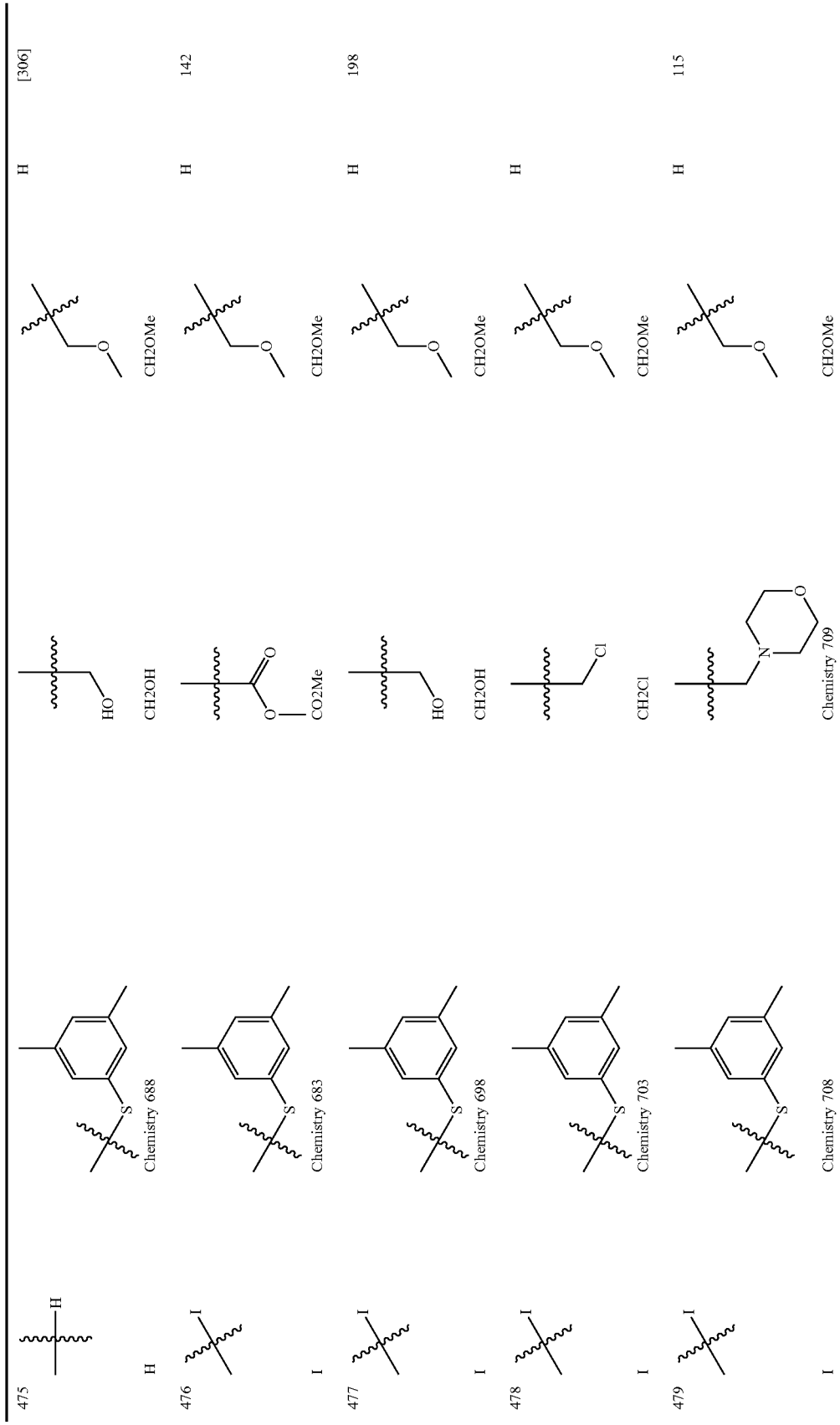

| | | | | |
|---|---|---|---|---|
| 480 | I | 3,5-dimethylphenyl-S- (Chemistry 713) | N-morpholinylmethyl- (Chemistry 714) | H | [487] |
| 481 | I | 3,5-dimethylphenyl-O- (Chemistry 718) | -CH2-S-CH2CH2-N(CH3)2 (Chemistry 719) | CH2OH | 230 |
| 482 | I | 3,5-dimethylphenyl-O- (Chemistry 723) | pyrazinyl-CH2-S- (Chemistry 724) | Me | 168 |
| 483 | I | 3,5-dimethylphenyl-O- (Chemistry 728) | 2-methylthiazol-4-yl-CH2-S-CH2- (Chemistry 729) | Me | [513] |

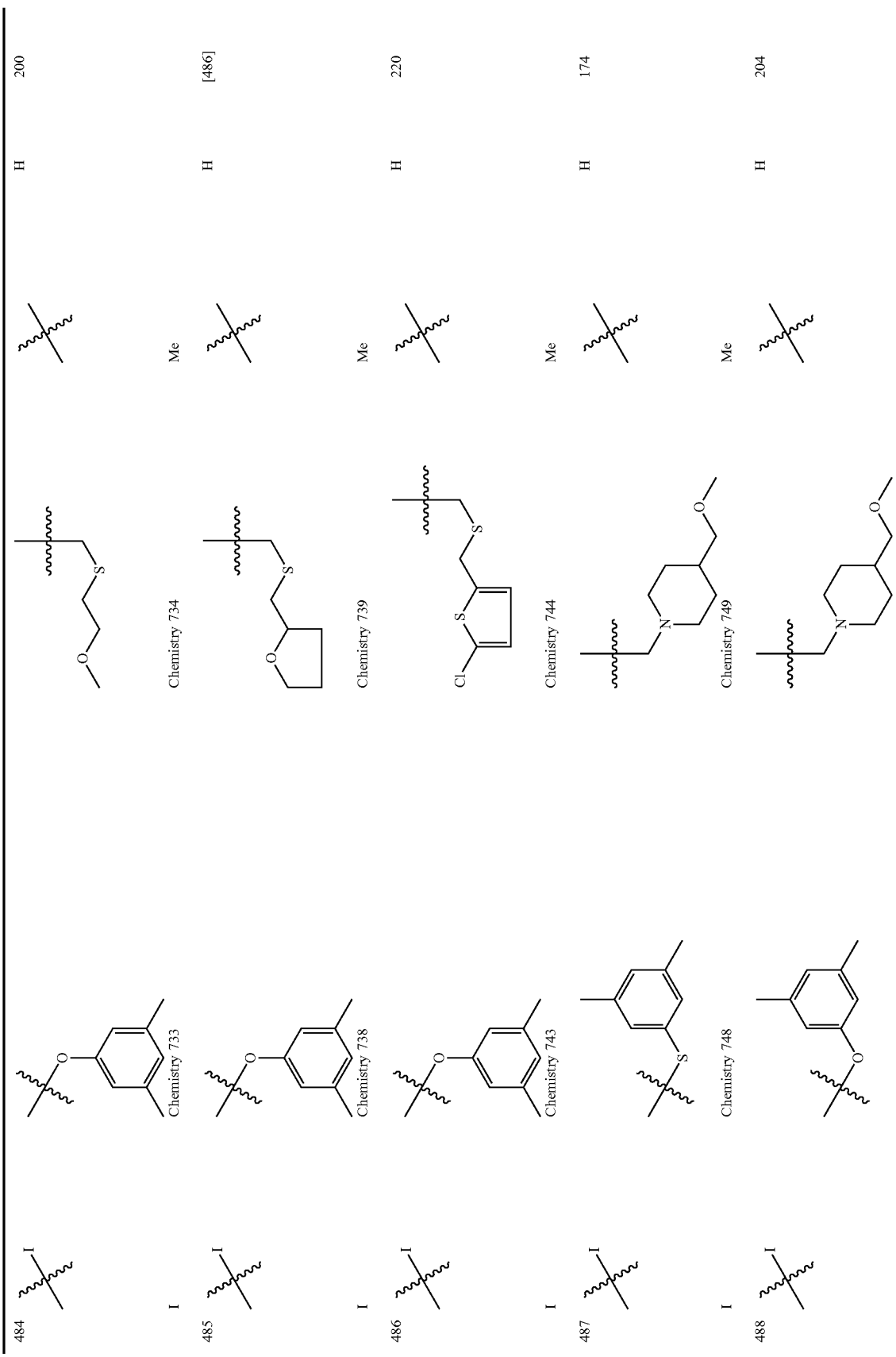

| | | | | | |
|---|---|---|---|---|---|
| 489 | I | Chemistry 753 | Chemistry 754 | Me | >250 H |
| 490 | I | Chemistry 758 | Chemistry 759 | Me | 162 H |
| 491 | I | Chemistry 763 | Chemistry 764 | Me | [600] H |
| | I | Chemistry 768 | Chemistry 769 | Me | |

| | | | | |
|---|---|---|---|---|
| 492 | 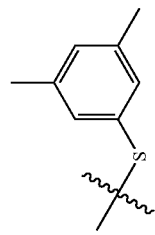 | 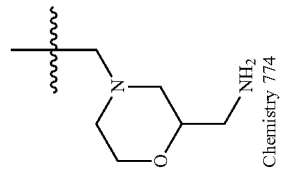 Chemistry 773 |  | H | [500] |
| 493 | 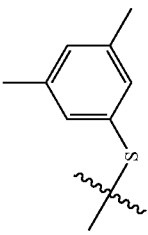 | 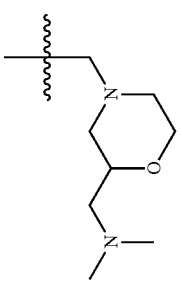 Chemistry 778 | 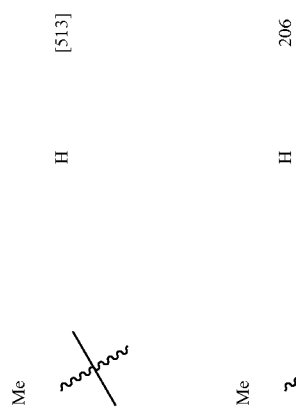 Chemistry 774 | H | 164 |
| | | | Chemistry 779 | | |
| 494 | 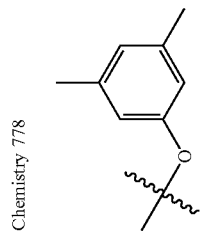 | 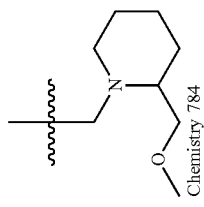 Chemistry 783 | | H | [513] |
| 495 | 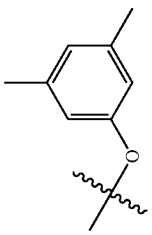 | 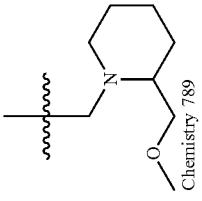 Chemistry 788 |  Chemistry 784 | H | 206 |
| | | | Chemistry 789 | Me | |
| | | | | Me | |
| | | | | Me | |
| | | | | Me | |
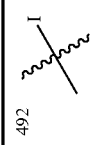

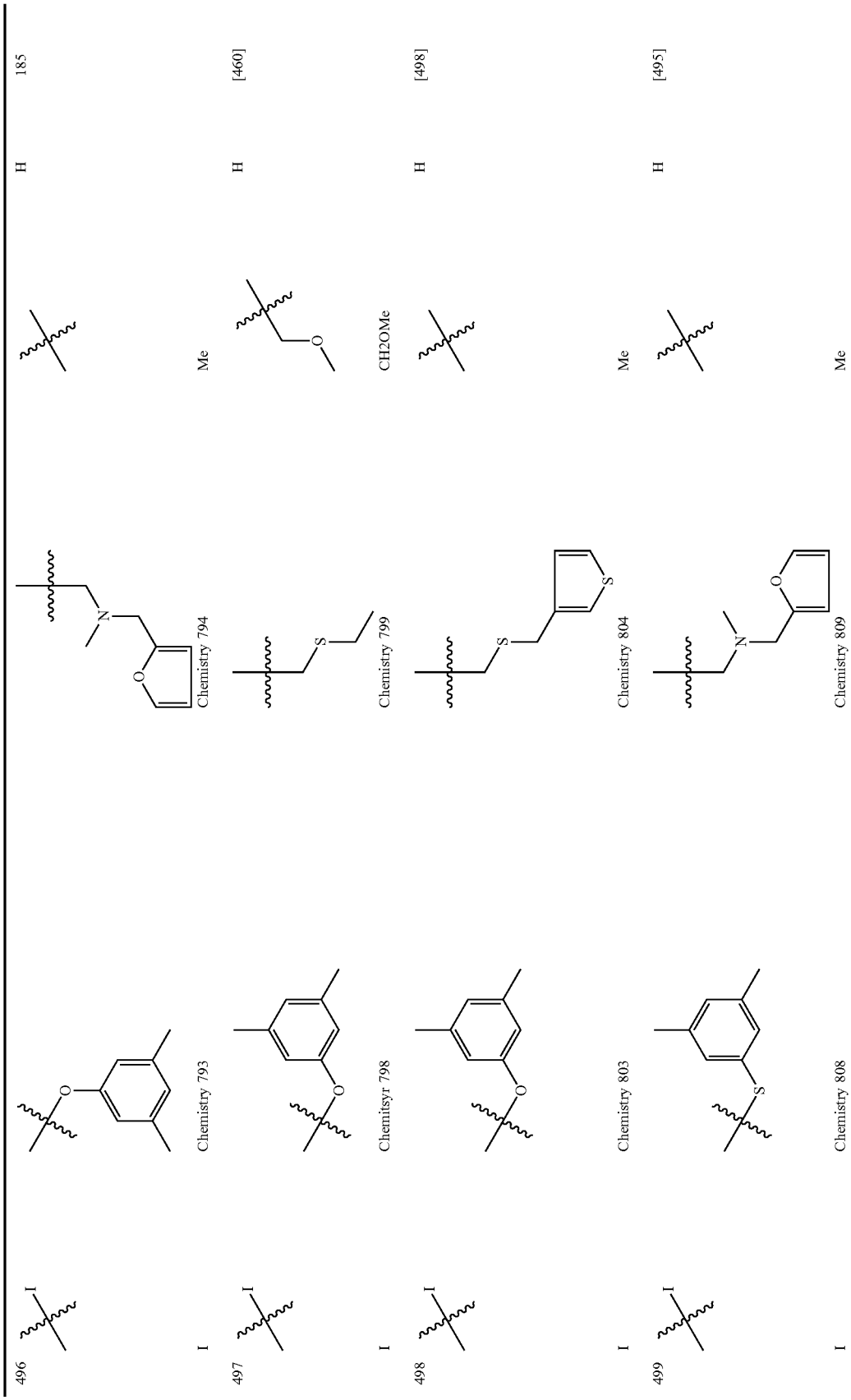

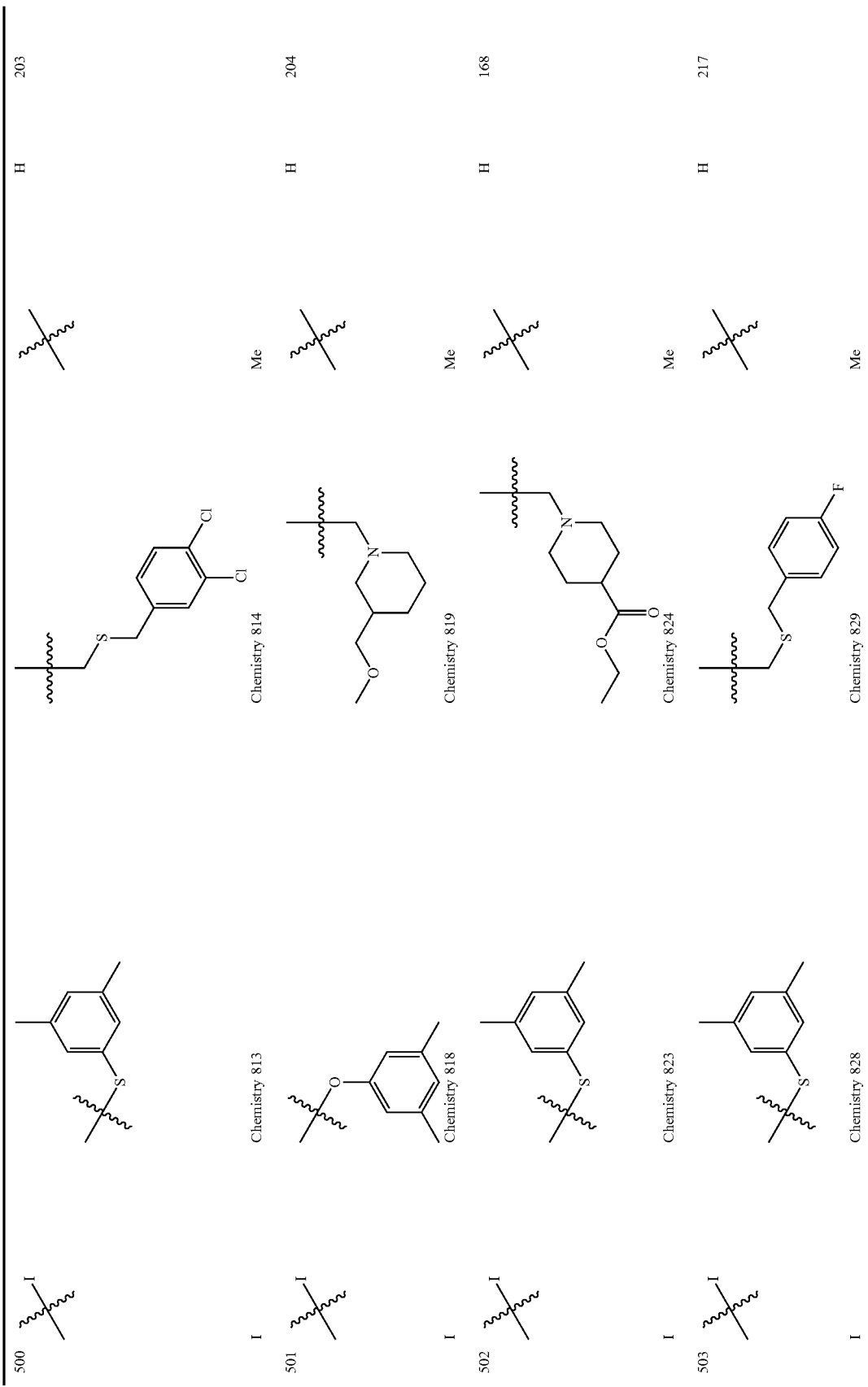

| | | | | |
|---|---|---|---|---|
| 504 | I | 3,5-dimethylphenyl-S- | 3-(trifluoromethyl)benzyl-S-CH2- Chemistry 834 | H | 200 |
| 505 | I | 3,5-dimethylphenyl-S- Chemistry 833 | CH2Cl | H | — |
| 506 | Me | 3,5-dimethylphenyl-S- Chemistry 838 | furan-2-yl-CH2-S-CH2- Chemistry 844 | H | 206 |
| 507 | Me | 3,5-dimethylphenyl-S- Chemistry 843 | CO2Et | H | 170 |

-continued
| | | | | |
|---|---|---|---|---|
| 508 | 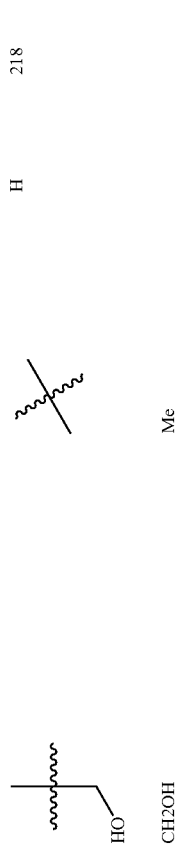 Chemistry 853 | 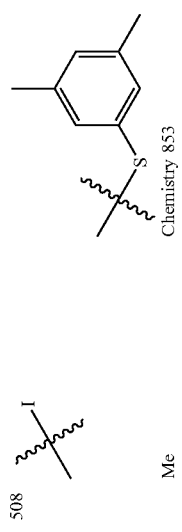 HO | 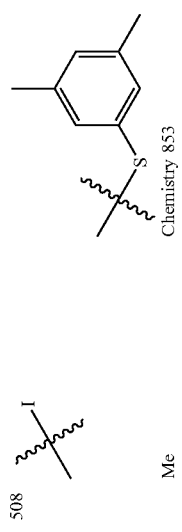 | H | 218 |
| 509 Me | 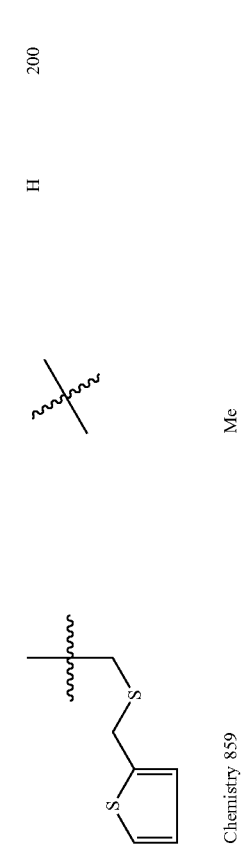 Chemistry 858 | CH2OH | Me | H | 200 |
| 510 Me | 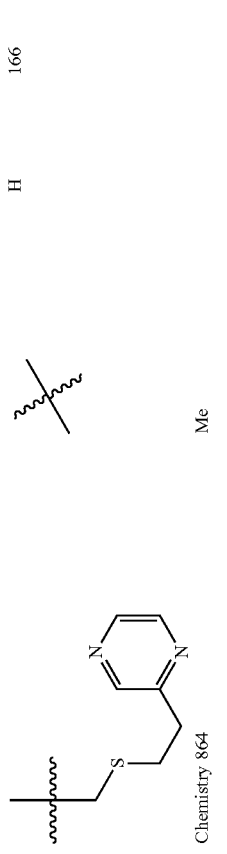 Chemistry 863 | 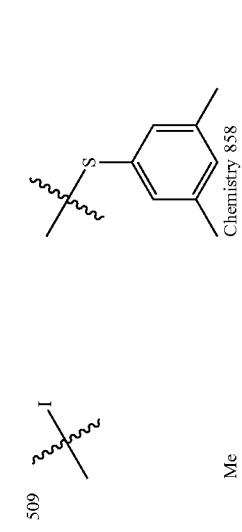 Chemistry 859 | Me | H | 166 |
| 511 | 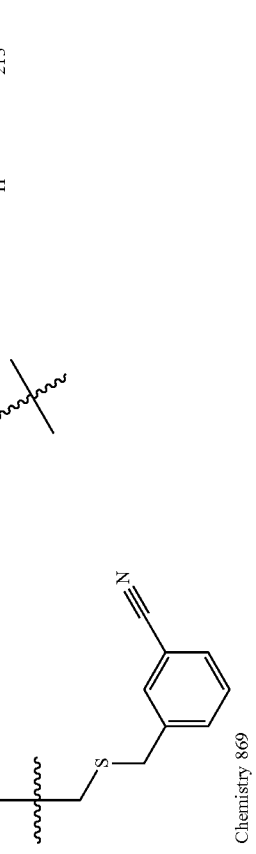 Chemistry 868 | 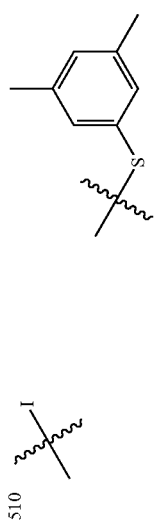 Chemistry 864 | Me | H | 213 |
| | | 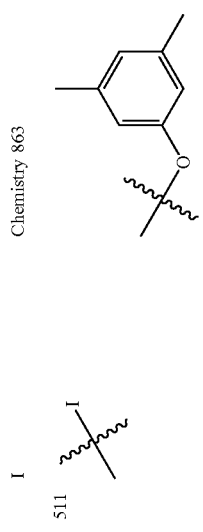 Chemistry 869 | | |

| | | | | |
|---|---|---|---|---|
| 512 | Chemistry 873 | Chemistry 874 | | H | [610] |
| 513 | Chemistry 878 | CO2Et | Me | H | [751] |
| 514 | Chemistry 883 | Chemistry 884 | Me | H | [567] |
| 515 | Chemistry 888 | Et | Me | H | [418, 420] |

-continued

| | | | | | |
|---|---|---|---|---|---|
| 516 | I | Chemistry 893 (dimethyl ester with O-link) | (wavy ethyl) | H | [472] |
| 517 | I | Chemistry 898 (Br-CH2, Me, O-link) | Et | Me | [621] |
| 518 | I | Chemistry 903 (HOCH2, HOCH2, O-link) | (wavy ethyl) | Me | [416] |
| 519 | I | Chemistry 908 (CHO, Me, O-link) | Et | Me | [556] |
| 520 | I | Chemistry 909 (ClCH2, ClCH2, O-link) | (wavy ethyl) | Me | [452, 454, 456] |

| | | | | |
|---|---|---|---|---|
| 521 | I | Chemistry 913 | Et | Me | H | [434, 436] |
| 522 | I | Chemistry 918 | Et | Me | H | [476] |
| 523 | I | Chemistry 923 | Et | Me | H | [517] |
| | | Chemistry 928 | Chemistry 929 | Me | H | [362] |
| 524 | Chemistry 932 | Chemistry 933 | Et | Me | |

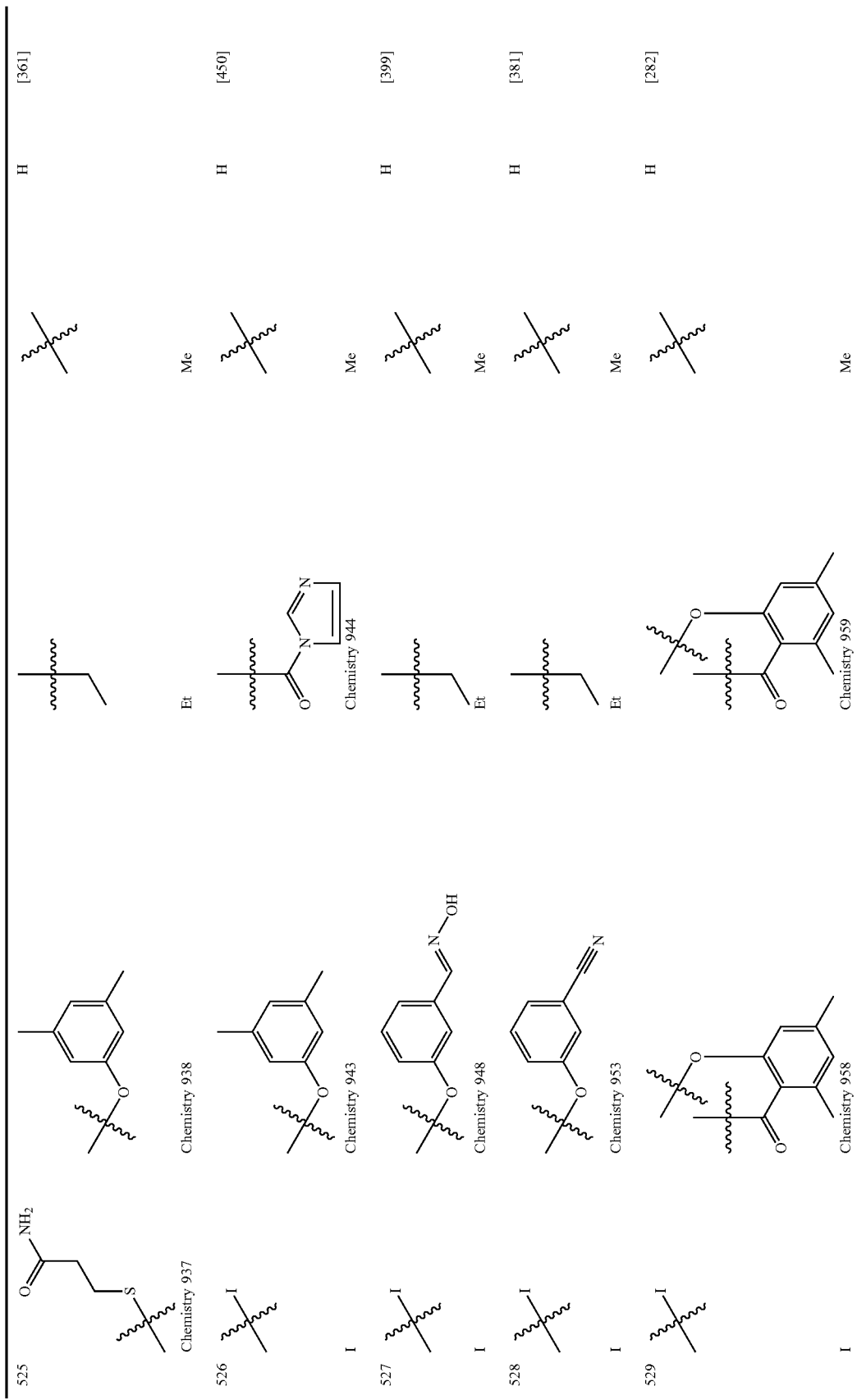

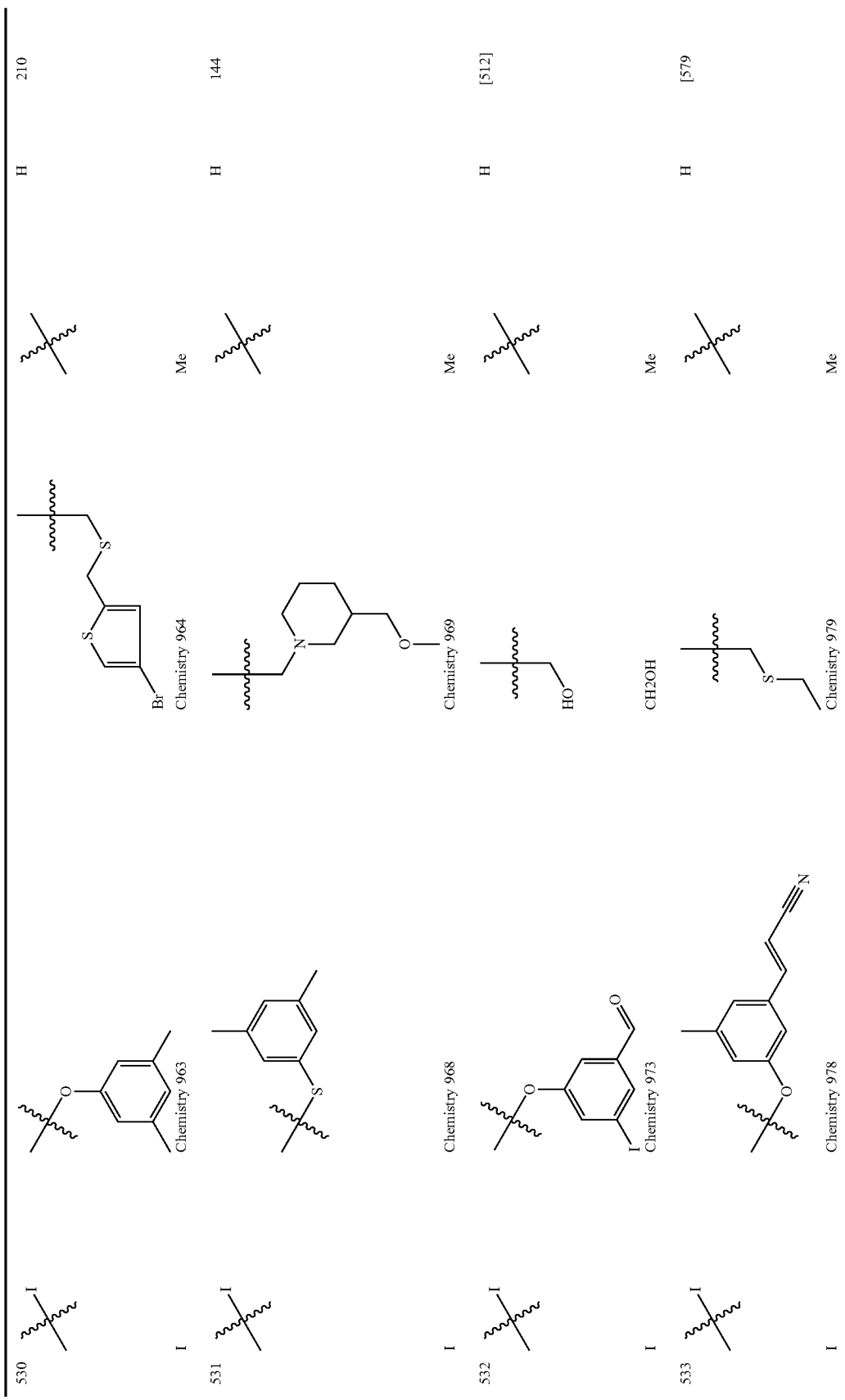

| | | | | |
|---|---|---|---|---|
| 534 | 3,5-dimethylphenoxy (Chemistry 983) | morpholine amide (Chemistry 984) | H | [469] |
| 535 | 3,5-dimethylphenoxy (Chemistry 988) | thiomorpholine amide (Chemistry 989) | Me | [485] |
| 536 | 3-ethynylphenoxy (Chemistry 993) | Et | Me | [380] |
| 537 | 3-(1H-tetrazol-5-yl)phenoxy (Chemistry 998) | Et | Me | [424] |
| 538 | 3,5-dimethylphenoxy (Chemistry 1003) | 4-fluorobenzyloxymethyl (Chemistry 1004) | Me | [494] |

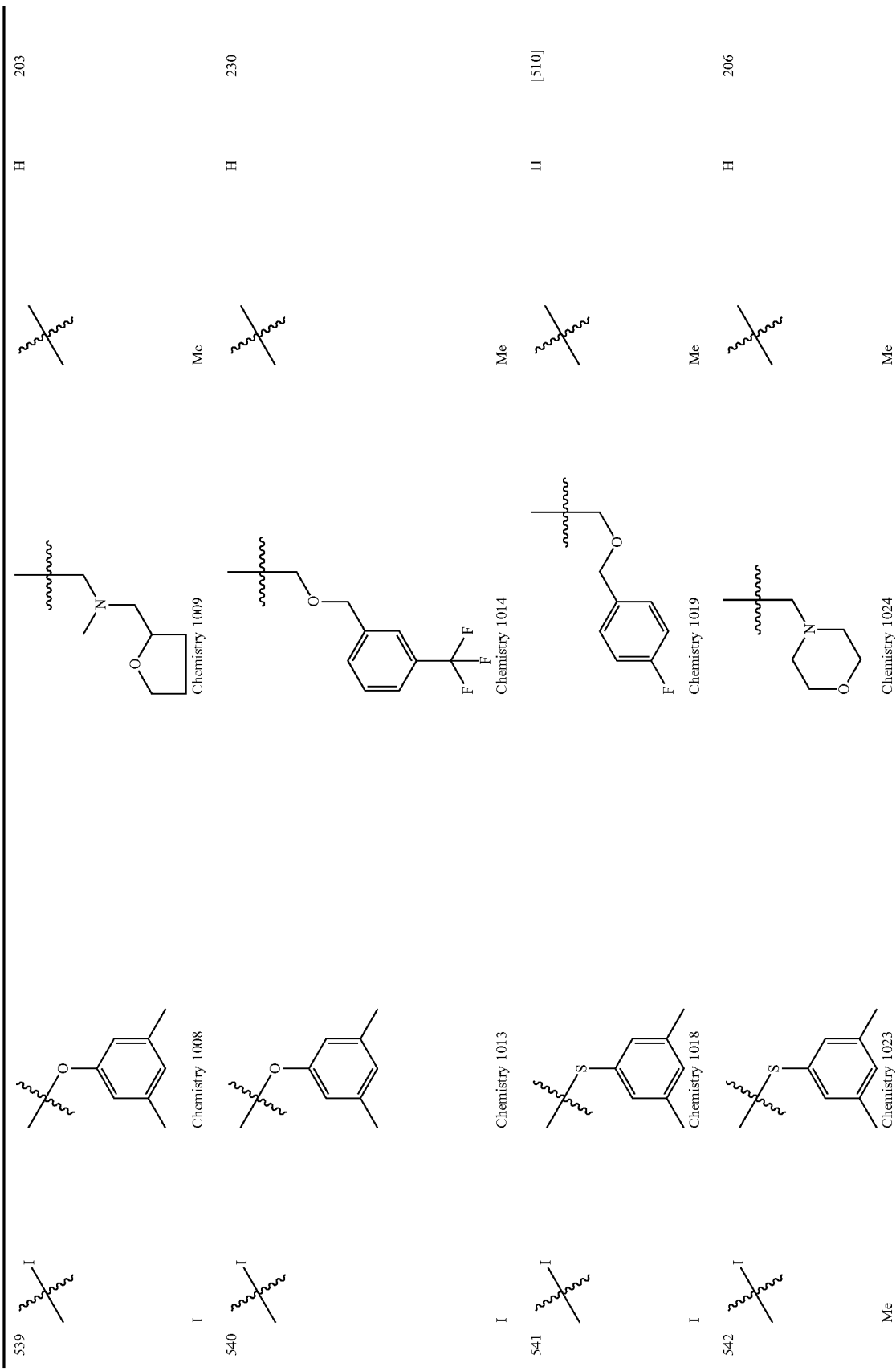

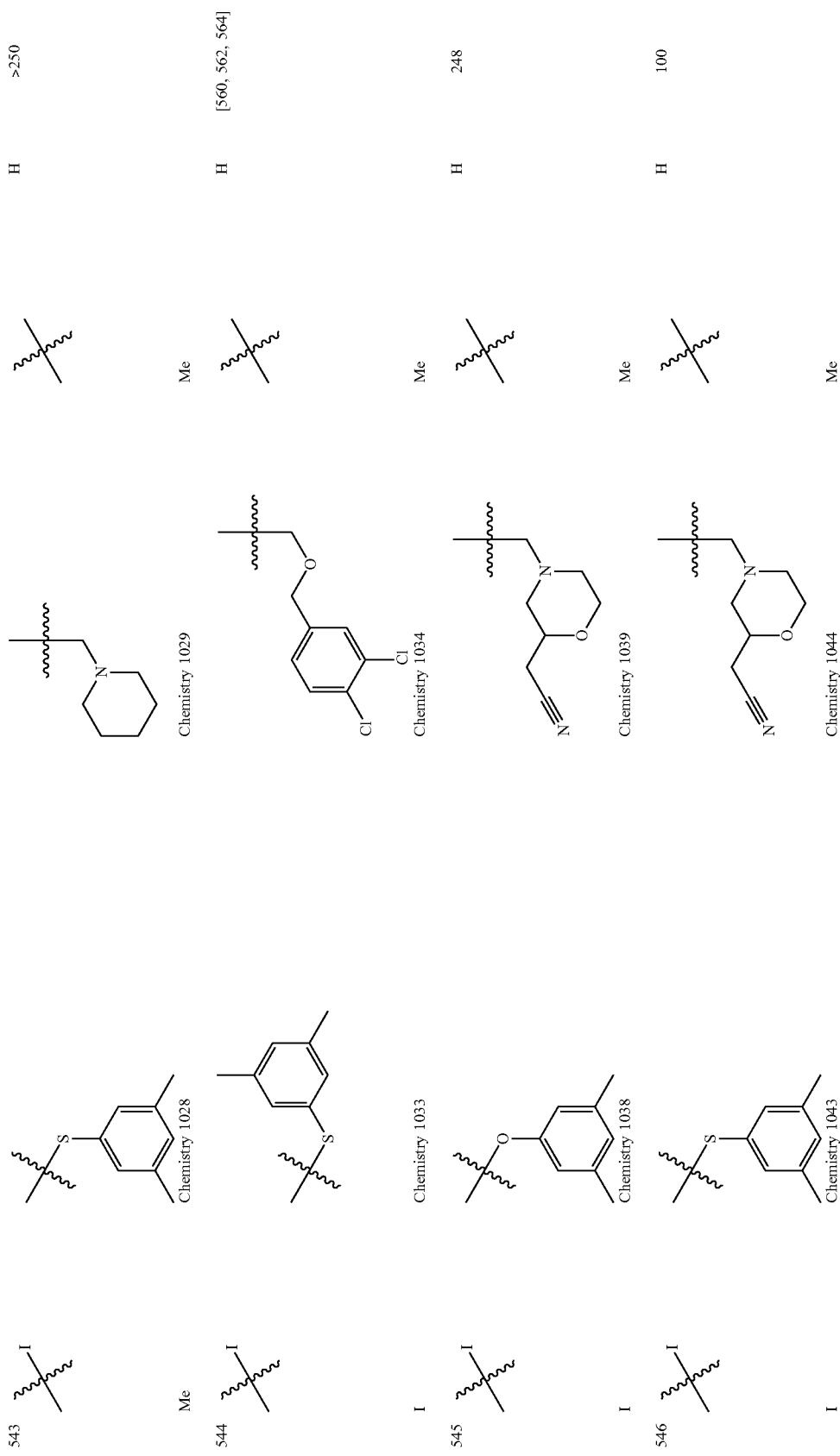

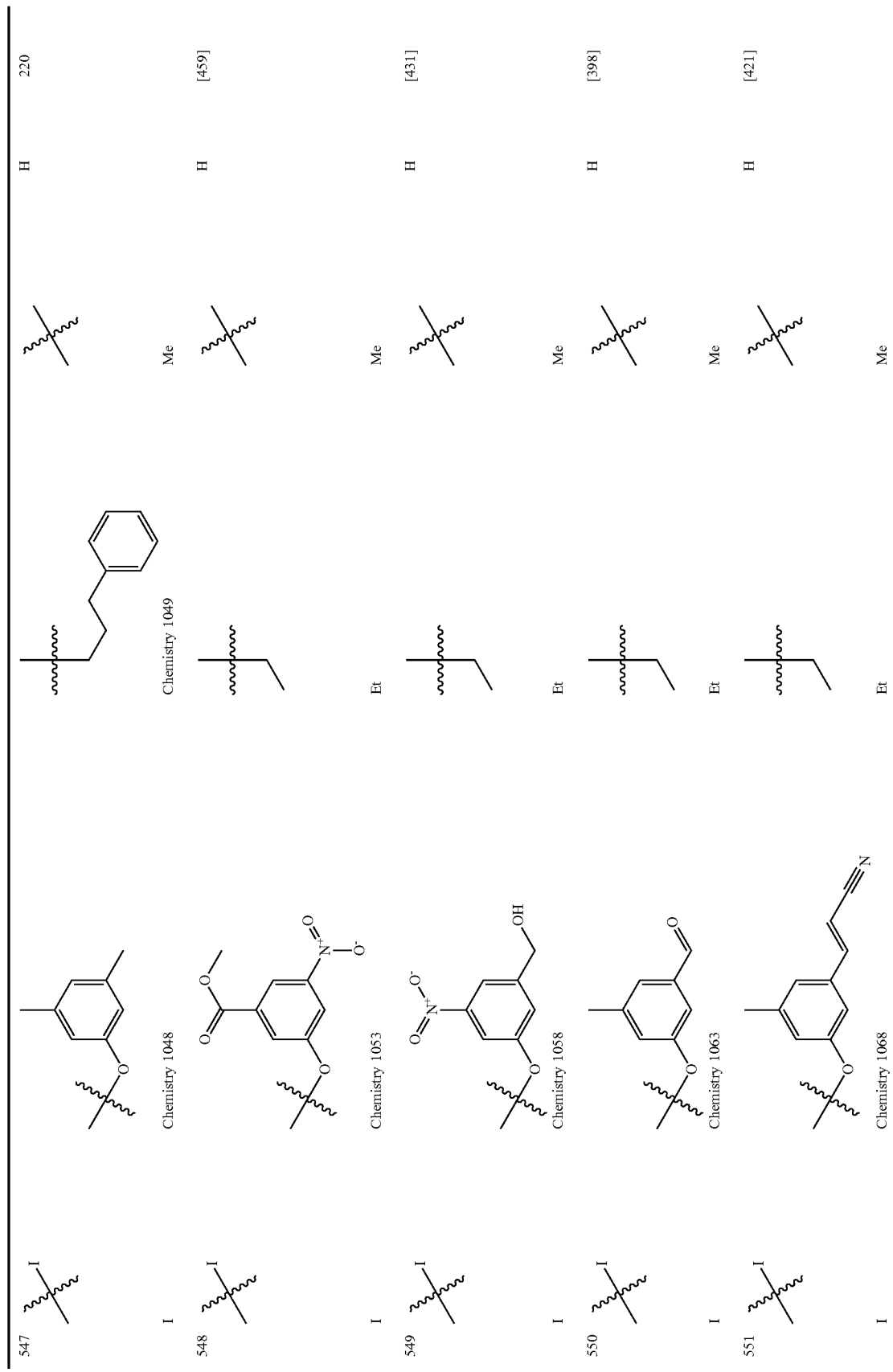

| | | | | | |
|---|---|---|---|---|---|
| 552 | ethyl ester group | | | | |
| 553 | H | | Et | Me | H | [370] |
| 554 | H | Chemistry 1073 | Et | Me | H | [298] |
| 555 | I | Chemistry 1078 | Et | Me | H | [424] |
| 556 | Br | Chemistry 1083 | Et | Me | H | [376, 378] |
| | I | Chemistry 1088 | Et | Me | H | [600] |
| | | Chemistry 1093 | Et | Me | | |

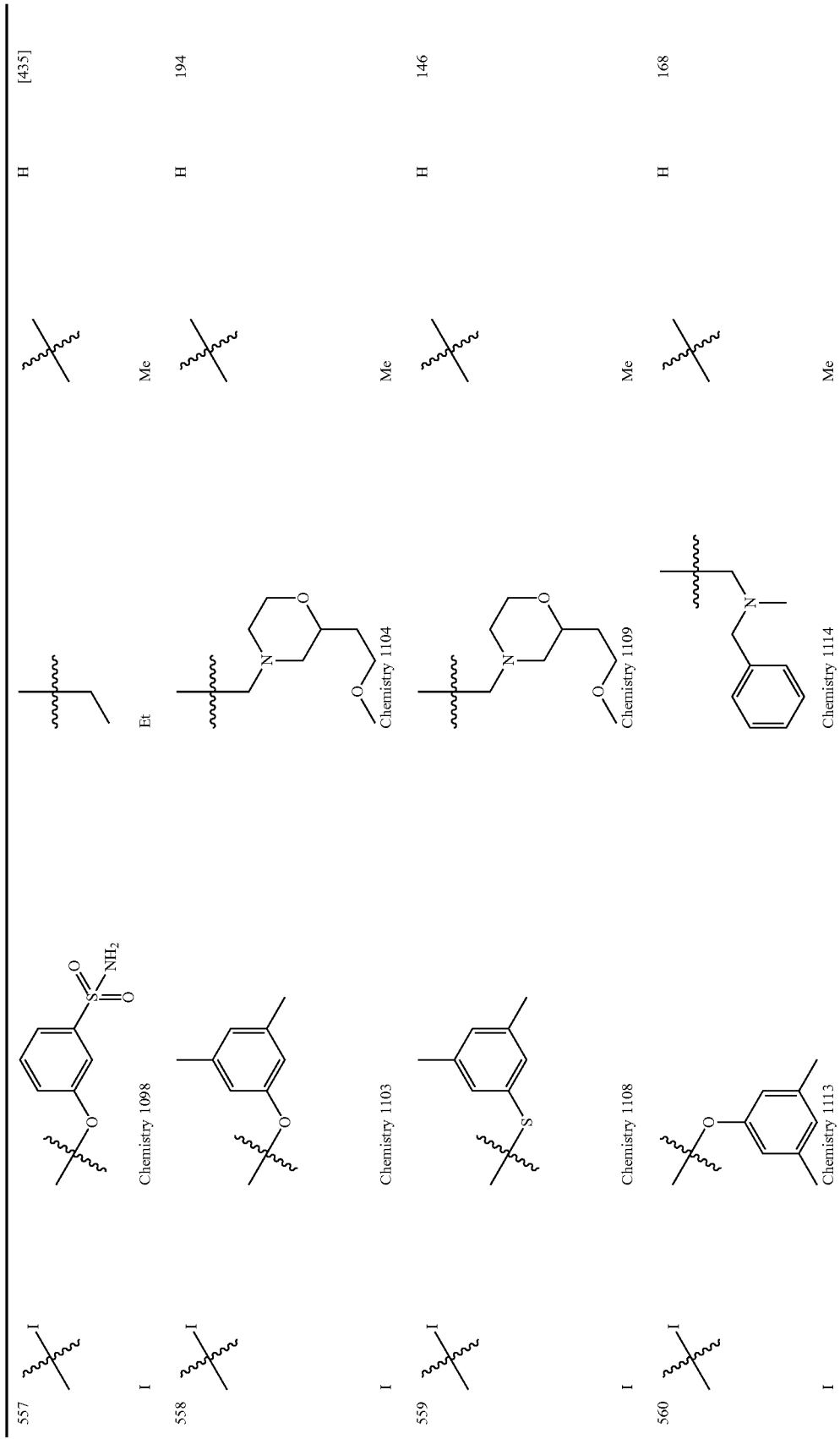

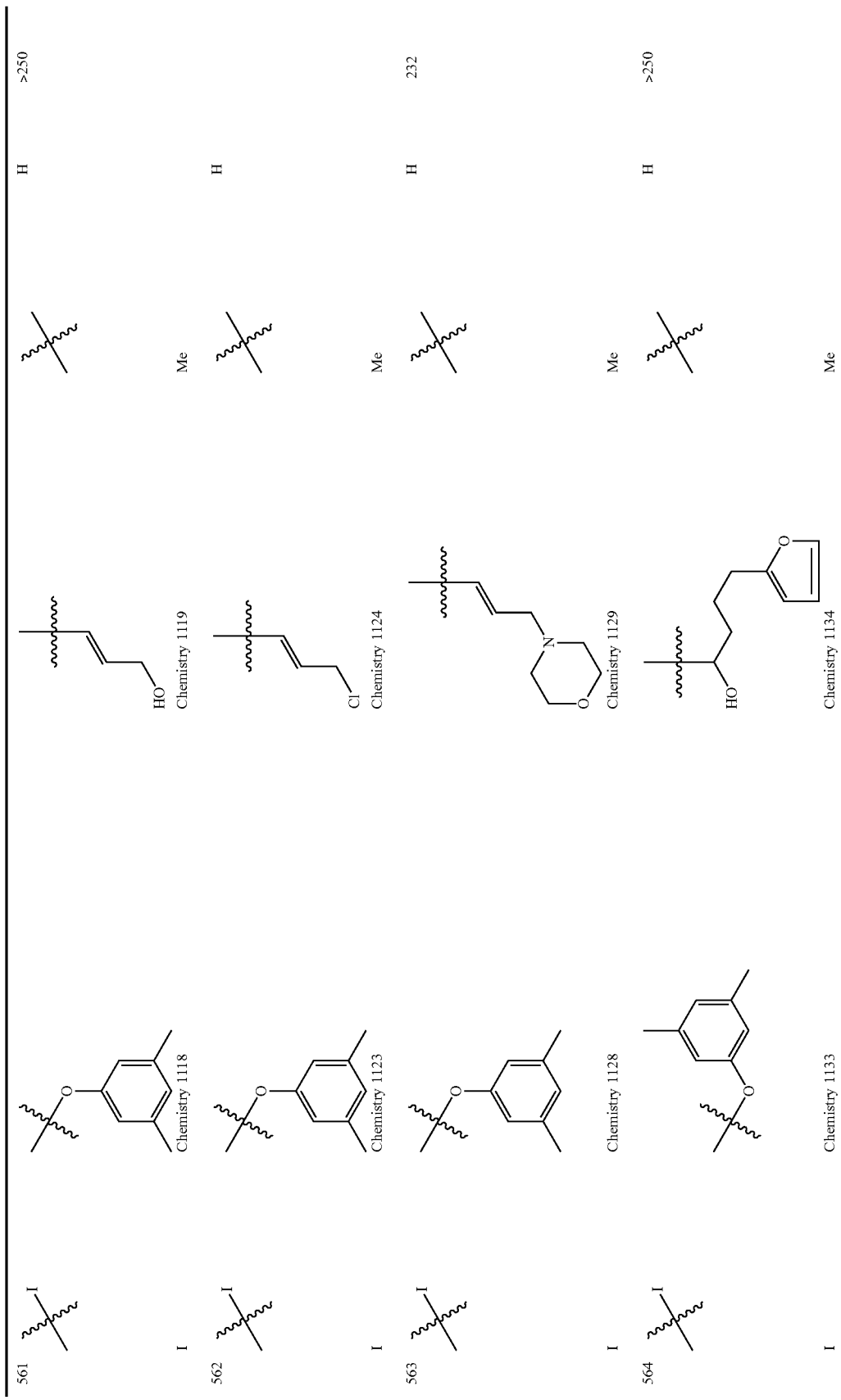

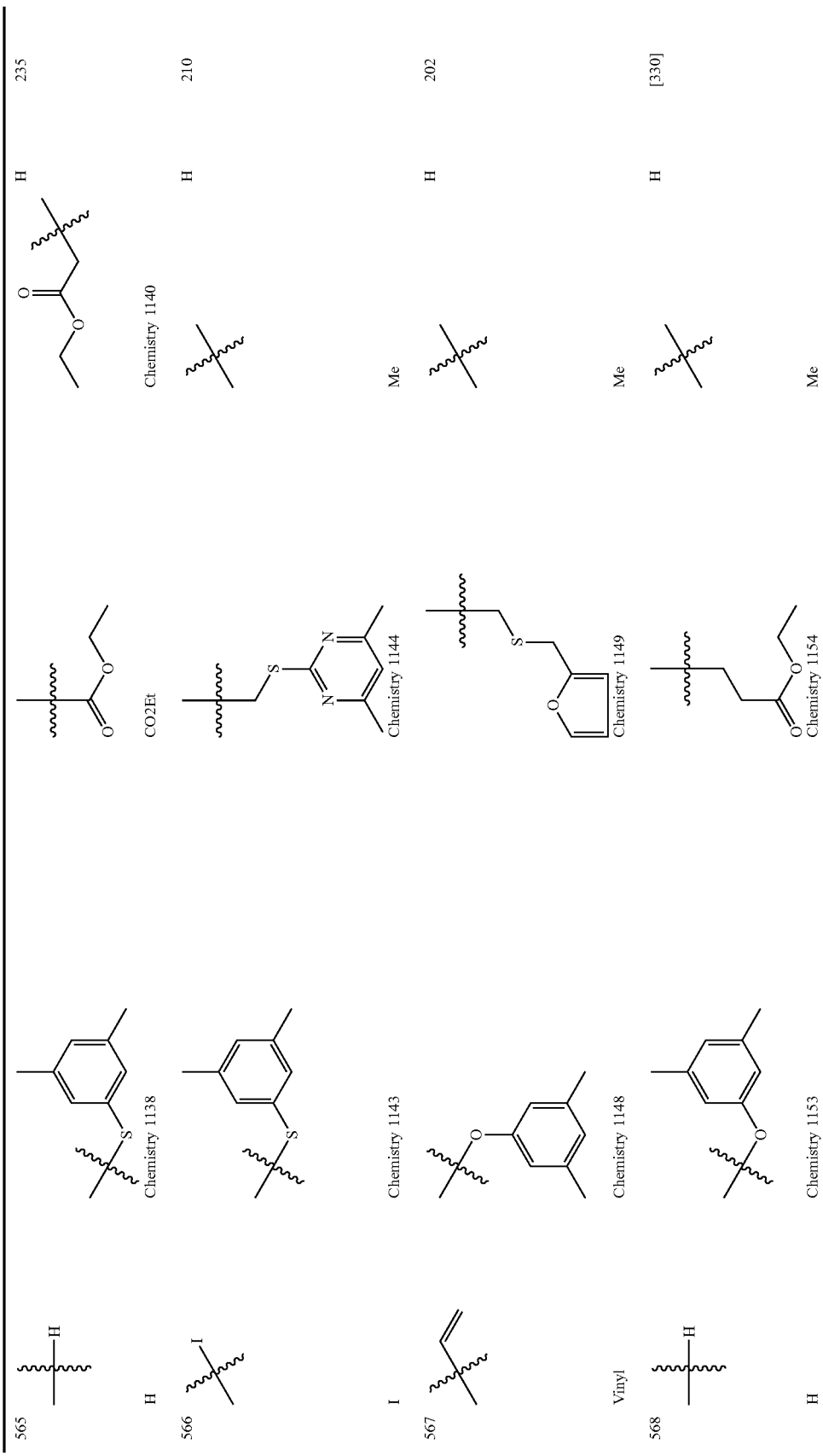

| | | | | |
|---|---|---|---|---|
| 569 | | | ![3,5-dimethylphenoxy](Chemistry 1158) | H | [302] |
| 570 | -NHMe) | ![morpholine amide](Chemistry 1164) Me | ![3,5-dimethylphenoxy](Chemistry 1163) | H | [371] |
| 571 | H | ![morpholine amide](Chemistry 1169) Me | ![3,5-dimethylphenoxy](Chemistry 1168) | H | >250 |
| 572 | I | ![pyrazole](Chemistry 1174) Me | ![3,5-dimethylphenoxy](Chemistry 1173) | H | 230 |

-continued
| | | | | |
|---|---|---|---|---|
| 573 | I | 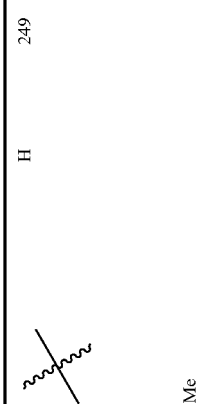 Chemistry 1178 | 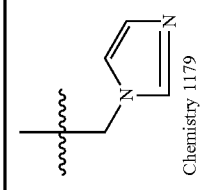 Chemistry 1179 | H | 249 |
| 574 | I |  Chemistry 1183 | 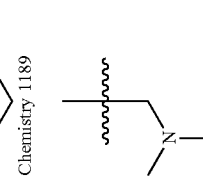 Chemistry 1184 | Me | >250 |
| 575 | I | Chemistry 1188 | Chemistry 1189 | Me | 216 |
| 576 | I | Chemistry 1193 | Chemistry 1194 | Me | >250 |
| 577 | I | Chemistry 1198 | Et | Me | [472] |

| | | | | | |
|---|---|---|---|---|---|
| 578 I | 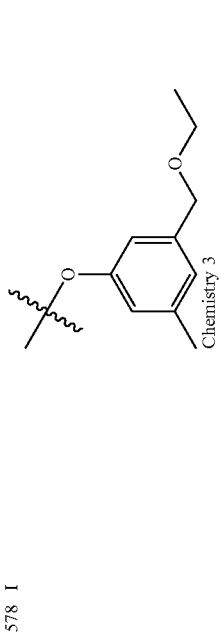 Chemistry 3 |  | Me | H | [427] |
| 579 I | 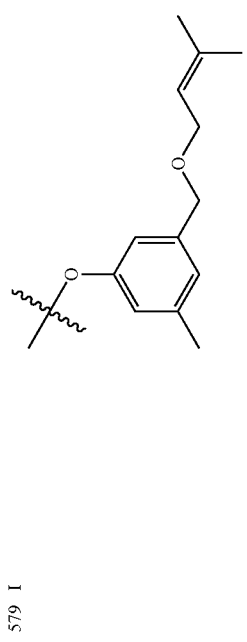 Chemistry 8 |  Et | Me | H | [468] |
| 580 I | 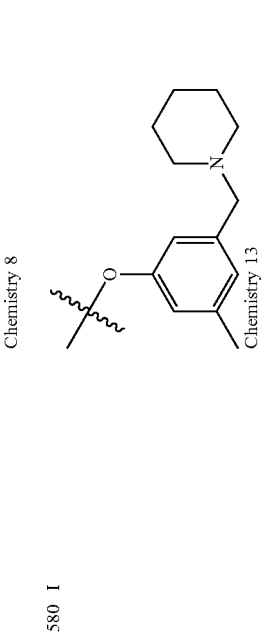 Chemistry 13 |  Et | Me | H | [467] |
| 581 I | 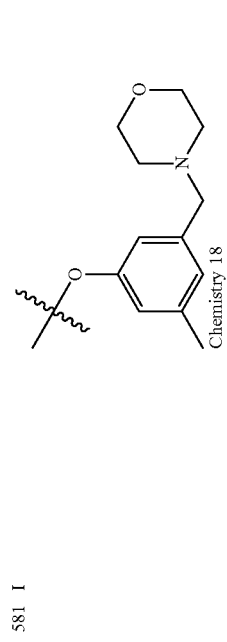 Chemistry 18 | 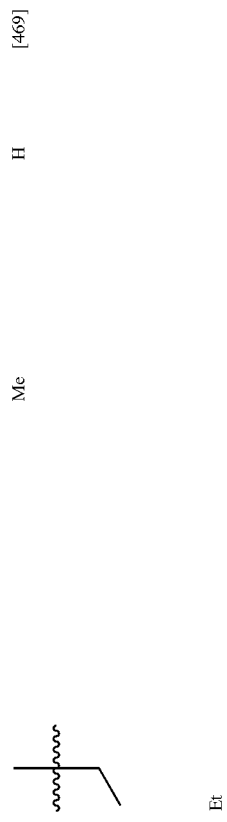 Et | Me | H | [469] |

-continued
| | | | | | |
|---|---|---|---|---|---|
| 582 | I | 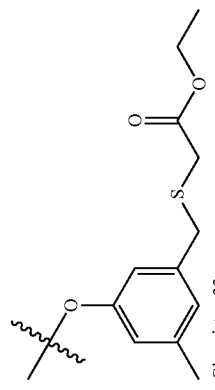 Chemistry 23 | 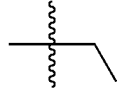 | Me | H | [502] |
| 583 | I | 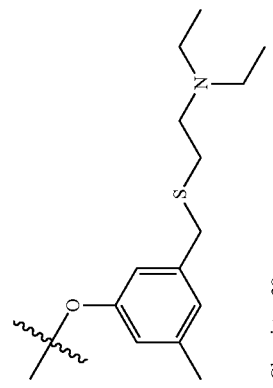 Chemistry 28 | 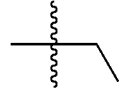 Et | Me | H | [515] |
| 584 | I | 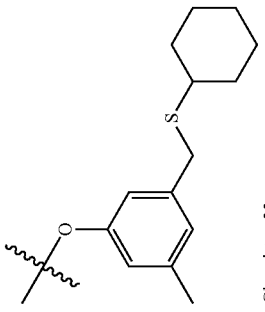 Chemistry 33 | 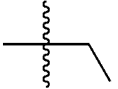 Et | Me | H | [498] |
| 585 | I | 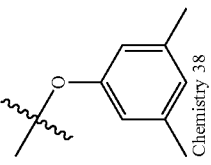 Chemistry 38 | 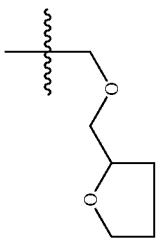 Et Chemistry 39 | Me | H | 180 |

| | | | | | |
|---|---|---|---|---|---|
| 586 I | ![3,5-dimethylphenoxy] Chemistry 43 | ![CH2N(CH2CH2OMe)2] Chemistry 44 | Me | H | 168 |
| 587 I | ![3,5-dimethylphenoxy] Chemistry 48 | ![CH2N(Me)Et] Chemistry 49 | Me | H | 236 |
| 588 I | ![3,5-dimethylphenoxy] Chemistry 53 | ![CH2N(Me)CH2CH2NMe2] Chemistry 54 | Me | H | 228 |
| 589 I | ![3,5-dimethylphenylthio] Chemistry 58 | ![CH2-pyrazole] Chemistry 59 | Me | H | >250 |
| 590 H | ![3,5-dimethylphenoxy] | ![CH2CH2C(O)-3-methoxypiperidine] | Me | H | [399] |

-continued
| | | | | |
|---|---|---|---|---|
| 591 I | 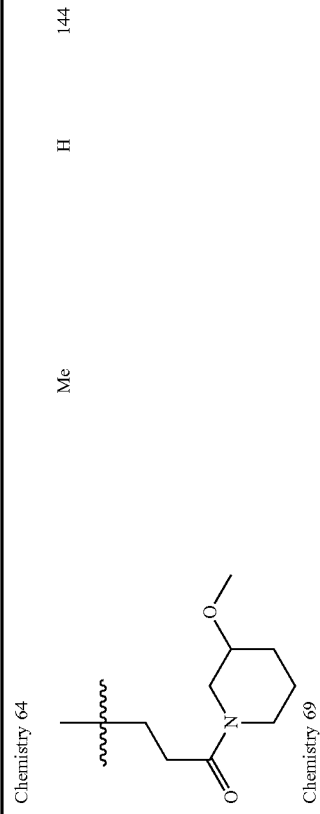 Chemistry 63 | 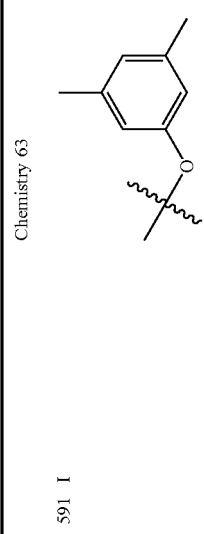 Chemistry 64 | Me | H | 144 |
| 592 I | 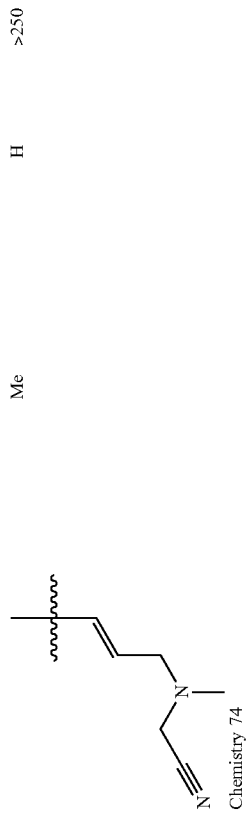 Chemistry 68 | 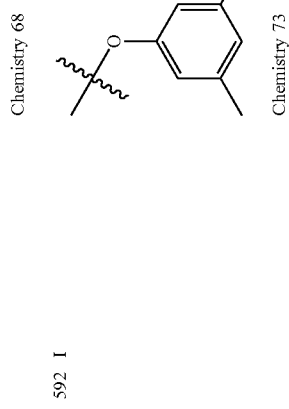 Chemistry 69 | Me | H | >250 |
| 593 I | 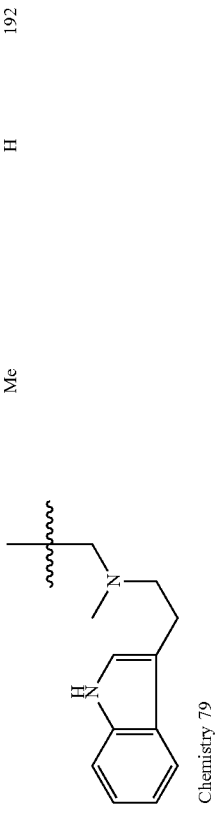 Chemistry 73 |  Chemistry 74 | Me | H | 192 |
| 594 I |  Chemistry 78 |  Chemistry 79 | Me | H | 212 |
| | | 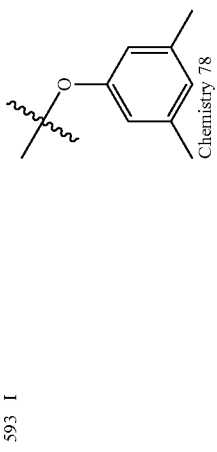 Chemistry 83 | | | |
| | | 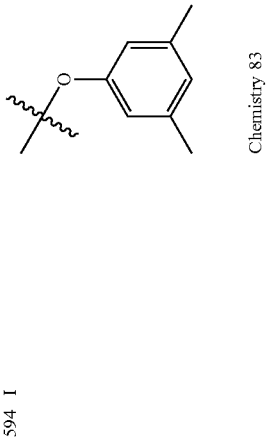 Chemistry 84 | | | |

-continued
| | | | | |
|---|---|---|---|---|
| 595 | I | 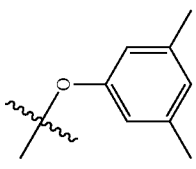 Chemistry 88 | 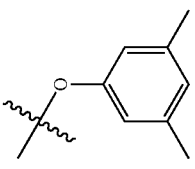 Chemistry 89 | Me | H | >250 |
| 596 | I | 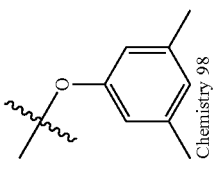 Chemistry 93 | 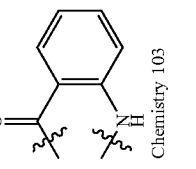 Chemistry 94 | Me | H | [466] |
| 597 | I | 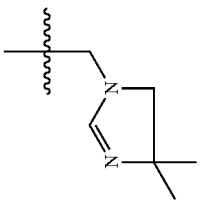 Chemistry 98 | 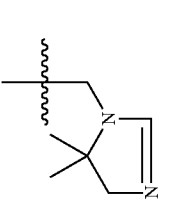 Chemistry 99 | Me | H | >250 |
| 598 | Chemistry 102 | 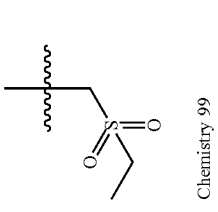 Chemistry 103 | 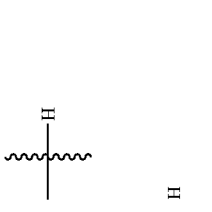 | Me | H | [227] |

| | | | | | |
|---|---|---|---|---|---|
| 599 Chemistry 107 | 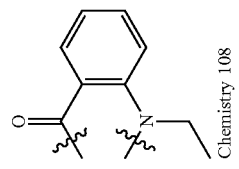 Chemistry 108 | H | Me | H | [255] |
| 600 Chemistry 112 | 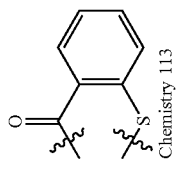 Chemistry 113 | H | Me | H | [244] |
| 601 Chemistry 117 | 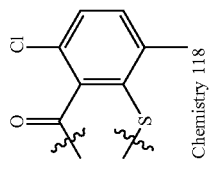 Chemistry 118 | H | Me | H | [291] |

-continued
| | | | | | |
|---|---|---|---|---|---|
| 602 | I |  | 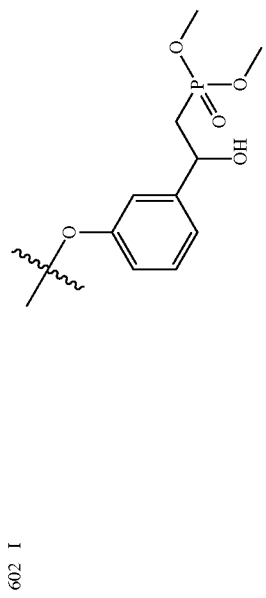 | Me | H | [508] |
| 603 | I | 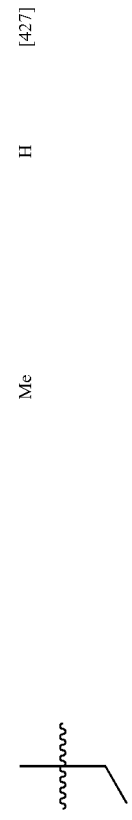 Et | 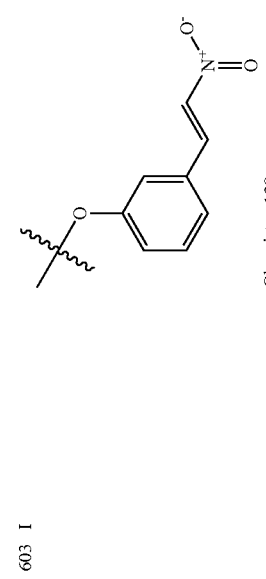 | Me | H | [427] |
| 604 | I | 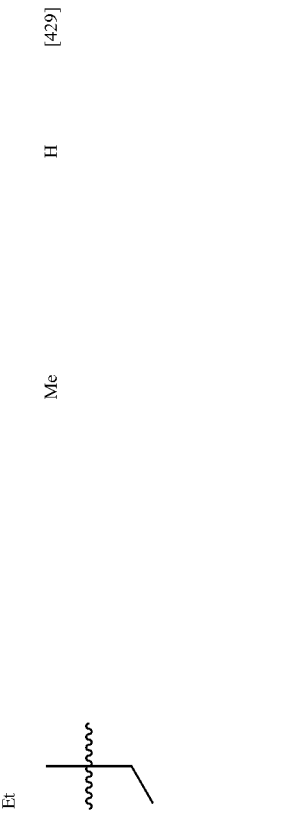 Et | 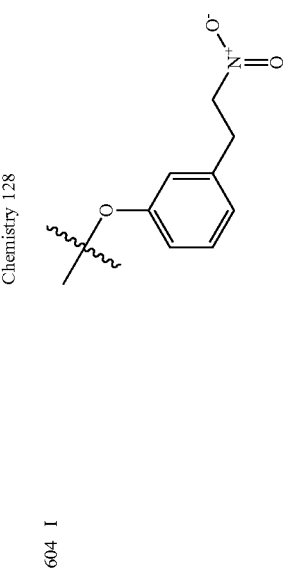 | Me | H | [429] |
Chemistry 123
Chemistry 128
Chemistry 133

| | | | | | |
|---|---|---|---|---|---|
| 605 | I | 3,5-dimethylphenoxy (Chemistry 138) | pentenyl-methoxypiperidine (Chemistry 139) | Me | H | 178 |
| 606 | I | 3,5-dimethylphenylthio (Chemistry 143) | imidazolyl-ethyl (Chemistry 144) | Me | H | 120 |
| 607 | I | 3,5-dimethylphenoxy (Chemistry 148) | N,N-bis(cyanoethyl)aminomethyl (Chemistry 149) | Me | H | >250 |
| 608 | I | 3,5-dimethylphenoxy (Chemistry 153) | dihydropyrrolyl-methyl (Chemistry 154) | Me | H | [437] |

| | | | | |
|---|---|---|---|---|
| 609 | I |   Chemistry 158 | 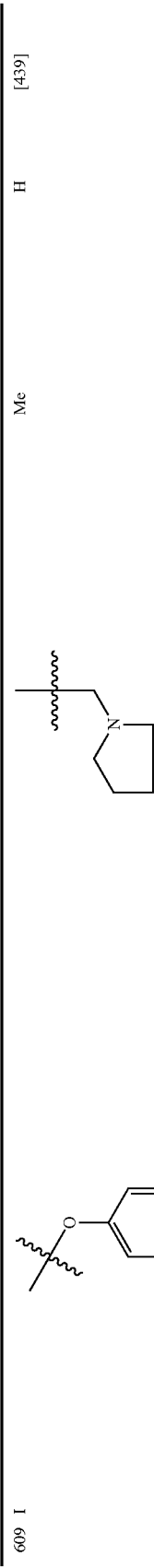  Chemistry 159 | Me | H | [439] |
| 610 | I |   Chemistry 163 | 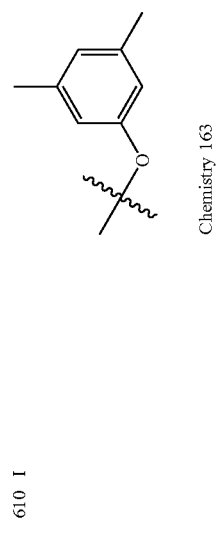  Chemistry 164 | Me | H | [426] |
| 611 | I | Chemistry 168 |   Chemistry 169 | Me | H | >250 |

| | | | | |
|---|---|---|---|---|
| 612 | H | Chemistry 173 | CO2Et) CO2Et | Me | H | [302] |
| 613 | Br | Chemistry 178 | CO2Et | Me | H | [381] |
| 614 | Br | Chemistry 183 | CH2OH | Me | H | [338, 340] |
| 615 | Br | Chemistry 188 | CH2Cl | Me | H |  |
| 616 | Br | Chemistry 193 | Chemistry 194 (morpholinylmethyl) | Me | H | >250 |

| | | | | |
|---|---|---|---|---|
| 617 | I | 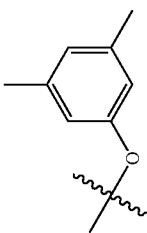  Chemistry 198 | 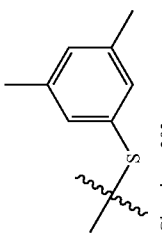  Chemistry 199 | Me | H | >250 |
| 618 | I | 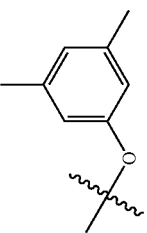  Chemistry 203 | 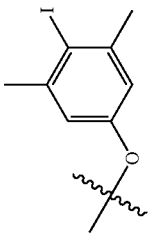  Chemistry 204 | Me | H | [451] |
| 619 | I | 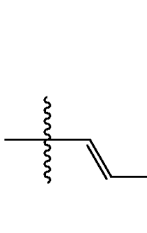  Chemistry 508 | 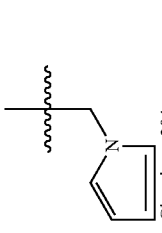  Chemistry 209 | Me | H | [513] |
| 620 | I | 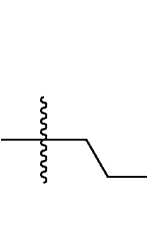  Chemistry 213 | 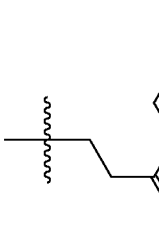  Chemistry 214 | Me | H | [639] |

| | | | | | |
|---|---|---|---|---|---|
| 621 | I | ![Chemistry 218] | ![Chemistry 219] | Me | H | [456] |
| 622 | I | ![Chemistry 223] | ![Chemistry 224] | Me | H | [582] |
| 623 | I | ![Chemistry 228] | ![Chemistry 229] CH2CH2CO2H | Me | H | [428] |
| 624 | I | ![Chemistry 233] | ![Chemistry 234] CH2CH2CO2H | Me | H | [554] |

| | | | | | |
|---|---|---|---|---|---|
| 626 | ![3,5-dimethylphenoxy] Chemistry 238 | ![N-(pyridin-3-ylmethyl)-N-(2-cyanoethyl)amino] Chemistry 239 | Me | H | [529] |
| 626 | ![3,5-dimethylphenoxy] Chemistry 243 | ![N-methylacrylamide] Chemistry 244 | Me | H | [453] |
| 627 | ![3,5-dimethylphenoxy] Chemistry 248 | ![N,N-diethylacrylamide] Chemistry 249 | Me | H | [481] |

| 628 | I |  | 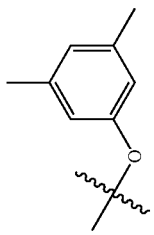 Chemistry 254 | Me | H | [541] |
| 629 | I | | 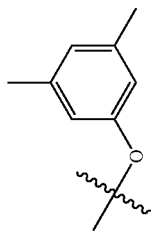 Chemistry 259 | Me | H | [510] |
| 630 | I | 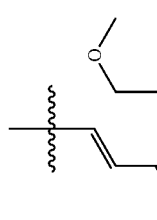 CHemistry 258 | 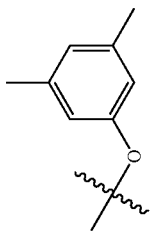 Chemistry 264 | Me | H | [483] |
| 631 | I |  Chemistry 263 | 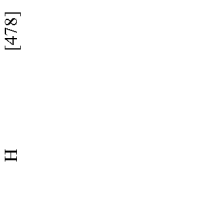 | Me | H | [478] |
(Note: table reconstructed — rows 628–631 with dimethylphenoxy group in column 3, acrylamide variants in column 4, Me, H, and bracketed numbers.)

| | | | | |
|---|---|---|---|---|
| 632 | Chemistry 268 | Chemistry 269 | Me | H | [492] |
| 633 | Chemistry 273 | Chemistry 274 | Me | H | [586] |
| 634 | Chemistry 278 | Chemistry 279 | Me | H | [493] |

| | | | | | |
|---|---|---|---|---|---|
| 635 | I | ![3,5-dimethylphenoxy] | ![N-methylpiperidine amide] Chemistry 289 | Me | H | [536] |
| 636 | I | ![3,5-dimethylphenoxy] Chemistry 293 | ![thiomorpholine amide] Chemistry 294 | Me | H | [511] |
| 637 | I | ![3,5-dimethylphenoxy] Chemistry 293 | ![dimethylmorpholine amide] Chemistry 299 | Me | H | [523] |
| 638 | I | ![3,5-dimethylphenoxy] Chemistry 298 | ![N-methylpiperazine amide] | Me | H | [508] |

-continued
| | | | | |
|---|---|---|---|---|
| 639 | I | 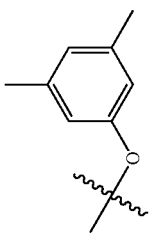 Chemistry 303 | 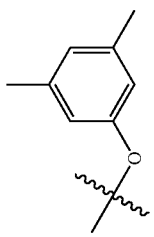 Chemistry 304 | Me | H | [584] |
| 640 | I | 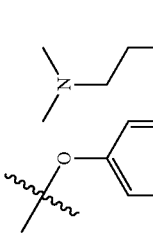 Chemistry 308 | 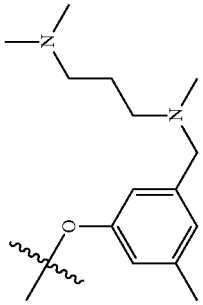 Chemistry 309 | Me | H | [571] |
| 641 | I | 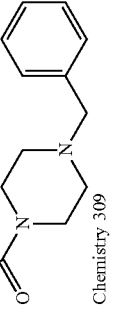 Chemistry 313 | 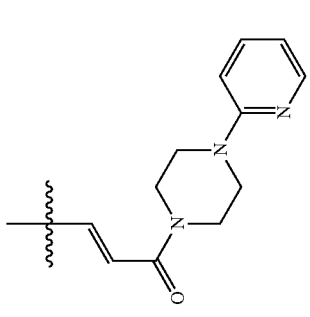 Chemistry 314 | Me | H | [484] |
| 642 | I |  Chemistry 318 | 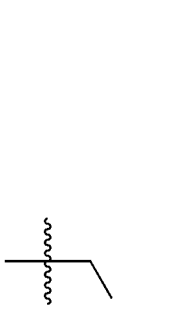 Et | Me | H | [498] |

| | | | | | |
|---|---|---|---|---|---|
| 643 | I | 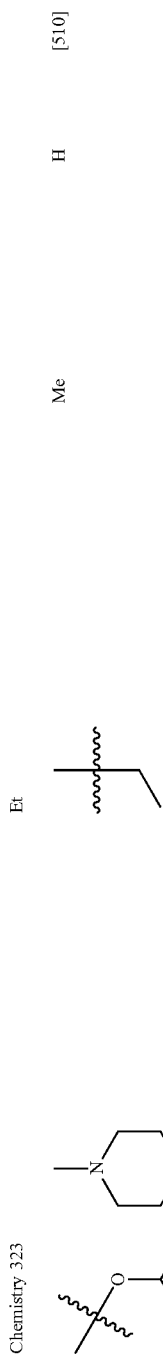 Chemistry 323 | Et | Me | H | [510] |
| 644 | I | 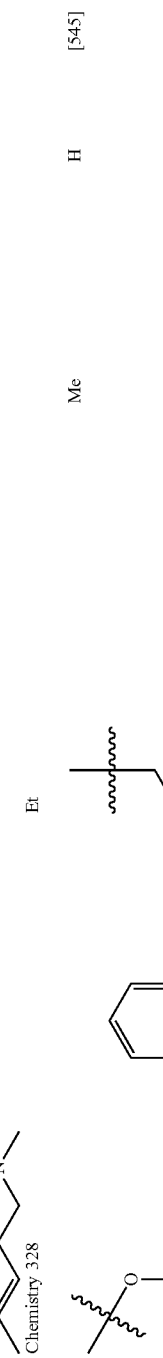 Chemistry 328 | Et | Me | H | [545] |
| 645 | I | 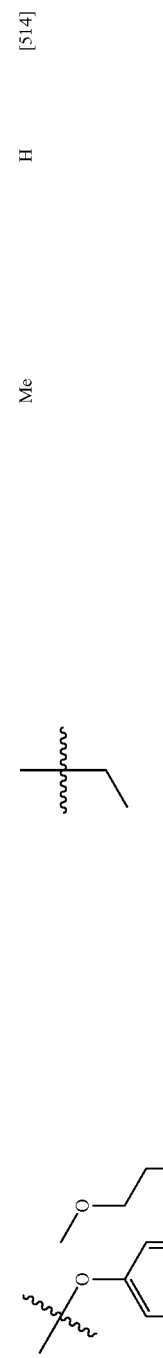 Chemistry 333 | Et | Me | H | [514] |
| 646 | I | 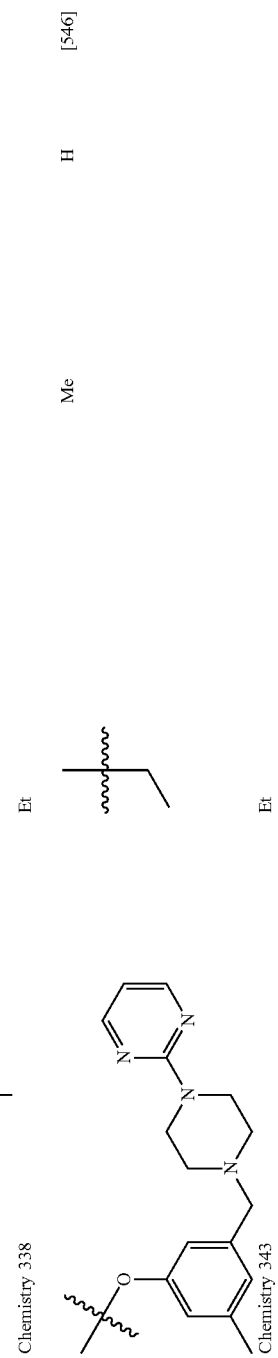 Chemistry 338 | Et | Me | H | [546] |

| | | | | |
|---|---|---|---|---|
| 647 I | 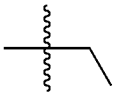 Chemistry 348 | 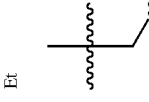 | Me | H | [497] |
| 648 I | 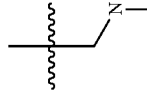 Chemistry 353 | Et | Me | H | >250 |
| 649 I | 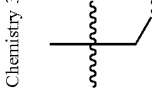 Chemistry 354 | 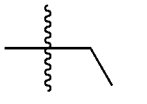 Chemistry 354 | Me | H | 165 |
| 650 I | 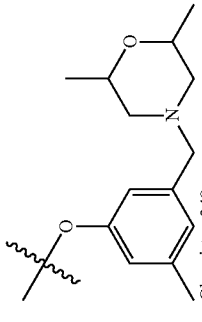 Chemistry 358 | 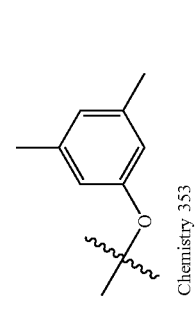 Chemistry 359 | Me | H | 181 |
| 651 I | 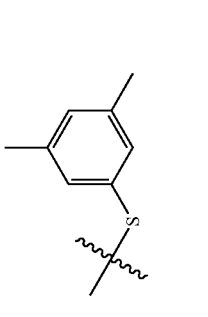 Chemistry 363 | 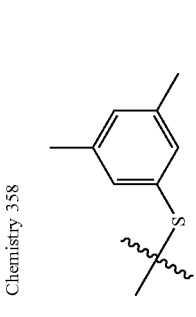 Chemistry 364 | Me | H | [497] |
| | 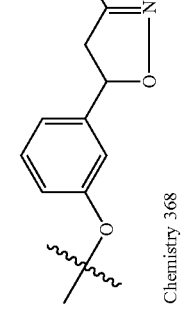 Chemistry 368 | Et | | | |

| | | | | |
|---|---|---|---|---|
| 652 I | (3-(3-(p-tolyl)-4,5-dihydroisoxazol-5-yl)phenoxy) | Et | Me | H | [515] |
| 653 I | (3,5-dimethylphenoxy) | NH-C(O)-O-Et (NHCO2Et) | Me | H | [443] |
| 654 I | (2-aminophenoxy) | Et | Me | H | [371] |
| 655 H | (2-aminophenoxy) | Et | Me | H | [245] |
| 656 I | (3-methoxyphenoxy) | Et | Me | H | [386] |

Chemistry 373, Chemistry 378, Chemistry 383, Chemistry 388, Chemistry 393

-continued
| | | | | | |
|---|---|---|---|---|---|
| 657 | I |  Chemistry 398 | 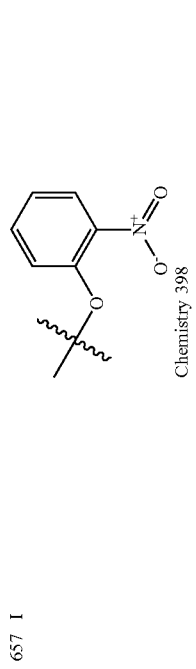 | Me | H | [401] |
| 658 | I |  Chemistry 403 | 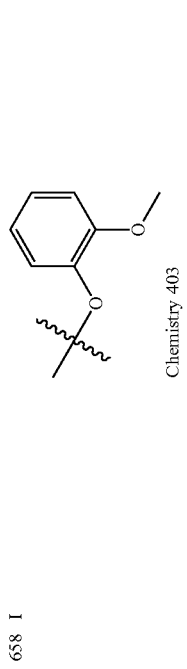 Et | Me | H | [386] |
| 659 | I |  Chemistry 408 | 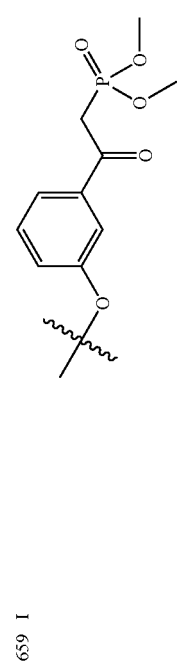 Et | Me | H | [506] |
| 660 | Br | 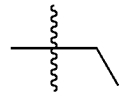 Chemistry 413 | 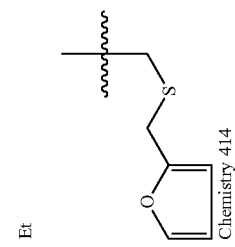 Chemistry 414 | Me | H | >250 |
| 661 | Br | 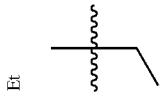 Chemistry 418 | 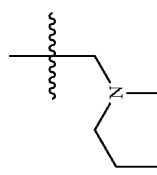 Chemistry 419 | Me | H | >250 |

| | | | | | |
|---|---|---|---|---|---|
| 662 | Chemistry 423 | Chemistry 424 | Me | H | >250 |
| 663 | Chemistry 428 | Chemistry 429 | Me | H | [552] |
| 664 | Chemistry 433 | Chemistry 434 | Me | H | [483] |

| | | | | |
|---|---|---|---|---|
| 665 | 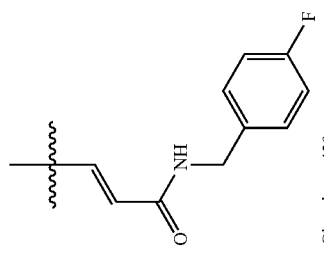 | 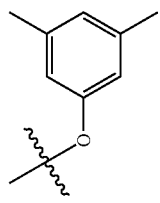Chemistry 439 | Me | H | [533] |
| 666 | 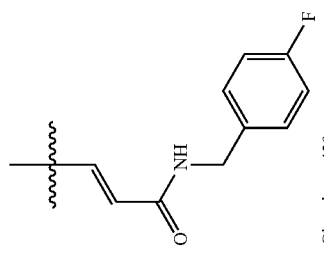<br>Chemistry 443 | 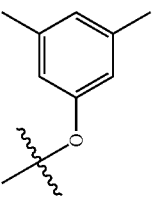Chemistry 444 | Me | H | [559] |

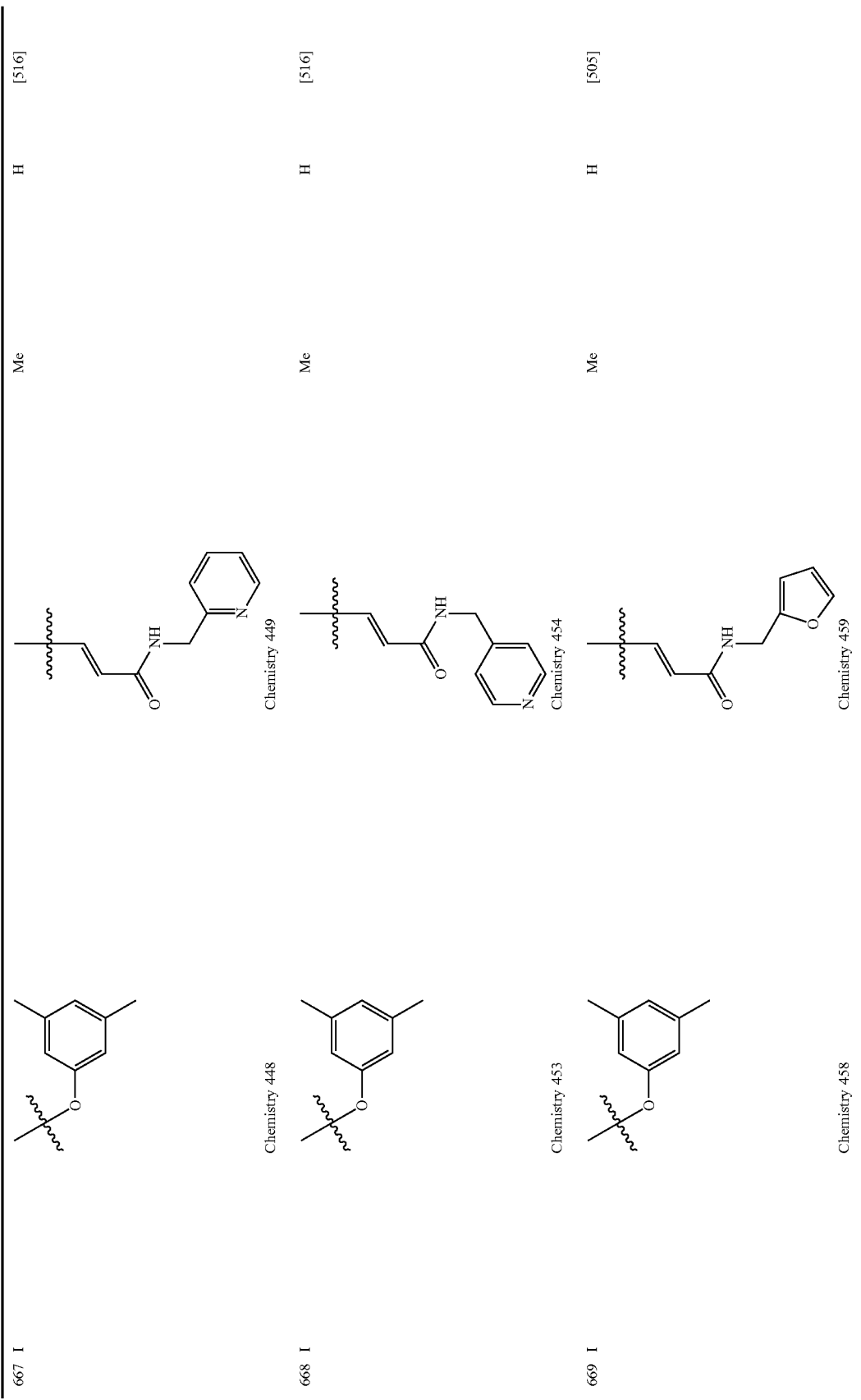

-continued
| | | | | | |
|---|---|---|---|---|---|
| 670 | I | 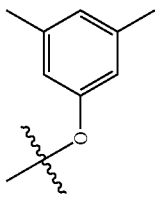Chemistry 463 | 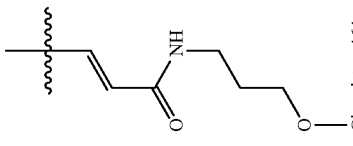Chemistry 464 | Me | H | [497] |
| 671 | I | 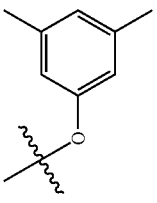Chemistry 468 | Chemistry 469 | Me | H | [513] |

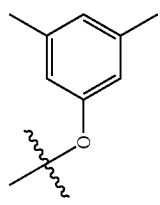
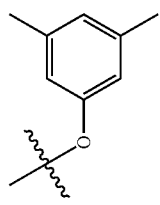

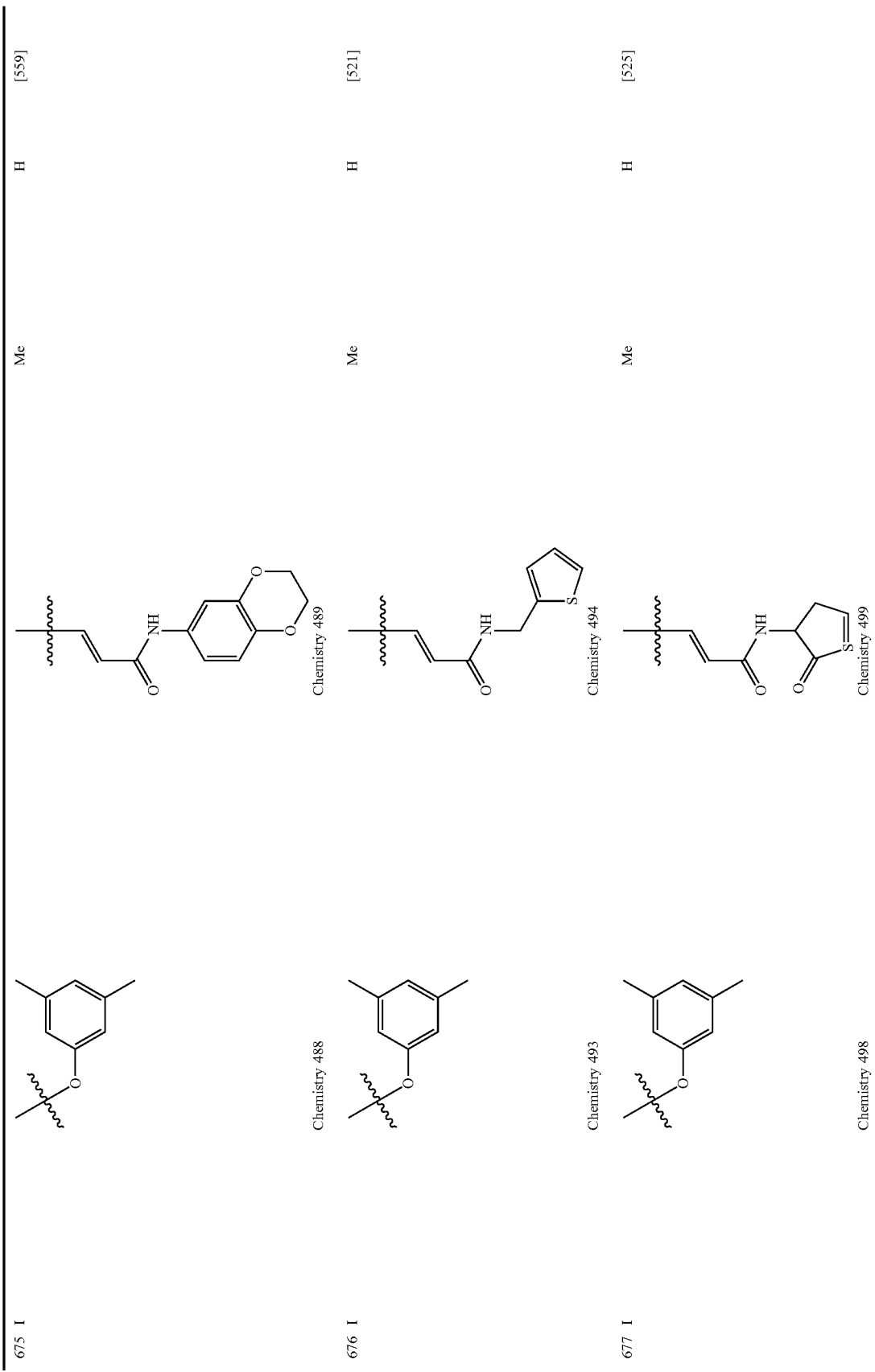

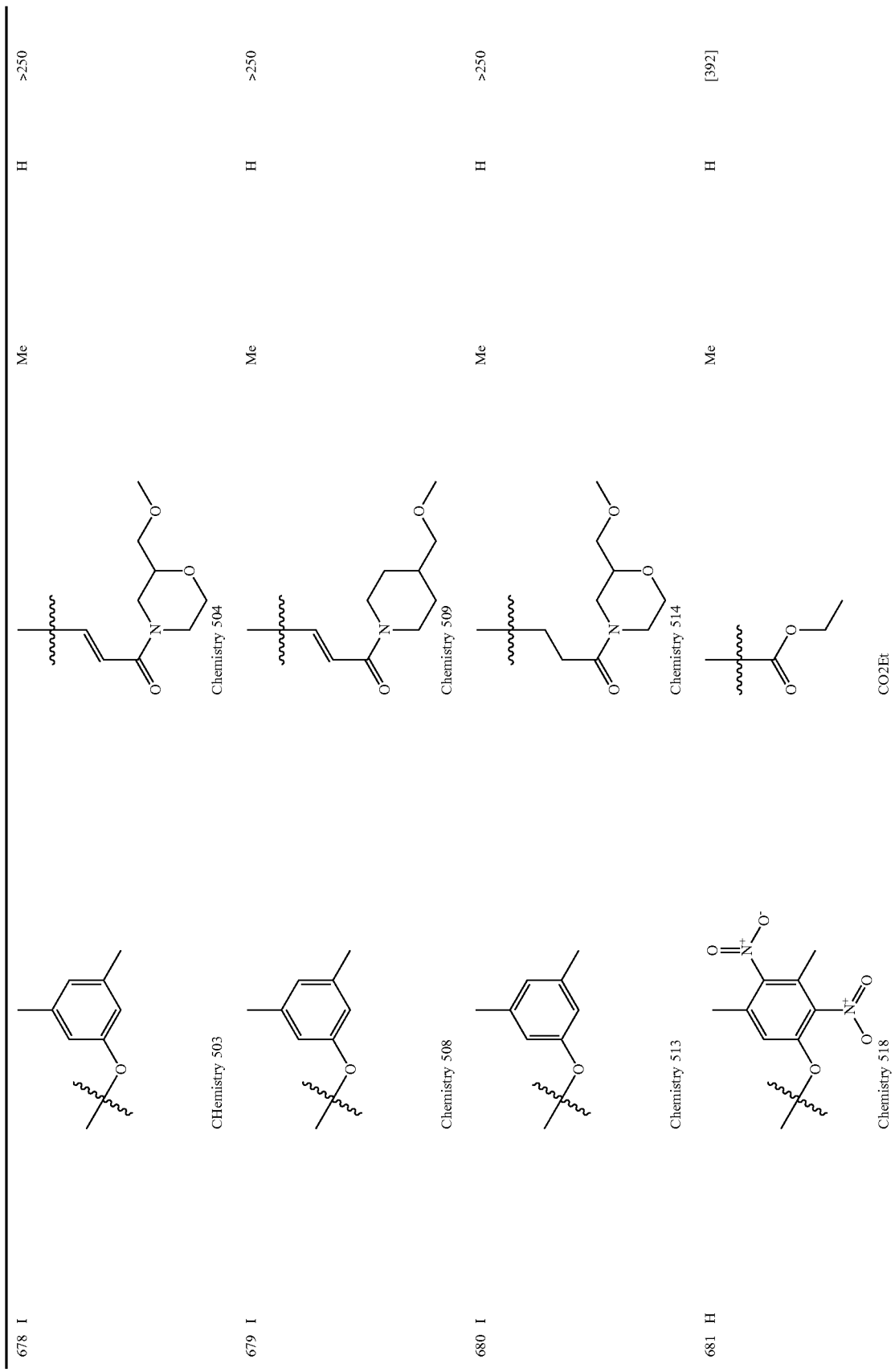

| | | | | |
|---|---|---|---|---|
| 682 I | ![Chemistry 523] | Et | Me | H | [440] |
| 683 I | ![Chemistry 528] | Et | Me | H | [492] |
| 684 I | ![Chemistry 533] | Et | Me | H | [486] |
| 685 I | ![Chemistry 538] | Et | Me | H | [412] |

| | | | | |
|---|---|---|---|---|
| 686 | I | ![structure with OH, Chemistry 543] | ![wavy Et] | Me | H | [414] |
| 687 | I | ![Chemistry 548] | ![wavy Et] | Me | H | [398] |
| 688 | H | ![Chemistry 553] | ![wavy Et] | Me | H | [272] |
| 689 | CO2Et | ![Chemistry 558] | ![wavy Et] | Me | H | [344] |

| | | | | |
|---|---|---|---|---|
| 690 | H |  | 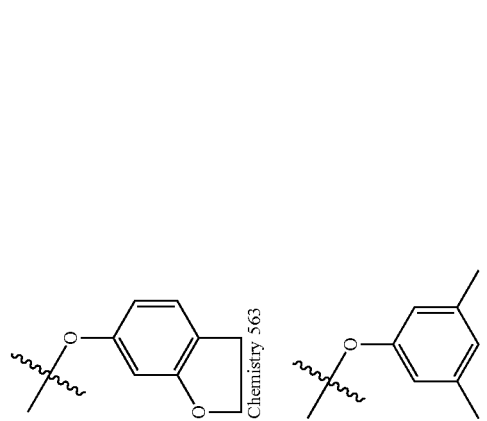 | Me | H | [272] |
| 691 | I |  Chemistry 568 | Et | Me | H | [471] |
| 692 | I |  Chemistry 573 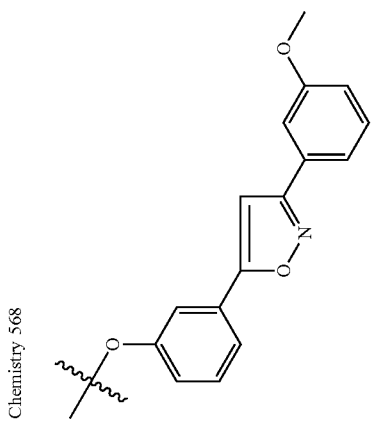 | 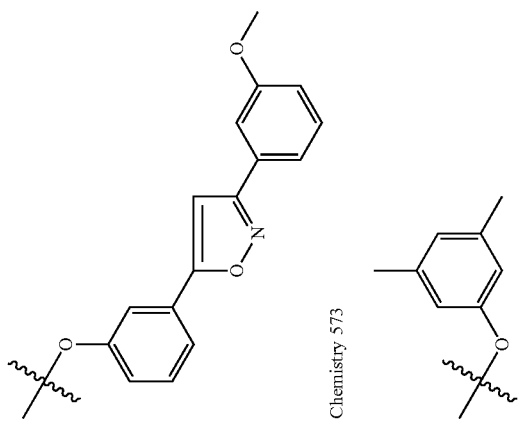 | Me | H | [531] |
| 693 | I |  | Et | Me | H | [468] |

| | | | | | |
|---|---|---|---|---|---|
| 694 | I | 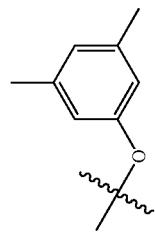 Chemistry 578 | 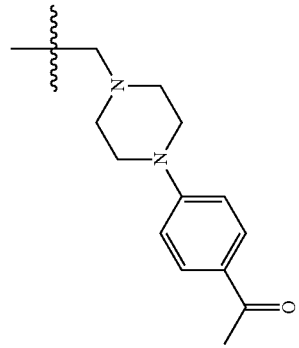 Chemistry 579 | Me | H | [572] |
| 695 | I | 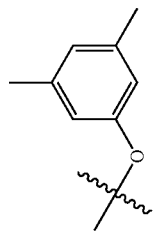 Chemistry 583 | 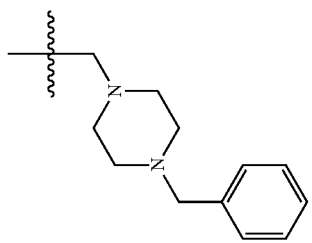 Chemistry 584 | Me | H | [544] |
| 696 | I | 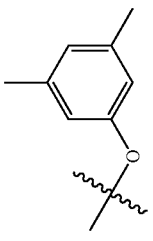 Chemistry 588 | 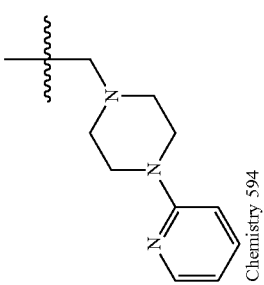 Chemistry 589 | Me | H | [531] |

| | | | | |
|---|---|---|---|---|
| 697 I | 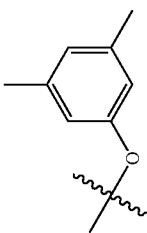 Chemistry 598 | 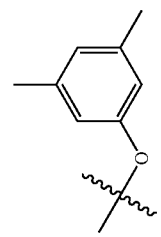 Chemistry 599 | Me | H | [482] |
| 698 I | 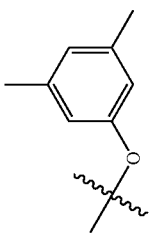 Chemistry 603 | 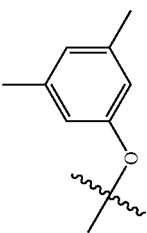 Chemistry 604 | Me | H | [557] |
| 699 I | 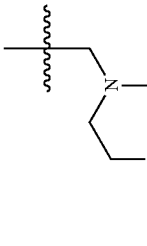 Chemistry 608 | 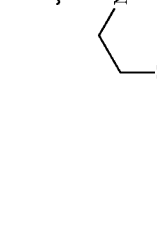 Chemistry 609 | Me | H | [598, 600, 602] |
| 700 I | 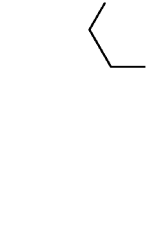 Chemistry 613 | 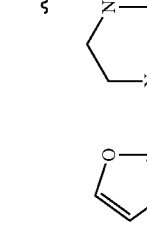 Chemistry 614 | Me | H | [548] |

| | | | | | |
|---|---|---|---|---|---|
| 701 | I | 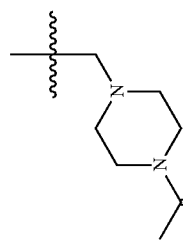 | 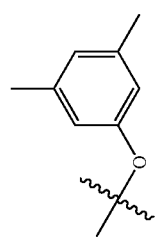 Chemistry 619 | Me | H | [496] |
| 702 | I | 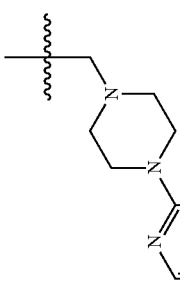 | 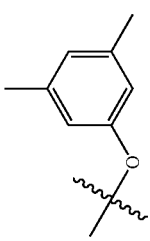 Chemistry 624 | Me | H | [532] |
| 703 | I | 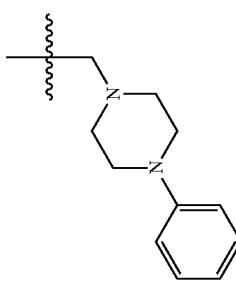 | 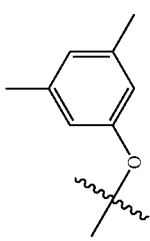 Chemistry 629 | Me | H | [544] |
| 704 | I | 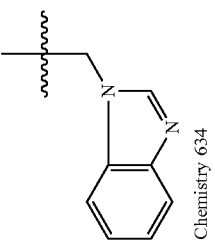 | 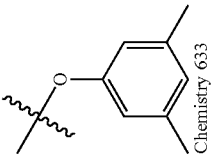 Chemistry 634 | Me | H | >250 |

| | | | | |
|---|---|---|---|---|
| 705 I |  Chemistry 638 |  Chemistry 639 | Me | H | [530] |
| 706 I |  Chemistry 643 |  Chemistry 644 | Me | H | [450] |
| 707 I |  Chemistry 648 |  Chemistry 649 | Me | H | [542, 544] |
| 708 I | 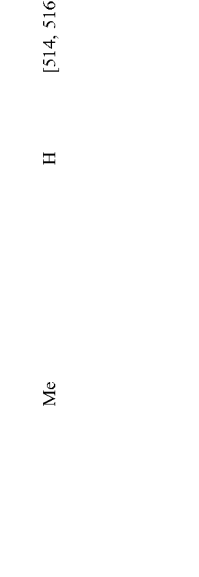 Chemistry 653 |  Chemistry 654 | Me | H | [514, 516] |

-continued

| | | | | |
|---|---|---|---|---|
| 709 | I | ![3,5-dimethylphenoxy] Chemistry 658 | ![4-Br-pyrazolylmethyl] Chemistry 659 | Me | H | [528, 530] |
| 710 | I | ![3,5-dimethylphenoxy] Chemistry 663 | ![3-phenyl-triazolylmethyl] Chemistry 664 | Me | H | [513] |
| 711 | I | ![3,5-dimethylphenoxy] Chemistry 668 | ![triazolylmethyl] Chemistry 669 | Me | H | [438] |
| 712 | I | ![3,5-dimethylphenoxy] Chemistry 673 | ![3-amino-pyrazolylmethyl] Chemistry 674 | Me | H | [451] |

| | | | | |
|---|---|---|---|---|
| 713 I | 3,5-dimethylphenoxy (Chemistry 678) | CH2-pyrazole (Chemistry 679) | Me | H | [437] |
| 714 I | 3,5-dimethylphenoxy (Chemistry 683) | CH2-(5-methyl-3-amino-pyrazole) (Chemistry 684) | Me | H | [465] |
| 715 I | 3,5-dimethylphenoxy (Chemistry 688) | CH2-(2-pyridyl-imidazole) (Chemistry 689) | Me | H | [513] |
| 716 I | 3,5-dimethylphenoxy (Chemistry 693) | CH2-(2-(4-fluorophenyl)-imidazole) (Chemistry 694) | Me | H | [530] |

| | | | | |
|---|---|---|---|---|
| 717 I | ![3,5-dimethylphenoxy] Chemistry 698 | ![1-benzyl-5-phenylimidazole] Chemistry 699 | Me | H | [512] |
| 718 I | ![3,5-dimethylphenoxy] Chemistry 703 | ![1-benzyl-4-methylimidazole] Chemistry 704 | Me | H | [450] |
| 719 I | ![3,5-dimethylphenoxy] Chemistry 708 | ![1-benzyl-4-hydroxymethylimidazole] Chemistry 709 | Me | H | [466] |
| 720 I | ![3,5-dimethylphenoxy] Chemistry 713 | ![1-benzyl-2-phenylimidazole] Chemistry 714 | Me | H | [512] |

| | | | | | |
|---|---|---|---|---|---|
| 721 I | Chemistry 718 (3,5-dimethylphenoxy) | Chemistry 719 (N-CH2-imidazole) | Me | H | [464] |
| 722 I | Chemistry 723 (3,5-dimethylphenoxy) | Chemistry 724 (N-CH(CH3)-imidazole) | Me | H | [478] |
| 723 I | Chemistry 728 (3,5-dimethylphenoxy) | Chemistry 729 (N-CH2-2-methylimidazole) | Me | H | [450] |
| 724 I | Chemistry 733 (3,5-dimethylphenoxy) | Chemistry 734 (N-CH2-2-(p-tolyl)imidazole) | Me | H | [526] |

| | | | | |
|---|---|---|---|---|
| 725 I | 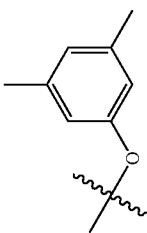 Chemistry 738 | 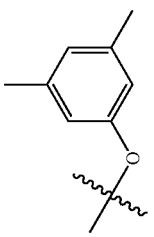 Chemistry 739 | Me | H | [537] |
| 726 I | 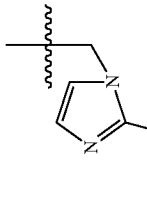 Chemistry 743 | 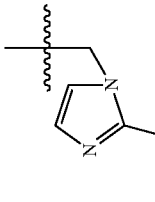 Chemistry 744 | Me | H | [537] |
| 727 I |  Chemistry 748 |  Chemistry 749 | Me | H | >250 |

| | | | | | |
|---|---|---|---|---|---|
| 728 | I | 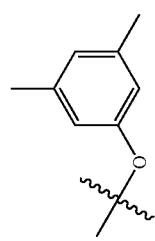 Chemistry 753 | 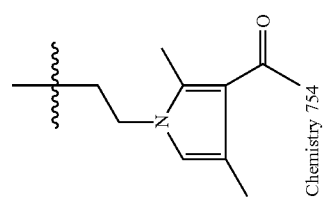 Chemistry 754 | Me | H | 164 |
| 729 | H | 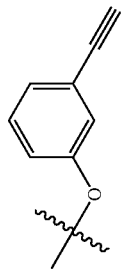 Chemistry 758 | 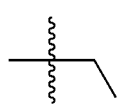 | Me | H | [254] |
| 730 | I | 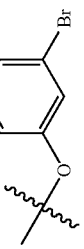 Chemistry 763 | 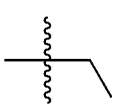 | Me | H | [464, 466] |
| 731 | H | 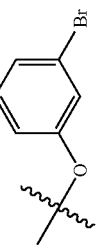 Chemistry 768 | 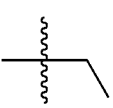 | Me | H | [338, 340] |

-continued
| | | | | | |
|---|---|---|---|---|---|
| 732 | H | 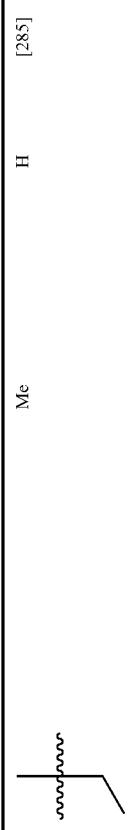 Chemistry 773 | 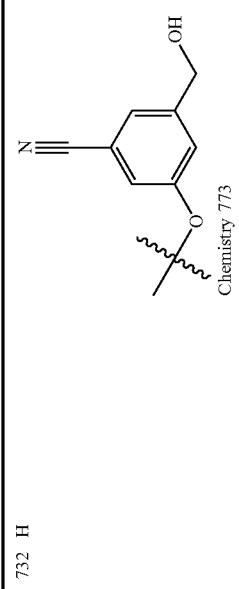 | Me | H | [285] |
| 733 | I |  Chemistry 778 | 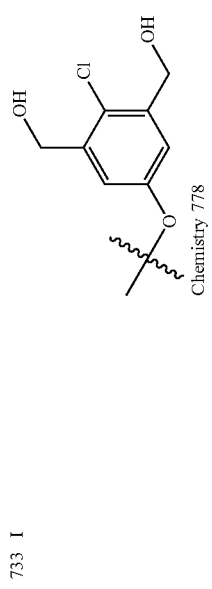 Et | Me | H | [450, 451] |
| 734 | I | 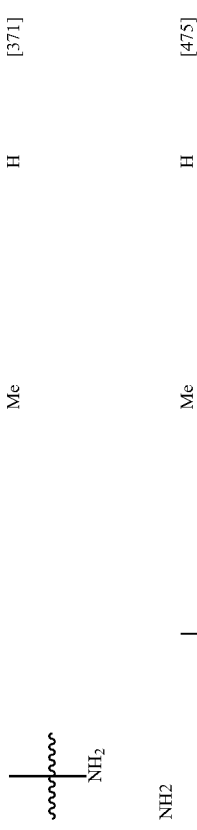 Chemistry 783 | Et NH$_2$ | Me | H | [371] |
| 735 | I | 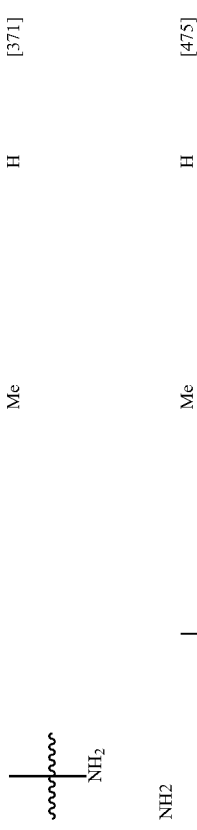 Chemistry 788 | NH2 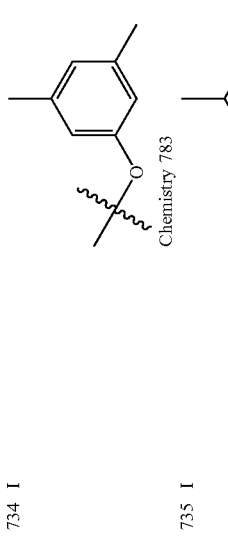 Chemistry 789 | Me | H | [475] |
| 736 | I |  | 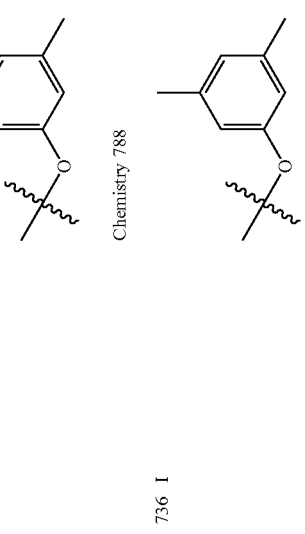 | Me | H | [491] |

| | | | | |
|---|---|---|---|---|
| 737 | I | 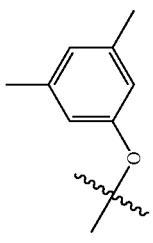Chemistry 793 | 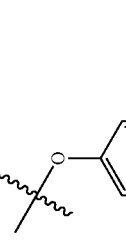Chemistry 794 | Me | H | [399] |
| 738 | CO2Et | 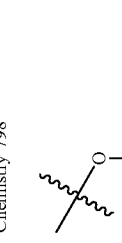Chemistry 798 | NMe2 | Me | H | [428] |
| 739 | I | 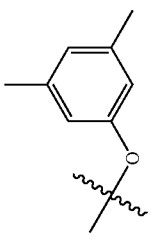Chemistry 803 | 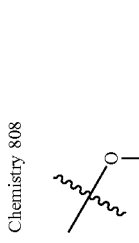Et | Me | H | [461] |
| 740 | I | 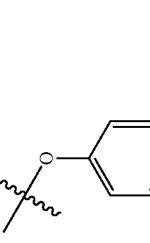Chemistry 808 | 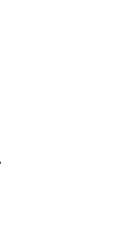Chemistry 809 | Me | H | 248 |
(Note: Chemistry 813 and Chemistry 814 correspond to the structures in row 740)

-continued

| | | | | | |
|---|---|---|---|---|---|
| 741 I | 3,5-dimethylphenoxy (Chemistry 818) | 2-Br-imidazolyl-N-CH2 (Chemistry 819) | Me | H | >250 |
| 742 I | 3,5-dimethylphenoxy (Chemistry 823) | 4,5-dicyano-imidazolyl-N-CH2 (Chemistry 824) | Me | H | [486] |
| 743 I | 3,5-dimethylphenoxy (Chemistry 828) | 4,5-dichloro-imidazolyl-N-CH2 (Chemistry 829) | Me | H | [504, 506, 508] |
| 744 I | 3,5-dimethylphenoxy (Chemistry 833) | 2-(4-pyridyl)-imidazolyl-N-CH2 (Chemistry 834) | Me | H | [513] |

| | | | | |
|---|---|---|---|---|
| 745 | I | 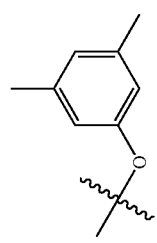 Chemistry 838 | 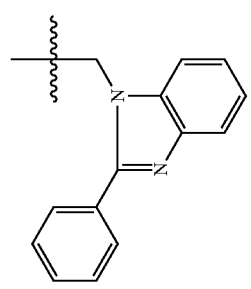 Chemistry 839 | Me | H | [562] |
| 746 | I | 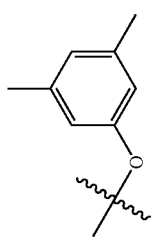 Chemistry 843 | 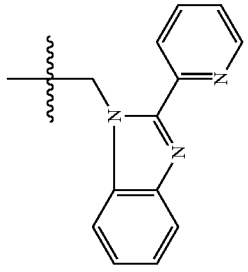 Chemistry 844 | Me | H | [563] |
| 747 | I | 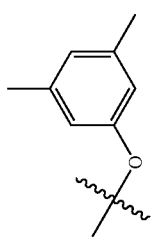 Chemistry 848 | 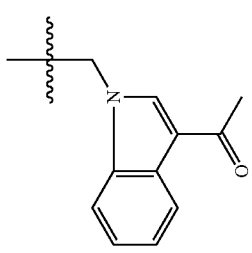 Chemistry 849 | Me | H | [527] |
| 748 | I | 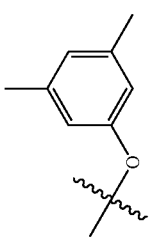 Chemistry 853 | 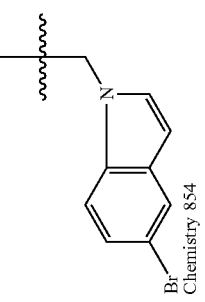 Chemistry 854 | Me | H | [563, 565] |

| | | | | |
|---|---|---|---|---|
| 749 | I | 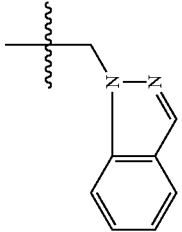 Chemistry 858 | 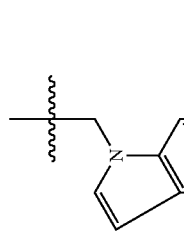 Chemistry 859 | Me | H | [486] |
| 750 | I | 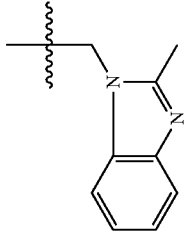 Chemistry 863 | 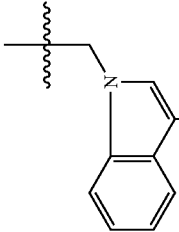 Chemistry 864 | Me | H | [515] |
| 751 | I | 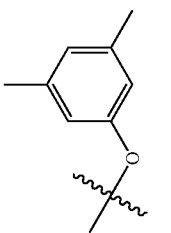 Chemistry 868 | 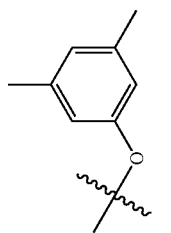 Chemistry 869 | Me | H | [500] |
| 752 | I | 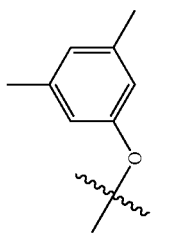 Chemistry 873 | 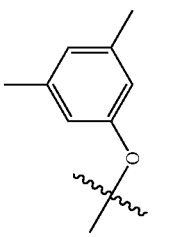 Chemistry 874 | Me | H | [499] |

-continued
| | | | | | |
|---|---|---|---|---|---|
| 753 | I |  Chemistry 878 |  Chemistry 879 | Me | H | [514] |
| 754 | I | 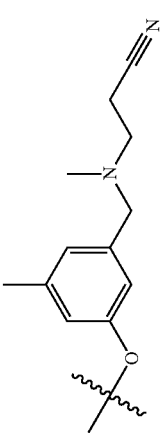 Chemistry 883 | Chemistry 884 | Me | H | >250 |
| 755 | I | Chemistry 888 | Et | Me | H | [466] |
| 756 | I | Chemistry 893 | Chemistry 894 | Me | H | [478] |

-continued
| | | | | | |
|---|---|---|---|---|---|
| 757 | I | 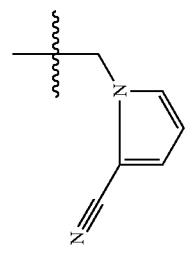 Chemistry 898 | 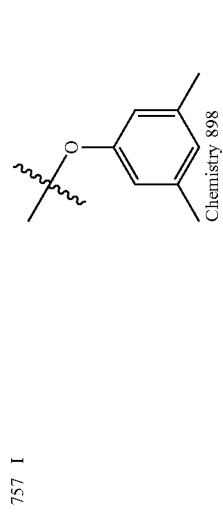 Chemistry 899 | Me | H | >250 |
| 758 | I | 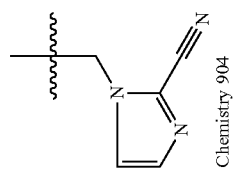 Chemistry 903 | 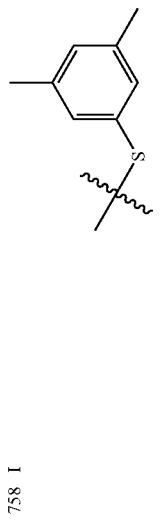 Chemistry 904 | Me | H | >250 |
| 759 | I | 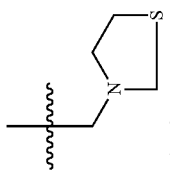 Chemistry 908 | Chemistry 909 | Me | H | 213 |
| 760 | I | 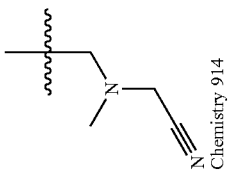 Chemistry 913 | 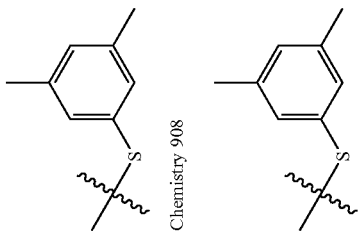 Chemistry 914 | Me | H | 207 |

| | | | | |
|---|---|---|---|---|
| 761 | I | Chemistry 918 | Me | H | >250 |
| 762 | I | Chemistry 923 | Et | H | [437] |
| 763 | I | Chemistry 928 | Et | H | [458] |
| 764 | Vinyl | Chemistry 933 | Et | H | [321] |

-continued

| | | | | | |
|---|---|---|---|---|---|
| 765 | H | [structure with phenyl, vinyl, CH2OH] Chemistry 938 | Et | Me | H | [286] |
| 766 | I | [structure with phenyl, NO2, CHO] Chemistry 943 | Et | Me | H | [429] |
| 767 | H | [structure with phenyl, vinyl, CHO] Chemistry 948 | Et | Me | H | [284] |
| 768 | CO2Et | [structure with phenyl, CF3, F] Chemistry 953 | Et | Me | H | [388] |

| | | | | |
|---|---|---|---|---|
| 769 | H | 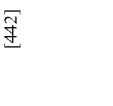 Chemistry 958 | 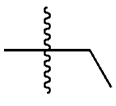 Me | H [316] |
| 770 | I | 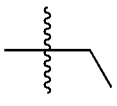 Chemistry 963 | Et Me | H [442] |
| 771 | CO2Et | 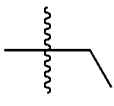 Chemistry 968 | Et Me | H [380, 382] |
| 772 | H | Chemistry 973 | Et Me | H [308, 310] |

-continued
| | | | | |
|---|---|---|---|---|
| 773 I |  Chemistry 978 | 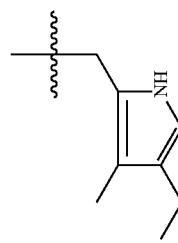 Chemistry 979 | Me | H | >250 |
| 774 I |  Chemistry 983 | 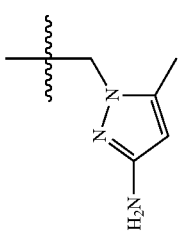 Chemistry 984 | Me | H | [481] |
| 775 I | 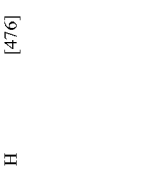 Chemistry 988 | 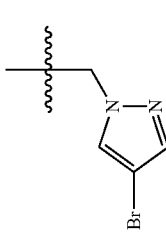 Chemistry 989 | Me | H | [545] |
| 776 I | 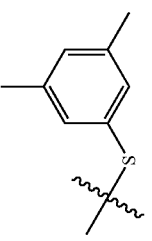 Chemistry 993 | 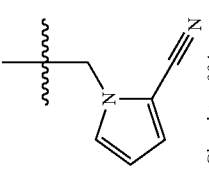 Chemistry 994 | Me | H | [476] |

-continued

| | | | | |
|---|---|---|---|---|
| 777 I | 3,5-dimethylphenyl-S- (Chemistry 998) | N-methylpiperazinyl-CH2- (Chemistry 999) | Me | H | [484] |
| 778 I | 3,5-dimethylphenyl-S- (Chemistry 1003) | 4-(4-acetylphenyl)piperazinyl-CH2- (Chemistry 1004) | Me | H | [588] |
| 779 I | 3,5-dimethylphenyl-S- (Chemistry 1008) | 4-benzylpiperazinyl-CH2- (Chemistry 1009) | Me | H | [560] |

-continued
| | | | | |
|---|---|---|---|---|
| 780 I |  Chemistry 1013 |  Chemistry 1014 | Me | H | [547] |
| 781 I |  Chemistry 1018 |  Chemistry 1019 | Me | H | [591] |
| 782 I |  Chemistry 1023 |  Chemistry 1024 | Me | H | [580] |

| | | | | |
|---|---|---|---|---|
| 783 | I | ![3,5-dimethylphenyl-S-] Chemistry 1028 | ![piperazine-phenyl] Chemistry 1029 | Me | H | [546] |
| 784 | I | ![3,5-dimethylphenyl-S-] Chemistry 1033 | ![piperazine-3,4-dimethylphenyl] Chemistry 1034 | Me | H | [574] |
| 785 | I | ![3,5-dimethylphenyl-S-] Chemistry 1038 | ![piperazine-3,4-dichlorophenyl] Chemistry 1039 | Me | H | [614, 616, 618] |
| 786 | I | ![3,5-dimethylphenyl-S-] Chemistry 1043 | ![piperazine-furoyl] Chemistry 1044 | Me | H | [564] |

-continued

| | | | | |
|---|---|---|---|---|
| 787 | 3,5-dimethylphenyl-S- (Chemistry 1048) | piperazinyl-pyrimidine CH2- (Chemistry 1049) | Me | H | [548] |
| 788 | 3,5-dimethylphenyl-S- (Chemistry 1053) | piperazinyl-cyclohexyl CH2- (Chemistry 1054) | Me | H | [552] |
| 789 | 3,5-dimethylphenyl-S- (Chemistry 1058) | piperazinyl-phenyl CH2- (Chemistry 1059) | Me | H | [560] |
| 790 | 3,5-dimethylphenyl-S- | cinnamyl-piperazinyl-CH2- | Me | H | [586] |

-continued

| | | | | |
|---|---|---|---|---|
| 791 I | Chemistry 1063 | Chemistry 1064 | Me | H | [530, 532] |
| 792 I | Chemistry 1068 | Chemistry 1069 | Me | H | [604] |
| 793 I | Chemistry 1073 | Chemistry 1074 | Me | H | [580] |
| 794 I | Chemistry 1078 | Chemistry 1079 | Me | H | [493] |
| | | Chemistry 1083 | Chemistry 1084 | | |

-continued
| | | | | |
|---|---|---|---|---|
| 795 | H | 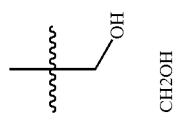 Chemistry 1088 | 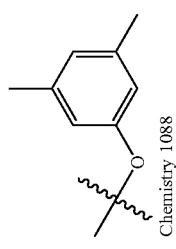 CH2OH | Me | H | [260] |
| 796 | H | 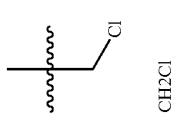 Chemistry 1093 | 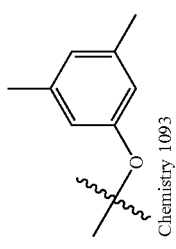 CH2Cl | Me | H | |
| 797 | H | 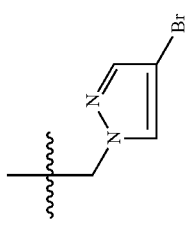 Chemistry 1098 | 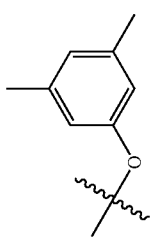 Chemistry 1099 | Me | H | >250 |
| 798 | I | 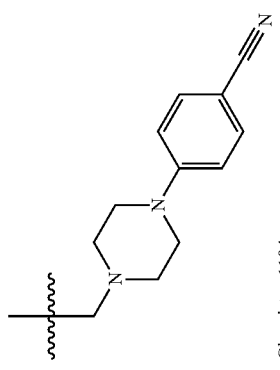 Chemistry 1103 | 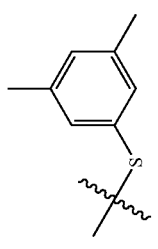 Chemistry 1104 | Me | H | 245 |

| | | | | | |
|---|---|---|---|---|---|
| 799 | I | 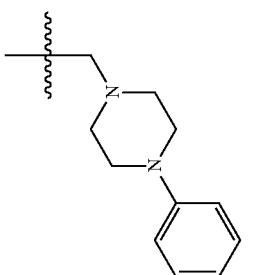 | 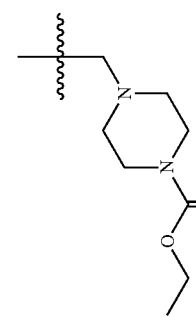 | Me | H | >250 |
| 800 | I | 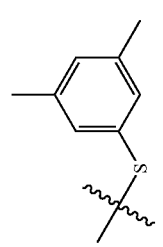 |  | Me | H | 232 |
| 801 | I | | | Me | H | 224 |

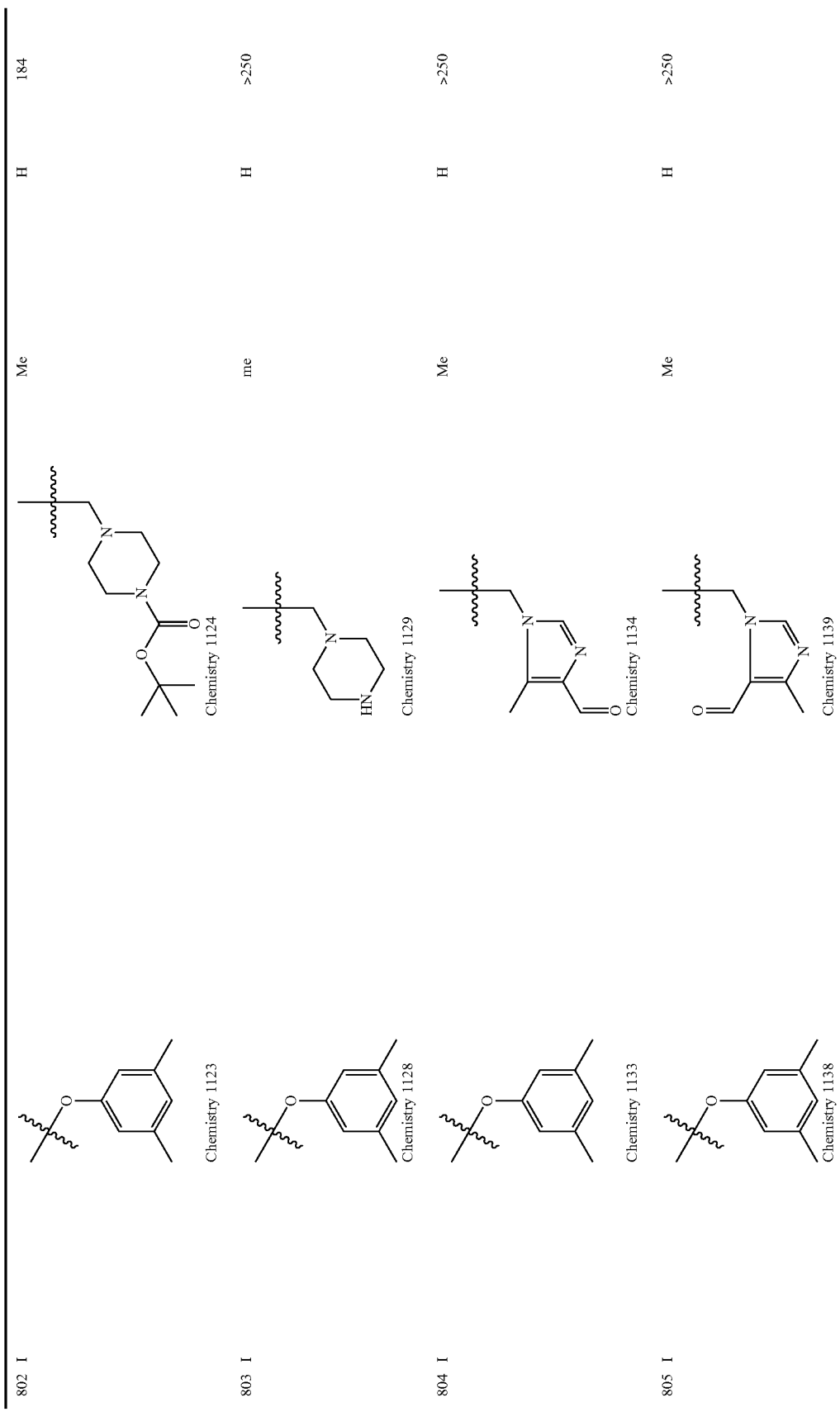

| | | | | |
|---|---|---|---|---|
| 806 | I | 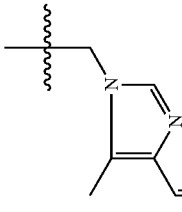 Chemistry 1143 | 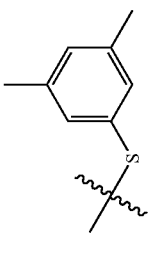 Chemistry 1144 | Me | H | >250 |
| 807 | I | 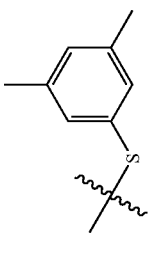 Chemistry 1148 | 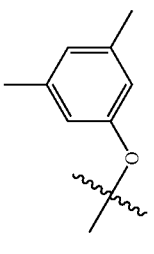 Chemistry 1149 | Me | H | 250 |
| 808 | I | 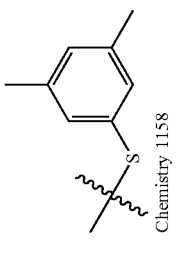 Chemistry 1153 | 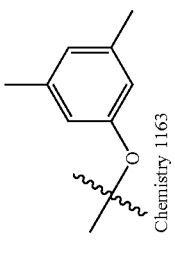 Chemistry 1154 | Me | H | 198 |
| 809 | NO2 | 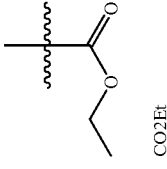 Chemistry 1158 | CO2Et | Me | H | [363] |
| 810 | NH2 | Chemistry 1163 | CO2Et | Me | H | [317] |

| | | | | | |
|---|---|---|---|---|---|
| 811 | NMe2 | 3,5-dimethylphenyl-S- (Chemistry 1168) | CO2Et (ethyl ester) | Me | H | [361] |
| 812 | NMe2 | 3,5-dimethylphenyl-O- (Chemistry 1173) | CH2OH | Me | H | 146 |
| 813 | NMe2 | 3,5-dimethylphenyl-O- (Chemistry 1178) | CH2OH | Me | H | [337] |
| 814 | NMe2 | 3,5-dimethylphenyl-O- (Chemistry 1183) | CH2-morpholine (Chemistry 1184) | Me | H | 178 |
| 815 | NMe2 | 3,5-dimethylphenyl-O- | CH2-pyrazole | Me | H | 168 |

US 7,115,608 B2
| | | | | | |
|---|---|---|---|---|---|
| 816 I | 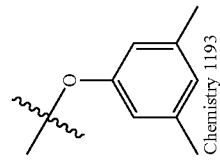 Chemistry 1193 |  Chemistry 1194 | Me | H | [493] |
| 817 I | 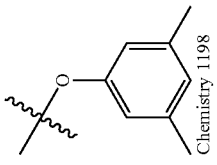 Chemistry 1198 |  Chemistry 1199 | Me | H | [493] |
| 818 I | 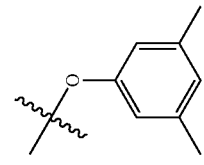 |  | Me | H | >250 |

| | | | | | |
|---|---|---|---|---|---|
| 819 | I | 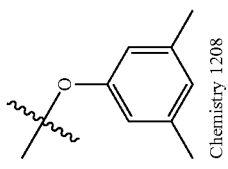 Chemistry 1203 | 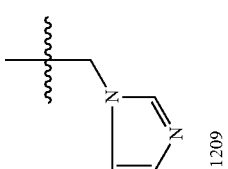 Chemistry 1204 | Me | H | >250 |
| 820 | I | 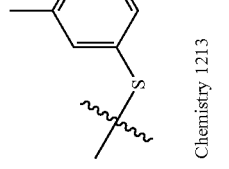 Chemistry 1208 | 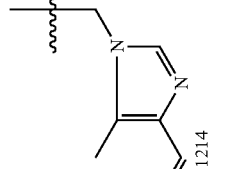 Chemistry 1209 | Me | H | [509] |
| 821 | I | 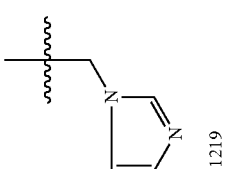 Chemistry 1213 | 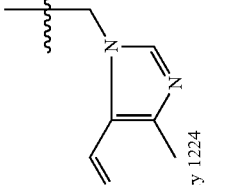 Chemistry 1214 | Me | H | >250 |
| 822 | I | Chemistry 1218 | Chemistry 1219 | Me | H | >250 |
| | | Chemistry 1223 | Chemistry 1224 | | | |

| | | | | | |
|---|---|---|---|---|---|
| 823 | I | 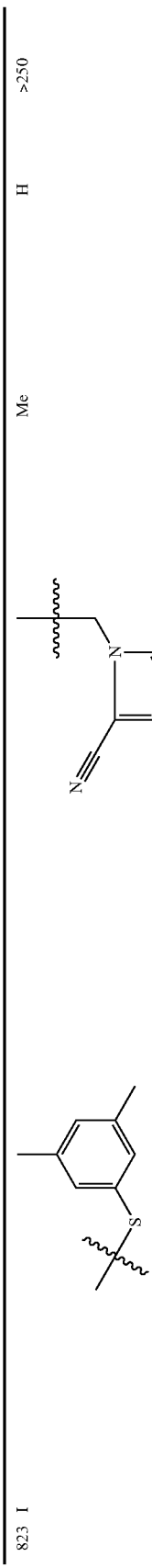 Chemistry 1228 |  Chemistry 1229 | Me | H | >250 |
| 824 | I | 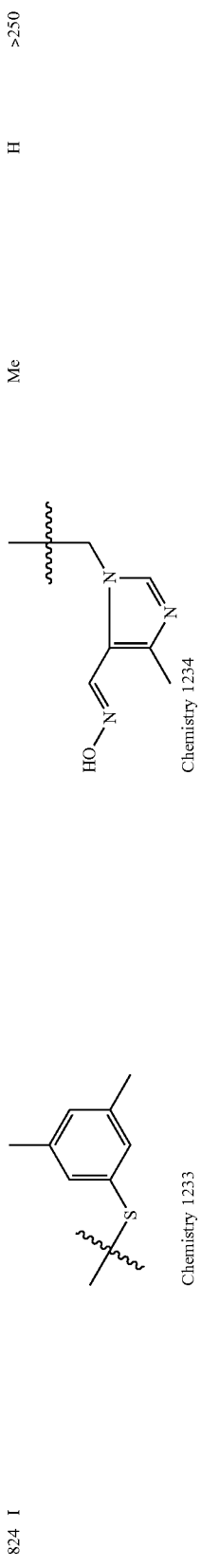 Chemistry 1233 | Chemistry 1234 | Me | H | >250 |
| 825 | I | 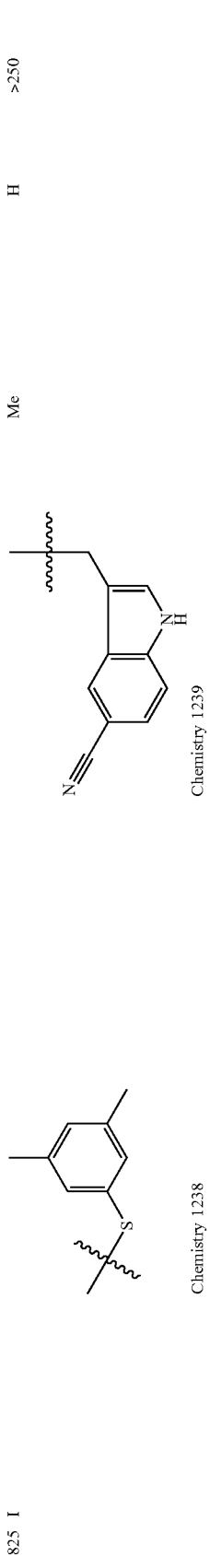 Chemistry 1238 | Chemistry 1239 | Me | H | >250 |

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, (1985), 36, 445–451) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in μM) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}}$$

expressed in %, whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in μM). The ratio of $CC_{50}$ to $IC_{50}$ was defined as the selectivity index (SI). The compounds of formula (I) were shown to inhibit HIV-1 effectively. Particular $IC_{50}$, $CC_{50}$ and SI values are listed in Table 2 hereinbelow.

TABLE 2

| N° | IC50(μm) | c | SI | c | CC50(μm) |
|---|---|---|---|---|---|
| 242 | 0,0006 | > | 158489 | > | 100 |
| 255 | 0,0006 | > | 15849 | > | 10 |
| 684 | 0,0008 | > | 125893 | > | 100 |
| 43 | 0,0010 |  | 10000 |  | 10 |
| 264 | 0,0010 | > | 10000 | > | 10 |
| 470 | 0,0010 |  | 12589 |  | 13 |
| 483 | 0,0010 | > | 100000 | > | 100 |
| 551 | 0,0010 |  | 12589 |  | 13 |
| 124 | 0,0013 | > | 7943 | > | 10 |
| 249 | 0,0013 | > | 25119 | > | 32 |
| 298 | 0,0013 | > | 7943 | > | 10 |
| 326 | 0,0013 |  | 7943 |  | 10 |
| 375 | 0,0013 | > | 79433 | > | 100 |
| 589 | 0,0013 | > | 7943 | > | 10 |
| 606 | 0,0013 |  | 15849 |  | 20 |
| 133 | 0,0016 | > | 6310 | > | 10 |
| 241 | 0,0016 | > | 63096 | > | 100 |
| 253 | 0,0016 | > | 6310 | > | 10 |
| 306 | 0,0016 | > | 19953 | > | 32 |
| 328 | 0,0016 | > | 63096 | > | 100 |
| 370 | 0,0016 | > | 63096 | > | 100 |
| 662 | 0,0016 | > | 63096 | > | 100 |
| 426 | 0,0016 |  | 39811 |  | 63 |
| 46 | 0,0020 | > | 50119 | > | 100 |
| 105 | 0,0020 | > | 5012 | > | 10 |
| 234 | 0,0020 |  | 5012 |  | 10 |
| 254 | 0,0020 | > | 15849 | > | 32 |
| 256 | 0,0020 | > | 5012 | > | 10 |
| 272 | 0,0020 |  | 12589 |  | 25 |
| 284 | 0,0020 | > | 5012 | > | 10 |
| 296 | 0,0020 |  | 12589 |  | 25 |
| 319 | 0,0020 | > | 50119 | > | 100 |
| 574 | 0,0020 | > | 50119 | > | 100 |

TABLE 2-continued

| N° | IC50(μm) | c | SI | c | CC50(μm) |
|---|---|---|---|---|---|
| 618 | 0,0020 |  | 25119 |  | 50 |
| 650 | 0,0020 | > | 50119 | > | 100 |
| 83 | 0,0025 |  | 3162 |  | 8 |
| 88 | 0,0025 | > | 39811 | > | 100 |
| 108 | 0,0025 |  | 19953 |  | 50 |
| 109 | 0,0025 |  | 12589 |  | 32 |
| 115 | 0,0025 |  | 3162 |  | 8 |
| 277 | 0,0025 | > | 39811 | > | 100 |
| 286 | 0,0025 | > | 12589 | > | 32 |
| 299 | 0,0025 |  | 32 |  | 0 |
| 713 | 0,0025 | > | 39811 | > | 100 |
| 45 | 0,0032 | > | 31623 | > | 100 |
| 85 | 0,0032 | > | 31623 | > | 100 |
| 86 | 0,0032 | > | 31623 | > | 100 |
| 231 | 0,0032 |  | 3162 |  | 10 |
| 409 | 0,0032 |  | 12589 |  | 40 |
| 244 | 0,0040 | > | 25119 | > | 100 |
| 297 | 0,0040 | > | 7943 | > | 32 |
| 250 | 0,0050 |  | 5012 |  | 25 |
| 257 | 0,0050 | > | 6310 | > | 32 |
| 307 | 0,0050 | > | 6310 | > | 32 |
| 324 | 0,0050 |  | 6310 |  | 32 |
| 81 | 0,0063 |  | 1995 |  | 13 |
| 92 | 0,0063 | > | 5012 | > | 32 |
| 140 | 0,0063 | > | 1585 | > | 10 |
| 143 | 0,0063 | > | 1585 | > | 10 |
| 217 | 0,0063 | > | 1585 | > | 10 |
| 221 | 0,0063 | > | 3162 | > | 20 |
| 230 | 0,0063 |  | 1259 |  | 8 |
| 232 | 0,0063 | > | 5012 | > | 32 |
| 245 | 0,0063 | > | 15849 | > | 100 |
| 309 | 0,0063 |  | 1585 |  | 10 |
| 321 | 0,0063 | > | 15849 | > | 100 |
| 322 | 0,0063 | > | 15849 | > | 100 |
| 547 | 0,0063 | > | 15849 | > | 100 |
| 31 | 0,0079 | > | 12589 | > | 100 |
| 218 | 0,0079 | > | 1259 | > | 10 |
| 222 | 0,0079 |  | 251 |  | 2 |
| 700 | 0,0079 | > | 1000 | > | 8 |
| 314 | 0,0079 | > | 3981 | > | 32 |
| 701 | 0,0100 |  | 6310 |  | 63 |
| 8 | 0,0100 | > | 10000 | > | 100 |
| 99 | 0,0100 | > | 10000 | > | 100 |
| 121 | 0,0100 | > | 10000 | > | 100 |
| 219 | 0,0100 | > | 3162 | > | 32 |
| 233 | 0,0100 | > | 1000 | > | 10 |
| 694 | 0,0100 |  | 39811 |  | 63 |
| 280 | 0,0100 |  | 2512 |  | 25 |
| 696 | 0,0158 | > | 2512 | > | 40 |

The invention claimed is:
1. Compounds of formula (I)

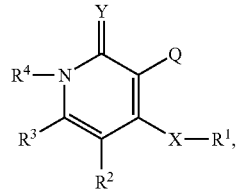

(I)

the N-oxides, the pharmaceutically acceptable addition salts, the quaternary amines and stereochemically isomeric forms thereof, wherein
Y is O or S;
Q is halo;
X is a bivalent radical of formula —$(CH_2)_p$— (a-1)

or

—(CH$_2$)$_q$-Z-(CH$_2$)$_r$—  (a-2);

wherein p is an integer of value 1 to 5;
q is an integer of value 0 to 5;
r is an integer of value 0 to 5;
Z is O, S, NR$^7$, C(=O), S(=O), S(=O)$_2$, CHOR$^{13}$, CH=CH, CH(NR$^7$R$^8$) or CF$_2$;
and wherein each hydrogen atom may be replaced by C$_{1-4}$alkyl or hydroxyC$_{1-4}$alkyl;

R$^1$ is C$_{3-6}$cycloalkyl, C$_{2-6}$alkenyl or aryl;

R$^2$ is selected from hydrogen; formyl; cyano; azido; hydroxy; oxiranyl; amino; mono- or di(C$_{1-4}$alkyl)amino; formylamino; mercapto(C$_{1-6}$)alkyl; hydrazino; R$^{5a}$R$^{6a}$N—C(=O)—; R$^9$—N=C(R$^{10}$)—; C$_{2-6}$alkenyl optionally substituted with one or two substituents each independently selected from halo, hydroxy, cyano, formyl, C$_{1-6}$alkyloxy, C$_{1-6}$alkylcarbonyl, C$_{1-6}$alkyloxycarbonyl, C$_{1-6}$alkylcarbonyloxy, di(C$_{1-4}$alkyl)carbamoyl, [di(C$_{1-4}$alkyl)amino(C$_{1-6}$alkyl)](C$_{1-4}$alkyl)carbamoyl, [di(C$_{1-4}$alkyl)amino(C$_{1-6}$alkyl)](arylC$_{1-4}$alkyl)carbamoyl, di(C$_{1-4}$alkyloxy)(C$_{1-4}$alkyl)carbamoyl, (cyanoC$_{1-6}$alkyl)(C$_{1-6}$alkyl)aminoC$_{1-6}$alkyl, N-hydroxy-imino, aryl, Het$^2$, Het$^2$carboxamido, Het$^2$(C$_{1-6}$alkyl)carbamoyl; C$_{2-6}$alkynyl optionally substituted with one or two substituents each independently selected from halo, hydroxy, cyano, formyl, C$_{1-6}$alkyloxy, C$_{1-6}$alkylcarbonyl, C$_{1-6}$alkyloxycarbonyl, C$_{1-6}$alkylcarbonyloxy, N-hydroxy-imino, aryl or Het$^2$; C$_{1-6}$alkyloxy; hydroxyC$_{1-6}$alkyloxy; aminoC$_{1-6}$alkyloxy; mono- or di(C$_{1-4}$alkyl)aminoC$_{1-6}$alkyloxy; C$_{1-6}$alkylcarbonyl; arylcarbonyl; Het$^2$carbonyl; C$_{1-6}$alkyloxycarbonyl; C$_{1-6}$alkylcarbonyloxy; aryl; aryloxy; arylC$_{1-6}$alkyloxy; arylthio; arylC$_{1-6}$alkylthio; mono- or di(aryl)amino; Het$^2$; Het$^2$oxy; Het$^2$thio; Het$^2$C$_{1-6}$alkyloxy; Het$^2$C$_{1-6}$alkylthio; Het$^2$SO$_2$; Het$^2$SO; mono- or di(Het$^2$)amino; C$_{3-6}$cycloalkyl; C$_{3-6}$cycloalkyloxy; C$_{3-6}$cycloalkylthio; C$_{1-6}$alkylthio; hydroxyC$_{1-6}$alkylthio; aminoC$_{1-6}$alkylthio; mono- or di(C$_{1-4}$alkyl)aminoC$_{1-6}$alkylthio; C$_{1-6}$alkyl optionally substituted with one or two substituents each independently selected from halo, hydroxy, cyano, carboxyl, C$_{1-6}$alkyloxy, C$_{1-6}$alkylthio, C$_{1-6}$alkylsulfonyl, C$_{1-6}$alkycarbamoylC$_{1-4}$alkylthio, hydroxyC$_{1-6}$alkyloxy, C$_{1-6}$alkyloxyC$_{1-6}$alkyloxy, C$_{1-6}$alkyloxyC$_{1-6}$alkylthio C$_{1-6}$alkylcarbonyl, C$_{1-6}$alkylcarbonyloxy, aminocarbonyloxy, mono- or di(C$_{1-4}$alkyl)aminocarbonyloxy, C$_{1-6}$alkyloxycarbonyl, C$_{1-6}$alkyloxycarbonylC$_{1-6}$alkyloxy, C$_{1-6}$alkyloxycarbonylC$_{1-6}$alkylthio, aryl, Het$^2$, aryloxy, arylthio, arylC$_{1-6}$alkyloxy, arylC$_{1-6}$alkylthio, Het$^2$C$_{1-6}$alkyloxy, Het$^2$C$_{1-6}$alkylthio, C$_{1-6}$alkyl-S(=O)$_2$-oxy, amino, mono- or di(C$_{1-4}$alkyl)amino, di(C$_{1-4}$alkyl)aminoC$_{1-6}$alkylthio, [di(C$_{1-4}$alkyl)amino(C$_{1-6}$alkyl)](C$_{1-4}$alkyl)amino, di(cyanoC$_{1-6}$alkyl)amino, C$_{1-6}$alkyloxycarbonylamino, C$_{1-6}$alkyloxyC$_{1-6}$alkylcarbonylamino, mono- or di(aryl)amino, mono- or di(arylC$_{1-4}$alkyl)amino, mono- or di(C$_{1-4}$alkyloxyC$_{1-4}$alkyl)amino, mono- or di(C$_{1-4}$alkylthioC$_{1-4}$alkyl)amino, mono- or di(Het$^2$C$_{1-4}$alkyl)amino, (Het$^2$C$_{1-4}$alkyl)(C$_{1-4}$alkyl)amino, (cyanoC$_{1-6}$alkyl)(C$_{1-4}$alkyl)amino, C$_{3-6}$cycloalkylthio, R$^{11}$—(C=O)—NH—, R$^{12}$—NH—(C=O)—NH—, R$^{14}$—S(=O)$_2$—NH—, C$_{1-6}$alkyl-P(O—R$^{15}$)2=O, C$_{1-6}$alkyl-P(O—C$_{1-6}$alkyl-O)=O or a radical of formula

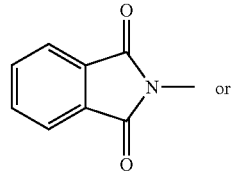  (c-1)

or

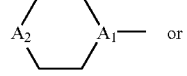  (c-2)

or

  (c-3)

with A$_1$ being CH or N, and A$_2$ being CH$_2$, NR$^{13}$, S or O, provided that when A$_1$ is CH then A$_2$ is other than CH$_2$, said radical (c-1), (c-2) and (c-3) being optionally substituted with one or two substituents each independently selected from H, C$_{1-6}$ alkyl, C$_{1-6}$ alkyloxy, hydroxy C$_{1-4}$alkyl, C$_{1-6}$alkyloxycarbonyl, C$_{1-6}$alkyloxycarbonylC$_{1-4}$alkyl, aminoC$_{1-6}$alkyl, C$_{1-4}$alkylcarbonyl, arylcarbonyl, aryl, Het$^1$, Het$^1$—(C=O)—, hydroxy, cyano, C$_{1-4}$alkylcyano, CONR$^{16}$R$^{17}$ with R$^{16}$ and R$^{17}$ being independently H or alkyl, mono or di(C$_{1-4}$alkyl)aminoalkyl, 4-hydroxy-4-phenyl or 4-cyano-4-phenyl;

R$^3$ is selected from hydrogen; halo; formyl; cyano; azido; hydroxy; oxiranyl; amino; mono- or di(C$_{1-4}$alkyl)amino; formylamino; mercapto(C$_{1-6}$)alkyl; hydrazino; R$^{5a}$R$^{6a}$N—C(=O)—; R$^9$—N=C(R$^{10}$)—; C$_{2-6}$alkenyl optionally substituted with one or two substituents each independently selected from halo, hydroxy, cyano, formyl, C$_{1-6}$alkyloxy, C$_{1-6}$alkylcarbonyl, C$_{1-6}$alkyloxycarbonyl, C$_{1-6}$alkylcarbonyloxy, di(C$_{1-4}$alkyl)carbamoyl, [di(C$_{1-4}$alkyl)amino(C$_{1-6}$alkyl)](CC$_{1-4}$alkyl)carbamoyl, [di(C$_{1-4}$alkyl)amino(C$_{1-6}$alkyl)](arylC$_{1-4}$alkyl)carbamoyl, di(C$_{1-4}$alkyloxy)(C$_{1-4}$alkyl)carbamoyl, (cyanoC$_{1-6}$alkyl)(CC$_{1-6}$alkyl)aminoC$_{1-6}$alkyl, N-hydroxy-imino, aryl, Het$^2$, Het$^2$carboxamido, Het$^2$(C$_{1-6}$alkyl)carbamoyl; C$_{2-6}$alkynyl optionally substituted with one or two substituents each independently selected from halo, hydroxy, cyano, formyl, C$_{1-6}$alkyloxy, C$_{1-6}$alkylcarbonyl, C$_{1-6}$alkyloxycarbonyl, C$_{1-6}$alkylcarbonyloxy, N-hydroxy-imino, aryl or Het$^2$; C$_{1-6}$alkyloxy; hydroxyC$_{1-6}$alkyloxy; aminoC$_{1-6}$alkyloxy; mono- or di(C$_{1-4}$alkyl)aminoC$_{1-6}$alkyloxy; C$_{1-6}$alkylcarbonyl; arylcarbonyl; Het$^2$carbonyl; C$_{1-6}$alkyloxycarbonyl; C$_{1-6}$alkylcarbonyloxy; aryl; aryloxy; arylC$_{1-6}$alkyloxy; arylthio; arylC$_{1-6}$alkylthio; mono- or di(aryl)amino; Het$^2$; Het$^2$oxy; Het$^2$thio; Het$^2$C$_{1-6}$alkyloxy; Het$^2$C$_{1-6}$alkylthio; Het$^2$SO$_2$; Het$^2$SO; mono- or di(Het$^2$)amino; C$_{3-6}$cycloalkyl; C$_{3-6}$cycloalkyloxy; C$_{3-6}$cycloalkylthio; C$_{1-6}$alkylthio; hydroxyC$_{1-6}$alkylthio; aminoC$_{1-6}$alkylthio; mono- or di(C$_{1-4}$alkyl)aminoC$_{1-6}$alkylthio; C$_{1-6}$alkyl optionally substituted with one or two substituents each independently selected from halo, hydroxy, cyano, carboxyl, C$_{1-6}$alkyloxy, C$_{1-6}$alkylthio, C$_{1-6}$alkylsulfonyl, C$_{1-6}$alkycarbamoylC$_{1-4}$alkylthio, hydroxyC$_{1-6}$alkyloxy, C$_{1-6}$alkyloxyC$_{1-6}$alkyloxy, C$_{1-6}$alkyloxyC$_{1-6}$alkylthio, C$_{1-6}$alkylcarbonyl, C$_{1-6}$alkylcarbonyloxy, aminocarbonyloxy, mono- or di(C$_{1-4}$alkyl)

aminocarbonyloxy, $C_{1-6}$alkyloxycarbonyl, $C_{1-6}$alkyloxycarbonyl$C_{1-6}$alkyloxy, $C_{1-6}$alkyloxycarbonyl$C_{1-6}$alkylthio, aryl, Het$^2$, aryloxy, arylthio, aryl$C_{1-6}$alkyloxy, aryl$C_{1-6}$alkylthio, Het$^2C_{1-6}$alkyloxy, Het$^2C_{1-6}$alkylthio, $C_{1-6}$alkyl-S(=O)$_2$-oxy, amino, mono- or di($C_{1-6}$alkyl)amino, di($C_{1-6}$alkyl)amino$C_{1-6}$alkylthio, [di($C_{1-6}$alkyl)amino($C_{1-6}$alkyl)]($C_{1-6}$alkyl)amino, di(cyano$C_{1-6}$alkyl)amino, $C_{1-6}$alkyloxycarbonylamino, $C_{1-6}$alkyloxy$C_{1-6}$alkylcarbonylamino, mono- or di(aryl)amino, mono- or di(aryl$C_{1-4}$alkyl)amino, mono- or di($C_{1-4}$alkyloxy$C_{1-4}$alkyl)amino, mono- or di($C_{1-4}$alkylthio$C_{1-4}$alkyl)amino, mono- or di(Het$^2C_{1-4}$alkyl)amino, (Het$^2C_{1-4}$alkyl)($C_{1-4}$alkyl)amino, (cyano$C_{1-6}$alkyl)($C_{1-4}$alkyl)amino, $C_{3-6}$cycloalkylthio, $R^{11}$—(C=O)—NH—, $R^{12}$—NH—(C=O)—NH—, $R^{14}$—S(=O)$_2$—NH—, $C_{1-6}$alkyl-P(O—$R^{15}$)2=O, $C_{1-6}$alkyl-P(O—$C_{1-6}$alkyl-O)=O or a radical of formula

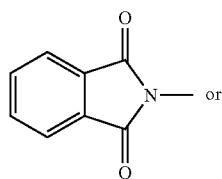

(c-1)

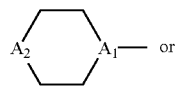

(c-2)

(c-3)

with $A_1$ being CH or N, and $A_2$ being CH$_2$, NR$^{13}$, S or O, provided that when $A_1$ is CH then $A_2$ is other than CH$_2$, said radical (c-1), (c-2) and (c-3) being optionally substituted with one or two substituents each independently selected from H, $C_{1-6}$alkyl, $C_{1-6}$alkyloxy, hydroxy$C_{1-4}$alkyl, $C_{1-6}$alkyloxycarbonyl, $C_{1-6}$alkyloxycarbonyl$C_{1-4}$alkyl, amino$C_{1-6}$alkyl, $C_{1-4}$alkylcarbonyl, arylcarbonyl, aryl, Het$^1$, Het$^1$-(C=O)—, hydroxy, cyano, $C_{1-4}$alkylcyano, CONR$^{16}$R$^{17}$ with R$^{16}$ and R$^{17}$ being independently H or alkyl, mono or di($C_{1-4}$alkyl)aminoalkyl, 4-hydroxy-4-phenyl or 4-cyano-4-phenyl;

or R$^2$ and R$^3$ may be taken together to form a bivalent radical of formula

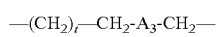 (d-1)

with t being an integer of 0, 1 or 2 and $A_3$ being CH$_2$, O, S, NR$^{7a}$ or N[C(=O)R$^{8a}$] and wherein each hydrogen in said formula (d-1) may be substituted with halo, $C_{1-4}$alkyl, $C_{1-4}$alkyloxy, $C_{1-4}$alkylcarbonyl, halo$C_{1-4}$alkylcarbonyl or arylcarbonyl;

R$^4$ is hydrogen;

R$^{5a}$ and R$^{6a}$ each independently are hydrogen; $C_{1-4}$alkyl optionally substituted with cyano, $C_{1-4}$alkyloxy, $C_{1-4}$alkylthio, amino, mono- or di($C_{1-4}$alkyl)amino or a radical of formula

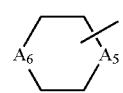 (f-1)

with $A_5$ and $A_6$ each independently being CH$_2$, NR$^{13}$ or O;

R$^7$, R$^{7a}$ and R$^{7b}$ each independently are hydrogen, formyl or $C_{1-4}$alkyl;

R$^8$, R$^{8a}$ and R$^{8b}$ each independently are hydrogen or $C_{1-4}$alkyl;

R$^9$ is hydrogen, hydroxy, $C_{1-4}$alkyloxy, carboxyl$C_{1-4}$alkyloxy, $C_{1-4}$alkyloxycarbonyl$C_{1-4}$alkyloxy, $C_{2-4}$alkenyloxy, $C_{2-4}$alkynyloxy or aryl$C_{1-4}$alkyloxy;

R$^{10}$ is hydrogen, carboxyl or $C_{1-4}$alkyl;

R$^{11}$ is hydrogen; $C_{1-4}$alkyl optionally substituted with cyano, $C_{1-4}$alkyloxy, $C_{1-4}$alkyl-S(=O)$_2$—, aryl or Het$^3$; $C_{1-4}$alkyloxy; $C_{2-4}$alkenyl; aryl$C_{2-4}$alkenyl; Het$^3C_{2-4}$alkenyl; $C_{2-4}$alkynyl; Het$^3C_{2-4}$alkynyl, aryl $C_{2-4}$alkynyl; $C_{3-6}$cycloalkyl; aryl; naphthyl or Het$^3$;

R$^{12}$ is $C_{1-4}$alkyl, aryl$C_{1-4}$alkyl, aryl, arylcarbonyl, $C_{1-4}$alkylcarbonyl, $C_{1-4}$alkyloxycarbonyl or $C_{1-4}$alkyloxycarbonyl$C_{1-4}$alkyl;

R$^{13}$ is hydrogen, $C_{1-4}$alkyl or $C_{1-4}$alkylcarbonyl;

R$^{14}$ is $C_{1-4}$alkyl optionally substituted with aryl or Het$^4$; polyhalo$C_{1-4}$alkyl or $C_{2-4}$alkenyl optionally substituted with aryl or Het$^4$;

R$^{15}$ is $C_{1-4}$alkyl;

Het$^1$ and Het$^2$ each independently are a heterocycle selected from pyrrolyl, furanyl, thienyl, imidazolyl, oxazolyl, isoxazolyl, thiazolyl, pyridyl, pyrimidinyl, pyrazinyl, pyridazinyl, pyrrolidinyl, tetrahydrofuranyl, tetrahydrothienyl, tetrahydropyrimidinyl, imidazolidinyl, oxazolidinyl, thiazolidinyl, piperidinyl, hexahydropyrimidinyl, piperazinyl, hexahydropyridazinyl, morpholinyl, thiomorpholinyl triazolyl, tetrazolyl, pyrrolyl, pyrazolyl, benzopyrrolyl, benzofuranyl, benzothienyl, benzimidazolyl, benzoxazolyl, benzothiazolyl, benzotriazolyl, indolyl, indazolyl, benzodioxanyl, quinolinyl, 2-oxo-1,2-dihydro-quinolinyl, imidazopyridinyl, dihydropyrrolyl or dihydroisoxazolyl, said heterocycle optionally being substituted with one, two or three substituents each independently selected from O, S, halo, formyl, amino, hydroxy, cyano, $C_{1-4}$alkyl, hydroxy$C_{1-4}$alkyl, carboxy$C_{1-4}$alkyl, carbamoyl$C_{1-4}$alkyl, carbamoyl$C_{1-4}$alkoxy, $C_{1-4}$alkyloxy, $C_{1-4}$alkylcarbonyl, $C_{1-4}$alkyloxy$C_{1-4}$alkyl, cyano$C_{1-4}$alkyl, di($C_{1-4}$alkyl)amino$C_{1-4}$alkyl, —OCONH$_2$, $C_{1-4}$alkoxy$C_{1-4}$alkyl, aryl, Het$^2C_{1-4}$alkyl, polyhalo$C_{1-4}$alkyl, $C_{3-6}$cycloalkyl or aryl$C_{2-6}$alkenyl;

Het$^3$ is a monocyclic or bicyclic heterocycle selected from pyrrolyl, furanyl, thienyl, imidazolyl, oxazolyl, thiazolyl, pyridinyl, pyrimidinyl, pyrazinyl, pyridazinyl, benzopyrrolyl, benzofuranyl, benzothienyl, benzimidazolyl, benzoxazolyl, benzothiazolyl, quinolinyl, 2-oxo-1,2-dihydro-quinolinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl or a radical of formula

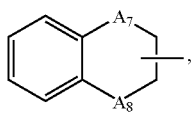

(g-1)

with $A_7$ or $A_8$ each independently being selected from $CH_2$ or O; each of said monocyclic or bicyclic heterocycles may optionally be substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

$Het^4$ is a monocyclic heterocycle selected from pyrrolyl, furanyl, thienyl, imidazolyl, oxazolyl, thiazolyl, pyridyl, pyrimidinyl, pyrazinyl, pyridazinyl, said heterocycle optionally being substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

$Het^5$ is pyridyl, pyrimidyl, pyridazinyl, pyrazinyl, pyrrolyl, thienyl, furanyl, imidazolyl, thiazolyl, oxazolyl, tetrazolyl, piperidinyl, morpholinyl or pyrrolidinyl;

aryl is phenyl optionally substituted with one, two or three substituents each independently selected from halo; hydroxy; carboxyl; cyano; formyl; acetyl; nitro; amino; mono- or di($C_{1-4}$alkyl)amino; $C_{1-4}$alkylcarbonylamino; mono- or di($C_{1-4}$alkyl)aminocarbonylamino; $C_{1-4}$alkyl-S(=O)$_2$—NH—; $Het^5$(=S)—S—$C_{1-4}$alkyl; $C_{1-6}$alkyloxy; sulfamoyl; $C_{1-4}$alkyl)sulfamoyl; arylsulfamoyl; $Het^2$sulfamoyl; O—P=O$R^{15}$; $C_{1-6}$alkyl optionally substituted with halo, hydroxy, cyano, nitro, formyl, amino, mono- or di($C_{1-4}$alkyl)amino, $C_{1-6}$alkyloxycarbonyl, $C_{1-6}$alkyloxy, $C_{1-6}$alkyloxy$C_{1-6}$alkyloxy, $C_{2-6}$alkenyloxy, $C_{1-6}$alkylcarbonyloxy, $C_{1-6}$alkyloxycarbonylthio, N-hydroxyimino, phenyl or $Het^5$; $C_{2-6}$alkenyl optionally substituted with halo, hydroxy, cyano, nitro, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or $Het^5$; $C_{2-6}$alkynyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or $Het^5$; phenyl; phenyloxy; phenyl($C_{1-4}$alkyl)thio$C_{1-4}$alkyl; ($C_{3-6}$)cyclohexylthio$C_{1-4}$alkyl or isoxazolinyl optionally substituted by $C_{1-4}$alkyloxycarbonyl or morpholinyl$C_{1-4}$alkyl provided that 3-iodo-6-methyl-4-phenoxy-2(1H)-pyridinone is not included.

2. A compound according to claim 1 wherein

Q is halo;

X is a bivalent radical of formula

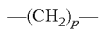  (a-1)

or

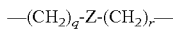  (a-2);

wherein p is an integer of value 1 to 5;

q is an integer of value 0 to 5;

r is an integer of value 0 to 5;

Z is O, S, $NR^7$, C(=O), S(=O), S(=O)$_2$, $CHOR^{13}$, CH=CH, CH($NR^7R^8$) or $CF_2$;

and wherein each hydrogen atom may be replaced by $C_{1-4}$alkyl or hydroxy$C_{1-4}$alkyl;

$R^1$ is $C_{3-6}$cycloalkyl; or aryl;

$R^2$ is selected from hydrogen; formyl; cyano; azido; hydroxy; oxiranyl; amino; mono- or di($C_{1-4}$alkyl) amino; formylamino; $R^{5a}R^{6a}N$—C(=O)—; $R^9$—N=C($R^{10}$)—; $C_{2-6}$alkenyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or $Het^2$; $C_{2-6}$alkynyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or $Het^2$; $C_{1-6}$alkyloxy; hydroxy$C_{1-6}$alkyloxy; amino$C_{1-6}$alkyloxy; mono- or di($C_{1-4}$alkyl)amino$C_{1-6}$alkyloxy; $C_{1-6}$alkylcarbonyl; arylcarbonyl; $Het^2$carbonyl; $C_{1-6}$alkyloxycarbonyl; $C_{1-6}$alkylcarbonyloxy; aryl; aryloxy; aryl$C_{1-6}$alkyloxy; arylthio; aryl$C_{1-6}$alkylthio; mono- or di(aryl)amino; $Het^2$; $Het^2$oxy; $Het^2$thio; $Het^2C_{1-6}$alkyloxy; $Het^2C_{1-6}$alkylthio; mono- or di($Het^2$)amino; $C_{3-6}$cycloalkyl; $C_{3-6}$cycloalkyloxy; $C_{3-6}$cycloalkylthio; $C_{1-6}$alkylthio; hydroxy$C_{1-6}$alkylthio; amino$C_{1-6}$alkylthio; mono- or di($C_{1-4}$alkyl)amino$C_{1-6}$alkylthio; $C_{1-6}$alkyl optionally substituted with one or two substituents each independently selected from halo, hydroxy, cyano, $C_{1-6}$alkyloxy, $C_{1-6}$alkylthio, hydroxy$C_{1-6}$alkyloxy, $C_{1-6}$alkyloxy$C_{1-6}$alkyloxy, $C_{1-6}$alkylcarbonyl, $C_{1-6}$alkylcarbonyloxy, aminocarbonyloxy, mono- or di($C_{1-4}$alkyl)aminocarbonyloxy, $C_{1-6}$alkyloxycarbonyl, $C_{1-6}$alkyloxycarbonyl$C_{1-6}$alkyloxy, $C_{1-6}$alkyloxycarbonyl$C_{1-6}$alkylthio, aryl, $Het^2$, aryloxy, arylthio, aryl$C_{1-6}$alkyloxy, aryl$C_{1-6}$alkylthio, $Het^2C_{1-6}$alkyloxy, $Het^2C_{1-6}$alkylthio, $C_{1-6}$alkyl-S(=O)$_2$-oxy, amino, mono- or di($C_{1-6}$alkyl)amino, $C_{1-6}$alkyloxy-carbonylamino, $C_{1-6}$alkyloxy$C_{1-6}$alkylcarbonylamino, mono- or di(aryl)amino, mono- or di(aryl$C_{1-4}$alkyl)amino, mono- or di($C_{1-4}$alkyloxy$C_{1-4}$alkyl)amino, mono- or di($C_{1-4}$alkylthio$C_{1-4}$alkyl)amino, mono- or di($Het^2C_{1-4}$alkyl)amino, $R^{11}$—(C=O)—NH—, $R^{12}$—NH—(C=O)—NH—, $R^{14}$—S(=O)$_2$—NH—, $C_{1-6}$alkyl-P(O—$R^{15}$)2=O, $C_{1-6}$alkyl-P(O—$C_{1-6}$alkyl-O)=O or a radical of formula

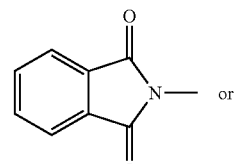  (c-1)

or

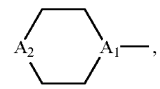  (c-2)

with $A_1$ being $CH_2$ or N, and $A_2$ being $CH_2$, $NR^{13}$, S or O, provided that when $A_1$ is $CH_2$ then $A_2$ is other than $CH_2$, said radical (c-1) and (c-2) being optionally substituted with one or two substituents each independently selected from H, $C_{1-6}$alkyl, $C_{1-6}$alkyloxy, hydroxy $C_{1-4}$alkyl, $C_{1-6}$alkyloxycarbonyl, $C_{1-6}$alkyloxycarbonyl$C_{1-4}$alkyl, amino$C_{1-6}$alkyl, carbonyl, hydroxy, cyano, $CONR^{16}R^{17}$ with $R^{16}$ and $R^{17}$ being independently H or alkyl, mono or di($C_{1-4}$alkyl)aminoalkyl, 4-hydroxy-4-phenyl or 4-cyano-4-phenyl;

$R^3$ is selected from hydrogen; halo; formyl; cyano; azido; hydroxy; oxiranyl; amino; mono- or di($C_{1-4}$alkyl) amino; formylamino; mercapto($C_{1-6}$)alkyl; hydrazino;

$R^{5a}R^{6a}N-C(=O)-$; $R^9-N=C(R^{10})-$; $C_{2-6}$alkenyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, di($C_{1-4}$alkyl)carbamoyl, [di($C_{1-4}$alkyl)amino($C_{1-6}$alkyl)]($C_{1-4}$alkyl)carbamoyl, [di($C_{1-4}$alkyl)amino($C_{1-6}$alkyl)](aryl$C_{1-4}$alkyl)carbamoyl, di($C_{1-4}$alkyloxy)($C_{1-4}$alkyl)carbamoyl, (cyano$C_{1-6}$alkyl)($C_{1-4}$alkyl)amino$C_{1-6}$alkyl, N-hydroxy-imino, aryl, $Het^2$, $Het^2$carboxamido, $Het^2(C_{1-6}$alkyl)carbamoyl; $C_{2-6}$alkynyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or $Het^2$; $C_{1-6}$alkyloxy; hydroxy$C_{1-6}$alkyloxy; amino$C_{1-6}$alkyloxy; mono- or di($C_{1-4}$alkyl)amino$C_{1-6}$alkyloxy; $C_{1-6}$alkylcarbonyl; arylcarbonyl; $Het^2$carbonyl; $C_{1-6}$alkyloxycarbonyl; $C_{1-6}$alkylcarbonyloxy; aryl; aryloxy; aryl$C_{1-6}$alkyloxy; arylthio; aryl$C_{1-6}$alkylthio; mono- or di(aryl)amino; $Het^2$; $Het^2$oxy; $Het^2$thio; $Het^2C_{1-6}$alkyloxy; $Het^2C_{1-6}$alkylthio; $Het^2SO_2$; $Het^2SO$; mono- or di($Het^2$)amino; $C_{3-6}$cycloalkyl; $C_{3-6}$cycloalkyloxy; $C_{3-6}$cycloalkylthio; $C_{1-6}$alkylthio; hydroxy$C_{1-6}$alkylthio; amino$C_{1-6}$alkylthio; mono- or di($C_{1-4}$alkyl)amino$C_{1-6}$alkylthio; $C_{1-6}$alkyl optionally substituted with one or two substituents each independently selected from halo, hydroxy, cyano, carboxyl, $C_{1-6}$alkyloxy, $C_{1-6}$alkylthio, $C_{1-6}$alkylsulfonyl, $C_{1-6}$alkycarbamoyl$C_{1-4}$alkylthio, hydroxy$C_{1-6}$alkyloxy, $C_{1-6}$alkyloxy$C_{1-6}$alkyloxy, $C_{1-6}$alkyloxy$C_{1-6}$alkylthio$C_{1-6}$alkylcarbonyl, $C_{1-6}$alkylcarbonyloxy, aminocarbonyloxy, mono- or di($C_{1-4}$alkyl)aminocarbonyloxy, $C_{1-6}$alkyloxycarbonyl, $C_{1-6}$alkyloxycarbonyl$C_{1-6}$alkyloxy, $C_{1-6}$alkyloxycarbonyl$C_{1-6}$alkylthio, aryl, $Het^2$, aryloxy, arylthio, aryl$C_{1-6}$alkyloxy, aryl$C_{1-6}$alkylthio, $Het^2C_{1-6}$alkyloxy, $Het^2C_{1-6}$alkylthio, $C_{1-6}$alkyl-S(=O)$_2$-oxy, amino, mono- or di($C_{1-6}$amino, di($C_{1-6}$alkyl)amino$C_{1-6}$alkylthio, [di($C_{1-6}$alkyl)amino($C_{1-6}$alkyl)]($C_{1-6}$alkyl)amino, di(cyano$C_{1-6}$alkyl)amino, $C_{1-6}$alkyloxycarbonylamino, $C_{1-6}$alkyloxy$C_{1-6}$alkylcarbonylamino, mono- or di(aryl)amino, mono- or di(aryl$C_{1-4}$alkyl)amino, mono- or di($C_{1-4}$alkyloxy$C_{1-4}$alkyl)amino, mono- or di($CC_{1-4}$alkylthio$C_{1-4}$alkyl)amino, mono- or di($Het^2CC_{1-4}$alkyl)amino, ($Het^2C_{1-4}$alkyl)($C_{1-4}$alkyl)amino, (cyano$C_{1-6}$alkyl)($C_{1-4}$alkyl)amino, $C_{3-6}$cycloalkylthio, $R^{11}-(C=O)-NH-$, $R^{12}-NH-(C=O)-NH-$, $R^{14}-S(=O)_2-NH-$, $C_{1-6}$alkyl-P(O-$R^{15}$)$_2$=O, $C_{1-6}$alkyl-P(O-$C_{1-6}$alkyl-O)=O or a radical of formula

  (c-1)

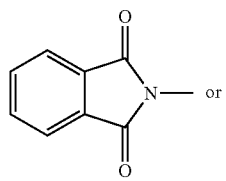 or  (c-2)

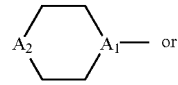 (c-3)

with $A_1$ being CH or N, and $A_2$ being $CH_2$, $NR^{13}$, S or O, provided that when $A_1$ is CH then $A_2$ is other than $CH_2$, said radical (c-1), (c-2) and (c-3) being optionally substituted with one or two substituents each independently selected from H, $C_{1-6}$alkyl, $C_{1-6}$alkyloxy, hydroxy$C_{1-4}$alkyl, $C_{1-6}$alkyloxycarbonyl, $C_{1-6}$alkyloxycarbonyl$C_{1-4}$alkyl, amino$C_{1-6}$alkyl, $C_{1-4}$alkylcarbonyl, arylcarbonyl, aryl, $Het^1$, $Het^1$-(C=O)—, hydroxy, cyano, $C_{1-4}$alkylcyano, $CONR^{16}R^{17}$ with $R^{16}$ and $R^{17}$ being independently H or alkyl, mono or di($C_{1-4}$alkyl)aminoalkyl, 4-hydroxy-4-phenyl or 4-cyano-4-phenyl;

or $R^2$ and $R^3$ may be taken together to form a bivalent radical of formula

—$(CH_2)_t$—$CH_2$-$A_3$-$CH_2$—  (d-1)

with t being an integer of 0, 1 or 2 and $A_3$ being $CH_2$, O, S, $NR^{7a}$ or $N[C(=O)R^{8a}]$ and wherein each hydrogen in said formula (d-1) may be substituted with halo, $C_{1-4}$alkyl, $C_{1-4}$alkyloxy, $C_{1-4}$alkylcarbonyl, halo$C_{1-4}$alkylcarbonyl or arylcarbonyl;

$R^4$ is hydrogen;

$R^{5a}$ and $R^{6a}$ each independently are hydrogen; $C_{1-4}$alkyl optionally substituted with cyano, $C_{1-4}$alkyloxy, $C_{1-4}$alkylthio, amino, mono- or di($C_{1-4}$alkyl)amino or a radical of formula

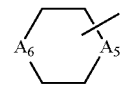  (f-1)

with $A_5$ and $A_6$ each independently being $CH_2$, $NR^{13}$ or O;

$R^7$, $R^{7a}$ and $R^{7b}$ each independently are hydrogen, formyl or $C_{1-4}$alkyl;

$R^8$, $R^{8a}$ and $R^{8b}$ each independently are hydrogen or $C_{1-4}$alkyl;

$R^9$ is hydrogen, hydroxy, $C_{1-4}$alkyloxy, carboxyl$C_{1-4}$alkyloxy, $C_{1-4}$alkyloxycarbonyl$C_{1-4}$alkyloxy, $C_{2-4}$alkenyloxy, $C_{2-4}$alkynyloxy or aryl$C_{1-4}$alkyloxy;

$R^{10}$ is hydrogen, carboxyl or $C_{1-4}$alkyl;

$R^{11}$ is hydrogen; $C_{1-4}$alkyl optionally substituted with cyano, $C_{1-4}$alkyloxy, $C_{1-4}$alkyl-S(=O)$_2$—, aryl or $Het^3$; $C_{1-4}$alkyloxy; $C_{2-4}$alkenyl; aryl$C_{2-4}$alkenyl; $Het^3C_{2-4}$alkenyl; $C_{2-4}$alkynyl; $Het^3C_{2-4}$alkynyl, aryl $C_{2-4}$alkynyl; $C_{3-6}$cycloalkyl; aryl; naphthyl or $Het^3$;

$R^{12}$ is $C_{1-4}$alkyl, aryl$C_{1-4}$alkyl, aryl, arylcarbonyl, $C_{1-4}$alkylcarbonyl, $C_{1-4}$alkyloxycarbonyl or $C_{1-4}$alkyloxycarbonyl$C_{1-4}$alkyl;

$R^{13}$ is hydrogen, $C_{1-4}$alkyl or $C_{1-4}$alkylcarbonyl;

$R^{14}$ is $C_{1-4}$alkyl optionally substituted with aryl or $Het^4$; polyhalo$C_{1-4}$alkyl or $C_{2-4}$alkenyl optionally substituted with aryl or $Het^4$;

$R^{15}$ is $C_{1-4}$ alkyl;

$Het^1$ and $Het^2$ each independently are a heterocycle selected from pyrrolyl, furanyl, thienyl, imidazolyl, oxazolyl, thiazolyl, pyridyl, pyrimidinyl, pyrazinyl, pyridazinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl, benzopyrrolyl, benzofuranyl, benzothienyl, benzimidazolyl, benzoxazolyl, benzothiazolyl, quinolinyl or 2-oxo-1,2-dihydro-quinolinyl, said heterocycle optionally being substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

$Het^3$ is a monocyclic or bicyclic heterocycle selected from pyrrolyl, furanyl, thienyl, imidazolyl, oxazolyl, thiazolyl, pyridinyl, pyrimidinyl, pyrazinyl, pyridazinyl, benzopyrrolyl, benzofuranyl, benzothienyl, benzimidazolyl, benzoxazolyl, benzothiazolyl, quinolinyl, 2-oxo-1,2-dihydro-quinolinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl or a radical of formula

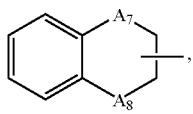

(g-1)

with $A_7$ or $A_8$ each independently being selected from $CH_2$ or O; each of said monocyclic or bicyclic heterocycles may optionally be substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

$Het^4$ is a monocyclic heterocycle selected from pyrrolyl, furanyl, thienyl, imidazolyl, oxazolyl, thiazolyl, pyridyl, pyrimidinyl, pyrazinyl, pyridazinyl, said heterocycle optionally being substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

$Het^5$ is pyridyl, pyrimidyl, pyridazinyl, pyrazinyl, pyrrolyl, thienyl, furanyl, imidazolyl, thiazolyl or oxazolyl;

aryl is phenyl optionally substituted with one, two or three substituents each independently selected from halo; hydroxy; carboxyl; cyano; formyl; nitro; amino; mono- or di($C_{1-4}$alkyl)amino; $C_{1-4}$alkylcarbonylamino; mono- or di($C_{1-4}$alkyl)aminocarbonylamino; $C_{1-4}$alkyl-S(=O)$_2$—NH—; $C_{1-6}$alkyloxy; $C_{1-6}$alkyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkyloxy$C_{1-6}$alkyloxy, $C_{1-6}$alkylcarbonyloxy, N-hydroxy-imino, phenyl or $Het^5$; $C_{2-6}$alkenyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or $Het^5$; $C_{2-6}$alkynyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or $Het^5$; phenyl or phenyloxy.

3. A compound according to claim 1 wherein

Q is halo;

X is (a-2) with q and r being 0 and Z being O, S or SO; $R_1$ is phenyl optionally substituted with one, two or three substituents each independently selected from halo; hydroxy; carboxyl; cyano; formyl; nitro; amino; mono- or di($C_{1-4}$alkyl)amino; $C_{1-4}$alkylcarbonylamino; mono- or di($C_{1-4}$alkyl)aminocarbonylamino; $C_{1-4}$alkyl-S(O)$_2$—NH—; $C_{1-6}$alkyloxy; $C_{1-6}$alkyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkyloxy$C_{1-6}$alkyloxy, $C_{1-6}$alkylcarbonyloxy, N-hydroxy-imino, phenyl or $Het^5$; $C_{2-6}$alkenyl optionally substituted with halo, hydroxy, cyano, formyl, amino, mono- or di($C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or $Het^5$; $C_{1-6}$alkynyl optionally substituted with halo, hydroxy, cyano, formyl, amino, mono- or di $C_{1-4}$alkyl)amino, $C_{1-6}$alkyloxycarbonyl, $C_{1-6}$alkyloxy, $C_{1-6}$alkylcarbonyl, $C_{1-6}$alkylcarbonyloxy, N-hydroxy-imino, phenyl or $Het^5$; phenyl or phenyloxy;

$R_2$ is selected from formyl; $C_{1-6}$alkyloxycarbonylalkyl; $Het^2$; $Het^2C_{1-6}$alkyl; $C_{1-6}$alkylthio; $C_{1-6}$alkyl optionally substituted with one or two substituents each independently selected from hydroxy or halo;

$R_3$ is selected from formyl or $C_{1-6}$alkyl optionally substituted with one or two $C_{1-6}$alkyloxy; and $R_4$ is hydrogen.

4. A compound as according to claim 1 wherein Q is iodo.

5. A compound according to claim 1 wherein Q is iodo, X—$R_1$ is a 3,5-dimethylphenylthio or a 3,5-dimethylphenyloxy and $R_2$ is a hydroxymethyl or a N-morpholinomethyl, or a 3-phenylpropyl or a furan-2-yl-methylthiomethyl.

6. A compound according to claim 1 wherein Q is iodo, X—$R_1$ is a 3-(2-cyano-vinyl)-5-iodophenyloxy or 5-bromo-3-(2-cyano-vinyl) and $R_2$ is ethyl.

7. A compound according to claim 1 wherein the compounds are listed in the following table;

| No | Y | Q | X–R1 | R2 | R3 | R4 |
|---|---|---|---|---|---|---|
| 8 | O | I | 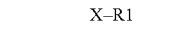 | 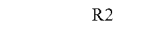 | Me | H |

-continued
| No | Y | Q | X–R1 | R2 | R3 | R4 |
|---|---|---|---|---|---|---|
| 31 | O | I | 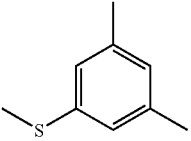 | 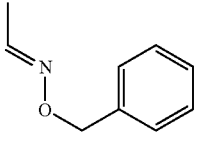 | Me | H |
| 43 | O | I | 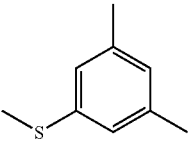 | 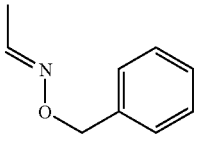 | Me | H |
| 45 | O | I | 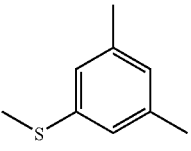 | 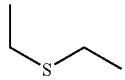 | Me | H |
| 46 | O | I | 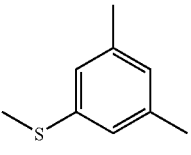 | 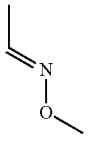 | Me | H |
| 81 | O | I | 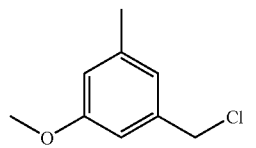 | Et | Me | H |
| 83 | O | I | 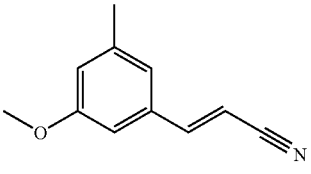 | Et | Me | H |
| 85 | O | Br | 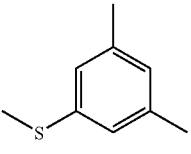 | 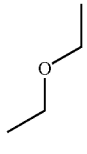 | Me | H |
| 86 | O | I | 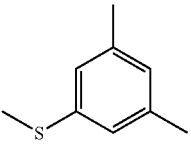 | 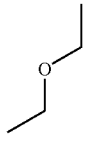 | Me | H |
| 88 | O | I | 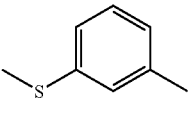 | Et | Me | H |
| 92 | O | I | 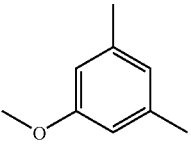 | 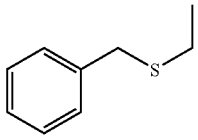 | Me | H |

-continued
| No | Y | Q | X-R1 | R2 | R3 | R4 |
|---|---|---|---|---|---|---|
| 99 | O | I | 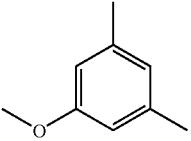 | 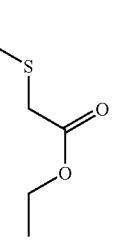 | Me | H |
| 105 | O | I | 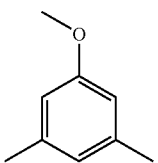 | Et | 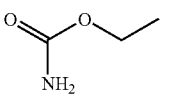 | H |
| 108 | O | I | 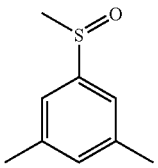 | Et | Me | H |
| 109 | O | I | 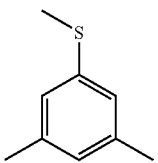 | Et | Me | H |
| 115 | O | I | 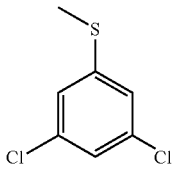 | Et | Me | H |
| 121 | O | I | 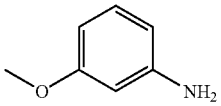 | Et | Me | H |
| 124 | O | I | 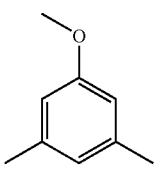 | 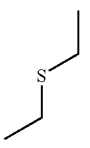 | Me | H |
| 133 | O | I | 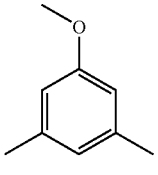 | Et | CH2OH | H |
| 140 | O | I | 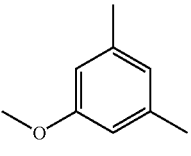 | CH=CHCN | Me | H |

-continued
| No | Y | Q | X–R1 | R2 | R3 | R4 |
|----|---|---|------|-----|-----|-----|
| 143 | O | I | 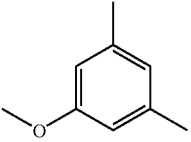 | 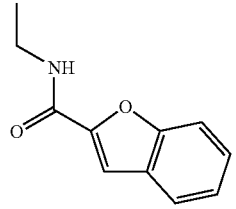 | Me | H |
| 217 | O | I | 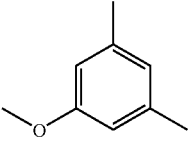 | Et | 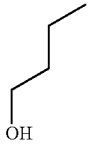 | H |
| 218 | O | I | 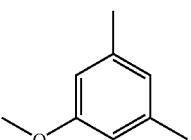 | 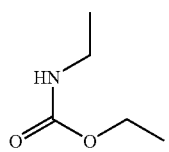 | Me | H |
| 219 | O | I | 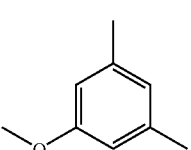 | 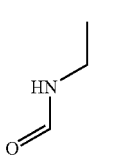 | Me | H |
| 221 | O | I | 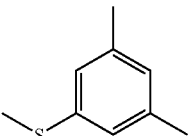 | 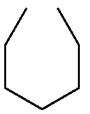 | | H |
| 222 | O | I | 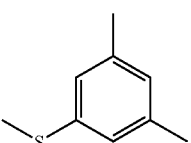 |  | | H |
| 232 | O | I | 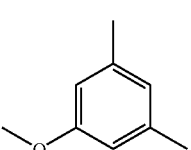 | 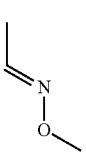 | Me | H |
| 233 | O | I | 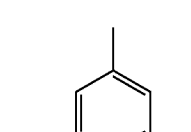 | 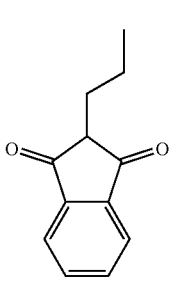 | Me | H |

-continued
| No | Y | Q | X–R1 | R2 | R3 | R4 |
|---|---|---|---|---|---|---|
| 241 | O | I | 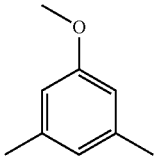 | 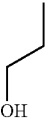 | Me | H |
| 242 | O | I | 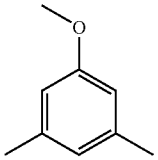 | 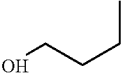 | Me | H |
| 244 | O | I | 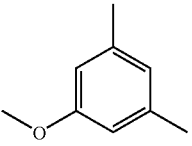 | 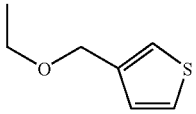 | Me | H |
| 245 | O | I | 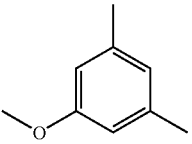 | 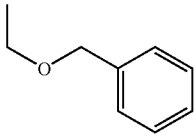 | Me | H |
| 249 | O | I | 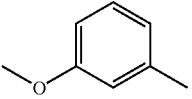 | 2-methoxyethyl | Me | H |
| 250 | O | I | 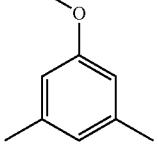 | 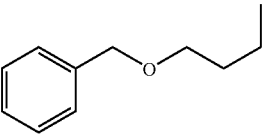 | Me | H |
| 253 | O | I | 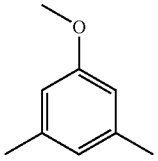 | 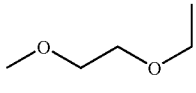 | Me | H |
| 254 | O | I | 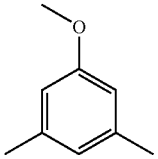 | 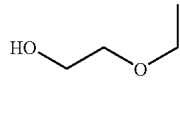 | Me | H |
| 255 | O | I | 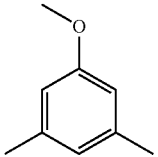 | 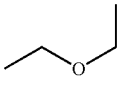 | Me | H |

-continued
| No | Y | Q | X–R1 | R2 | R3 | R4 |
|---|---|---|---|---|---|---|
| 256 | O | I | 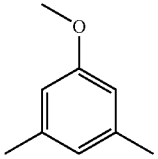 | 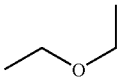 | H | H |
| 257 | O | I | 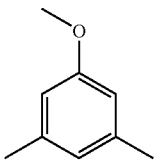 | CH2OH | Me | H |
| 264 | O | I | 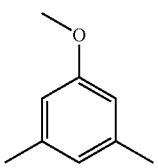 | 2-methoxyethyl | Me | H |
| 284 | O | Br | 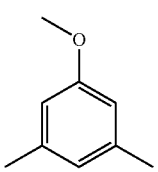 | Et | Me | H |
| 286 | O | I | 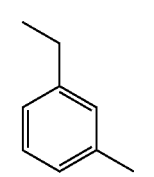 | Et | Me | H |
| 296 | O | I | 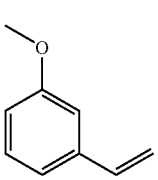 | Et | Me | H |
| 297 | O | I | 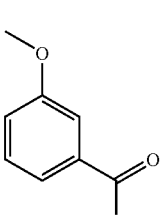 | Et | Me | H |
| 298 | O | I | 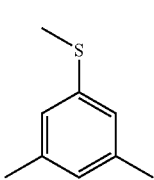 | Et | Me | H |

-continued

| No | Y | Q | X–R1 | R2 | R3 | R4 |
|---|---|---|---|---|---|---|
| 299 | O | I | 3-methoxyphenyl-pentadienyne | Et | Me | H |
| 306 | O | I | 2-methyl-methoxybenzene | Et | Me | H |
| 307 | O | I | 1-bromo-3-methoxybenzene | Et | Me | H |
| 309 | O | I | 3-methoxyphenyl-propenyl-N-methylimine | Et | Me | H |
| 314 | O | I | 3-methylphenyl methyl ether | Et | H | H |
| 319 | O | I | 3-methoxyphenyl-butenyne | Et | Me | H |
| 321 | O | I | 3-methoxybenzaldehyde | Et | Me | H |
| 322 | O | I | 3-methoxybenzyl alcohol | Et | Me | H |
| 326 | O | I | 3,5-dimethyl methoxybenzene | Et | Me | H |
| 328 | O | I | OPh | Et | Me | H |
| 370 | O | I | 3,5-dimethylphenyl methylsulfide | ethylthio-N-methylacetamide | Me | H |

-continued
| No | Y | Q | X–R1 | R2 | R3 | R4 |
|---|---|---|---|---|---|---|
| 375 | O | I | 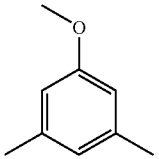 | 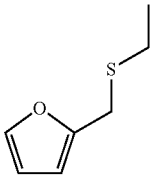 | Me | H |
| 426 | O | I | 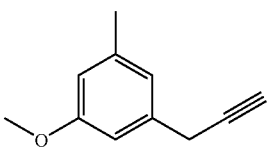 | Et | Me | H |
| 470 | O | I | 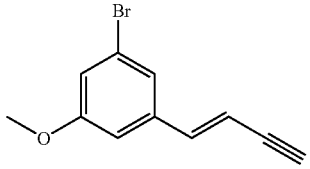 | Et | Me | H |
| 483 | O | I | 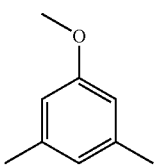 | 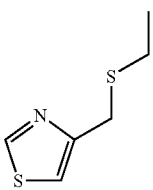 | Me | H |
| 547 | O | I | 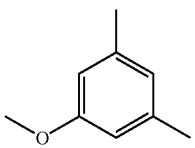 | 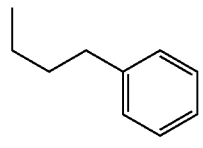 | Me | H |
| 551 | O | I | 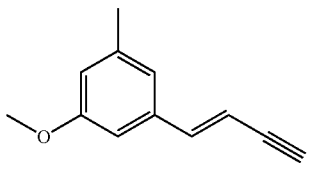 | Et | Me | H |
| 574 | O | I | 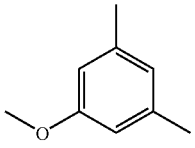 | 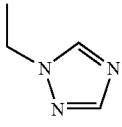 | Me | H |
| 589 | O | I | 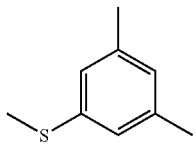 | 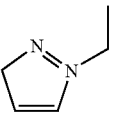 | Me | H |
| 606 | O | I | 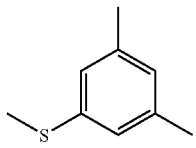 | 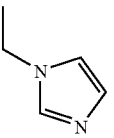 | Me | H |

-continued
| No | Y | Q | X–R1 | R2 | R3 | R4 |
|---|---|---|---|---|---|---|
| 618 | O | I | 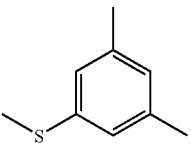 | 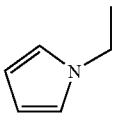 | Me | H |
| 650 | O | I | 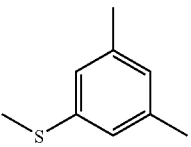 | 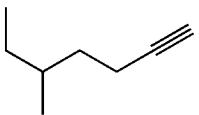 | Me | H |
| 662 | O | I | 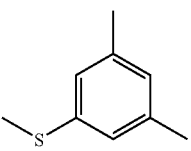 | 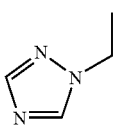 | Me | H |
| 684 | O | I | 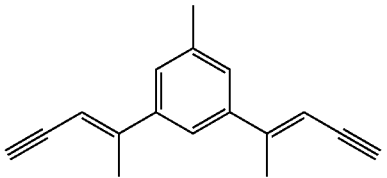 | Et | Me | H |
| 694 | O | I | 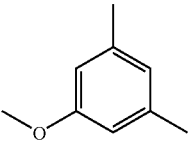 | 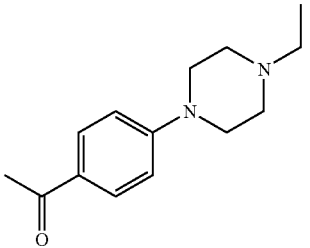 | Me | H |
| 696 | O | I | 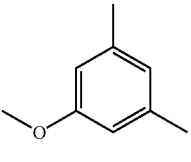 | 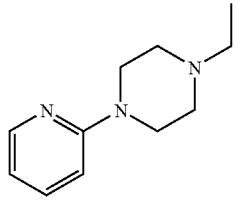 | Me | H |
| 700 | O | I | 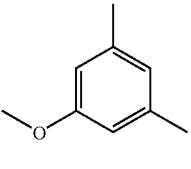 | 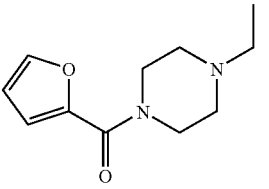 | Me | H |
| 701 | O | I | 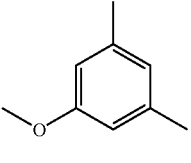 | 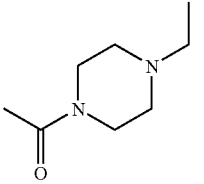 | Me | H |

-continued

| No | Y | Q | X–R1 | R2 | R3 | R4 |
|---|---|---|---|---|---|---|
| 709 | O | I | 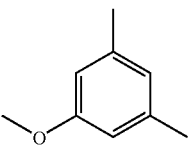 | 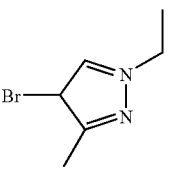 | Me | H |
| 713 | O | I | 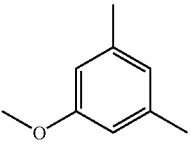 | 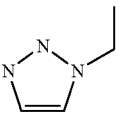 | Me | H |

8. A method for treating subjects suffering from Human Immuno Deficiency Virus infection by administering a therapeutically effective amount of a compound according to claim 1.

9. A pharmaceutical composition comprising a pharmaceutically acceptable carrier and a therapeutically active amount of a compound according to claim 1.

* * * * *